US010328276B2

(12) United States Patent
Williams et al.

(10) Patent No.: US 10,328,276 B2
(45) Date of Patent: Jun. 25, 2019

(54) SINUSOIDAL DRIVE SYSTEM AND METHOD FOR PHOTOTHERAPY

(71) Applicant: Applied BioPhotonics Limited, Cupertino, CA (US)

(72) Inventors: Richard K. Williams, Cupertino, CA (US); Keng Hung Lin, Chupei (TW); Daniel Schell, Los Gatos, CA (US); Joseph P. Leahy, Los Gatos, CA (US)

(73) Assignee: Applied BioPhotonics Ltd., Hong Kong (CN)

( * ) Notice: Subject to any disclaimer, the term of this patent is extended or adjusted under 35 U.S.C. 154(b) by 336 days.

(21) Appl. No.: 14/461,147

(22) Filed: Aug. 15, 2014

(65) Prior Publication Data

US 2015/0231408 A1 Aug. 20, 2015

Related U.S. Application Data

(60) Provisional application No. 61/940,209, filed on Feb. 14, 2014.

(51) Int. Cl.
*A61N 5/06* (2006.01)
*A61B 17/00* (2006.01)

(52) U.S. Cl.
CPC ...... *A61N 5/06* (2013.01); *A61B 2017/00159* (2013.01); *A61N 2005/0626* (2013.01);
(Continued)

(58) Field of Classification Search
CPC ............... A61B 18/203; A61B 5/0059; A61B 2018/0047; A61B 2017/00159; A61B 18/20–18/28; A61N 5/06–2005/073
(Continued)

(56) References Cited

U.S. PATENT DOCUMENTS 5,409,445 A * 4/1995 Rubins ................. A61M 21/00
600/27
6,049,471 A * 4/2000 Korcharz .......... H02M 3/33515
363/20
(Continued)

FOREIGN PATENT DOCUMENTS

GB 2212010 A 7/1989
JP H11192315 A 7/1999
(Continued)

OTHER PUBLICATIONS

Ilango and Vijayalakshmi, Effectiveness of vision stimulation therapy in congenitally blind children, Jul.-Aug. 2008, Indian Journal of Ophthalmology, 342-343.*
(Continued)

*Primary Examiner* — Lynsey C Eiseman
*Assistant Examiner* — Jonathan Kuo
(74) *Attorney, Agent, or Firm* — Patentability Associates; David E. Steuber

(57) ABSTRACT

The LEDs in a phototherapy LED pad are controlled so that the intensity of the light varies in accordance with a sinusoidal function, thereby eliminating the harmonics that are generated when the LEDs are pulsed digitally, in accordance with a square-wave function. This is accomplished analogically by using a sinusoidal wave to control the gate of a MOSFET connected in series with the LEDs or by using a digital-to-analog converter to control the gate of the MOSFET with a stair step function representative of the values of a sinusoidal function at predetermined intervals. Alternatively, pulse-width modulation is used to control the gate of the MOSFET in such a way that the average current through the LEDs simulates a sinusoidal function. In additional to using a simple sine wave function, the LED current may also
(Continued)

be controlled in accordance with "chords" containing multiple sine waves of different frequencies.

28 Claims, 89 Drawing Sheets

(52) U.S. Cl.
CPC ................. *A61N 2005/0629* (2013.01); *A61N 2005/0652* (2013.01)

(58) Field of Classification Search
USPC .................. 606/2, 9–19; 607/88–95, 66–76; 702/112; 708/845
See application file for complete search history.

(56) References Cited

U.S. PATENT DOCUMENTS

| | | | | |
|---|---|---|---|---|
| 6,395,555 | B1* | 5/2002 | Wilson | G01N 33/5008 436/2 |
| 6,586,890 | B2* | 7/2003 | Min | B60Q 1/2607 315/224 |
| 7,645,226 | B2* | 1/2010 | Shealy | A61M 21/00 600/27 |
| 7,744,590 | B2* | 6/2010 | Eells | A61N 5/0613 128/898 |
| 8,236,037 | B2* | 8/2012 | Weisbart | A61N 5/0613 606/9 |
| 8,779,696 | B2 | 1/2014 | Williams et al. | |
| 9,071,139 | B2* | 6/2015 | Williams | H02M 3/158 |
| 9,232,587 | B2 | 1/2016 | Williams et al. | |
| 9,288,861 | B2 | 3/2016 | Williams et al. | |
| 9,877,361 | B2 | 1/2018 | Williams | |
| 9,895,550 | B2 | 2/2018 | Williams et al. | |
| 2003/0231495 | A1* | 12/2003 | Searfoss, III | A61B 5/00 362/249.12 |
| 2005/0245998 | A1 | 11/2005 | Pruitt et al. | |
| 2007/0129776 | A1* | 6/2007 | Robins | A61N 5/0613 607/88 |
| 2007/0219604 | A1* | 9/2007 | Yaroslavsky | A61N 5/0613 607/100 |
| 2009/0112296 | A1* | 4/2009 | Weisbart | A61N 5/0613 607/89 |
| 2012/0143285 | A1* | 6/2012 | Wang | A61B 5/024 607/59 |
| 2013/0313996 | A1* | 11/2013 | Williams | H02M 3/158 315/291 |
| 2015/0297126 | A1* | 10/2015 | Atsumori | A61B 5/7475 600/328 |

FOREIGN PATENT DOCUMENTS

| | | |
|---|---|---|
| RU | 2116089 C1 | 7/1998 |
| WO | 9507731 A1 | 3/1995 |
| WO | 2010033630 A1 | 3/2010 |
| WO | 2013102183 A1 | 7/2013 |

OTHER PUBLICATIONS

Nygaard and Frumkes, LEDs: Convenient, Inexpensive Sources for Visual Experimentation, 1982, Vision Research, vol. 22, pp. 435 to 440.*

Wikipedia page on Current source; Wikipedia; https://en.wikipedia.org/wiki/Current_source; accessed Jan. 9, 2018.*

* cited by examiner

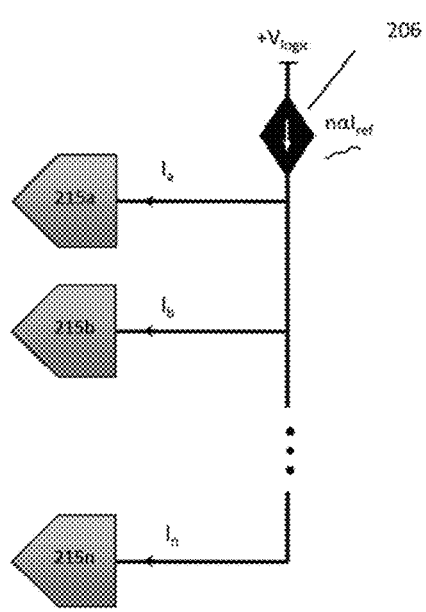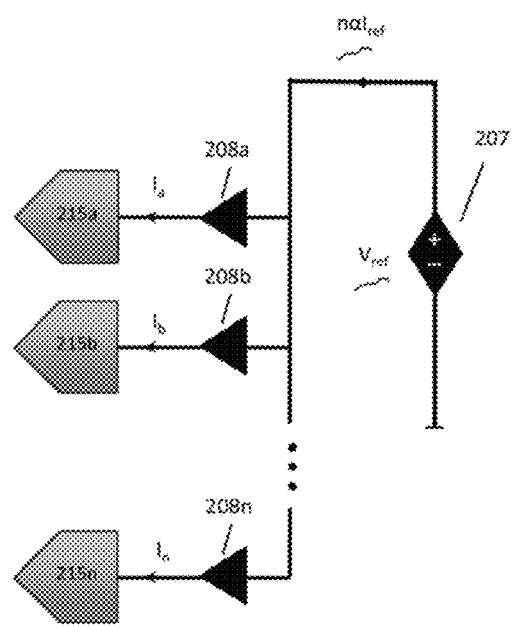
Figure 16A
Figure 16B

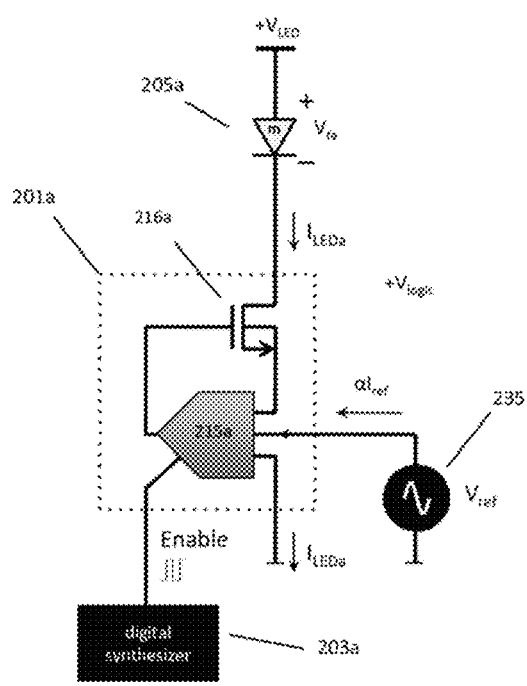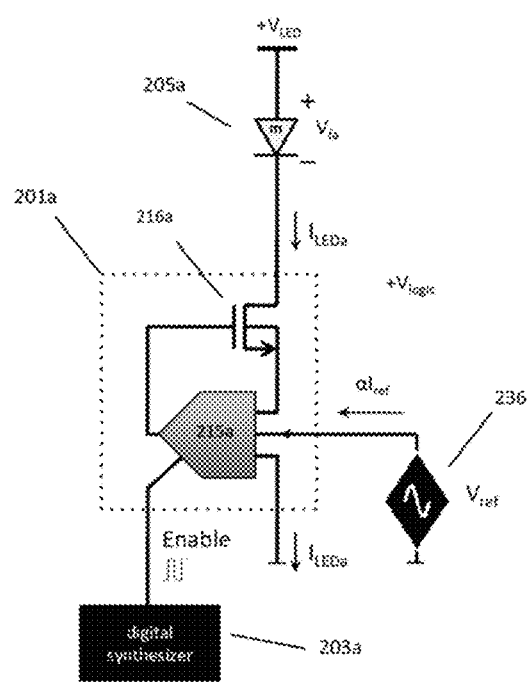
Figure 17A
Figure 17B

815a

| arc° | time (ms) | PWM count | Hex | Synth D out |
|---|---|---|---|---|
| 0 | 0.00 | 128 | 80 | 50.2% |
| 5 | 0.01 | 139 | 8B | 54.5% |
| 10 | 0.02 | 150 | 96 | 58.8% |
| 15 | 0.04 | 160 | A0 | 62.7% |
| 20 | 0.05 | 171 | AB | 67.1% |
| 25 | 0.06 | 181 | B5 | 71.0% |
| 30 | 0.07 | 191 | BF | 74.9% |
| 35 | 0.08 | 201 | C9 | 78.8% |
| 40 | 0.10 | 209 | D1 | 82.0% |
| 45 | 0.11 | 218 | DA | 85.5% |
| 50 | 0.12 | 225 | E1 | 88.2% |
| 55 | 0.13 | 232 | E8 | 91.0% |
| 60 | 0.14 | 238 | EE | 93.3% |
| 65 | 0.15 | 243 | F3 | 95.3% |
| 70 | 0.17 | 247 | F7 | 96.9% |
| 75 | 0.18 | 251 | FB | 98.4% |
| 80 | 0.19 | 253 | FD | 99.2% |
| 85 | 0.20 | 255 | FF | 100.0% |
| 90 | 0.21 | 255 | FF | 100.0% |
| 95 | 0.23 | 255 | FF | 100.0% |
| 100 | 0.24 | 253 | FD | 99.2% |
| 105 | 0.25 | 251 | FB | 98.4% |
| 110 | 0.26 | 247 | F7 | 96.9% |
| 115 | 0.27 | 243 | F3 | 95.3% |
| 120 | 0.29 | 238 | EE | 93.3% |

815b

| arc° | time (ms) | PWM count | Hex | Synth D out |
|---|---|---|---|---|
| 120 | 0.29 | 238 | EE | 93.3% |
| 125 | 0.30 | 232 | E8 | 91.0% |
| 130 | 0.31 | 225 | E1 | 88.2% |
| 135 | 0.32 | 218 | DA | 85.5% |
| 140 | 0.33 | 209 | D1 | 82.0% |
| 145 | 0.34 | 201 | C9 | 78.8% |
| 150 | 0.36 | 191 | BF | 74.9% |
| 155 | 0.37 | 181 | B5 | 71.0% |
| 160 | 0.38 | 171 | AB | 67.1% |
| 165 | 0.39 | 160 | A0 | 62.7% |
| 170 | 0.40 | 150 | 96 | 58.8% |
| 175 | 0.42 | 139 | 8B | 54.5% |
| 180 | 0.43 | 128 | 80 | 50.2% |
| 185 | 0.44 | 116 | 74 | 45.5% |
| 190 | 0.45 | 105 | 69 | 41.2% |
| 195 | 0.46 | 95 | 5F | 37.3% |
| 200 | 0.48 | 84 | 54 | 32.9% |
| 205 | 0.49 | 74 | 4A | 29.0% |
| 210 | 0.50 | 64 | 40 | 25.1% |
| 215 | 0.51 | 54 | 36 | 21.2% |
| 220 | 0.52 | 46 | 2E | 18.0% |
| 225 | 0.54 | 37 | 25 | 14.5% |
| 230 | 0.55 | 30 | 1E | 11.8% |
| 235 | 0.56 | 23 | 17 | 9.0% |
| 240 | 0.57 | 17 | 11 | 6.7% |

815c

| arc° | time (ms) | PWM count | Hex | Synth D out |
|---|---|---|---|---|
| 240 | 0.57 | 17 | 11 | 6.7% |
| 245 | 0.58 | 12 | 0C | 4.7% |
| 250 | 0.59 | 8 | 08 | 3.1% |
| 255 | 0.61 | 4 | 04 | 1.6% |
| 260 | 0.62 | 2 | 02 | 0.8% |
| 265 | 0.63 | 0 | 00 | 0.0% |
| 270 | 0.64 | 0 | 00 | 0.0% |
| 275 | 0.65 | 0 | 00 | 0.0% |
| 280 | 0.67 | 2 | 02 | 0.8% |
| 285 | 0.68 | 4 | 04 | 1.6% |
| 290 | 0.69 | 8 | 08 | 3.1% |
| 295 | 0.70 | 12 | 0C | 4.7% |
| 300 | 0.71 | 17 | 11 | 6.7% |
| 305 | 0.73 | 23 | 17 | 9.0% |
| 310 | 0.74 | 30 | 1E | 11.8% |
| 315 | 0.75 | 37 | 25 | 14.5% |
| 320 | 0.76 | 46 | 2E | 18.0% |
| 325 | 0.77 | 54 | 36 | 21.2% |
| 330 | 0.78 | 64 | 40 | 25.1% |
| 335 | 0.80 | 74 | 4A | 29.0% |
| 340 | 0.81 | 84 | 54 | 32.9% |
| 345 | 0.82 | 95 | 5F | 37.3% |
| 350 | 0.83 | 105 | 69 | 41.2% |
| 355 | 0.84 | 116 | 74 | 45.5% |
| 360 | 0.86 | 128 | 80 | 50.2% |

Figure 37B

SINUSOIDAL DRIVE SYSTEM AND METHOD FOR PHOTOTHERAPY

SCOPE OF INVENTION

This invention relates to biotechnology for medical applications, including photobiomodulation, phototherapy, and bioresonance.

BACKGROUND OF INVENTION

Introduction

Biophotonics is the biomedical field relating to the electronic control of photons, i.e. light, and its interaction with living cells and tissue. Biophotonics includes surgery, imaging, biometrics, disease detection, and phototherapy. Phototherapy is the controlled application of light photons, typically infrared, visible and ultraviolet light for medically therapeutic purposes including combating injury, disease, and immune system distress. More specifically, phototherapy involves subjecting cells and tissue undergoing treatment to a stream of photons of specific wavelengths of light either continuously or in repeated discontinuous pulses to control the energy transfer and absorption behavior of living cells and tissue.

History of Pulsed Phototherapy Technology

For more than a century, doctors, researchers, and amateur experimentalists have dabbled with the response of living cells and tissue to non-ionizing energy, including ultraviolet and visible light, infrared light and heat, microwaves, radio waves, alternating current (specifically microcurrents), ultrasound and sound. In many cases, the energy source is modulated with oscillations or pulses, reportedly resulting in "biomodulation" effects that are different from the effects resulting from the steady application of energy. Even the famous scientist and father of alternating current Nicholas Tesla was known to have subjected himself to high-frequency modulated electrical shocks or "lightning strikes" in theatrical public demonstrations to showcase the supposed benefits of AC technology and oscillatory energy. Unfortunately, despite all the interest and activity, rather than producing a systematic comprehensive knowledge of the cellular interactions with constant and oscillatory directed energy, the consequence of these sensationalized and poorly controlled experiments has produced a confusing, and even self-contradictory, mix of science, pseudo-science, mysticism, and religion. Promulgating these conflicting and sometimes extraordinary claims, today's publications, literature, and web sites range from hard science and biotechnology research to holistic medicine and spiritualism, and often represent sensational pseudo-science (devoid of technical evidence) purely for the purpose of enticing clients and promoting product sales.

Topically, while the greatest interest in directed-energy therapy today is focused on low-level pulsed light for healing (i.e. phototherapy), the earliest studies concerning the influence of oscillatory energy on the process of healing in animal and human tissue did not utilize light, but instead involved stimulating tissue with sinusoidal electrical microcurrents. Performed by the acupuncturist Dr. Paul Nogier in the mid 1950s, this poorly-documented empirically-based work concluded that certain frequencies stimulate healing faster than others and manifest tissue-specificity. The studies were performed in the audio frequency range from zero (DC) to 20 kHz.

Absent clear documentation of the treatment conditions and the apparatus employed, to our knowledge, exact scientific reproduction of Nogier's experiments and verification of his results have not occurred and no scientific technical reports appear in the refereed published literature. So rather than constituting a specific method to cure disease or combat pain, Nogier's reported observations have served as a roadmap, i.e. a set of guiding principles, in the subsequent exploration and development of the field, including the following premises:

- In human patients, the healing of injured or diseased tissue and a patient's perceived pain varies with the oscillating frequency of electrical stimulation (especially 292 Hz or "D" in the musical scale)
- Specific frequencies in the audio range of 20 kHz and below, appear to stimulate different tissue and organs more than others, i.e. tissue specificity is frequency dependent
- Doubling a given frequency appears to behave similar to the original frequency in tissue specificity, in effect, and in efficacy.

It is curious to note in the last bullet point, that even-multiples of a frequency behave similarly, implies harmonic behavior in cellular biology and physiological processes. Such harmonic behavior is analogous to the design of a piano and its keyboard, where doubling or halving a frequency is musically equivalent to the same note one octave, i.e. eight whole tones, higher or lower than the original. Also, the reported benefit of "even" harmonics is consistent with mathematical analysis of physical systems showing even-harmonics couple energy more efficiently, and behave more predictably than circuits or systems exhibiting odd harmonics.

While Nogier's observations have become a serious research topic in the medical research community (especially in its applicability to phototherapy), they also have fueled fanatical claims promoting highly-dubious metaphysical and religious principles that life comprises a single pure frequency, that anything that disturbs that frequency represents disease or injury, and that eliminating or cancelling these bad frequencies somehow will restore health. Even though such incredulous claims for maintaining health have been debunked scientifically, proponents of this theory continue to offer for profit products or services for "enhancing" a person's healthy frequency using so-called "bioresonance" for better health and longer life.

In the context of this application, any discussion of bioresonance herein does not refer to this metaphysical interpretation of the word but instead refers to well defined biochemical processes in cells and in tissue resulting from photobiomodulation. In fact, scientific measurements reveal that not one, but many dozens of frequencies simultaneously coexist in a human body. These measured frequencies—some random, some fixed frequency, and some time-varying, exist mostly in the audio spectrum, i.e. below 20 kHz. These naturally occurring frequencies include ECG signals controlling heart function, EEG signals in the brain controlling thought, visual signals carried by the optic nerve, time-varying muscle stimulation in the peripheral muscles, peristaltic muscle contractions in the intestines and uterus, nerve impulses from tactile sensations carried by the central nervous system and spinal cord, and more. Similar signals are observed in humans, other mammals and in birds. So clearly there is no one frequency that uniformly describes a healthy condition for life.

Starting in the late 1960s, medical interest turned from microcurrents to phototherapy, as pioneered by the Russians and the Czechs and later in the 1980s by NASA-sponsored research in the United States. In the course of researching phototherapy, also known as low-level light therapy (LLLP), the same question of modulating frequency arose, comparing pulsed light to continuous irradiation for phototherapy treatment. The efforts primarily focused on red and infrared light pulsed at frequencies in the audio range, i.e. below 20 kHz.

Numerous studies and clinical trials have since compared various pulsed infrared laser methods to continuous wave treatments for phototherapy. In the journal paper "Effect of Pulsing in Low-Level Light Therapy" published in Lasers Surg. Med. August 2010, volume 42(6), pp. 450-466, the authors and medical doctors Hashmi et al. from Massachusetts General Hospital, Harvard Medical School, and other hospitals, critically reviewed nine direct comparative trials of pulsed wave (PW) and continuous wave (CW) tests. Of these trials, six studies showed pulsed treatments outperformed continuous wave illumination, and only in two cases did the continuous wave treatment outperform light pulsing. In these published works, however, no agreement or consensus was reached defining the optimum pulse conditions for therapeutic efficacy.

One such study showing that pulsed-light phototherapy outperforms continuous light, published in *Laser Medical Science*, 10 Sep. 2011, entitled "Comparison of the Effects of Pulsed and Continuous Wave Light on Axonal Regeneration in a Rat Model of Spinal Cord Injury," by X. Wu et al. addresses the subject of nerve repair. Excerpts include an introduction stating: "Light therapy (LT) has been investigated as a viable treatment for injuries and diseases of the central nervous system in both animal trials and in clinical trials. Based on in vivo studies, LT has beneficial effects on the treatment of spinal cord injury (SCI), traumatic brain injury, stroke, and neurodegenerative diseases."

The study then concentrated its effect on a comparison of continuous wave (CW) light therapy versus pulsed wave (PW) treatments on SCI. The rats were transcutaneously irradiated within 15 minutes of SCI surgery with an 808 nm (infrared) diode laser for 50 minutes daily and thereafter for 14 consecutive days. After an extended discussion, the authors reported: "In conclusion, CW and pulsed laser light support axonal regeneration and functional recovery after SCI. Pulsed laser light has the potential to support axonal regrowth to spinal cord segments located farther from the lesion site. Therefore, the use of pulsed light is a promising non-invasive therapy for SCI."

While the majority of these studies utilized pulsed lasers, similar systems were subsequently developed using digitally pulsed light-emitting diodes (LEDs). These studies (e.g. *Laser Med. Sci.*, 2009) showed that, all things being equal, LED phototherapy matches or outperforms laser phototherapy. Moreover, LED therapy solutions are cheaper to implement and intrinsically offer greater safety than laser methods and apparatus. Given these considerations, this application shall focus on LED based systems, but with the caveat that many of the disclosed inventive methods are equally applicable for both LED or semiconductor-laser based solutions.

Pulsed LED Phototherapy Systems

FIG. 1 illustrates elements of a phototherapy system capable of continuous or pulsed light operation including an LED driver 1 controlling and driving LEDs as a source of photons 3 emanating from LED pad 2 on tissue 5 for the patient. Although a human brain is shown as tissue 5, any organ, tissue or physiological system may be treated using phototherapy. Before and after, or during treatment, doctor or clinician 7 may adjust the treatment by controlling the settings of LED driver 1 in accordance with monitor observations.

While there are many potential mechanisms, as shown in FIG. 2, it is generally agreed that the dominant photobiological process 22 responsible for photobiomodulation during phototherapy treatment occurs within a mitochondrion 21, an organelle present in every eukaryotic cell 20 comprising both plants and animals including birds, mammals, horses, and humans. To the present understanding, photobiological process 22 involves a photon 23 impinging, among others, a molecule cytochrome-c oxidase (CCO) 24, which acts as a battery charger increasing the cellular energy content by transforming adenosine monophosphate (AMP) into a higher energy molecule adenosine diphosphate (ADP), and converting ADP into an even higher energy molecule adenosine triphosphate (ATP). In the process of increasing stored energy in the AMP to ADP to ATP, charging sequence 25, cytochrome-c oxidase 24 acts similar to that of a battery charger with ATP 26 acting as a cellular battery storing energy, a process which could be considered animal "photosynthesis". Cytochrome-c oxidase 24 is also capable of converting energy from glucose resulting from digestion of food to fuel in the ATP charging sequence 25, or through a combination of digestion and photosynthesis.

To power cellular metabolism, ATP 26 is able to release energy 29 through an ATP-to-ADP-to-AMP discharging process 28. Energy 29 is then used to drive protein synthesis including the formation of catalysts, enzymes, DNA polymerase, and other biomolecules.

Another aspect of photobiological process 22 is that cytochrome-c oxidase 24 is a scavenger for nitric oxide (NO) 27, an important signaling molecule in neuron communication and angiogenesis, the growth of new arteries and capillaries. Illumination of cytochrome-c oxidase 24 in cells treated during phototherapy releases NO 27 in the vicinity of injured or infected tissue, increasing blood flow and oxygen delivery to the treated tissue, accelerating healing, tissue repair, and immune response.

To perform phototherapy and stimulate cytochrome-c oxidase 24 to absorb energy from a photon 23, the intervening tissue between the light source and the tissue absorbing light cannot block or absorb the light. The electromagnetic radiation (EMR) molecular absorption spectrum of human tissue is illustrated in a graph 40 of absorption coefficient versus the wavelength of electromagnetic radiation λ (measured in nm) as shown in FIG. 3. FIG. 3 shows the relative absorption coefficient of oxygenated hemoglobin (curve 44a), deoxygenated hemoglobin (curve 44b), cytochrome c (curves 41a, 41b), water (curve 42) and fats and lipids (curve 43) as a function of the wavelength of the light. As illustrated, deoxygenated hemoglobin (curve 44b) and also oxygenated hemoglobin, i.e. blood, (curve 44a) strongly absorb light in the red portion of the visible spectrum, especially for wavelengths shorter than 650 nm. At longer wavelengths in the infrared portion of the spectrum, i.e. above 950 nm, EMR is absorbed by water ($H_2O$) (curve 42). At wavelengths between 650 nm to 950 nm, human tissue is essentially transparent as illustrated by transparent optical window 45.

Aside from absorption by fats and lipids (curve 43), EMR comprising photons 23 of wavelengths λ within in transparent optical window 45, is directly absorbed by cytochrome-c oxidase (curves 41aa, 41b). Specifically, cytochrome-c oxidase 24 absorbs the infrared portion of the spectrum represented by curve 41b unimpeded by water or blood. A secondary absorption tail for cytochrome-c oxidase (curve 41a) illuminated by light in the red portion of the visible spectrum is partially blocked by the absorption properties of deoxygenated hemoglobin (curve 44b), limiting any photobiological response for deep tissue but still activated in epithelial tissue and cells. FIG. 3 thus shows that phototherapy for skin and internal organs and tissue requires different treatments and light wavelengths, red for skin and infrared for internal tissue and organs.

Present Photonic Delivery Systems

In order to achieve maximum energy coupling into tissue during phototherapy, it is important to devise a consistent delivery system for illuminating tissue with photons consistently and uniformly. While early attempts used filtered lamps, lamps are extremely hot and uncomfortable for patients, potentially can burn patient and doctors, and are extremely difficult in maintaining uniform illumination during a treatment of extended durations. Lamps also suffer short lifetimes, and if constructed using rarified gasses, can also be expensive to replace regularly. Because of the filters, the lamps must be run very hot to achieve the required photon flux to achieve an efficient therapy in reasonable treatment durations. Unfiltered lamps, like the sun, actually deliver too broad of a spectrum and limit the efficacy of the photons by simultaneously stimulating both beneficial and unwanted chemical reactions, some involving harmful rays, especially in the ultraviolet portion of the electromagnetic spectrum.

As an alternative, lasers have been and continue to be employed to perform phototherapy. Like lamps, lasers risk burning a patient, not through heat, by exposing tissue to intense concentrated optical power. To prevent that problem, special care must be taken that laser light is limited in its power output and that unduly high current producing dangerous light levels cannot accidentally occur. A second, more practical problem arises from a laser's small "spot size", the illuminated area. Because a laser illuminates a small focused area, it is difficult to treat large organs, muscles, or tissue and it is much easier for an overpower condition to arise.

Another problem with laser light results from its "coherence," the property of light preventing it from spreading out, making it more difficult to cover large areas during treatment. Studies reveal there is no inherent extra benefit from phototherapy using coherent light. For one thing, bacterial, plant and animal life evolved on and naturally absorbs scattered, not coherent light because coherent light does not occur naturally from any known light sources. Secondly, the first two layers of epithelial tissue already destroy any optical coherence, so the presence of coherence is really relegated to light delivery but not to its absorption.

Moreover, the optical spectrum of a laser is too narrow to fully excite all the beneficial chemical and molecular transitions needed for to achieve high efficacy phototherapy. The limited spectrum of a laser, typically a range of ±3 nm around the laser's center wavelength value, makes it difficult to properly excite all the beneficial chemical reactions needed in phototherapy. It is difficult to cover a range of frequencies with a narrow bandwidth optical source. For example, referring again to FIG. 3, clearly the chemical reactions involved in making the CCO absorption spectra (curve 41b) is clearly different than the reactions giving rise to absorption tail (curve 41a). Assuming the absorption spectra of both regions are shown to be beneficial it is difficult to cover this wide range with an optical source having a wavelength spectrum only 6 nm wide.

So just as sunlight is an excessively broad spectrum, photobiologically exciting many competing chemical reactions with many EMR wavelengths, some even harmful, laser light is too narrow and does not stimulate enough chemical reactions to reach full efficacy in phototherapeutic treatment. This subject is discussed in greater detail in a related application entitled "Phototherapy System And Process Including Dynamic LED Driver With Programmable Waveform", by Williams (U.S. application Ser. No. 14/073, 371), now U.S. Pat. No. 9,877,361, issued Jan. 23, 2018, incorporated herein by reference.

To deliver phototherapy by exciting the entire range of wavelengths in the transparent optical window 45, i.e. the full width from approximately 650 nm to 950 nm, even if four different wavelength light sources are employed to span the range, each light source would require a bandwidth almost 80 nm wide. This is more than an order of magnitude wider than the bandwidth of a laser light source. This range is simply too wide for lasers to cover in a practical manner. Today, LEDs are commercially available for emitting a wide range of light spectra from the deep infrared through the ultraviolet portion of the electromagnetic spectrum. With bandwidths of ±30 nm to ±40 nm, it is much easier to cover the desired spectrum with center frequencies located in the red, the long red, the short near infrared (NIR) and the mid NIR portions of the spectrum, e.g. 670 nm, 750 nm, 825 nm, and 900 nm.

FIG. 4 illustrates a preferred solution to light delivery problem is to employ a flexible LED pad, one that curves to a patient's body as shown in pictograph 59. As shown, flexible LED pad 50 is intentionally bent to fit a body appendage, in this case leg comprising tissue 61, and pulled taught by Velcro strap 57. To prevent slippage, flexible LED pad 50 includes Velcro strips 58 glued to its surface. In use, Velcro strap 57 wrapped around the pad attaches to the Velcro strips 58 holding flexible LED pad 50 firmly in position conforming to a patient's leg, arm, neck, back, shoulder, knee, or any other appendage or body part comprising tissue 61.

The resulting benefit, also shown in FIG. 4 illustrates that the resulting light penetration depth 63 into subdermal tissue 62 from LEDs 52 embedded in flexible pad 50 is perfectly uniform along the lateral extent of the tissue 62. Unlike devices where the light source is a stiff LED wand or inflexible LED panel held above the tissue being treated, in this example the flexible LED pad 50 is positioned adjacent to the patient's skin, i.e. epithelial 61, separated from the skin only by a disposable aseptic sanitation barrier 51, typically a clear hypoallergenic biocompatible plastic layer, which prevents the inadvertent spread of virulent agents through contact with LED pad 50. Close proximity between the LEDs 52 and the tissue 62 is essential to maintain consistent illumination for durations of 20 minutes to over 1 hour, an interval too long to hold a device in place manually. This is one reason handheld LED devices and gadgets, including brushes, combs, wands, and torchlights, have been shown to offer little or no medical benefit for phototherapy treatment.

A prior art phototherapy system for controlled light delivery available today and shown in the pictograph of FIG. 5 comprises an electronic driver 70 connected to one or more sets of flexible LED pads 71a-71e through cables 72a and 72b and connected to one other through short electrical connectors 73a-73d.

Specifically, one electrical output of electronic LED driver 70 is connected to center flexible LED pad 71*a* by electrical cable 72*a*, which is in turn connected to associated side flexible LED pads 71*b* and 71*c* through electrical connectors 73*a* and 73*b*, respectively. A second set of LED pads connected to a second electrical output of electronic driver 70 is connected to center flexible LED pad 71*c* by electrical cable 72*b*, which is in turn connected to associated side flexible LED pads 91*d* and 91*e* through electrical connectors 73*c* and 73*d*, respectively, located on the edge of LED pad 71*c* perpendicular to the edge where electrical cable 72*b* attaches. The use of flexible LED pads and the ability of electronic LED driver 70 to independently drive two sets of LED pads with up to 900 mA of current, with each comprising a set of three pads, renders the phototherapy system a best-in-class product offering today.

Despite its technical superiority, the prior art phototherapy system suffers from numerous limitations and drawbacks, including poor reliability for its LED pads, the inability to control LED current (and therefore light uniformity) across the LED pads, limited control in the excitation patterns driving the LEDs, limited safety and diagnostic features, and the inability to communicate or receive updates via the internet, wirelessly, or by cloud services. These various inadequacies are addressed by a number of related patents.

Improving the reliability of the flexible LED pads is addressed in detail in a related application entitled "Improved Flexible LED Light Pad for Phototherapy," by Williams et. al. (U.S. application Ser. No. 14/460,638) now U.S. Pat. No. 9,895,550, issued Feb. 20, 2018, which is incorporated herein by reference. FIG. 6A illustrates a view of the improved flexible LED pad set, which virtually eliminates all discrete wires and any wires soldered directly into PCBs within the LED pads (except for those associated with center cable 82) while enabling significantly greater flexibility in positioning and arranging the flexible LED pads upon a patient undergoing phototherapy.

As shown, the LED pad set includes three flexible LED pads comprising center flexible LED pad 80*a* with associated electrical cable 82, and two side flexible LED pads 80*b* and 80*c*. All three LED pads 80*a*-80*c* include two connector sockets 84 for connecting pad-to-pad cables 85*a* and 85*b*. Although connector socket 84 is not visible in this perspective drawing as shown, its presence is easily identified by the hump 86 in the polymeric flexible LED pad 80*b*, and similarly in flexible LED pads 80*a* and 80*c*. Pad-to-pad cables 85*a* and 85*b* electrically connect center LED pad 80*a* to LED pads 80*b* and 80*c*, respectively.

Industry standard USB connectors maintain high performance and consistent quality at competitive costs manufactured through a well established high-volume supply chain, using sockets 84 that securely mount to a printed circuit board, and USB cables 85*a* and 85*b*, thereby integrating electrical shielding and molded plugs and resisting breakage from repeated flexing and bending. Moreover, the USB connector cables 85*a* and 85*b* are capable of reliably conducting up to 1 A of current and avoid excessive voltage drops or electromigration failures during extended use. Aside from USB cables, other connector and cable set options include min-USB, IEEE-1394, and others. In the example shown in FIG. 6A, an 8-pin rectangular USB connector format was chosen for its durability, strength, and ubiquity.

In the embodiment shown in FIG. 6A, center flexible LED pad 80*a* is rectangular and includes a strain relief 81 for connecting to cable 82 and two USB sockets 84, all located on the same edge of center LED pad 80*a*, shown as the pad edge parallel to the x-axis. Similarly, each of side LED pads 80*b* and 80*c* is also rectangular and includes two USB sockets also located on the same edge. This connection scheme is markedly different from the prior art device shown in FIG. 5, where the connector sockets are proprietary and located on edges of the LED pads 71*a*-71*c* and 71*c*-71*e* that face one another.

The benefit of this design change greatly improves a physician's or clinician's choices in positioning the LED pads on a patient being treated. Because the connector sockets do not face one another as they do in prior art devices, connector cables 85*a* and 85*b* need not be short in order to allow close placement of the LED pads. In fact, in the example shown, LED pads 80*a*, 80*b* and 80*c* may, if desired, actually abut one another without putting any stress on the cables 85*a* and 85*b* whatsoever, even if long cables are employed. With the LED pads touching, the versatility of the disclosed flexible LED pad set offers a doctor the ability to utilize the highest number of LEDs in the smallest treatment area.

Alternatively, the flexible LED pads may be placed far apart, for example across the shoulder and down the arm, or grouped with two pads positioned closely and the third part positioned farther away. With electrical shielding in cables 85*a* and 85*b*, the pads may be positioned far apart without suffering noise sensitivity plaguing the prior art solutions shown previously.

The design shown in FIG. 6A also makes it easy for a clinician to position the flexible LED pads 80*a*-80*c*, bend them to fit to the patient's body, e.g. around the stomach and kidneys, and then secure the pads 80*a*-80*c* by Velcro belt 93 attaching to Velcro straps 92 attached firmly to the LED pads 80*a*-80*c*. The bending of the individual flexible LED pads 80*a*-80*c* and the Velcro belt 93 binding them together is illustrated in FIG. 6B, where the belt 93 and the pads 80*a*-80*c* are bent to fit around a curved surface with curvature in the direction of the x-axis. In order to bend in the direction of the x-axis, no rigid PCB oriented parallel to the x-axis can be embedded within any of the LED pads 80*a*-80*c*.

In center LED pad 80*a*, cable 82 and an RJ45 connector 83 are used to electrically connect the LED pads 80*a*-80*c* to the LED controller in order to preserve and maintain backward compatibility with existing LED controllers operating in clinics and hospitals today. If an adapter for converting RJ45 connector 83 to a USB connector is included, flexible LED pad 80*a* may be modified to eliminate cable 82 and strain relief 81, instead replacing the center connection with a third USB socket 84 and replacing cable 82 with another USB cable similar to USB cable 85*a* but typically longer in length.

Methods of controlling LED current to improve light uniformity, providing enhanced safety and self-diagnostic capability while augmenting control of LED excitation patterns are described in the above-referenced U.S. Pat. No. 9,877,361.

Control of LED Excitation Patterns

To precisely control the excitation pattern of the light pulses requires more sophisticated phototherapy system comprising advanced electronic control. Such circuitry can be adapted from pre-existing driver electronics, e.g. that used in HDTV LED backlight systems, re-purposed for application to phototherapy.

As shown in FIG. 7, one such advanced electronic drive system adapted from LED TV drive circuitry employs individual channel current control to insure that the current in every LED string is matched regardless of LED forward conduction voltages. As shown, current sinks 96a, 96b, ..., 96n are coupled to power N LED strings 97a, 97b, ..., 97n, respectively, acting as switched constant current devices having programmable currents when they are conducting and the ability to turn on and off any individual channel or combination thereof dynamically under control of digital signals 98a, 98b, ..., 98n, respectively. The number n can be any number of channels that are practical.

As shown, controlled current in current sink 96a is set relative to a reference current 99 at a magnitude Iref and maintained by a feedback circuit monitoring and adjusting the circuit biases accordingly in order to maintain current $I_{LEDa}$ in the string of m series-connected LEDs 97a. The number m can be any number of LEDs that are practical. The current control feedback is represented symbolically by a loop and associated arrow feeding back into current sink 96a. The digital enable signals are then used to "chop" or pulse the LED current on and off at a controlled duty factor and, as disclosed in the above-referenced U.S. Pat. No. 9,877,361, also at varying 27-29 frequencies. An LED controller 103 is powered by low-dropout (LDO) linear regulator 102 and instructed by a microcontroller 104 through a SPI digital interface 105. A switch mode power supply 100 powers LED strings 97a-97n at a high voltage $+V_{LED}$ which may be fixed or varied dynamically.

Despite employing analog current control, the resulting waveforms, and PWM control are essentially digital waveforms, i.e. a string of sequential pulses as shown in FIG. 8A, controlling the average LED brightness and setting the excitation frequency by adjusting the repetition rate and LED on-times. As shown in the simplified timing diagram of FIG. 8A, a string of clock pulses is used to generate a sequential waveform of LED light, which may comprise different wavelength LEDs of wavelengths $\lambda_a$, $\lambda_b$, and $\lambda_c$, each illuminated at different times and different durations.

As shown by the illustrative waveforms 110 and 111 in FIG. 8A, a pulse generator within LED controller 103 generates clock pulses at intervals $T_\Theta$ and a counter located within LED controller 103 associated with generating the waveform 111 counts 9 clock pulses and then turns on the specific channel's current sink and $\lambda_a$ LED string for a duration of 4 pulses before turning it off again. As shown by waveform 112, a second counter, also within LED controller 103, turns on the $\lambda_b$ channel immediately after one clock pulse for a duration of 8 clock pulses, and then turns the channel's LED string off for a duration of 4 clock pulses (while the $\lambda_a$ LED string is on) and then turns the $\lambda_b$ LED string on again for another 3 clock pulses thereafter. As shown by waveform 113, a third counter in LED controller 103 waits 22 pulses before turning on the $\lambda_c$ LED string for a duration of 4 pulses then off again.

In this sequenced manner, $\lambda_b$ LED string conducts for a duration $\Delta_{t1}$ (8 clock pulses), then $\lambda_a$ LED string conducts for a duration $\Delta_{t2}$ (4 clock pulses), then when it turns off $\lambda_b$ LED string conducts for a duration $\Delta_{t3}$ (3 clock pulses), waiting for a duration $\Delta_{t4}$ when no LED string is conducting, and followed by $\lambda_c$ LED string conducting for a duration $\Delta_{t5}$ (4 clock pulses). The timing diagrams 110-113 illustrate the flexibility of the new control system in varying the LED wavelength and the excitation pattern frequency.

The improved LED system allows precise control of the duration of each light pulse emitted by each of LED strings $\lambda_a$, $\lambda_b$ and $\lambda_c$. In practice however, biological systems such as living cells cannot respond to single sub-second pulses of light, so instead one pattern comprising a single wavelength and a single pattern frequency of pulses is repeated for long durations before switching to another LED wavelength and excitation pattern frequency. A more realistic LED excitation pattern is shown in FIG. 8B, where the same clock signal (waveform 110) is used to synthesize, i.e. generate, a fixed frequency excitation pattern 116 of a single $\lambda_a$ wavelength light with an synthesized pattern frequency of $f_{synth}$, where $f_{synth} = 1/nT_\Theta$, where the time $T_\Theta$ is the time interval at which successive clock pulses are generated, and "n" is the number of clock pulses in each period of the synthesized waveform. As shown in waveform 116, until time $t_1$ the LED string is on 50% of the time so the duty factor D is 50% and the brightness of the LED is equal to one-half of what it would be if it were on all the time. After the time $t_2$, the duty factor is increased to 75%, increasing average LED brightness but maintain the same synthesized pattern frequency $f_{synth}$.

Timing diagram 117 illustrates a similar synthesized waveform of a single $\lambda_a$ wavelength light at a fixed brightness and duty factor D=50% until time $t_1$. However, instead of varying the brightness at time $t_2$, the synthesized pattern frequency changes from $f_{synth1}=1/nT_\Theta$ to a higher frequency $f_{synth2}=1/mT_\Theta$, m being less than n. So at time $t_2$, the synthesized frequency increases from $f_{synth1}$ to $f_{synth2}$, even though the duty factor (50%) and LED brightness stay constant. In summary, the improved LED drive system allows the controlled sequencing of arbitrary pulse strings of multiple and varying wavelength LEDs with control over the brightness and the duration and digital repetition rate, i.e. the excitation or pattern frequency.

To avoid any confusion, it should noted that the pattern frequency $f_{synth}$ is not the LED's light frequency. The light's frequency, i.e. the color of the emitted light, is equal to the speed of light divided by the light's wavelength $\lambda$, or mathematically as $\upsilon_{EMR} = c/\lambda \approx (3 \cdot 10^8 \text{ m/s})/(0.8 \cdot 10^{-6} \text{ m}) = 3.8 \cdot 10^{14}$ cycles/s=380 THz For clarity's sake, the light's frequency as shown is referred to by the Greek letter nu or "$\upsilon$" and not by the small letter f or $f_{synth}$. As calculated, the light's electromagnetic frequency is equal to hundreds of a THz (i.e. tera-Hz) while the synthesized pattern frequency of the digital pulses $f_{synth}$ is general in the audio or "sonic" range (and at most in the ultrasound range) i.e. below 100 kHz, at least nine orders-of-magnitude lower. Unless noted by exception, throughout the remainder of this application we shall refer to the "color" of light only by its wavelength and not by its frequency. Conversely, the pulse rate or excitation pattern frequency $f_{synth}$ shall only be described as a frequency and not by a wavelength.

Summary of Limitations in Prior-Art Phototherapy

Prior-art phototherapy apparatus remain limited by a number of fundamental issues in their design and implementation including

- use of lasers (instead of LEDs) limited by their intrinsically narrow bandwidth of emitted light unable to simultaneously stimulate the required range of chemical reactions necessary to maximize photobiostimulation and optimize medical efficacy,
- safety concerns in the use of lasers
- LEDs mounted in a rigid housing unable to conform to treatment areas
- poor, improper, or ineffective modulation of phototherapy excitation patterns The last subject, ineffective modulation of phototherapy excitation patterns represents a major challenge and opportunity for improving photobiomodulation and treatment efficacy, one which represents the focus of this disclosure.

BRIEF SUMMARY OF THE INVENTION

In accordance with this invention, the intensity of light used in phototherapy is varied gradually and repeatedly with regular periodicity rather than being administered as a series of square-wave pulses that are either ON or OFF. In many embodiments the light is generated by strings of light-emitting diodes (LEDs), but in other embodiments other types of light sources, such as semiconductor lasers, may be used. In a preferred embodiment, the light is sometimes varied in accordance with a single frequency sinusoidal function, or a "chord" having two or more sine waves as components, but it will become apparent that the techniques described herein can be employed to generate an infinite variety of intensity patterns and functions.

In one group of embodiments, the intensity of light emitted by a string of LEDs is varied by analogically controlling the gate voltage of a current-sink MOSFET connected in series with the LEDs. A gate driver compares the current in the LED string against a sinusoidal reference current, and the gate voltage of the current-sink MOSFET is automatically adjusted by circuitry within the MOSFET driver until the LED and reference currents match and the LED current is at its desired value. In this way, the LED current mimics the sinusoidal reference current. The sinusoidal reference current can be generated in a variety of ways; for example, with an LC or RC oscillator, a Wien bridge oscillator or a twin T oscillator.

In an alternative version of these embodiments, the gate voltage of the current-sink MOSFET is varied using a digital-to-analog (D/A) converter. The D/A converter is supplied with a series of digital values that represent the values of a sine wave at predetermined instants of time, e. g. 24 values in a full 360° cycle. The digital values may represent not only a sine wave but also may be generated by or from a CD or DVD.

In a second group of embodiments, the LED current is controlled digitally, preferably using pulse-width modulation (PWM). As in the previous embodiment, a sine wave is broken down into a series of digital values that represent its level at particular intervals of time. These intervals are referred to herein as having a duration $T_{sync}$. A pulse is generated for each $T_{sync}$ interval, its width representing the value of the sine wave in that interval. To do this, each $T_{sync}$ interval is further broken down into a number of smaller intervals (each having a duration referred to herein as $T_\theta$), and the gate of the current-sink MOSFET is controlled such that the LED current is allowed to flow during a number of these smaller $T_\theta$ intervals that represent the value of the sine wave. Thus, the current-sink MOSFET is turned ON for part of each $T_{sync}$ interval and turned OFF during the remainder of each $T_{sync}$ interval. As a result, the level of the LED current is averaged (smoothed out) into the form of a sine wave.

The gate of the current-sink MOSFET may be controlled by a precision gate bias and control circuit that receives reference current from a reference current source and an enable signal from a digital synthesizer. The digital synthesizer contains a counter that is set to a number representative of the number of small $T_\theta$ intervals during which the current-sink MOSFET is to be turned ON. The current-sink MOSFET is turned ON, and the counter counts down to zero. When the counter reaches zero, the current-sink MOSFET is turned OFF. The current-sink MOSFET remains OFF for a number of $T_\theta$ intervals equal to the total number of $T_\theta$ intervals in a $T_{sync}$ interval less the number of $T_\theta$ intervals during which the current-sink MOSFET was turned on.

At the beginning of the next $T_{sync}$ interval, a new number representative of the next value of the sine wave is loaded into the counter in the precision gate bias and control circuit, and the process is repeated.

Controlling the LEDs in accordance with a sinusoidal function eliminates the harmonics that are produced when the LEDs are pulsed ON and OFF according to a square wave function, many of which may fall within the "audible" spectrum (generally less than 20,000 Hz) and may have deleterious effects on a phototherapy treatment. Using the technique of this invention, the frequencies of the smaller intervals used in producing the sinusoidal function ($1/T_{sync}$ and $1/T_\theta$) can typically be set at above 20,000 Hz, where they generally have little effect on phototherapy treatments.

Chords containing multiple sinusoidal functions may be generated by adding the values of the component sine waves together. With the analog technique, the sine waves may be added together with an analog mixer, or a chord may be generated using a polyphonic analog audio source in lieu of an oscillator. With the digital technique, the numerical values representing the component sine waves may be added together using an arithmetic logic unit (ALU). Another way of creating a chord is to combine an analog synthesized waveform with a second digital pulse frequency by "strobing" the analog waveform ON and OFF at a strobe frequency. The strobe frequency may be either higher or lower than the frequency of the analog waveform. The strobe pulse may be generated by feeding an analog sine wave to a divide by 2, 4 or 8 counter to produce a second waveform 1, 2 or 3 octaves above the analog sine wave, respectively.

An advantage of using a D/A converter to generate an analog voltage or using the digital technique is that treatment sequences (e.g., for particular organs or tissues) may be stored digitally in a memory (e.g., an EPROM) for convenient retrieval and use by a doctor or other clinician.

BRIEF DESCRIPTION OF THE DRAWINGS

FIG. 12B illustrates a graph showing that the spectral content of a 4,671 Hz digital pulse mostly contaminates the ultrasonic spectrum.

FIG. 16A schematically illustrates the problem of current sharing among multiple loads from a single reference current.

FIG. 16B schematically illustrates the use of transconductance amplifiers for distributing a reference current among multiple loads.

FIG. 17A schematically represents the use of a fixed-frequency voltage source to generate an oscillating current reference.

FIG. 17B schematically represents the use of an adjustable voltage source to generate an oscillating reference current.

FIG. 18A schematically represents an implementation of a single-channel current-controlled LED driver using a D/A converter to generate a reference current.

FIG. 19C illustrates an expanded view of digital steps present in a 18.25 Hz sine wave synthesized from a D/A converter generated reference current.

FIG. 19D illustrates a portion of a 18.25 Hz sine wave comprising a sequence of voltage changes occurring at a clock frequency of a D/A converter.

FIG. 34B graphically illustrates digital synthesis of a 292 Hz (D4) sine wave using 20° intervals.

FIG. 35D illustrates the frequency spectrum of a digitally synthesized 1,168 Hz (D6) sinusoid with a 20% amplitude offset by +60%.

FIG. 37B illustrates the pattern file for the digital synthesis of a 1,168 Hz (D6) sine wave using 4× oversampling.

FIG. 42B illustrates an alternative way of creating chords utilizing the algorithm described in FIG. 41 to generate individual sinusoidal pattern files with normalized mathematical functions.

DESCRIPTION OF THE INVENTION

Harmonic Spectra of Synthesized Patterns

Figure 1:
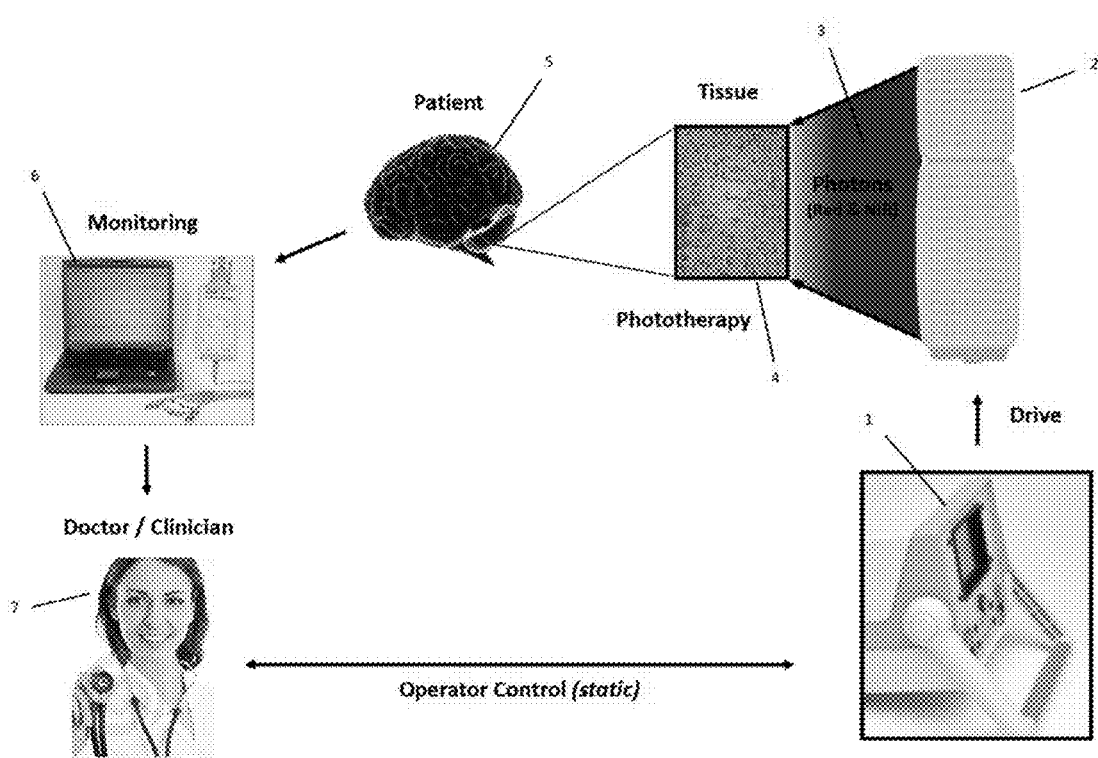
FIG. 1 is a simplified pictorial representation of a phototherapy treatment.

As described previously, the pulsing of light at prescribed frequencies in prior art phototherapy is based on empirical evidence and doctors' observations that pulsed laser light works better than continuous light in reducing pain and healing tissue. As stated previously, while this general conclusion appears credible, no consensus exists on what digital pulses produce the best results and highest treatment efficacies. To date, studies of laser phototherapy did not consider arbitrary waveforms (such as sine waves, ramp waves, sawtooth waveforms, etc.) but were restricted to direct comparisons between continuous wave laser operation (CW) to pulsed wave (PW) laser operation, i.e. square waves, likely because most lasers are designed only to operate by being pulsed on or off digitally. The pulse rates used were chosen to operate at a rate near the time-constants of specific, empirically-observed photobiological processes, i.e. in the audio range below 20 kHz.

In these studies, experimenters report the digital pulse rate and erroneously assume that this square-wave pulse frequency used to modulate the light is the only frequency present in the test. From communication theory, physics, electromagnetics, and the mathematics of Fourier, however, it is well known that digital pulses do not exhibit only the digital pulse frequency, but in fact exhibit an entire spectrum of frequencies. So, while it may seem reasonable to assume digital pulses operating at a fixed clock rate both emit and conduct only a single frequency—the fundamental switching frequency, this self-evident truth is, in fact, incorrect.

In fact, the harmonic content in switched digital systems can be significant both in energy and in the spectrum the harmonics contaminate—some harmonics occurring at frequencies that are orders of magnitude higher than the fundamental frequency. In electromagnetics, these harmonics are often responsible for unwanted conducted and radiated noise, potentially adversely affecting circuit operating reliability. At higher frequencies, these harmonics are known to generate electromagnetic interference, or EMI, radiated into the surroundings.

Mathematical analysis reveals that the speed of the digital on-and-off transitions (along with any possible ringing or overshoot) determine the generated harmonic spectra of a waveform. In power electronic systems such as the LED or laser drivers used in phototherapy systems, the problem is compounded by high currents, large voltages and high power delivered in such applications because more energy is being controlled. In fact. unless the precise rise time and fall time of a string of digital pulses is accurately recorded, the frequency spectrum resulting from the string of pulses is unknown.

The origin and magnitude of these unexpected frequencies can best be understood mathematically. Analysis of any physical system or an electrical circuit may be performed in the "time domain", i.e. where time is the key variable by which everything is measured and referenced, or alternatively in the "frequency domain", where every time-dependent waveform or function is considered as a sum of sinusoidal oscillating frequencies. In engineering, both time and frequency domains are used interchangeably, essentially because some problems are more easily solved in the time domain and others are better analyzed as frequencies.

One means to perform this translation between time and frequency is based on the $18^{th}$ century contributions of the French mathematician and physicist Jean Fourier which revealed that generalized functions may be represented by sums of simpler trigonometric functions, generally sine and cosine waveforms (a cosine may be considered as a sine wave shifted by 90° in phase). The methodology is bidirectional—Fourier analysis comprises decomposing or "transforming" a function into its simpler elements, or conversely, synthesizing a function from these simpler elements. In engineering vernacular, the term Fourier analysis is used to mean the study and application of both operations.

Figure 9A:
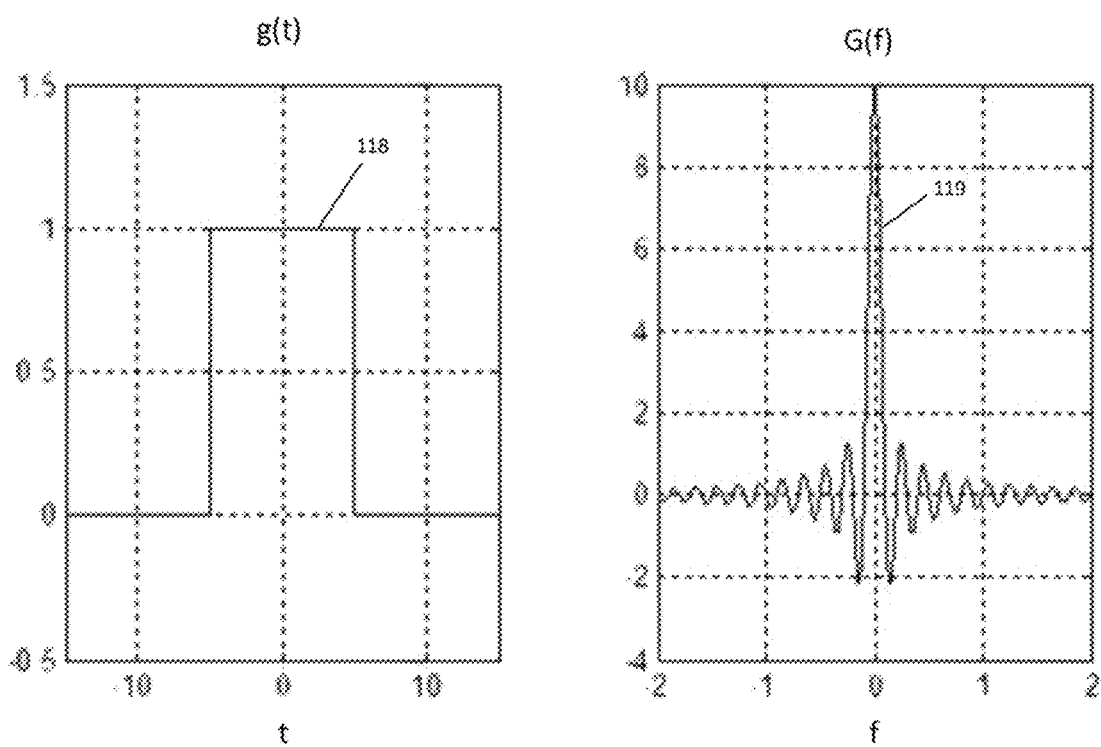
FIG. 9A illustrates the time domain and Fourier frequency domain representation of a digital (square wave) pulse.

A continuous Fourier transform refers to the transform of a continuous real argument into a continuous frequency distribution or vice versa. Theoretically, the continuous Fourier transform's ability to convert a time varying waveform into the precise frequency domain equivalent, requires summing an infinite number of sine waves of varying frequency and sampling the time dependent waveform for an infinite period of time. An example of this transform is shown in FIG. 9A, where graph g(t) illustrates a repeating time dependent waveform 118. The equivalent frequency domain spectrum is shown by graph G(f) illustrating that a simple square wave results in an continuous spectrum 119 of frequencies of varying magnitudes centered around the fundamental frequency f=0.

Of course, taking data samples for infinite time and summing an infinite number of sine waves are both idealized impossibilities. In mathematics and control theory, however, the word "infinite" can be safely translated into a "very large number", or even more practically in engineering to mean a "large number compared to what is being analyzed". Such an approximation of a series sum of a limited number of "discrete" sinusoids is referred to as a discrete Fourier transform or "Fourier series". In practice, measuring a regularly repeating time domain waveform for 2 to 5 periods can be very accurately emulated with the sum of less than 50 sinusoids of varying frequencies. Moreover, in cases where the original time-domain waveform is simple, regular and repeating for extended duration, reasonable approximations can occur by summing only a few sinusoids.

Figure 9B:
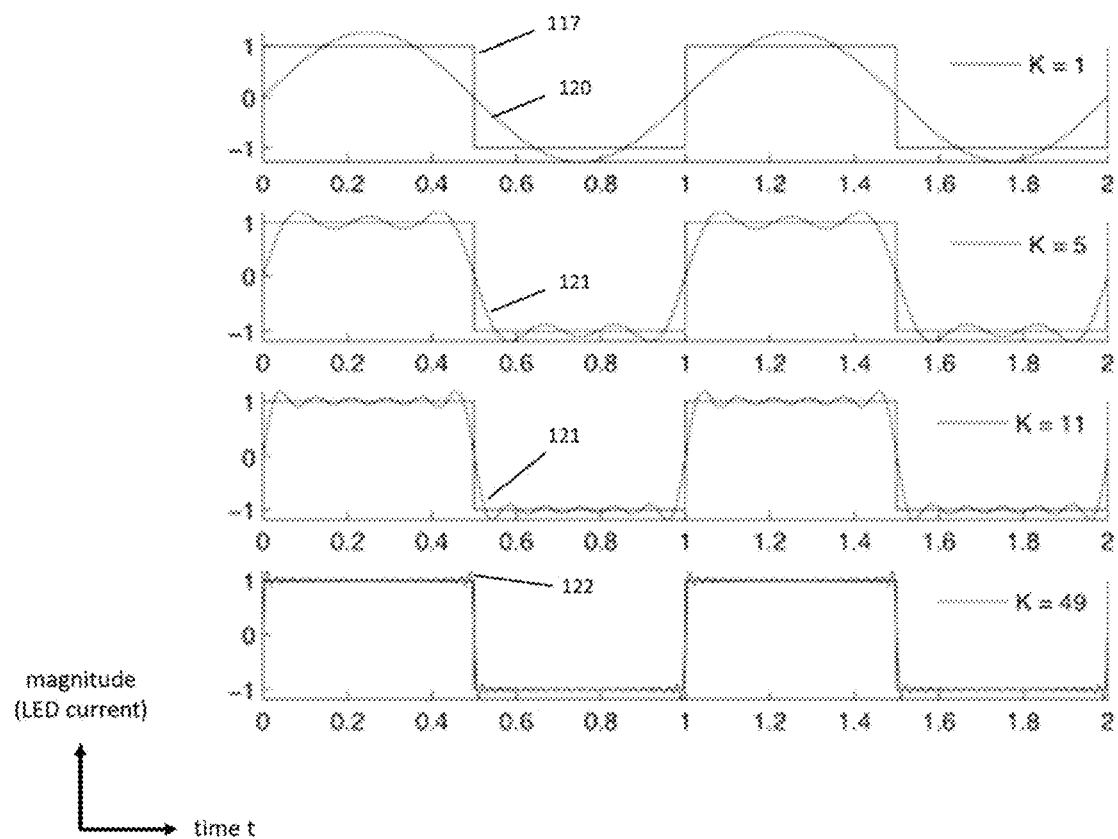
FIG. 9B illustrates a discrete Fourier transform representation using varying numbers of summed sine waves.

This principle is illustrated in FIG. 9B in a graph of signal magnitude, in this case LED current, versus time in four different cases approximating square wave 117 using the discrete Fourier transform method. In the four cases shown the number of sine waves K used in the transform vary from K=1 to K=49. Clearly, in the case of K=1, the single sinusoid only vaguely resembles square wave 117. When the number of sine waves of varying frequency used in the transform is increased to K=5, the resulting reconstructed waveform 121 and its match to square wave 117 improves dramatically. At K=11, the match of waveform 121 very closely tracks the original 117, while at K=49 the transform reconstruction and the original waveform are nearly indistinguishable.

Figure 9C:
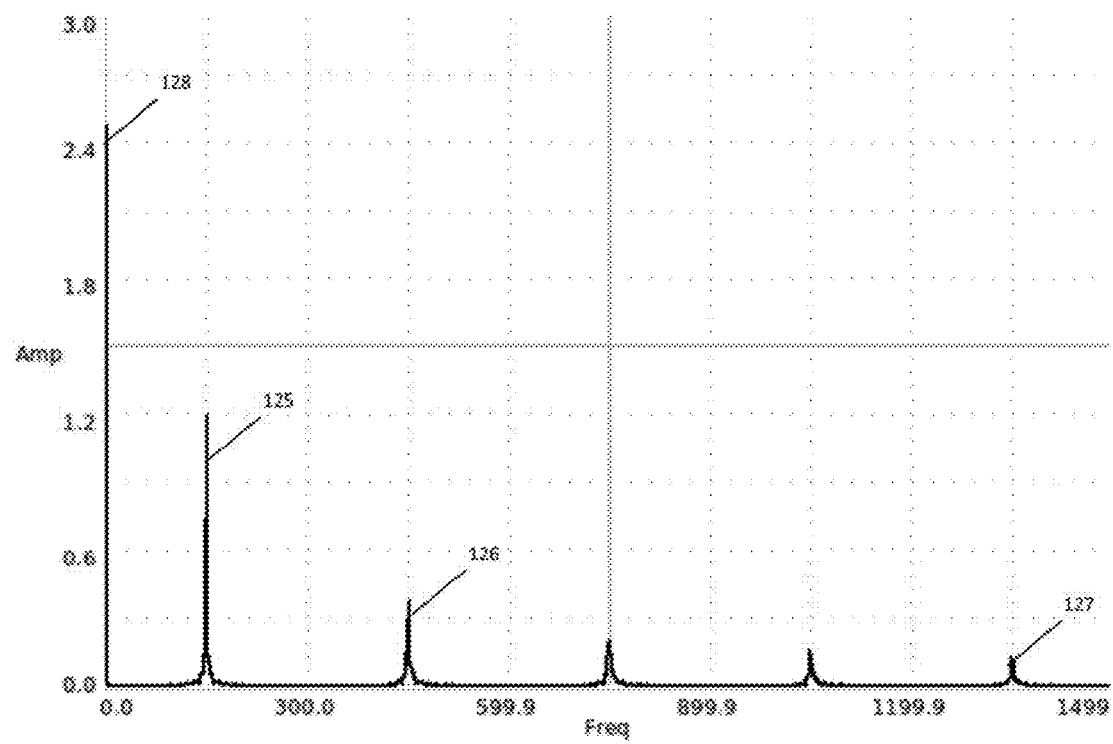
FIG. 9C illustrates the measured current harmonic content of a digitally pulsed power supply.

Through Fourier analysis, then, physicists can observe what frequencies are present in any time varying system or circuit by looking at the constituent components and the amount of energy present in each component. This principle is exemplified in the graph of FIG. 9C showing the measured spectral components of current in a power circuit comprising a 150 Hz square wave. The Fourier transform was performed by the measuring device employing a real time analytical algorithm called a FFT or fast Fourier transform to immediately estimate the measured spectra from a minimal data sample. As shown by spike 125, the fundamental pulse frequency is at 150 Hz and has an amplitude of 1.2 A. The fundamental frequency is accompanied by a series of harmonics at 450 Hz, 750 Hz, 1050 Hz, and 1350 Hz, corresponding to the $3^{rd}$, $5^{th}$, $7^{th}$ and $9^{th}$ harmonics of the fundamental frequency. The $9^{th}$ harmonic 127 has a frequency well into the kHz range despite the low fundamental pulse rate. Also, it should be noted the $3^{rd}$ harmonic 126 is responsible for 0.3 A of the current in the waveform, a substantial portion of the current flowing in the system. As shown, the circuit also included a 2.5 A DC component of current 128, i.e. at a frequency of 0 Hz. A steady DC component does not contribute to the spectral distribution and can be ignored in a Fourier analysis.

Figure 9D:
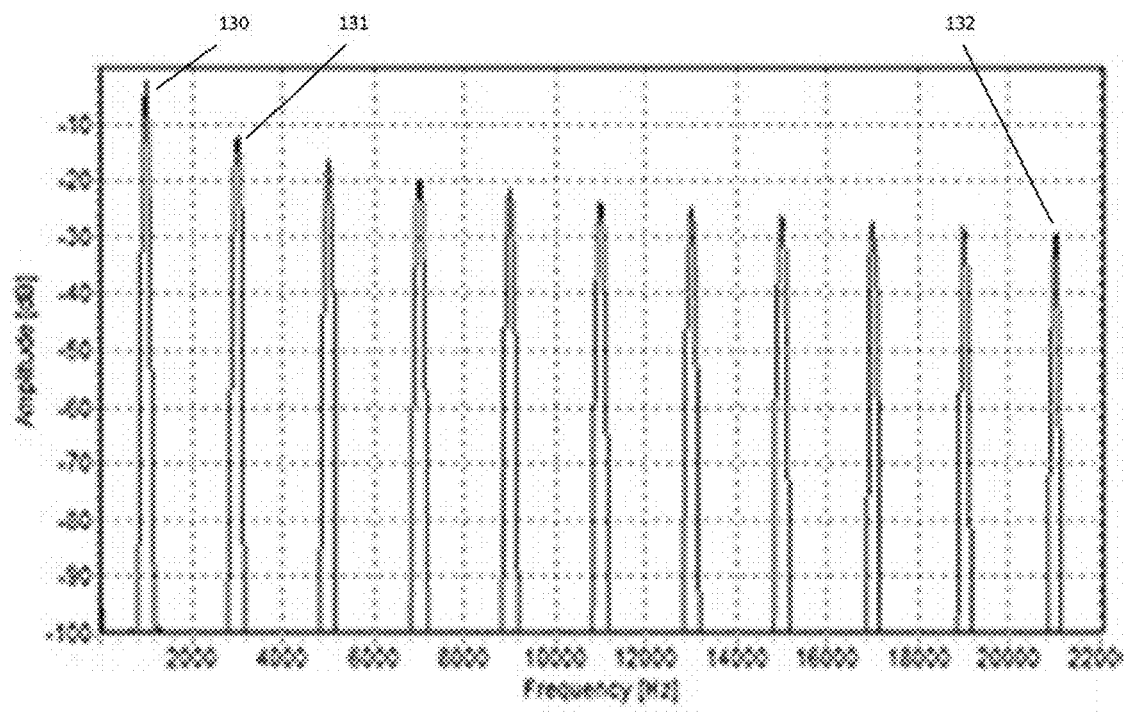
FIG. 9D illustrates a measured Fourier spectrum of amplitude harmonics.
Figure 9E:
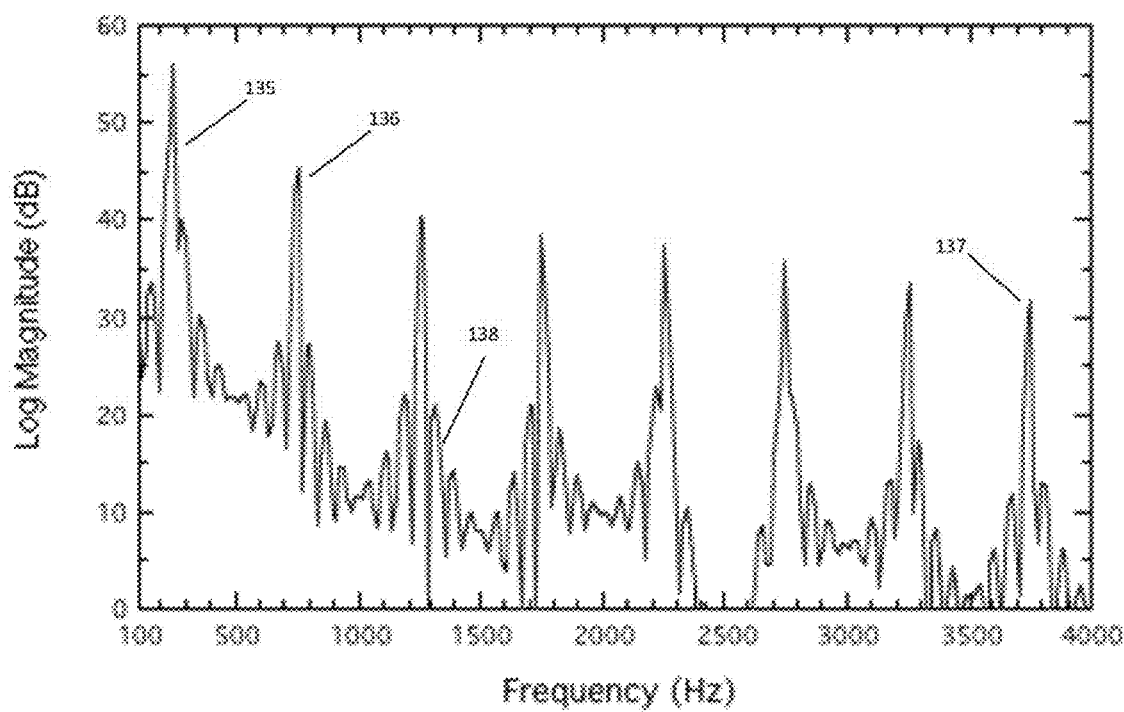
FIG. 9E illustrates a Fourier transform of a limited time sample of a measured amplitude data revealing the frequency "spurs" resulting from the short duration sample.

FIG. 9D illustrates another example of a FFT, this time with the signal amplitude measured in decibels (dB). As shown, the 1 kHz fundamental is accompanied by a sizeable $3^{rd}$ harmonic 131 at 3 kHz and includes spectral contributions 132 above—30 dB beyond 20 kHz. In contrast, FIG. 9E illustrates a less idealistic looking FFT output of a 250 Hz square wave with a fundamental frequency 135 of 250 Hz, a $3^{rd}$ harmonic 136 of 750 Hz, and a $15^{th}$ harmonic 137 of 3750 Hz. The lobes 138 around each significant frequency and the inaccuracy of the frequency can be caused to be two phenomena, either a small and inadequate time based sample measurement possibly with jitter in the signal itself, or the presence of high frequency fast transients that do not appear in normal oscilloscope waveforms but distort the waveform. In this case, as in every prior example shown, the FFTs of a square wave, i.e. a repeating digital pulse, exhibit purely odd harmonics of the fundamental.

Figure 9F:
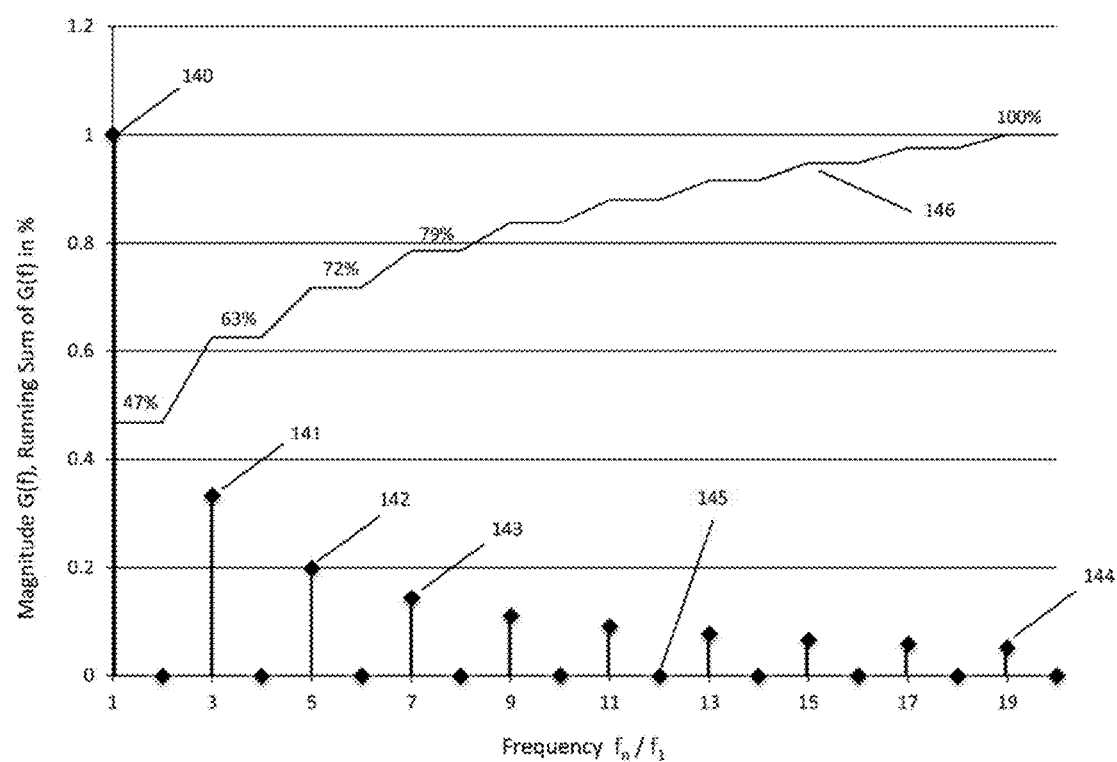
FIG. 9F illustrates the magnitude of odd and even harmonics and the cumulative energy over the spectrum of a continuous Fourier transform of a digital (square wave) pulse.

The behavior of a square wave or a string of digital pulses is summarized in the discrete Fourier transform calculation of a square wave shown in FIG. 9F, where the fundamental frequency 140 is accompanied only by odd harmonics 141, 142, 143 . . . 144 corresponding to the $3^{rd}$, $5^{th}$, $7^{th}$, . . . , $19^{th}$ harmonics. All even harmonics 145 of the fundamental frequency $f_1$ carry no energy, meaning their Fourier coefficient is zero, i.e. they do not exist. If the y-axis also represents the cumulative current or energy of the fundamental and each harmonic component, then assuming the total current is present in the first 20 harmonics and all other harmonics are filtered out, the fundamental alone represents only 47% of the total current as shown by curve 146. This means that less than half the current is oscillating at the desired frequency. Including the $3^{rd}$ harmonic 141, the total current is 63%, while adding the $5^{th}$ and the $7^{th}$ increases the content to 72% and 79% respectively.

While even harmonics, e.g. $2^{nd}$, $4^{th}$, $6^{th}$, ..., $(2n)^{th}$, tend to reinforce their fundamental frequency, it is well known that odd harmonics tend to interfere, i.e. fight, with one another. In the audio spectrum, for example, vacuum tube amplifiers produce even harmonic distortion, a sound that sounds good to the human ear. Bipolar transistors, on the other hand produce odd harmonics that interfere with one another, in the audio spectrum producing a scratchy uncomfortable sound, wasting energy. Whether these frequencies are exciting an audio membrane, e.g. a speaker transducer, a microphone transducer, or the human ear drum, or whether they are exciting a molecule or a group of molecules, the result is the same—orderly oscillations of even harmonics exhibit constructive interference enforcing the oscillations, while competing random oscillations of odd harmonics result in random and even time-varying waveforms manifesting destructive wave interference, producing erratic inefficient energy coupling in a system, and sometimes even giving rise to unstable conditions in the system.

Such is the case in any physical system that can absorb and temporarily store energy then release the energy kinetically. To understand the interaction of such a physical system excited with a spectrum of frequencies, however, the concept of oscillatory behavior and resonance must be considered. Thereafter, the behavior of chemical and biological systems, which follow the same laws of physics, can more thoroughly be considered.

Principles of Oscillations and Resonance

In any physical system capable of manifesting both kinetic energy, i.e. the energy of motion, and potential energy, i.e. stored energy, there exists the capability of oscillatory behavior and "resonance". Oscillations occur when energy repeatedly transfers from one form of potential energy into another. In mechanical examples the compression and expansion of a spring represent an oscillatory system where the spring's tension represents stored energy and where a swinging door represent the kinetic energy of motion and its associated friction leading to energy loss. A similar example is a pendulum or a child swinging in a swing, each time stopping at the top of each arc (where kinetic energy is zero and potential energy is maximum) and then falling back to earth as the swing reaches the bottom of its arc (where the potential energy is at is minimum value and the velocity and kinetic energy of the swing is at its maximum value). In such an example the potential energy is stored in the force due to gravity. Similar phenomena occur in buildings and bridges, sensitive to both wind and seismic vibrations. Each time the object oscillates friction removes some of the energy and the system loses its total energy. Unless that energy is replenished the system will eventually lose all of its energy and cease oscillating.

The mechanism of oscillatory behavior is also manifest in electrical circuits with magnetic and capacitive elements, where the energy may be stored in a magnetic field, or an electric field or some combination thereof. The current and voltage in inductive and capacitive elements are intrinsically out of phase and once energized, spontaneously oscillate, with stored energy being redistributed from the inductor to the capacitor, or vise versa. During the oscillations, whenever current is flowing between the energy storage elements, some of the system's energy is lost as heat as a result of electrical resistance.

At sufficiently high oscillating frequencies, however, the electric field and magnetic field can no longer be contained within the circuit elements. The resulting electro-magnetic field propagates through space as an electromagnetic "traveling" wave, also known as electromagnetic radiation or EMR. Depending on the oscillatory frequency, EMR may comprise radio waves, microwaves, infrared radiation, light, ultraviolet light, X-rays, or gamma-rays. In the vacuum of space EMR can travel indefinitely. By contrast, for any EMR traveling through matter, the wave is gradually attenuated and energy is lost as it travels, in a manner similar to the energy loss due to friction in mechanical systems or to losses due to resistance in electrical circuits.

In any system capable of exhibiting oscillatory behavior, the timing of when energy is put into the system determines its response. In the swing example, if an adult pushes the swing before it has returned fully to the apex of its height, the pushing force will act against the swing's swinging motion and reduce its energy lowering the maximum height to which the swing reaches on its next cycle. The action of pushing too early impedes or interferes with the swing's motion and can be referred to as destructive interference. Conversely, if the adult waits till after the swing reaches its peak height where the swing reverses direction, pushing at that time will put energy into the swing and reinforce the oscillation making the swing reach a higher height on its next oscillatory cycle. The action of pushing at just the right time, thereby reinforcing the swing's motion, can be referred to as constructive interference. If the pushing is done cyclically at just the right moment the swing will go higher with each cycle and the benefit from pushing at the right time maximizes the energy transfer into the swing's oscillations. The swing is said to be oscillating near its "resonant" frequency.

The same thing is true in an electrical system. In a system RLC oscillatory circuit or RLC "tank", energy "sloshes" back and forth between the inductor L and the capacitor C (hence the metaphor of water sloshing to and fro in a "tank"). If an oscillating source of energy such as an AC voltage source driving the network oscillates with a frequency approaching the value 1/SQRT(LC), the oscillations will reach their maximum magnitude and the energy coupling from the AC voltage source into the tank circuit will be greatest. The presence of resistance R causes a loss in energy in the tank circuit. Any excitation frequency below or above the resonant frequency will couple energy into the circuit less efficiently than at the resonant frequency.

To better envision this behavior, the frequency of the oscillating voltage source exciting the oscillating tank circuit is swept starting from a low frequency below resonance up and increased constantly to a higher value. At very low frequencies (near DC) the tank circuit may not react at all. As the frequency ramps, energy couples into the system and current begins to oscillate between the inductor and capacitor. As the driving frequency continues to increase, the response of the tank to the excitation and the corresponding magnitude of the oscillations will grow, steadily at first and then rapidly as the resonant frequency is approached. When the driving voltage source reaches the circuit's resonant frequency the oscillations will hit their peak value and most efficient energy transfer. Continuing to ramp the frequency beyond resonance will reduce the magnitude of the oscillations.

Figure 10:
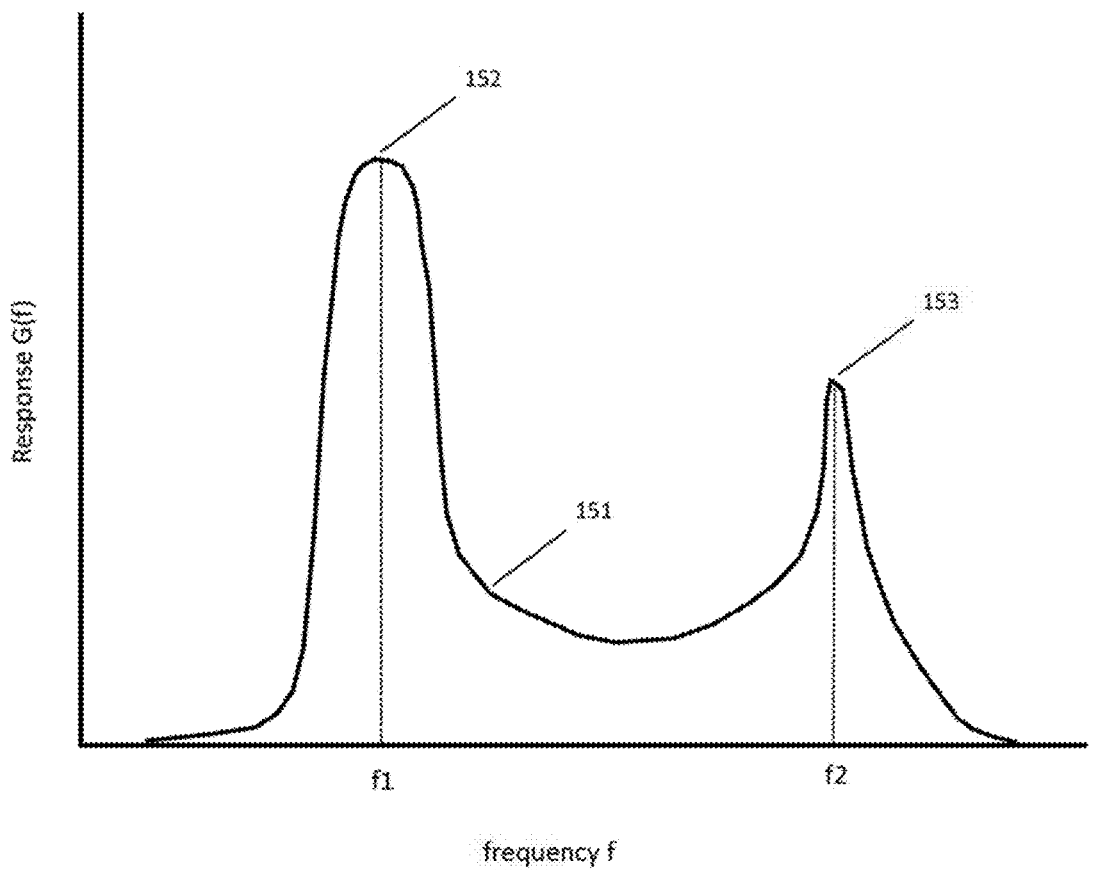
FIG. 10 illustrates a graph of the frequency response of an oscillatory system having two resonant frequencies.

While the example cited describes a system with a single resonant frequency, oftentimes a system contains more than two energy storage elements, conditions or mechanisms and may therefore exhibit two or more natural resonant frequencies. An example of a system with two resonant frequencies is shown in the graph of FIG. 10 as a plot of the magnitude of an oscillation G(f) on y-axis and with frequency f on the x-axis. As shown, response curve 151 includes a lower-frequency resonant peak 152 at a frequency f1 and a second higher-frequency resonant peak 153 at a frequency f2. As shown, resonant peak 152 is greater in magnitude and broader in frequency than resonant peak 153, which exhibits a lower magnitude and a sharper sensitivity to frequency. The magnitude of the system's response between the two resonant peaks never reaches zero, meaning the entire system of energy storage elements are interacting at those excitation frequencies.

So using the prior analytical method, sweeping a single AC voltage source from low to high frequency, will trace out curve 151 starting with an increase in G(f) until resonant peak 152 at frequency f1 is reached then declining and flattening at a lower magnitude until the response again grows as the driving frequency approaches f2 and resonant peak 153, beyond which the response declines. In many instances, physical systems include resonant peaks that are never observed because they are never excited under normal conditions. A classic example of this behavior is a building that sways harmlessly at a fixed frequency in the wind, but in an earthquake resonates severely at a lower frequency leading to building collapse. So in any oscillatory system, if the resonant frequencies are not known it is difficult to analyze a system's response to excitation, especially unintended excitation.

Even worse, if the energy source providing the excitation itself includes a broad and unknown spectrum of frequencies, it is difficult to predict, understand, or even interpret the system's response. Such is the problem with digital pulse excitation of an oscillatory system with multiple resonant frequencies. Since each digital pulse generates a fundamental frequency and a spectrum of harmonics, the various frequencies may stimulate unknown, unwanted, or even potentially harmful harmonics.

In other cases, it may be desirable to intentionally stimulate several specific resonant frequencies but not others. In such cases, digital pulses are also undesirable since the harmonics cover a range of frequencies and may stimulate unwanted resonances. Ideally then, it is preferable in such circumstances to generate oscillations at the two target frequencies, e.g. at f1 and f2. Unfortunately, even ignoring the problem of harmonics, another limitation of digital pulse control to generate pulses at or near a desired frequency, is that the fundamental excitation frequency is intrinsically monophonic, i.e. comprising a single frequency, pitch, or note.

Figure 11:
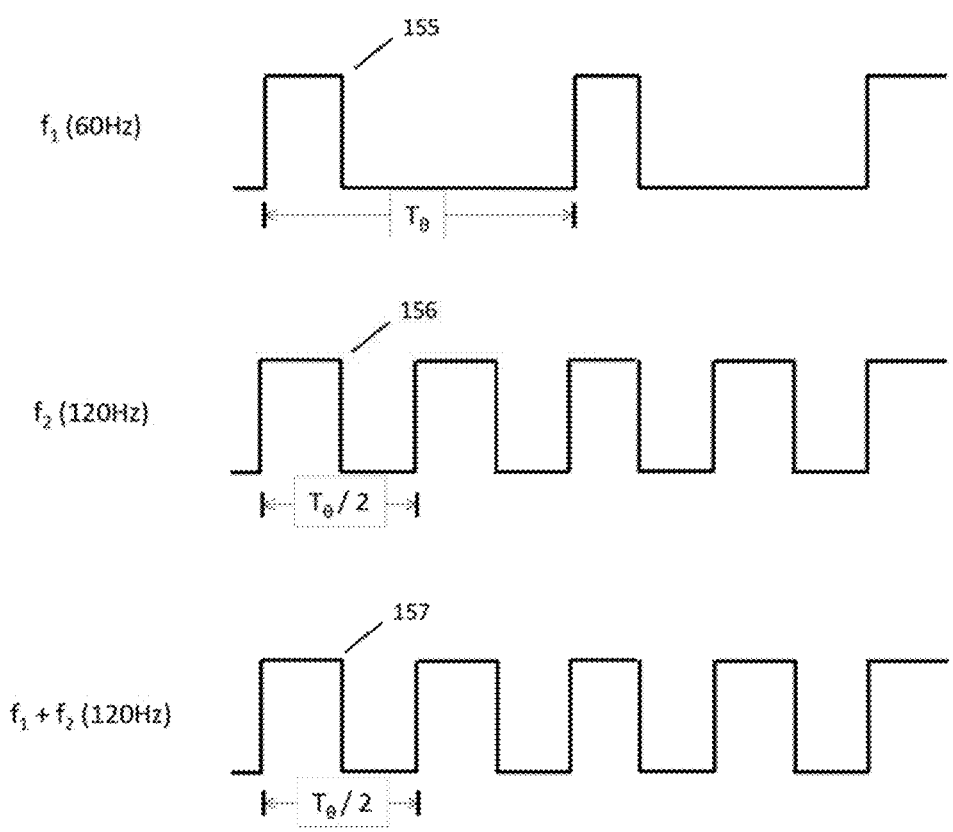
FIG. 11 illustrates the summation of two synchronized digital pulses of varying frequency.

For example, as shown in FIG. 11, if a system continuously generates digital pulses 191 at 60 Hz, and then we add a second series of digital pulses 155 at 120 Hz on top of and synchronized to the original 60 Hz pulses 156, the resulting waveform 193 is identical to the digital pulses 157 at 120 Hz with no 60 Hz component. This means for even multiples of synchronized digital pulses, only the highest frequency multiple is manifest. In essence, when using digital pulses modulated at or near a desired frequency, it is only possible to excite a circuit or an energy conversion device (such as a laser or LED) with one single fundamental frequency, so it is not possible to produce chords or multiple frequencies simultaneously with the digital technology and methods used in today's phototherapy apparatus.

Limitations of Pulsed Phototherapy

In conclusion, Fourier analysis reveals that using digital pulses to control the brightness and pattern frequency of an electrical load, such as an LED or a laser used in a phototherapy system, results in a spectrum of frequencies well beyond that of the fundamental frequency used to pulse the energy conversion device. The resulting harmonic spectrum, comprising odd harmonics, wastes energy and potentially compromises a phototherapy device's ability to acutely control and deliver a specific desired frequency of operation for an electronic circuit or in an energy conversion device (such as a laser or LED).

Applying principles of oscillation and resonance to phototherapy, digital modulation of LED or laser light results in a broad spectrum of frequencies potentially exciting various chemical and photobiological processes in an uncontrolled manner. Since the frequencies needed to activate particular chemical reactions in the healing process are not accurately known, stimulating tissue with an uncontrolled spectrum of harmonics renders identification and isolation of key beneficial frequencies and the systematic improvement of treatment efficacy impossible.

Along with ambiguity stemming from inadequately reported test conditions, harmonic spectral contamination resulting from square-wave pulsing of a light source during phototherapy experiments represents an uncontrolled variable responsible, at least in part, for the conflicting results and inconsistent efficacies observed reported in published studies attempting to optimize pulsed wave phototherapy. Assuming that most photobiological processes occur in the audio spectrum, i.e. below 20 kHz, then analysis shows the impact of spectral contamination from pulsed operation should be worse at lower digital pulse frequencies because unwanted harmonic spectrum generated more significantly overlaps and influences the frequencies sensitive to photobiological stimulation.

For example, the harmonic spectrum of a 292 Hz square wave pulse contaminates most of the audio spectrum, while significant harmonics generated from a 5 kHz square wave pulse occur in the ultrasonic range, i.e. >20 kHz, and beyond a cell's ability to react to such rapid frequencies.

Figure 12A:
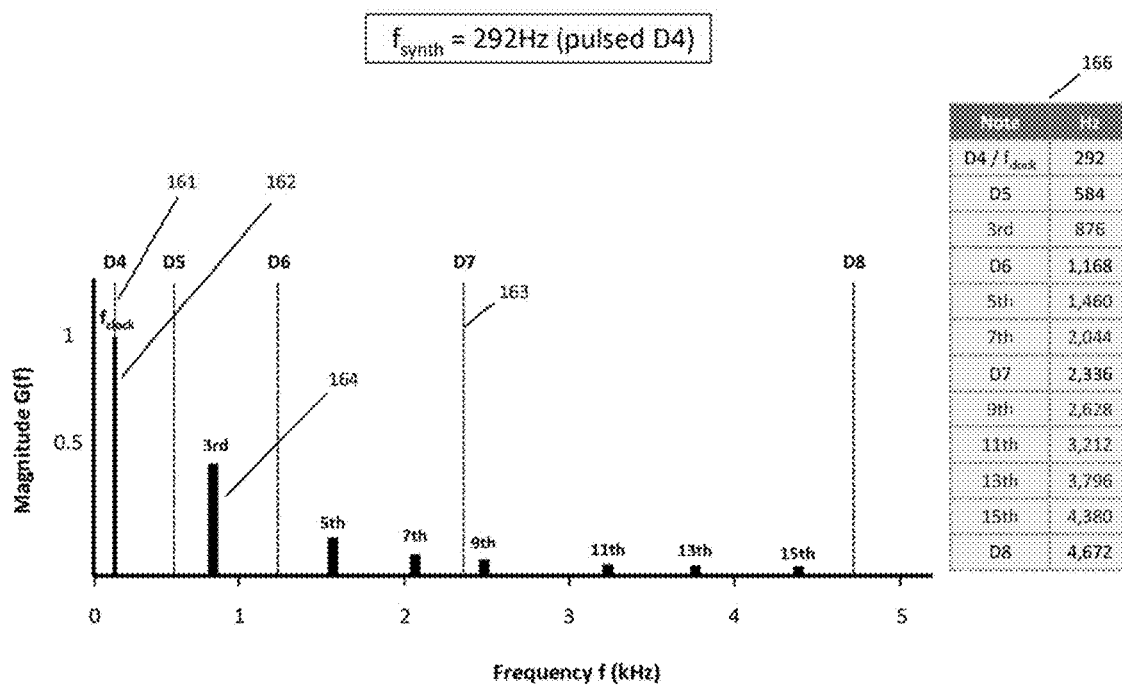
FIG. 12A illustrates a graph of spectral content of a 292 Hz digital pulse contaminating the audio spectrum to that of idealized octaves of D4 in the same range.
Figure 128:
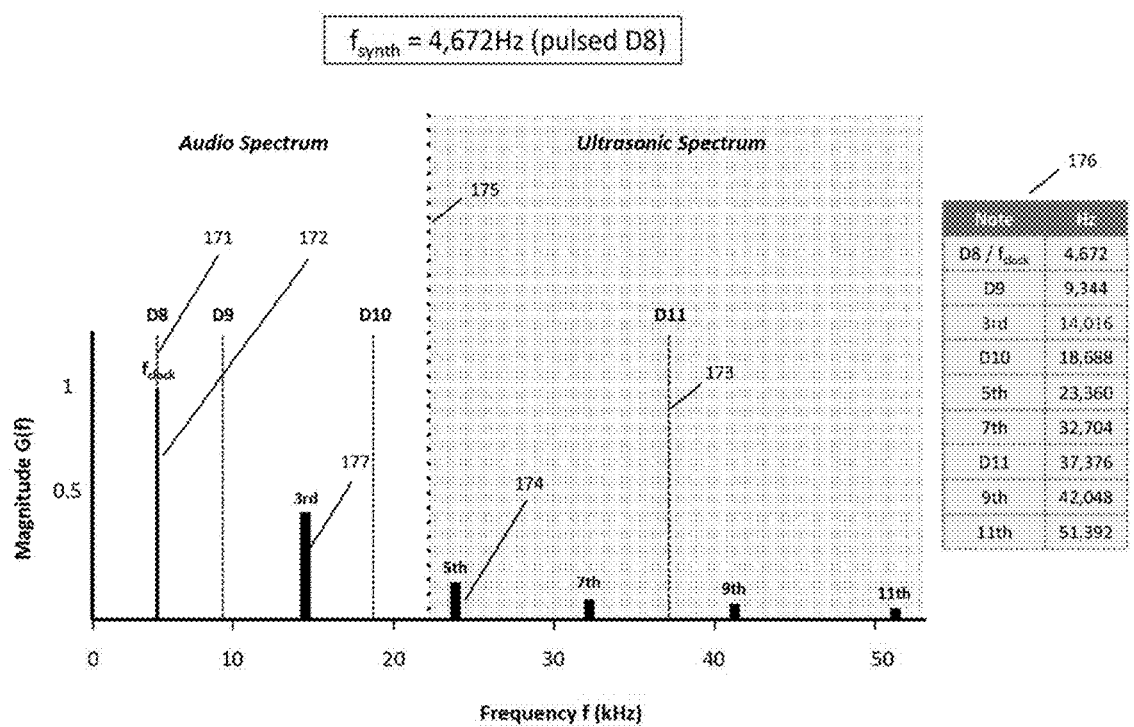

To elaborate on this point, FIG. 12A graphically contrasts the harmonic content of a 292 Hz digital pulse to that of a pure tone of 292 Hz, i.e. the fourth octave of D (or D4) and even multiples of this frequency, as recommended by Nogier's studies on healing. Using pure tones, a 292 Hz fundamental frequency 161 would exhibit constructive interference and improved energy transfer when blended with other harmonic multiples of D in the audio spectrum 163, for example D5, D6, D7, and D8 at corresponding frequencies of 584 Hz, 1,168 Hz, 2,336 Hz, and 4,672 Hz. Instead, a 292 Hz repeating digital pulse 162 results in odd harmonics 164 comprising $3^{rd}$, $5^{th}$, $7^{th}$, $9^{th}$, $11^{th}$, $13^{th}$, $15^{th}$, . . . , harmonic frequencies at 876 Hz, 1,460 Hz, 2,044 Hz, 2,628 Hz, 3,212 Hz, 3,796 Hz, 4,380 Hz and so on, none of which even remotely match the even harmonic frequencies recommended by physiological studies. Instead, the resulting spectrum content of odd harmonics 164 generated by 292 Hz digital pulse 162 contaminates much of the audio spectrum where adverse or non-beneficial interaction with many biochemical processes may occur and interfere with desired photobiomodulation.

While digital pulses produce unwanted harmonics, not all pulse frequencies should have an equally significant impact on biological processes and photobiomodulation. FIG. 12B contrasts a 4,672 Hz digital pulse 172 and its generated odd harmonics 174 to a pure tone of D in the eighth octave 171 (i.e. D8), which also has a frequency of 4,672 Hz, and even harmonics 173 of the pure tone D8. Specifically, a pure tone of D in the eighth octave 171 includes even multiples of this frequency, D9 and D10 at 9,344 Hz and 18,688 Hz, respectively, in the audio range where most photobiomodulation occurs. In contrast, at 37,376 Hz, the note D11 is in the ultrasonic spectrum, a range of notes above the frequency illustrated by line 175 that is too high to be heard and for most cells or tissue to react to chemically. The key point of this graph is that, despite the fact that a 4,672 Hz digital pulse 172 results in a whole spectrum of odd harmonics 174, only a single harmonic, the $3^{rd}$ harmonic at 14,016 Hz, falls within in the audio spectrum and below the frequency specified by line 175. All the other harmonics are too high in frequency for most tissues to respond or react to significantly.

In conclusion, the spectral contamination resulting from digital pulses is more significant at lower frequencies, because above 5 kHz pulse rates, most of the unwanted odd harmonics that occur are ultrasonic, above the audio frequency range and at frequencies too high to adversely impact beneficial photobiomodulation.

Also, aside from producing undesirable harmonics, controlling a laser or an array of LEDs with a digital excitation pattern of pulses in a desired frequency range is incapable of producing chords or multiple frequencies simultaneously, thereby limiting a phototherapy device's potential for controlling or optimizing energy coupling into cells, tissue, or organs.

What is needed is a means to control the excitation pattern operation of a laser or LED array to synthesize a specific desired frequency or group of frequencies (chords) without spectral contamination from unwanted and uncontrolled harmonics, especially those contaminating the audio spectrum, i.e. below 20 kHz.

Improving Photobiomodulation Through Harmonic Control

In order to provide complete control of photobiomodulation during phototherapy treatments (low-level light therapy or LLLT), the disclosed system described herein is capable of systematically driving arrays of various wavelength LEDs or lasers with user-selectable arbitrary waveforms (and sequences of waveforms) comprising continuous and time-varying modulation patterns, frequencies and duty factors, free of unwanted harmonics or spectral contamination. Time varying waveforms comprise digital pulses, sinusoids, pulsed sinusoids, continuous operation, and user-defined waveforms and mathematical functions.

The goal of this enhanced control is to improve treatment efficacy by adjusting device operation to synchronize to natural frequencies of particular biological processes specific to cells, tissue, organs, and physiological systems. By timing the energy delivery and controlling its frequencies and harmonics, tissue specificity can be enhanced. In order to ascertain these operating parameters, the biochemical and cytological origin of the frequency dependence of photobiomodulation must first be considered, starting with present-day knowledge and available technical literature.

Origin of Photobiomodulation Frequency Dependence

The frequency dependence of photobiomodulation and its influence on phototherapy efficacy is correlated to physical mechanisms within living cells, tissue, organs, and physiological systems.

According to the previously cited paper, "Effect of Pulsing in Low-Level Light Therapy" published in Lasers Surg. Med. August 2010, volume 42(6), pp. 450-466, "if there is a biological explanation of the improved effects of pulsed light it is either due to some fundamental frequency that exists in biological systems in the range of tens to hundreds of Hz, or alternatively due to some biological process that has a time scale of a few milliseconds."

This paper cites various natural frequencies occurring within living organisms, including electroencephalography studies identifying four distinct classes of brain waves, namely alpha waves at 8-13 Hz, beta waves at 14-40 Hz, delta waves at 1-3 Hz, and theta waves at 4-7 Hz. These various waves are present during different conditions or sleep, rest, meditation, visual, and cognitive mental activity and are affected by illness, concussion and traumatic brain injury, and age. The authors surmise "The possibility of resonance occurring between the frequency of the light pulses and the frequency of the brain waves may explain some of the results with transcranial LLLT using pulsed light."

Similar observations have been made by other authors in regards to electrocardiogram signals and regulation of heart function. Resting heart rates typically occur in the 60 to 100 beats per minute, or roughly 1 Hz to 2 Hz, depending on a person's age and health. Peristaltic contractions in the intestines can occur in sub 1 Hz frequencies. These systems and their optimum response conditions do not represent simple chemical or electrical reaction rates because they are operating as a clocked system with their own time regulation, generally electrochemical in nature. For example, through an electrochemical process, potassium is intimately involved in setting the heart's natural pulse rate in humans.

Another entirely different class of mechanisms present within cells and potentially responsible for the photobiomodulation frequency dependence appears related to chemical or ionic reaction rates and ionic transport. The Hashmi et al. paper continues, "the time scale for opening and closing of ion channels is of the order of a few milliseconds," with referenced citations having time constants for ion channels ranging from 0.1 to 100 milliseconds, i.e. 100 Hz to 10 Hz, including potassium and calcium ion channels in mitochondria. Other papers suggest sarcolemma, the lipid bilayer plasma membrane providing scaffolding for muscle cells, may also be responsible for photobiomodulation frequency dependence, since such membranes often serve as ion pumps.

Figure 2:
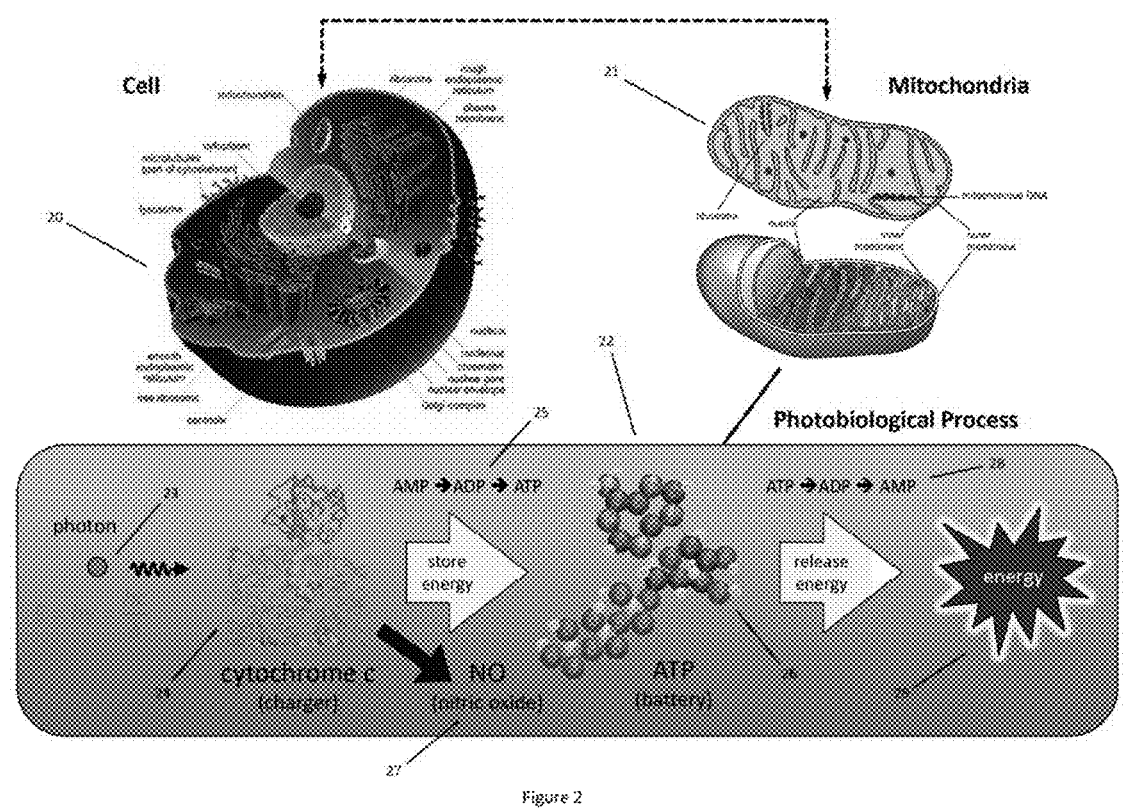
FIG. 2 is a simplified pictorial representation of photobiomodulation of cellular mitochondria.
Figure 3:
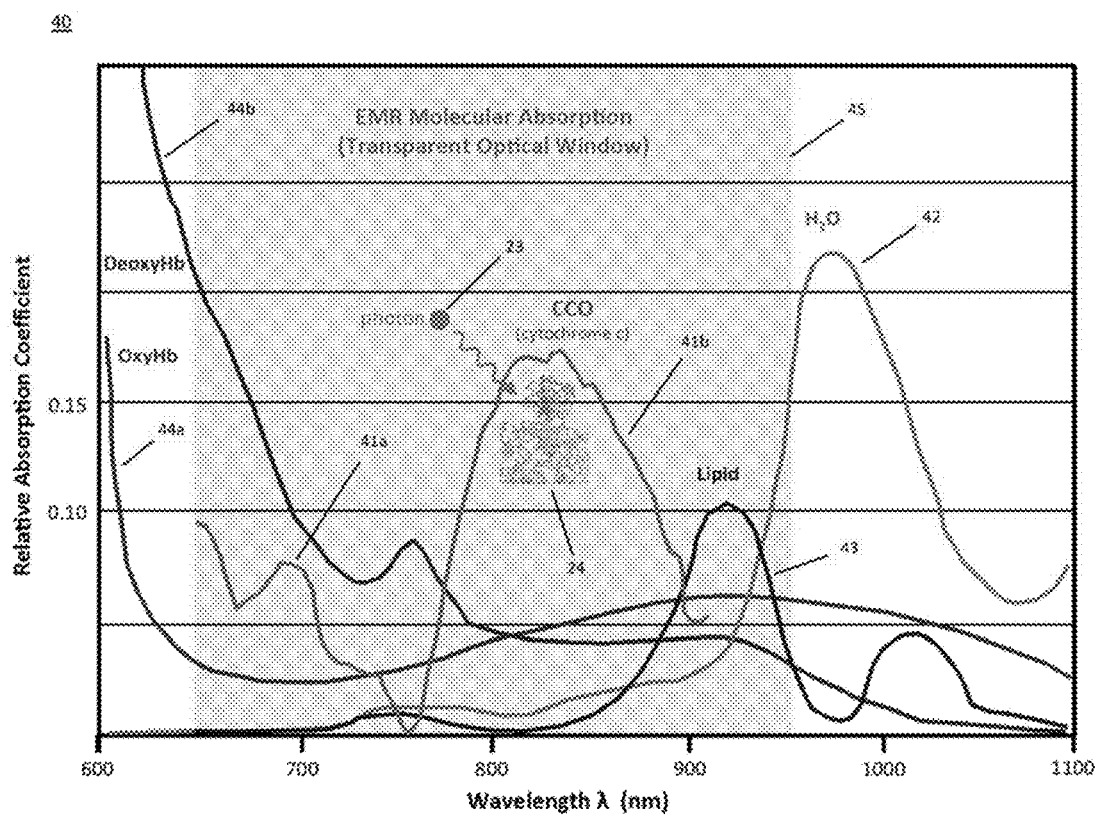
FIG. 3 is a graph showing the absorption spectra of cytochrome-c (CCO), blood (Hb), water and lipids.
Figure 4:
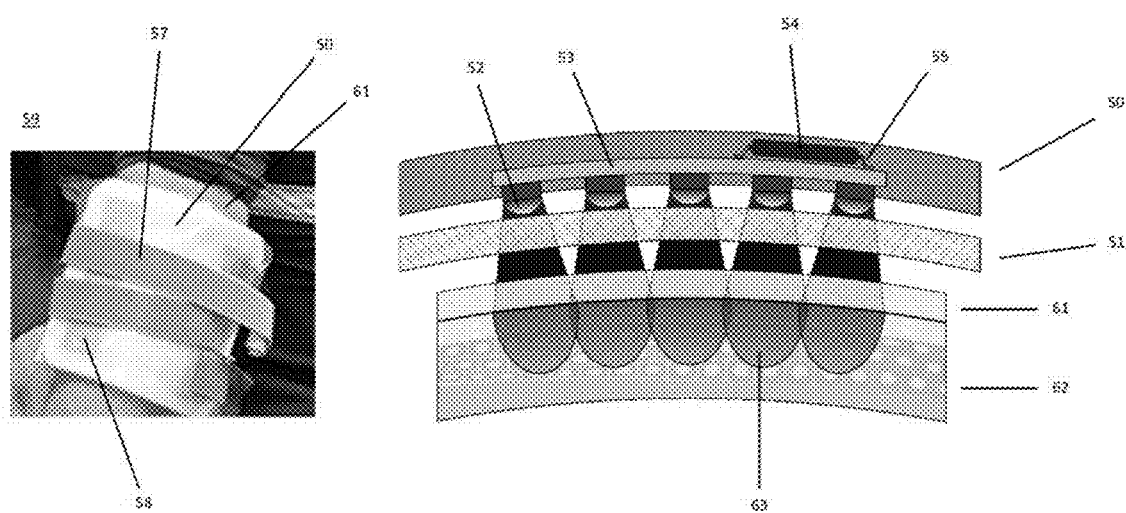
FIG. 4 is a photographic example and schematic representation of a LED pad being used in a phototherapy treatment.
Figure 5:
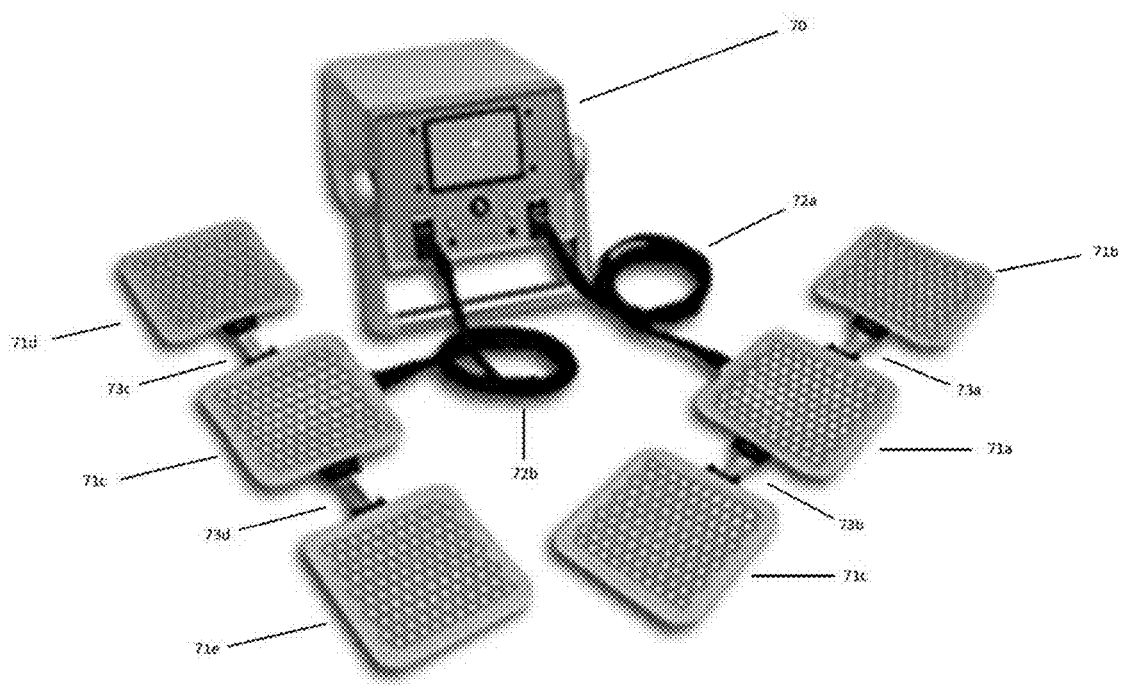
FIG. 5 is a view of a phototherapy system comprising a controller and six flexible polymeric LED pads.
Figure 6A:
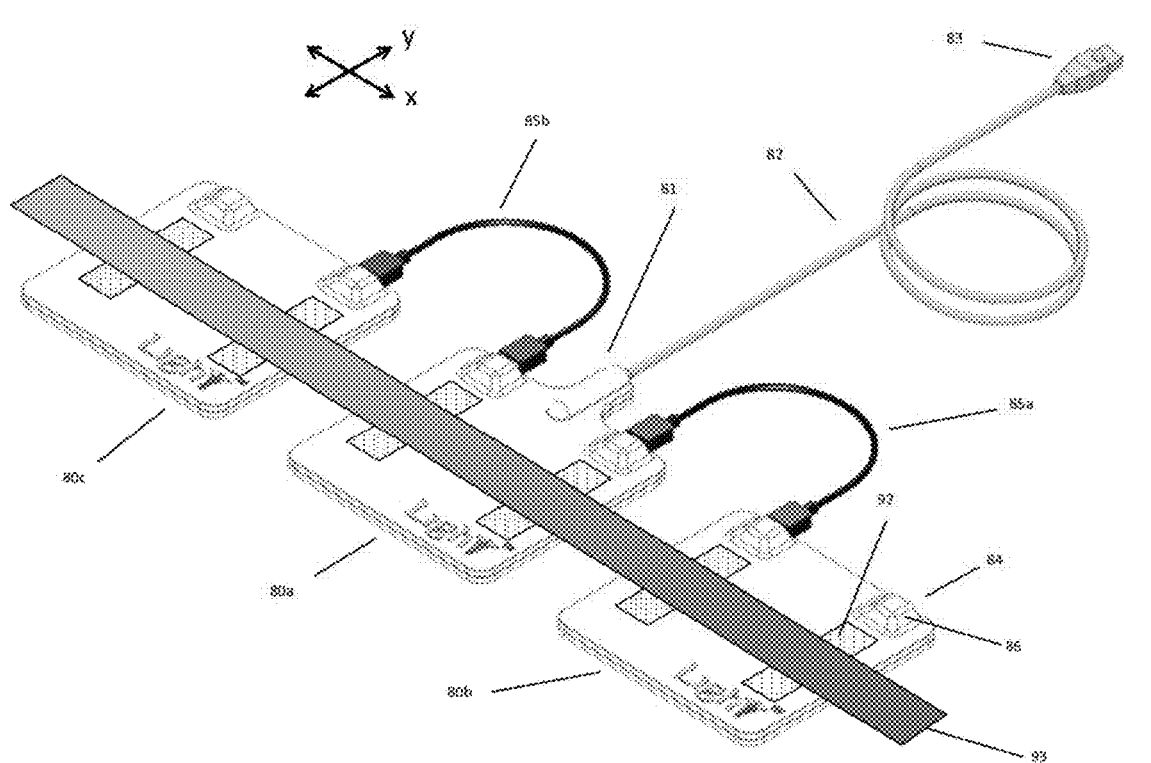
FIG. 6A is a schematic representation of a set of three flexible polymeric LED pads connected together and attached to a Velcro strap.
Figure 6B:
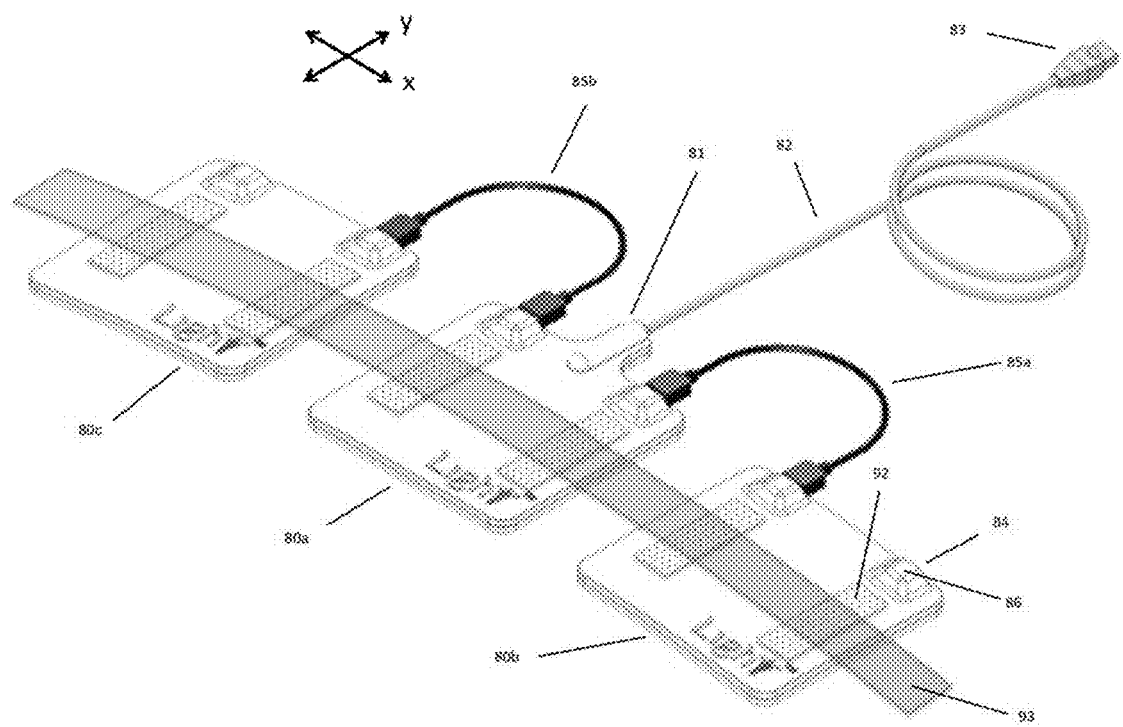
FIG. 6B is a schematic representation of the set of flexible polymeric LED pads shown in FIG. 6A, bent slightly to conform to a patient's body.
Figure 7:
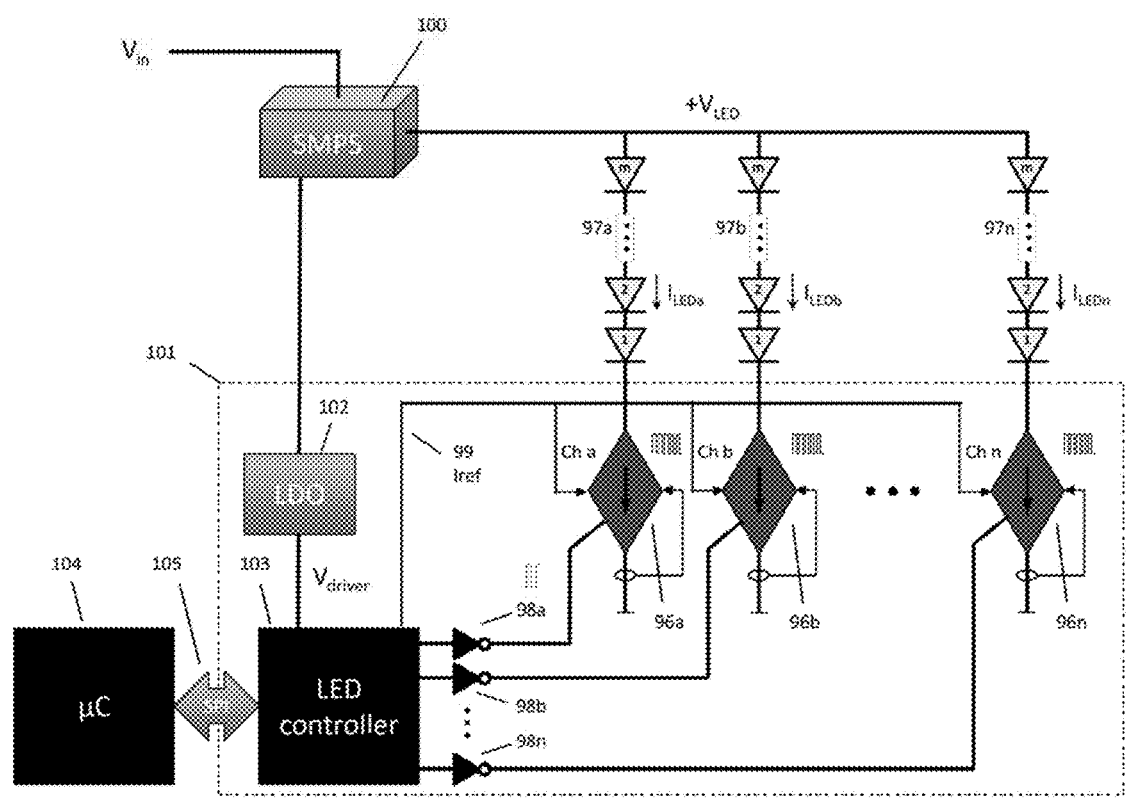
FIG. 7 is an electrical schematic diagram of a current controlled LED pulsed phototherapy system.

On a cellular level, another mechanism responsible for photobiomodulation frequency dependence is the photodissociation of nitric oxide (NO) from a protein bonding site (heme or copper) found in cytochrome c oxidase (CCO). CCO acts as a NO scavenger molecule providing negative feedback and NO regulation. As described earlier in reference to FIG. 2, in the presence of photobiomodulation, NO is released only where it is subjected to phototherapy, presumably only in the locale of diseased or injured tissue. The observed benefit of pulsed phototherapy, it is postulated, occurs because pulsed light can trigger multiple photodissociation events, while in continuous wave (CW) mode the release of NO will stabilize at a lower fixed rate, balancing NO release with the counter-reaction of NO reattachment.

Figure 13:
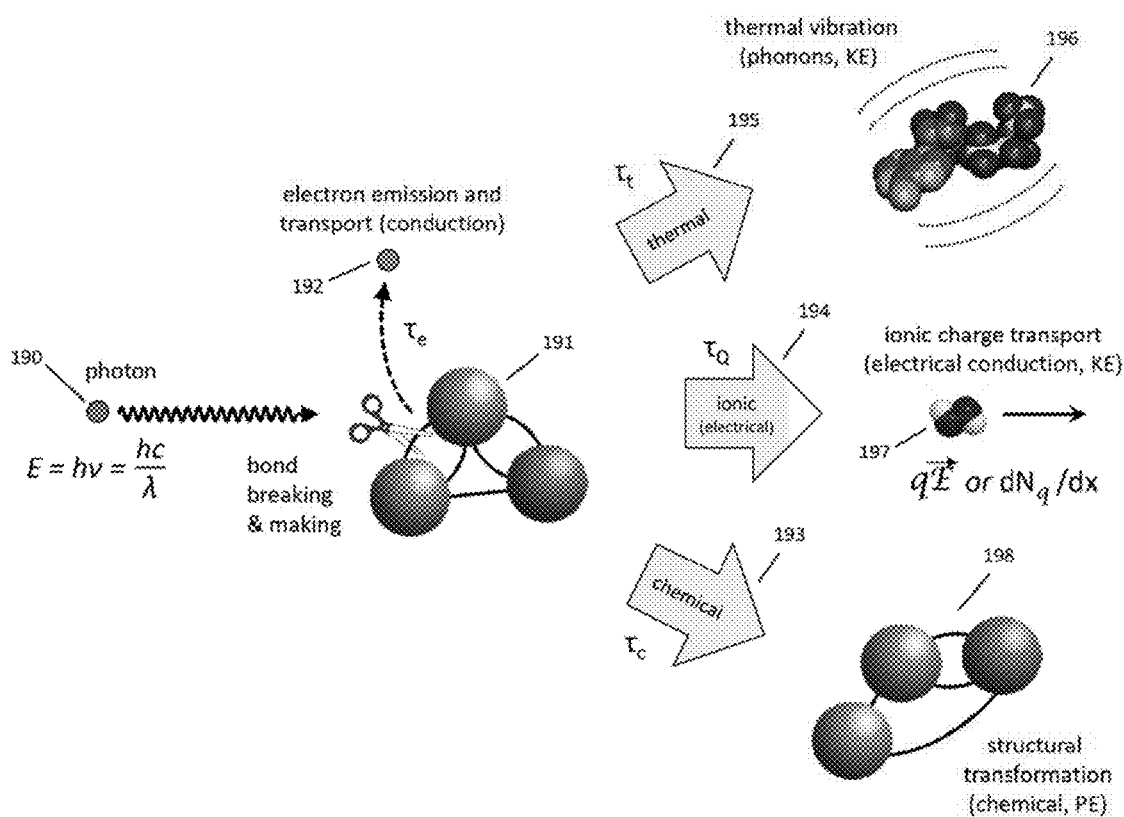
FIG. 13 illustrates various physical mechanisms of photobiomodulation

FIG. 13 schematically summarizes the physical mechanisms of photobiomodulation. As shown, photon 190 is absorbed by and interacts with molecule 191 to make or break new bonds. The energy of the impinging light depends on its wavelength as given by the Einstein relation $E=hc/\lambda$, or for convenience sake by the relation $E=1.24$ eV-$\mu$m/$\lambda$, where $\lambda$, is measured in $\mu$m. For 650 nm red light $E=1.91$ eV per photon while for 950 nm NIR light $E=1.31$ eV. While most chemical bonds, including hydrogen, ionic, and most covalent bonds range in bond energies from 0.2 eV to 10 eV, the making or breaking of a chemical bond from the energy of a photon is complicated by the fact that molecules and especially crystals comprise groups of atoms with many bonds working collectively, meaning breaking a single bond does not necessarily induce a bond transformation. Moreover, depending on the reaction, multiple sources of energy and enzymes may assist the photon in inducing a chemical transformation. For example, a single ATP molecule may release up to 0.6 eV of energy, thereby assisting singularly or collectively in fueling a photochemical reaction.

The result of the photobiomodulation of molecule 191 may be manifest itself in one of several mechanisms, namely electrical conduction 192, chemical transformations 193, ionic conduction 194, or thermal vibration 195. Release of free electrons 192 during ionization describes the purely electrical component of photobiomodulation. Electron transport occurring with a time constant $\tau_e$ is relatively fast and capable of responding to stimuli from kHz up to tens of kHz. Photobiomodulation inducing electrical conduction through electron emission and electron transport can be referred to as biophotoelectric conduction.

Chemical transitions 193 along with ionic electrical conduction 194 having respective time constants $\tau_c$ and $\tau_Q$ are slower, responding to photobiomodulation in to 10 Hz to the 1 kHz range. Chemical processes are complex, involving a structural transformation in the affected molecule 198 with a corresponding change in its chemical reactivity and its stored potential energy (PE). Ionic processes 194 are significantly slower than simple electron 192 conduction, because the conducting ions 197 are oftentimes large molecules conducting by diffusion (driven by a concentration gradient $dN_q/dx$) or by electrical conduction driven by intra- and intercellular electric field induced force qE, said electric fields existing as a result of spatially unevenly distributed ions. Photobiomodulation inducing electrical conduction through ionic transport can be referred to as biophotoionic conduction. Similarly photobiomodulation inducing structural transformations in molecules can be referred to as biophotochemical transformation.

The other mechanism, thermal vibrations 195 is the spread of heat, either classical kinetic energy or by quantized phonon conduction causing molecules 196 to vibrate at increased levels compared to their surroundings as energy escapes the photo-excited molecules and spreads thermally into its neighbors. Transient thermal effects, vibrations spreading across tissue can occur at a rate of 1 to 10 Hz while steady state conduction can take minutes to stabilize, i.e. responding to sub-Hz frequencies. Thermal vibration is another important mechanism in photobiomodulation because thermal excitation increases reaction rates by causing interacting ions and molecules to bump into one another more frequently and rapidly, the molecular version of stirring reactant chemicals in solution. Photobiomodulation inducing the diffusion of heat between and among molecules can be referred to as "biophotothermal" conduction or thermal vibration.

Frequency dependent photobiomodulation results from these physical processes interacting with the modulating or pulse frequencies of incoming photons. Overstimulation occurs when the digital pulse rate or light modulating frequency is faster then the physical process's ability to respond to it. In such cases, the response is reduced because the cell or molecule simply cannot keep up with the stimulus. Such a case is analogous to a busy freeway with entrance ramp metering lights stuck-on causing more-and-more cars to jam onto the freeway until no one is able to move. Understimulation occurs when the digital pulse rate or light modulating frequency is much slower than the cell's ability to absorb it in which case little or no photobiomodulation occurs. This condition is analogous to a freeway whose metering lights are allowing almost no one to get onto the freeway, with the similar result that no one gets anywhere. Only if the photobiomodulation frequency matches the system's natural response frequency is there an optimum result and efficient energy transfer. For example, if the metering lights onto the freeway are timed correctly, the optimum number of cars will fill the freeway and promptly travel to their destination without starting a traffic jam.

As detailed, understimulation at too low of a frequency and overstimulation at too high of a frequency results in a diminished photobiomodulation response, and only in between, at the optimum pulse rate or excitation frequency can the photobiomodulation response and phototherapeutic efficacy be maximized. This peak response condition occurring at a particular frequency appears very similar to the resonant curve of FIG. 10, especially since the prior analysis reveals multiple time constants exist in any cells, tissue or organs, each optimized to induce specific electrical, ionic, chemical and thermal mechanisms.

Therefore, the various peak response conditions can be referred to as bioresonance even though the mechanism may not involve energy storage and timed release as in the true resonant systems described above. Being able to stimulate these select resonant frequencies in a controlled manner free from spectral contamination is critical, especially in avoiding the inadvertent generation of frequencies causing destructive interference and loss of efficacy. Moreover, invoking multiple bioresonant mechanisms simultaneously is not possible using present-day digital pulse based phototherapy systems. The disclosed new electronic drive system described herein comprises both an inventive apparatus and novel methods for realizing sinusoidal drive and arbitrary waveform synthesis of LED or laser light for phototherapy, not available or even suggested in the prior art.

Waveform Synthesis System for Phototherapy

A key element in driving LEDs and laser diodes with controlled frequencies and harmonics is the circuitry and algorithms used in generating the device's waveforms, patterns, and driving conditions. While the following description details the means to drive arrays of multiple strings of series-connected LEDs, the same circuitry can be adapted to drive one or multiple semiconductor lasers.

Because the light output of an LED depends on its current and because its brightness is poorly correlated to the forward voltage present across the LED during conduction, it is preferable to use controlled current-sources (and current sinks) rather than constant voltage drive. For example if an series-connected string of LEDs is powered by a voltage source connected through a series resistor, the LED current $I_{LED}$ will unavoidably vary with the total series forward voltage drop $V_f$ of all the LEDs. Provided the power supply voltage $+V_{LED}$ is higher than the forward voltage drop $V_f$ of the LED string, i.e. $+V_{LED} > V_f$, then the LED current $I_{LED}$ is given by the series relation $I_{LED} = (+V_{LED} - V_f)/R$ illustrating that any change in the LED voltage will result in changes in LED current and hence in LED brightness. Since LED voltages cannot be accurately controlled or matched, unless each LED string comprises sorted LEDs with matched total voltages, any given LED string will invariably be brighter or dimmer than the next.

Figure 14:
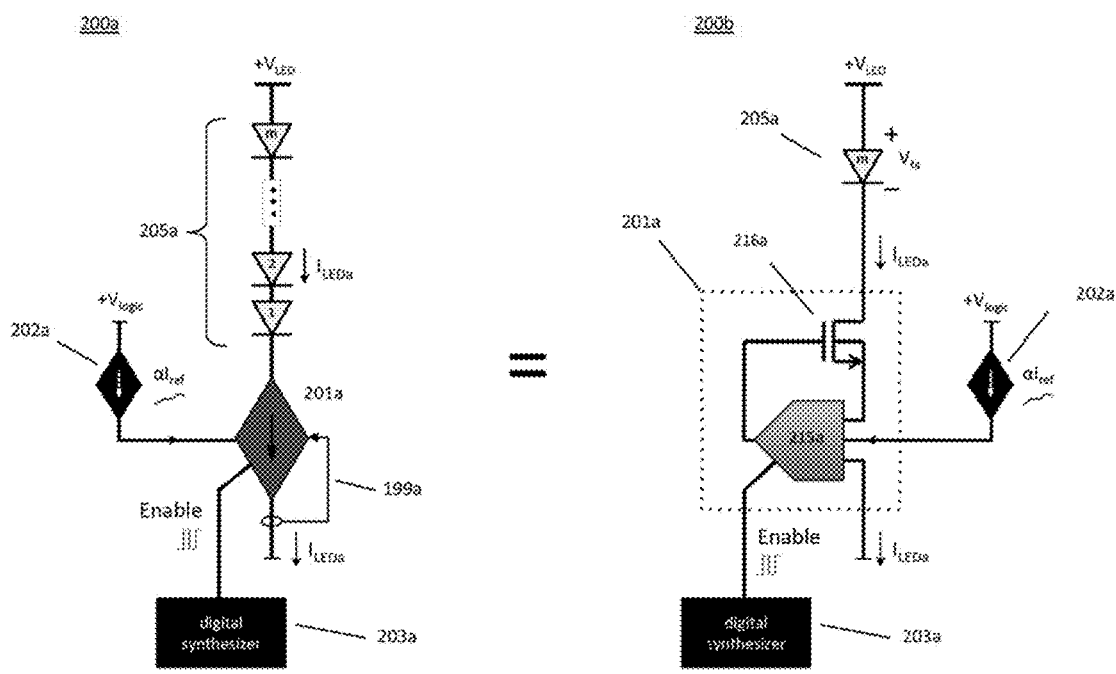
FIG. 14 illustrates two equivalent circuits of a single channel LED driver with current control.

FIG. 14 illustrates two equivalent representations 200a and 200b of a current sink controlling the current through a string of series-connected LEDs 205a. In schematic 200a, current sink 201a represents an idealized current controlled device with sensing and feedback designed to maintain a prescribed current $I_{LEDa}$ in LED string 205a. As shown, the LED string 205a comprises "m" anode-to-cathode series-connected LEDs, where m is a mathematical variable representing the number of LEDs in string 206. The schematic element 199a represents feedback from sensing the value of current $I_{LEDa}$ and using feedback to insure the current stays constant even if the voltage across current sink 201a varies.

When conducting the value of the LED current $I_{LEDa}$ is proportional to an analog input current $\alpha I_{ref}$ set by low-voltage current source 202a. When current sink 201a is not conducting, i.e. when current source 202a is not enabled, the voltage across the LEDs is minimal and the voltage supported across current sink 201a approaches the value $+V_{LED}$, a relatively high voltage, e.g. 40V, compared to the lower voltage of $+V_{logic}$, typically 3V to 5V. Current sink 201a may be digitally toggled on or off, i.e. conducting or not conducting, through its digital enable pin labeled "Enable" connected to digital synthesizer 203a. Note that the letter "a" represents one of multiple channels driving separate series-connected strings of LEDs in an LED pad. LED pads may contain many independently controlled strings of LEDs, namely LED output channels a, b, c, . . . , n, where "n" is a mathematical variable representing the number of channels.

In schematic circuit 200b, the series connection of "m" LEDs is symbolically replaced by a single LED with the number "m" inside the device and the voltage $+V_{fD}$ labeled across the LED. As shown, current sink 201a is further detailed showing an analog feedback circuit comprising MOSFET driver 215a driving the gate of high-voltage MOSFET 216a. In operation, MOSFET driver 215a provides a voltage on the gate of current-sink MOSFET 216a allowing current $I_{LEDa}$ to flow through the sensing circuitry contained with MOSFET driver 215a to ground. This current is then compared to a multiple $\beta_r$ of the analog input current $\alpha I_{ref}$ set by low-voltage current source 202a, and the gate voltage on current-sink MOSFET 216a automatically adjusted by the circuitry within MOSFET driver 215a until the multiple $\beta_r$ of the current $\alpha I_{ref}$ and the current $I_{LEDa}$ match and $I_{LEDa}$ is at is desired value. Because of its analog closed-loop circuitry, feedback from MOSFET driver 215a is nearly instantaneous, adjusting dynamically with fluctuating voltages and programmed changes in the reference current input from current source 202a.

The reference current $\alpha I_{ref}$ from current source 202a may be realized by a fixed, time varying, or adjustable reference voltage and a series resistor trimmed for accuracy to convert the precise voltage into a precise reference current. The accurate voltage source may comprise a fixed-value Zener diode or a bandgap voltage, a voltage-controlled oscillator (VCO), or a digital-to-analog converter (DAC) facilitating digital control of the analog current value output from current-source 202a. The digital pulse output from digital synthesizer 203a can be realized by counters and clock circuits, by programmable logic arrays (PLAs), or by a microprocessor executing firmware or software instructions.

Some implementations of the aforementioned circuitry are described in a previously-cited related U.S. Pat. No. 9,877,361. Other exemplary and novel analog, digital and mixed-mode circuits will be included herein later in the application.

Figure 15:
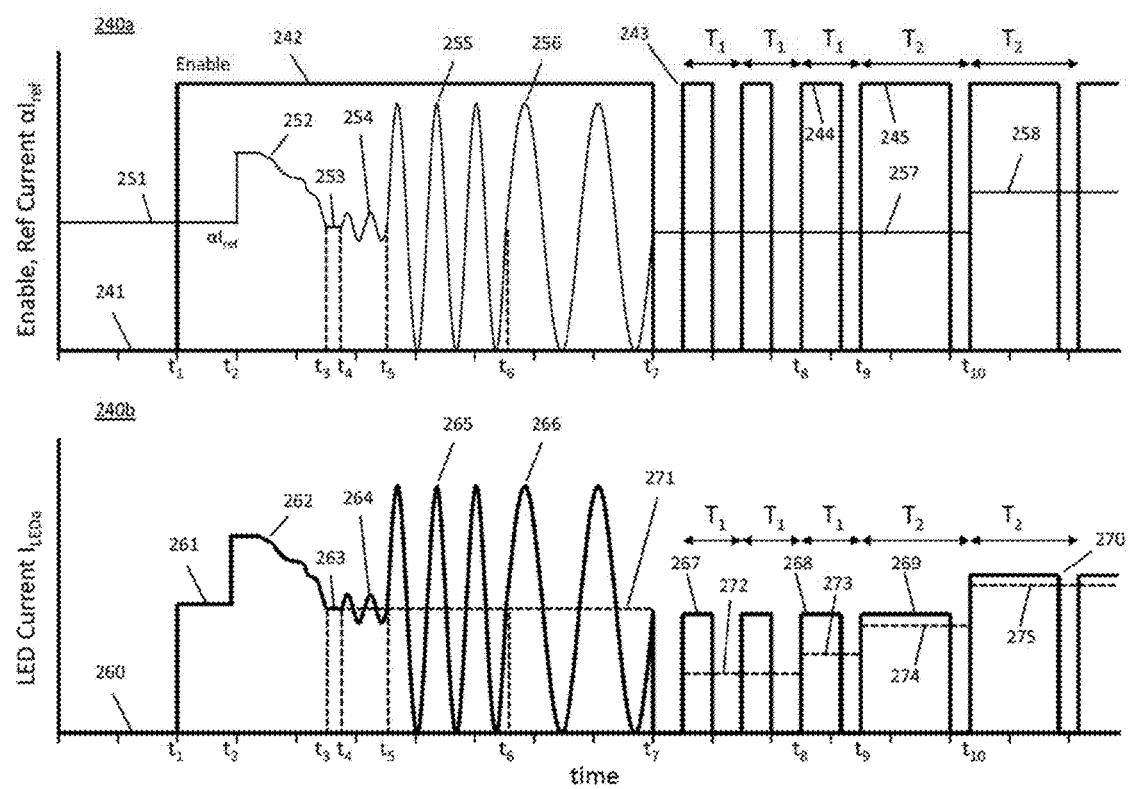
FIG. 15 illustrates various example combinations of reference current and enable signals and the resulting LED current waveforms.

FIG. 15 illustrates the diverse variety of waveforms that may be synthesized by the described driver circuitry. As shown, graph 240a illustrates the input waveforms of current sink 201a comprising the digital Enable signal output from digital synthesizer 203a, and the reference current $\alpha I_{ref}$ output from current source 202a. Graph 240b illustrates the resulting LED current conduction waveform with the same time references $t_1$, $t_2$, etc. as graph 240a included for easy comparison. The generated waveforms are examples, not intended to imply any specific operating condition attempting to avoid undesirable harmonics in phototherapy systems, but simply to illustrate that the combination of digital pulsing and analog current control offers nearly limitless control of LED excitation.

As shown in graph 240a, the digital Enable signal comprises line segments 241 through 245, and reference current $\alpha I_{ref}$ comprises curves 251 through 258. In the corresponding output of LED current in graph 240b, the instantaneous LED current is illustrated by curves 260 through 269, while the average LED current, where applicable, is represented by the dashed lines shown by line segments 271 through 275.

To understand the interaction between the analog and digital control of LED excitation, we will compare the two graphs in each corresponding time interval. Specifically, before time $t_1$, enable signal 241 is at a logic zero and reference current 251 is biased at some nominal value $\alpha I_{ref}$, e.g. at an input current corresponding to an $I_{LEDa}$ output current of 20 mA. Because digital enable signal 241 is at a logic zero, the LED current 260 is at zero and the string of LEDs remains off despite the non-zero value of reference current $\alpha I_{ref}$.

Between time $t_1$ and $t_2$ digital enable signal 242 jumps from a logic zero state to a logic one state while the value of reference current 251 remains biased at a value of $\alpha I_{ref}$ for example at 20 mA to 30 mA. As a result, LED current 261 jumps to the value of reference current 251. The off-to-on transition in LED conduction at time $t_1$ illustrates the effect of digitally "toggling" an analog current sink.

While digital enable signal 242 remains on, at time $t_2$ the analog magnitude $\alpha I_{ref}$ of reference current 252 jumps to a higher value and then declines in a specific but user settable manner until it finally settles at a value 253, which is the same as its original value 251. The LED current 262 similarly tracks the reference, jumping from 20 mA to a higher value, e.g. 27 mA, before settling back at 20 mA at time $t_3$, shown by LED current 263. The output waveform of LED currents 262 and 263 illustrates that the reference current can be used to facilitate purely analog control of LED current and brightness with no digital pulsing whatsoever.

At time $t_4$, as shown by curve 254, the reference current commences a controlled, small signal sinusoidal oscillation superimposed on an non-zero average DC value. The perturbation in the reference current may be considered small-signal because the amplitude of the oscillation is small compared to the average value of current $\alpha I_{ref}$. As a symmetric oscillation, the average current remains unchanged from the DC value (shown by curve 253) of the reference current existing before the oscillations commenced. While any oscillating frequency may be considered possible, practical considerations and the value of oscillating waveforms in phototherapy suggest the operating frequency should be 20 kHz or below. The corresponding LED current, depicted as curve 264 in graph 240b commencing at time $t_4$, tracks that of the reference current shown by curve 254, having an average current value (dashed line 271) of 20 mA and varying symmetrically around the average LED current by some fixed amount, for example ±1 mA. This means that the LED current varies sinusoidally, with peak-to-peak values ranging from 19 mA to 21 mA.

At time $t_5$, as shown by curve 255, the small signal oscillations in the reference current during the prior interval $t_4$-$t_5$ grow into large signal oscillations shown by curve 255 and having the same frequency of oscillation as the prior interval. In the example shown the minimum reference current $\alpha I_{ref}$ reaches zero (or nearly so) while the peak reference current reaches twice the average value, i.e. twice the value of the reference current represented by curve 253. As before, since the value of the digital enable signal (line segment 242) remains at a logic one state, the LED current (curve 265) tracks the value as a multiple of the reference current (curve 255) both in frequency and in wave shape, having an average LED current (dashed line 271) of 20 mA with peak-to-peak oscillations around that average of nearly ±20 mA, meaning the LED current varies sinusoidally from 0 mA to 40 mA with an average value of 20 mA.

Starting at time $t_6$, the same oscillatory operating conditions persist as existed in the interval $t_5$-$t_6$, except that the oscillation frequency of the reference current represented by curve 255 and correspond LED current represented by curve 265 is intentionally reduced to a lower oscillating frequency, shown by curve 256 for the reference current and by curve 266 for the corresponding LED current, with the output still maintaining an average LED current 71 of 20 mA, the same average as previously occurred for oscillatory LED currents shown by curves 264 and 265.

At time $t_7$, the roles of the digital enable signal and the reference current $\alpha I_{ref}$ are reversed, whereby the value of reference current becomes constant at some nominal value (shown by line segment 257) and the digital enable signal begins pulsed operation. Specifically at time $t_7$, the digital enable signal (shown by curve 243) commences pulsed operation with 50% duty factor, pulsing at a digital clock frequency of $1/T_1$, where $T_1$ is the period of each repeated cycle. At time $t_8$, as shown by curve 244, the pulse on-time of digital enable signal increases while the period $T_1$ and the corresponding pulse frequency remain the same as before. As a result, the 20 mA pulses of LED current at a 50% duty factor, represented by curve 267, become an LED current become an LED current at a 75% duty factor, represented by curve 268. This mode of operation comprises fixed-frequency PWM or pulsed width modulation operation, where the average LED current varies from 50% of 20 mA, i.e. 10 mA average LED current (represented by dashed line 272), to 75% of 20 mA or 15 mA average LED current (represented by dashed line 273) at time $t_8$.

At time $t_9$, while the value of the reference current remains unchanged (curve 257), the period of the pulses of the digital enable signal increases to a value $T_2$, as does the pulse on time, as shown by curve 245. This is reflected by the waveform of the LED current (curve 269). As shown, the duty factor, the pulse on time of the digital enable signal represented by curve 245, divided by the total period $T_2$ also increases, resulting in the LED current having a higher average value (shown by dashed line 274), corresponding to an increase of duty factor to 90%. The reduction in operating frequency from $1/T_1$ during the interval between times $t_7$ to $t_9$, to the lower operating frequency $1/T_2$ thereafter is an example of variable frequency PWM operation, and clarifies that PWM duty factor can be varied independently of the digital pulse frequency.

In the final waveform shown in FIG. 15, at time $t_{10}$ the value of reference current increases to a higher value (represented by the transition from curve 257 to curve 258), while the waveform of digital enable signal remains the same as it was in the prior interval $t_9$-$t_{10}$. The result is that the instantaneous value of the LED output current increases, as shown by the transition from curve 269 to curve 270 and the average LED current also increases, as shown by the transition from the dashed line 274 to the dashed line 275. Despite increasing the average and instantaneous LED brightness, the duty factor and the pulse frequency of the LED current remain unchanged from the corresponding values in the time interval $t_9$-$t_{10}$.

In conclusion, the instantaneous and time average value of the LED current can be controlled in numerous and flexible ways using analog control of the reference current and digital pulse control of the enable signal of the current sink schematic representations shown in FIG. 14. Realizing current sink 215a, reference current source 202a, and digital synthesizer 203a can be accomplished in many ways. Actual realization of these circuits must address issues of accuracy, reproducibility, and scalability into multichannel systems. Such circuitry can be divided into two broad categories—analog LED control and digital synthesis.

Analog LED Current Control

Referring again to FIG. 14, controlling LED current $I_{LEDa}$ requires analog control to implement the sense and LED drive circuitry within MOSFET driver 215a, as well as to implement precision reference current $I_{ref}$.

Current sink 201a comprises high-voltage MOSFET 216a biased to control the LED current $I_{LEDa}$ and MOSFET driver 215a which senses the LED current $I_{LEDa}$ compares the LED current $I_{LEDa}$ to the desired reference current $\alpha I_{ref}$ and dynamically adjusts the gate voltage on high-voltage MOSFET 216a until the LED current $I_{LEDa}$ matches the predefined scalar multiple $\beta_r$ of the reference current $\alpha I_{ref}$. Measurement and feedback must operate in a closed loop manner to adjust for any manufacturing variations in high-voltage MOSFET 216a affecting its transconductance and channel-to-channel matching such as threshold voltage and gate oxide thickness.

Although the reference current $\alpha I_{ref}$ is schematically represented as a controlled current, distributing precise currents across multiple channels, as shown in FIG. 16A, is problematic because the total current $n\alpha I_{ref}$ from current source 206 will not necessarily be distributed evenly among the inputs to MOSFET drivers 215a through 215n, i.e. $I_a \neq I_b \neq I_n$. The solution to this problem, shown conceptually in FIG. 16B, is to employ a reference voltage source 207 to distribute a voltage $V_{ref}$ rather than a current to each channel and to convert this voltage into identical currents using a transconductance amplifier 208a, 208b . . . 208n in each channel. For example, transconductance amplifier 208a converts $V_{ref}$ into current $I_a$ feeding MOSFET driver 215a, transconductance amplifier 208b converts the same $V_{ref}$ into current $I_b$ feeding MOSFET driver 215b, and so on.

Figure 16C:
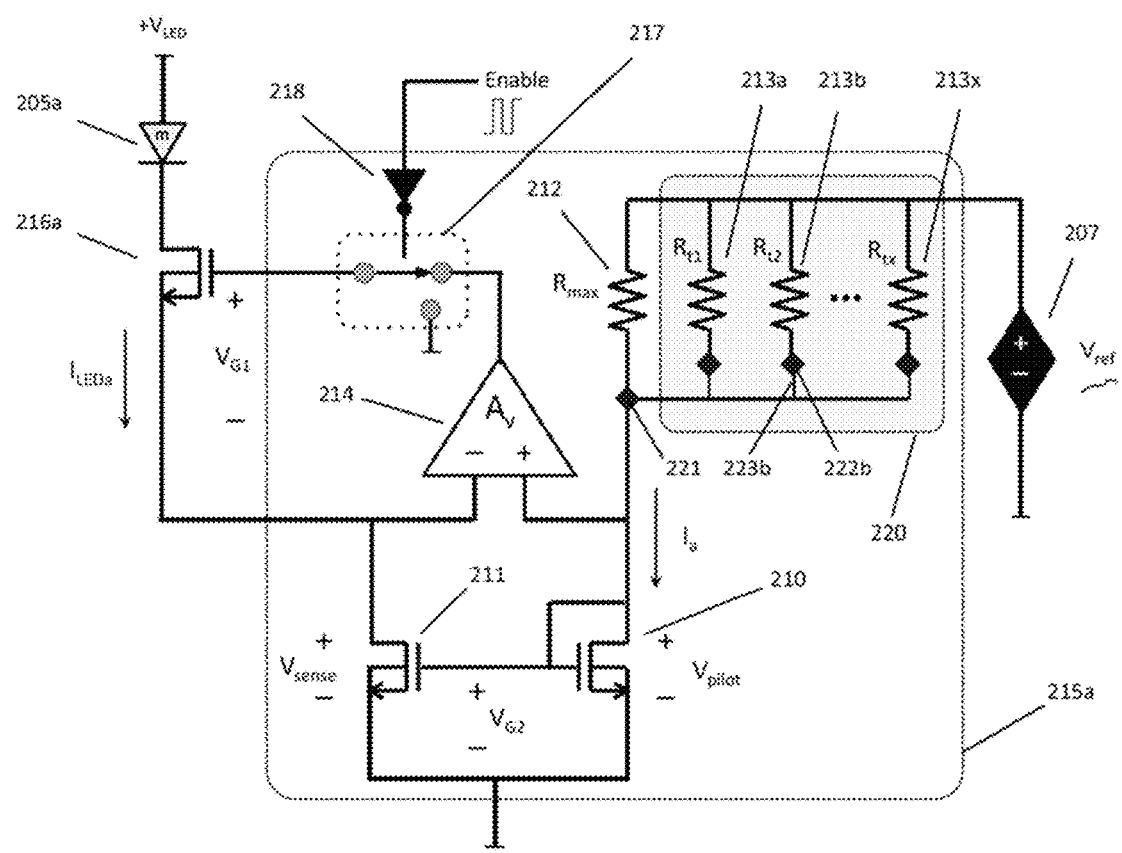
FIG. 16C schematically illustrates one implementation of a controlled current sink comprising a high voltage MOSFET and MOSFET driver circuit with resistor trimming.

In practice however, it is unnecessary to employ n-channels of transconductance amplifiers since the voltage conversion function can be performed inside the MOSFET driver's circuitry. For example, as shown in FIG. 16C, the current $I_a$ coming from reference voltage source 207 and feeding MOSFET driver 215a is used to bias a current mirror MOSFET 210 through bias resistor 212 and a parallel network 220 of trim resistors 213a through 213x. The subscript "x" is a mathematical variable representing the number of resistors in parallel network 220. Since the gate of MOSFET 210 is connected to its drain, i.e. MOSFET 210 is "threshold connected," the gate voltage of MOSFET 210 will naturally bias itself to a voltage $V_{G2}$ sufficient to conduct the desired reference current $I_a$ as set by series resistor 212 and the parallel trim network 220 comprising resistors 213a through 213x. MOSFET 210 and the parallel combination of resistor 212 and trim network 220 form a voltage divider, where the voltage across mirror MOSFET 210, $V_{pilot} = V_{ref} - I_a \cdot R_{equiv}$ where $1/R_{equiv} = 1/R_{max} + 1/R_{t1} + 1/R_{t2} + \ldots + 1/R_{tx}$. By changing the resistive value of the resistor network 220, $V_{pilot}$ adjusts itself to produce a gate voltage $V_{G2}$ on MOSFET 210 consistent with its drain current because its gate and drain are connected, i.e. $V_{GS} = V_{pilot}$. The gate voltage $V_{G2}$ of MOSFET 210 will be slightly larger than its threshold voltage, hence the designation "threshold connected."

This same gate voltage $V_{G2}$ biases a much larger MOSFET 211 to the same gate drive condition such that the ratio of nominal operating currents through current mirror MOSFETs 210 and 211 (i.e., the above-defined multiple $\beta_r$) is equal to the ratio of the gate widths of current mirror MOSFETs 210 and 211. For example, if reference current $I_a$ is nominally set at 2 µA and $I_{LEDa}$ is intended to be 20 mA, then the size ratio between MOSFETs 210 and 211 should be selected to be 20 mA/2 µA=10,000, meaning that the gate width of current mirror MOSFET 211 should be 10,000 times larger than the gate width of MOSFET 210. Because of their common gate biasing and fixed size ratio, only when current mirror MOSFET 211 is conducting 20 mA, will its drain-to-source voltage $V_{sense}$ be equal to $V_{pilot}$. During the illumination of LED string 205a, a differential amplifier 214, which is biased in a closed loop with a stable voltage gain Av, drives the gate of high-voltage MOSFET 216a with a gate voltage $V_{G1}$, till the current $I_{LEDa}$ flowing in MOSFETs 216a and 211 drives the difference between $V_{sense}$ and $V_{pilot}$ to zero, i.e. $V_{sense}-V_{pilot}=0$. In this way, the multiple $\beta_r$ of the reference current $I_a$ is "mirrored" in MOSFET 211, and a controlled and constant current flows in LED string 205a even if the LED supply voltage $+V_{LED}$ changes.

During manufacturing, the resistor network 220 in parallel with fixed resistor 212 is functionally trimmed to produce an accurate output current thereby eliminating the impact of variability coming from MOSFET transconductance of MOSFET 210 or in the resistor value $R_{max}$ of resistor 212. In the example shown, trimming is performed by measuring the current $I_{LEDa}$ and then blowing fuse links till the measured value of $I_{LEDa}$ reaches its target value. Because amplifier 214 controls the gate voltage of MOSFET 216a (and hence the current $I_{LEDa}$) and provided the size of MOSFETs 210 and 211 are equal, then the error voltage, the difference between $V_{sense}$ and $V_{pilot}$, will be driven to zero when the currents $I_a$ and $I_{LEDa}$ are equal. Should the gate width of MOSFET 211 be larger than that of MOSFET 210, then when the error voltage is zero, the LED current $I_{LEDa}$ will be larger than reference current $I_a$ by the ratio between the respective gate widths of MOSFETs 211 and 210, which as indicated above is equal to $\beta_r$.

For example, initially after manufacturing and immediately prior to trimming when all the resistors in resistor network 220 are still electrically connected in parallel with resistor 212, the total resistance of the resistor network 212 is at its minimum value, $I_a$ is higher than its target value, and therefore the value of $I_{LEDa}$ will also be too high, e.g. 22 mA (10% above its target value of 20 mA). On the integrated circuit (or on a printed circuit board) probes are electrically connected to common metal trim pad 221 and to all the specific resistor trim pads 222. For clarity's sake, only trim pad 222b in series with trim resistor 213b is labeled. A high current is then impressed by the tester between common trim pad 211 and a specific channel's trim pad, e.g. trim pad 222b, causing the thin portion of the metal fuse link 223b in series with trim resistor 213b to melt and become an electrical open circuit, disconnecting resistor 213b from trim network 220. With less parallel resistance, the total resistance increases, the value of reference current drops, and the LED current in LED string 205a decreases by a fixed amount.

This measurement and link blowing process is repeated until the proper number of metal fuse links have been blown reduce the magnitude of the reference current $I_{ref}$ by the factor α so as to produce the target value of the current $I_{LEDa}$. $\alpha I_{ref}$ thus represents the reference current after trimming. If all the fuse links are blown, the resistance in series with MOSFET 210 increases to its maximum value $R_{max}$, the resistance of resistor 212, and reference current $I_a$ reaches its lowest value. If that current is still above the target value, then that particular integrated circuit will be rejected as defective, lowering production yield and increasing product cost. As such, the resistance values $R_{t1}$, $R_{t2}$, ... $R_{tx}$ used in resistor network 220 must be chosen carefully to accommodate normal stochastic variability in integrated circuit manufacturing. Note that the schematic representation of fuse link 223b is illustrated by a line that is thinner than the rest of the conductors shown in the schematic of FIG. 16C.

Also, single-pole double-throw switch 217 is shown to illustrate the digital enable function within MOSFET driver 215a. When the digital input to digital gate buffer (shown as an inverter symbol) 218 is "high" or a logic one, switch 217 connects the gate of high-voltage MOSFET 216a to the output terminal of differential amplifier 214, turning MOSFET 216a on and illuminating LED string 205a. If the enable signal is biased to a logic zero state, the switch 217 connects the gate of high-voltage MOSFET 216a to ground, whereby $V_{G1}=0$ and MOSFET 216a turns off, cutting off the current in LED string 205a. While this function is shown as a mechanical switch, it is actually realized by a network of transistors configured as an analog switch or amplifier as commonly known to those skilled in the art. Also, during times when a specific channel is not enabled, the operation of differential amplifier 214 may be suspended or clamped in voltage so that it does not try to increase its output voltage in a futile attempt to increase the sense current in MOSFET 211.

Figure 16D:
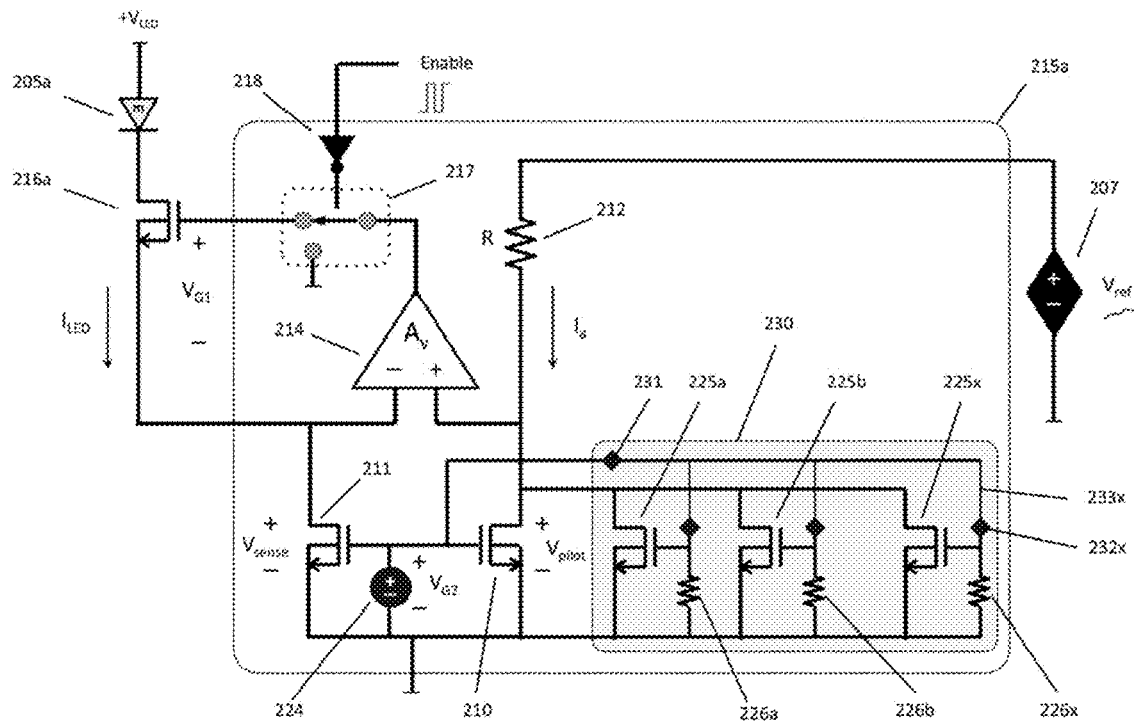
FIG. 16D schematically illustrates one implementation of a controlled current sink comprising a high voltage MOSFET and MOSFET driver circuit with MOSFET trimming.

While resistor trimming is commonplace, trimming the size, i.e. gate width, of a network of transistors is generally easier and more accurate and reproducible than using resistors. Such a circuit is shown in FIG. 16D, where resistor 212 has no parallel network of trim resistors but instead current mirror MOSFET 210 includes a parallel network 230 of trim MOSFETs 225a, 225b ... 225x. Another advantage of using MOSFET trimming rather than resistor trimming is that network 230 is generally smaller than network 220, shown in FIG. 16C. Like the resistor trim method, as shown fuse links (illustrated by fuse link 233x) are blown to disconnect, i.e. turn off, one or more of MOSFETs 225a ... 225X in parallel with current mirror MOSFET 210. For example, initially after manufacturing and immediately prior to trimming, when all of the MOSFETs 210 and 225a ... 225x are still connected in parallel, the size ratio between MOSFET 211 and the parallel combination of current mirror MOSFET 210 and trim network 230 is at a minimum and the current $I_{LED}$ will be below its targeted value, e.g. at 18 mA, 10% below its 20 mA target. By forcing a high current between common trim pad 231 and channel specific trim pad 232x, for example, fuse link 233x is blown and the gate of trim MOSFET 225x is no longer connected to the gate of MOSFET 210. Instead, with its gate disconnected, resistor 226x biases MOSFET 225x off. With less parallel gate width in MOSFET trim network 230, the current mirror gate ratio increases and for the same value of reference current $I_a$, the LED current $I_{LED}$ will increase commensurately.

Note that, in FIG. 16D, the gates of MOSFETs 210 and 211 along with those in MOSFET trim network 230 are biased by a voltage source 224 and not by connecting the gate of current mirror MOSFET 210 to its drain. The advantage of this method is that the current mirror MOSFET 211 may operate with a lower drain voltage $V_{sense}$ using this method. While some initial accuracy may be lost using this method, functional trimming is able to correct for this deficiency. Beneficially, the lower voltage drop across MOSFET 211 reduces power dissipation and improves overall system efficiency of the LED driver 215a.

An alternative method of trimming involves varying the reference current by adjusting the reference voltage. Adjusting the reference voltage also requires analog circuitry. Methods of manufacturing fixed value reference voltage sources are well known, including means to minimize variation in the voltage over temperature. Such methods include bandgap voltage references (see en.wikipedia.org/wiki/bandgap_voltage_reference) and Zener diode voltage references (see en.wikipedia.org/wiki/Zener_diode). Since these techniques are well known to those skilled in the art, they will not be discussed here.

Analog Sinusoidal Synthesis

While sinusoidal waveforms can be generated digitally as described later in this application, an inventive means disclosed herein by which to synthesize a sinusoidal waveform for driving LEDs in a phototherapy system is through the use of analog synthesis. While digital synthesis, as disclosed, involves pulsing an LED current on-and-off in constantly varying durations, i.e. pulse-width-modulation, to synthesize a sine wave (or chords of multiple frequency sine waves), analog synthesis involves sinusoidally varying the reference current or current bias to the LED current control circuit, i.e. the current mirror driving an LED string, in essence making the reference current into an oscillator. Referring to the exemplary waveforms shown in FIG. 15, analog waveform synthesis is illustrated by sinusoids 254, 255 and 256 occurring at times $t_4$, $t_5$, and $t_6$, and also by the arbitrary time dependent waveform representing the ability to implement any control function by waveform 252 at time $t_2$.

As shown in FIG. 17A, to perform analog sinusoidal synthesis, the reference voltage biasing MOSFET driver 215a is replaced with a fixed frequency sine-wave or sinusoidal oscillating reference voltage source 235, also known as a linear or "harmonic" oscillator. Harmonic oscillators in the audio range can be made using inductor-capacitor, i.e. LC, oscillators or using resistor-capacitor, i.e. RC, oscillators circuits including RC phase shift oscillators, Wien bridge oscillators, or twin-T oscillators (see wikieducator.org/sinusoidal_oscillator). During manufacturing, the output voltage of oscillating reference voltage source 235 must be trimmed using resistors or transistor arrays in a manner similar to the trimming of MOSFET driver 215a described previously. In contrast, other common RC circuits often used for clock generation comprising simple relaxation oscillators are not harmonic oscillators and are not applicable because they produce sawtooth or triangular shaped waveforms with unwanted broadband spectral content.

Figure 17C:
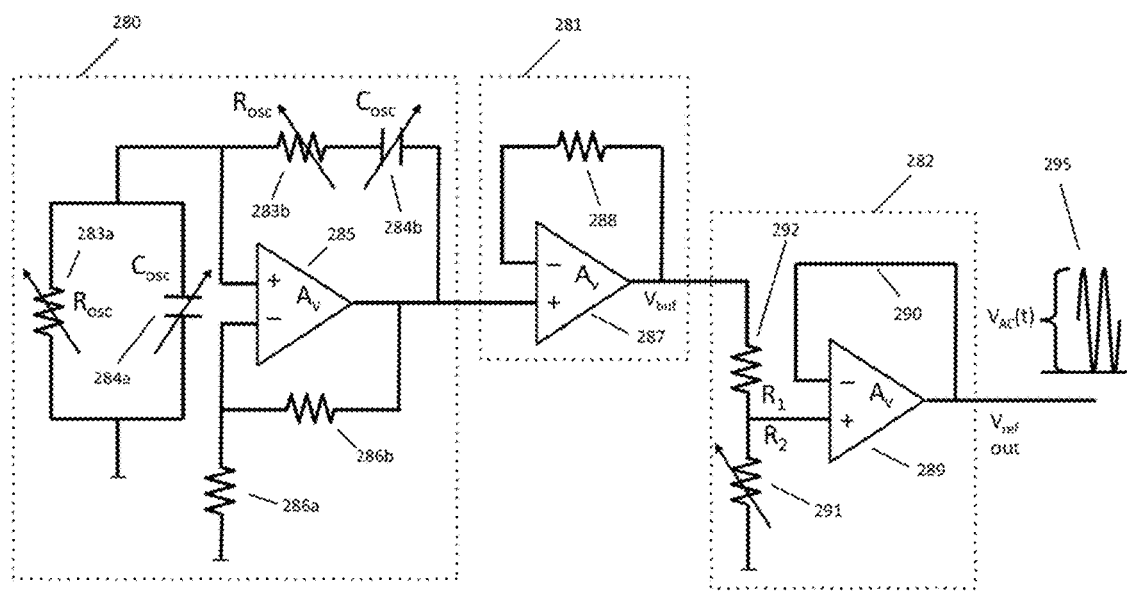
FIG. 17C schematically represents a frequency and voltage adjustable voltage source comprising a Wien-bridge used to generate an oscillating reference current.

In FIG. 17B, oscillating reference voltage source 235 is replaced by a controlled oscillating reference voltage source 236 with an adjustable frequency and an adjustable voltage. One example of such an oscillating reference is illustrated in FIG. 17C comprising a Wien oscillator 280 with a voltage follower 281 and a trimable variable voltage output buffer 282. Wien oscillator 280 comprises two matched variable capacitors 284a and 284b and two matched programmable resistors 283a and 283b. The two RC networks create a voltage divider and feedback network returning signals from the output of a high-gain differential amplifier 285 back to its positive input. A damping network comprising resistors 286a and 286b sets the gain and stability of the circuit to stabilize the oscillations.

The oscillating frequency may be adjusted by changing the resistance $R_{osc}$ of programmable resistors 283a and 283b or alternatively by changing the capacitance $C_{osc}$ of variable capacitors 284a and 284b. Variable resistance may be realized by varying the gate voltage and resistance of MOSFETs biased in their linear region of operation, or alternatively using a digital potentiometer comprising discrete resistors with parallel MOSFETs able to short out the various resistors. Variable capacitance may be realized by varactors comprising back-to-back PN junction diodes, one of which is reverse biased to a fixed voltage to establish the junction capacitance. Changing either the resistance or the capacitance adjusts the oscillating frequency of Wien oscillator 280.

To insure that loading by trimable variable voltage output buffer 282 does not affect the oscillating frequency of Wien oscillator 280, voltage follower 281 comprising a differential amplifier 287 with negative feedback through resistor 288 provides buffering. The voltage $V_{buf}$ of voltage follower 281 is then adjusted by a resistor divider comprising a fixed resistor 292 and a variable resistor 291 with resistance values $R_1$ and $R_2$ respectively. The variable resistance 291 may comprise a trim network as well as a digital potentiometer, as described previously. The voltage at the tap point located between resistors 291 and 292 and connected to the positive input of differential amplifier 289, is equal to the output voltage $V_{ref}$out of variable voltage output buffer 282 and is given by $V_{ref}\text{out}=(V_{buf}\cdot R_2)/(R_1+R_2)$. With its output connected to its negative input by wire 290, differential amplifier 289 behaves as a voltage follower faithfully reproducing the voltage waveform of its input while delivering the required current to an electrical load connected to its output $V_{ref}$out.

As shown by the output waveform 295, this output voltage $V_{ref}$out has an AC component $V_{AC}(t)$ extending from zero to its peak value of $+V_{AC}(t)$ with an average value of $V_{AC}(t)/2$ and contains no added DC offset (aside from the intrinsic DC average value of a sine wave). Since the only voltage component is AC, specifically the sine wave generated from Wien oscillator $280+V_{AC}(t)$, then the sine wave can be said to represent large-signal AC behavior. If it is desirable to also include a DC offset, the output of oscillating reference voltage source 236 may be further adjusted by the circuit shown in FIG. 17D. In this circuit, the $V_{ref}$out output of the circuit shown in FIG. 17C is fed into a voltage follower 300 comprising a differential amplifier 302 (or another type of voltage follower circuit) through an AC coupling capacitor 303. Differential amplifier 302 operates as a voltage follower because of negative feedback on wire 301, connecting its output to its negative input. The purpose of AC coupling capacitor 303 is to block any DC offsets present within the output of oscillating reference voltage source 236. If no offset is present capacitor 303 may be eliminated.

Although operational amplifier 302 is powered from logic supply+$V_{logic}$, its negative supply rail is not connected to ground but instead is connected to a generated voltage $+V_{neg}$ produced by a voltage bias circuit 309, an above ground voltage that acts as the negative supply rail for differential amplifier 302. Because of this re-referencing its negative supply rail, the output voltage $V_{ref}\text{out}_2$ of differential amplifier 302 is shifted in its voltage level from ground to a more positive voltage. As a result, the waveform of the output voltage $V_{ref}\text{out}_2$ appears the same as the waveform of its input $V_{ref}$out but $V_{ref}\text{out}_2$ is offset by a DC voltage equal to the generated voltage $+V_{neg}$, or mathematically as $$V_{ref}\text{out}_2 = V_{DC} + V_{AC}(t) + V_{neg} + V_{ref}\text{out}_2 < +V_{logic}$$

The circuit will faithfully reproduce the input so long that the sum of the DC bias (+$V_{neg}$) and the sine wave input signal AC(t) do not exceed the supply voltage +$V_{logic}$, otherwise the top of the sine wave will be "clipped", i.e. reach a constant maximum output voltage at +$V_{logic}$ during any interval where +$V_{neg}$+$V_{ref}$out$_2$≥+$V_{logic}$. Waveform clipping results in the distorting of the output waveform, producing unwanted harmonics and spectral contamination similar to (or even worse than) that of LED drive using digital pulses. Also note that if the difference in voltage (+$V_{logic}$−+$V_{neg}$) is too small, meaning that the level shifted bias is too high, differential amplifier 302 may not be able to function properly.

Figure 17D:
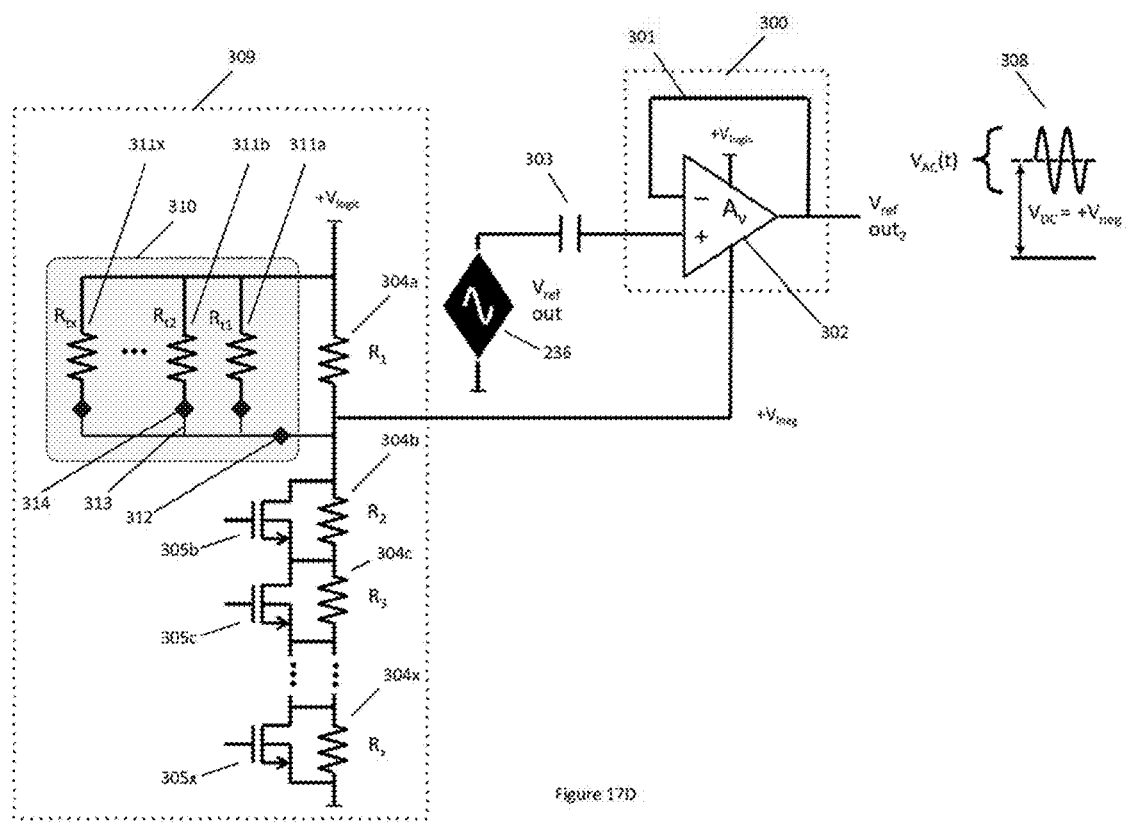
FIG. 17D schematically represents a programmable level shift circuit using a resistor ladder.

Generation of the DC voltage +$V_{neg}$ may be performed in any number of ways including a trimmed bandgap voltage followed by a variable gain amplifier, a voltage controlled amplifier, or varying resistor or switched-capacitor voltage divider networks. One such voltage divider method is illustrated in FIG. 17D as voltage generation circuit 309 using a resistor voltage divider technique. As shown, the logic supply voltage +$V_{logic}$ is connected to series resistor string comprising resistors 304a through 304x, where x is a mathematical variable representing the number of resistors in the series resistor string. Resistors 304b through 304x are connected in parallel with MOSFETs 305b through 305x, respectively. The number of resistors may commonly be 9, 13, or 17 allowing various 8-bit, 12,-bit and 16-bit combinations of voltage to be realized depending on the accuracy required, where the number of resistors needed equal one plus the number of bits of accuracy desired. For example, 8 bits of accuracy requires 9 resistors providing 256 levels of output voltage.

The output voltage +$V_{neg}$ taken from the voltage tap point between resistors 304a and 304b, is varied by shorting out various resistors by turning on and off MOSFETs 305b through 305x in various combinations. For example, if all the MOSFETs 305b through 305x are turned on and their resistance is designed to be small relative to that of the resistance value $R_1$ of resistor 304a, then the output voltage +$V_{neg}$ is near ground; if none of the transistors 305b through 305x is turned on, the output voltage +$V_{neg}$ becomes +$V_{logic}$, and for various other combinations an intermediate voltage may be selected. The resistor network 304a through 304x can further be modified to select a voltage from only a portion of the supply range. For example, a lower voltage than +$V_{logic}$ may be used to power the resistor string. The series ladder of resistors 304a through 304x forms a type of digital-to-analog converter because turning various MOSFETs on and off is essentially a digital function and the result is an analog, albeit quantized, voltage. For greater resolution the number of resistors can be increased or the voltage range reduced to that the least significant bit, i.e. LSB, represents a smaller voltage gradation.

Aside from the voltage generator function, resistor trim network 310 comprising parallel resistors 311a through 311x is placed in parallel with resistor 304a to provide a means to trim the voltage accuracy during manufacturing by blowing fuse links by impressing temporary high currents on trim pads on an IC. For example, by running high current between common trim pad 312 and trim pad 314, thin metal line 313 will act like a fuse and melt, creating an electrical open-circuit and removing resistor 311b from the parallel network of resistors in trim network 310.

In conclusion, the DC offset circuit shown in FIG. 17D, combined with the oscillating reference voltage circuit of FIG. 17C allow the electrical generation of a sine wave AC(t) of varying frequency and magnitude offset by a DC voltage. So long as it does not exceed the supply voltage +$V_{logic}$, the output voltage of this newly disclosed oscillating reference voltage is $V_{ref}$out$_2$=$V_{DC}$±$V_{AC}$(t)/2=+$V_{neg}$±$V_{ref}$out$_2$ having a peak output voltage of $V_{DC}$+$V_{AC}$(t)/2, a minimum output voltage of $V_{DC}$−$V_{AC}$(t)/2, and an average output voltage of $V_{DC}$. If the AC coupling capacitor 303 is removed, the average value of the output increases by the average voltage of the sign wave $V_{AC}$(t)/2, reducing the usable operating voltage range of differential amplifier 302.

As shown by the $V_{ref}$out$_2$ waveform 308, using the circuit of FIG. 17D or a similar circuit, the AC component of the signal is smaller than the DC offset voltage, i.e. $V_{AC}$(t)<$V_{DC}$. Since the main voltage component is DC and not the sinusoid, then the sine wave can be said to represent small-signal AC behavior. In a phototherapy application, the voltage value of $V_{ref}$out$_2$ actually represents the reference current that determines LED brightness whenever the LED string is enabled and conducting. Small signal operation of the inventive circuitry represents a completely new operating mode for phototherapy—one wherein the LED string is continuously illuminated at a fixed current and then modulated sinusoidally at bias condition with slight increases and decreases in current and corresponding changes in brightness.

As shown in FIG. 18A, another way to vary the reference current is to supply the reference voltage used to generate the reference current α$I_{ref}$ for MOSFET driver 215a from a digital-to-analog (D/A) converter 315. While any number of bits may be used to control accuracy, commonly available converters, for example those used in HDTVs, comprise 8 bits with 256 levels, 12 bits with 4096 levels, or 16 bits with 65,536 levels. Converter speed is not high because the highest frequency required for phototherapy is 20 kHz, and in most cases only 5 kHz. In operation, data is written into a latch or static memory, specifically $I_{LED}$ register 316, and loaded into D/A converter each time the converter receives a digital clock pulse on its Load input pin, i.e. between 5 kHz to 20 kHz, as desired.

While many methods including switched capacitor, resistor ladder and other types of D/A converters (DAC) exist, because only audio frequencies are required in phototherapy applications low cost solutions may be utilized. One such circuit is an 8-bit resistor ladder converter 315 shown in FIG. 18B comprising a precision reference voltage source 320, and a DAC resistor ladder comprising resistors 321a through 321x, along with DAC switches comprising MOSFETs 322b through 322x controlled by decoder 323. MOSFETs 322b through 322x are connected in parallel with resistors 321b through 321x, respectively. In operation, a decoder 323 loads an 8-bit word from its input line 8b upon receiving a clock pulse on its digital Load input, represented by digital inverter 344, and converts the 8-bit word into instructions of which of the MOSFETs 322b through 322x should be turned-on in various combinations to produce a linear output voltage on the DAC ladder tap point between resistors 321a and 321b. The DAC ladder voltage, ranging from zero to $V_{ref}$, is then fed to the positive input of a differential amplifier 335 configured as a voltage follower. A resistor trim network 325 comprising resistors 324a through 324x, trim pads (e.g. 326 and 328) and fuse links 327, is placed in parallel with resistor 321a in order to trim the output voltage during manufacturing. Alternatively, the internal reference voltage $V_{ref}$ provided by source 320 may be trimmed to provide the required precision.

As an inventive element, a switched filter capacitor 342 is optionally included to filter the ripple of the output voltage $V_{ref}$out, or if a high speed transient is desired to disable the filter depending on the digital control signal on the Filter Enable input represented by digital inverter 343. In operation when MOSFET 340 is turned on and MOSFET 341 is disabled capacitor 342 is connected in parallel with the output of buffer amplifier 335 and the output of reference 315 is filtered removing high frequency noise. When MOSFET 340 is turned off and MOSFET 341 is enabled, capacitor 342 is disconnected from the output of buffer amplifier 335 and the output of reference 315 is not filtered. By enabling MOSFET 341, the charge on capacitor 342 is discharged to prevent the accumulation of voltage from repeated operation. Other D/A converters may be employed in place of resistor ladder converter 315, as desired.

Figure 19A:
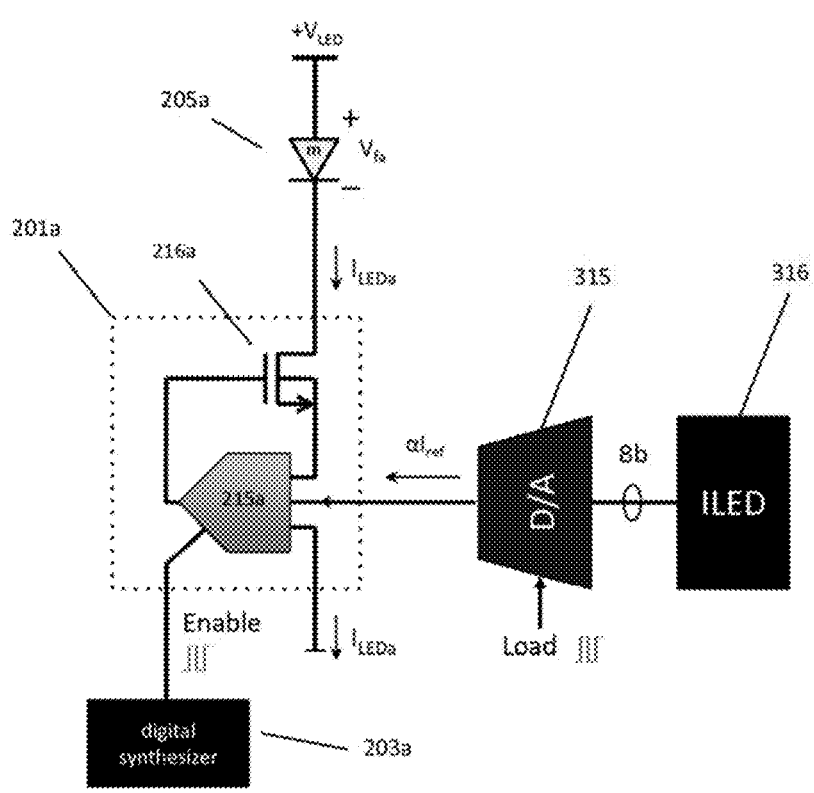
FIG. 19A illustrates a 292 Hz sine wave synthesized from a D/A converter.

An example of an 292 Hz (D4) oscillating reference voltage without any added DC offset generated in the disclosed manner is illustrated in FIG. 19A comprising a 1.2V sine wave 371 with a period of 3.42 msec and an average voltage output of 0.6V. The peak voltage is conveniently chosen to be similar to the output voltage of a bandgap voltage trimmed for a low temperature coefficient or near zero "tempco". Other voltages, however, may be employed as well to produce the desired input current to LED driver 215a.

It should be emphasized that sinusoid 350 as disclosed herein is synthesized, programmable, and low voltage, not the artifact of a rotating electromagnetic generator or alternator used in AC power generation in power plants. So while LEDs used in residential and commercial lighting applications can, at least theoretically, be driven directly from the 60 Hz AC line voltage, the sinusoidal characteristic of the AC line voltages and its application in general lighting is completely different than the proposed synthesized sine wave excitation of LEDs applicable for phototherapy.

First, the AC line voltage is high-voltage, typically 110 VAC or 220 VAC and unacceptably dangerous in medical applications where a device, in this case the LED array and pad, touches the skin. In LED drive for phototherapy, the total number of series connected LEDs is limited to operate at a maximum voltage below 40V, a voltage considered safe by Underwriter Laboratories (UL) for consumer and medical applications.

Second, the frequency of the AC line varies with loading of the utility customers and is contaminated by numerous undesirable spectral harmonics affecting the purity of the sinusoid and rendering it unsuitable for phototherapy applications.

Third, the frequency of the AC line, namely 60 Hz and its harmonic 120 Hz do not represent a frequency known to be beneficial in phototherapy, e.g. a multiple of 292 Hz. In fact 60 Hz does not represent a multiple of any pure or chromatic tone indicated for photobiomodulation.

Fourth, aside from its uncontrolled variation with loading, the frequency of the AC line is fixed and is not programmable or adjustable. It cannot be adjusted or varied dynamically or to match the time constants of natural biological processes and associated time constants. It also cannot be used to generate chords of multiple frequency sinusoids nor control the energy density and spectral content, i.e. the mix, of multiple frequency sinusoids.

Fifth, the reduction of the AC mains line voltage from 110 VAC or 220 VAC to a safe level, i.e. below 40V, requires a large and heavy iron-core transformer designed to operate at 60 Hz.

Sixth, LEDs used in phototherapy necessarily comprise relatively narrow spectral wavelengths in the red, near infrared, or blue portion of the spectrum. The LED light, typically ±35 nm in spectral width, emitted through the quantum-mechanical process of tunnel emission is determined by bandgap engineering of the manmade crystal used to realize the LED in manufacturing. LEDs used in lighting are designed to emit a broad spectrum of light, i.e. white light, comprising a number of colors in the rainbow. Unlike LEDs used in phototherapy, white light LEDs comprise blue or UV LEDs with a lens cap containing phosphor tuned to absorb blue or UV light. In operation, the light emitted from the LED semiconductor material is absorbed by the phosphor atoms in the lens cap and converted into broad spectrum "white" light similar to sunlight but more white and less yellow.

Finally, the direct drive of LEDs using AC sinusoids in general lighting applications is actually not in commercial practice today for a variety of intractable technical problems including poor power efficiency, poor power factor, electrical shock risk, and flicker. Today's LED bulbs use multi-stage PWM switching power supplies for power factor correction and voltage regulation. LED brightness is therefore controlled by digital pulses and not using sinusoids.

So LEDs driven in AC lighting are not applicable for phototherapy.

In the operation of D/A converter 315, the digital input to decoder 323 is repeatedly loaded during clocking of the Load pin, i.e. the input to inverter 344, occurring at fixed time intervals in order to generate a sine wave of an arbitrary and adjustable frequency. The following table represents examples of various time points used in the waveform synthesis.

| time (msec) | binary in | hex | DAC level | arc degree | output V |
|---|---|---|---|---|---|
| 0 | 0000 0000 | | 0 | 0° | 0.600000000 |
| 0.014 | 0000 0001 | 01 | 1 | 1.5° | 0.615706169 |
| 0.029 | 0000 0010 | 02 | 2 | 3.0° | 0.631401574 |
| 0.043 | 0000 0011 | 03 | 3 | 3.5° | 0.647075457 |
| 0.143 | 0000 1010 | 0A | 10 | 15° | 0.755291427 |
| 0.285 | 0001 0100 | 14 | 20 | 30° | 0.900000000 |
| 0.428 | 0001 1110 | 1E | 30 | 45° | 1.024264069 |
| 0.571 | 0010 1000 | 28 | 40 | 60° | 1.119615242 |
| 0.714 | 0011 0010 | 32 | 50 | 75° | 1.179555496 |
| 0.856 | 0011 1100 | 3C | 60 | 90° | 1.200000000 |
| 1.284 | 0101 1010 | 5A | 90 | 135° | 1.024264069 |
| 1.427 | 0110 0100 | 64 | 100 | 150° | 0.900000000 |
| 1.698 | 0111 0111 | 77 | 119 | 178.5° | 0.615706169 |
| 1.712 | 0111 1000 | 78 | 120 | 180° | 0.600000000 |
| 1.727 | 0111 1001 | 79 | 121 | 181.5° | 0.584293831 |
| 1.998 | 1000 1100 | 8C | 140 | 210° | 0.300000000 |
| 2.569 | 1011 0100 | B4 | 180 | 270° | 0.000000000 |
| 3.139 | 1101 1100 | DC | 220 | 330° | 0.300000000 |
| 3.396 | 1110 1110 | EE | 238 | 357° | 0.568598426 |
| 3.410 | 1110 1111 | EF | 239 | 358.5° | 0.584293831 |
| 3.425 | 1111 0000 | F0 | 240 | 360° (0°) | 0.600000000 |
| skipped | 1111 0001 | F1 | 241 | not used | N/A |
| skipped | 1111 1111 | FF | 255 | not used | N/A |

As shown, an 8-bit D/A converter exhibits 256 output states or 256 steps above its zero state, i.e. from 0000-0000 in binary or from 00 to FF in hexadecimal. To conveniently map these states to the 360 degrees of angle arc, only 240 steps (i.e. 241 states) of the D/A converter have been employed. As such, 240 steps corresponds to 360° or 1.5° per DAC step. The remaining DAC steps from 241 to 255, in hexadecimal corresponding to DAC input codes from F0 to FF are intentionally skipped and not used in sinusoid generation. As described, the DAC value is represented in three equivalent ways

Figure 18B:
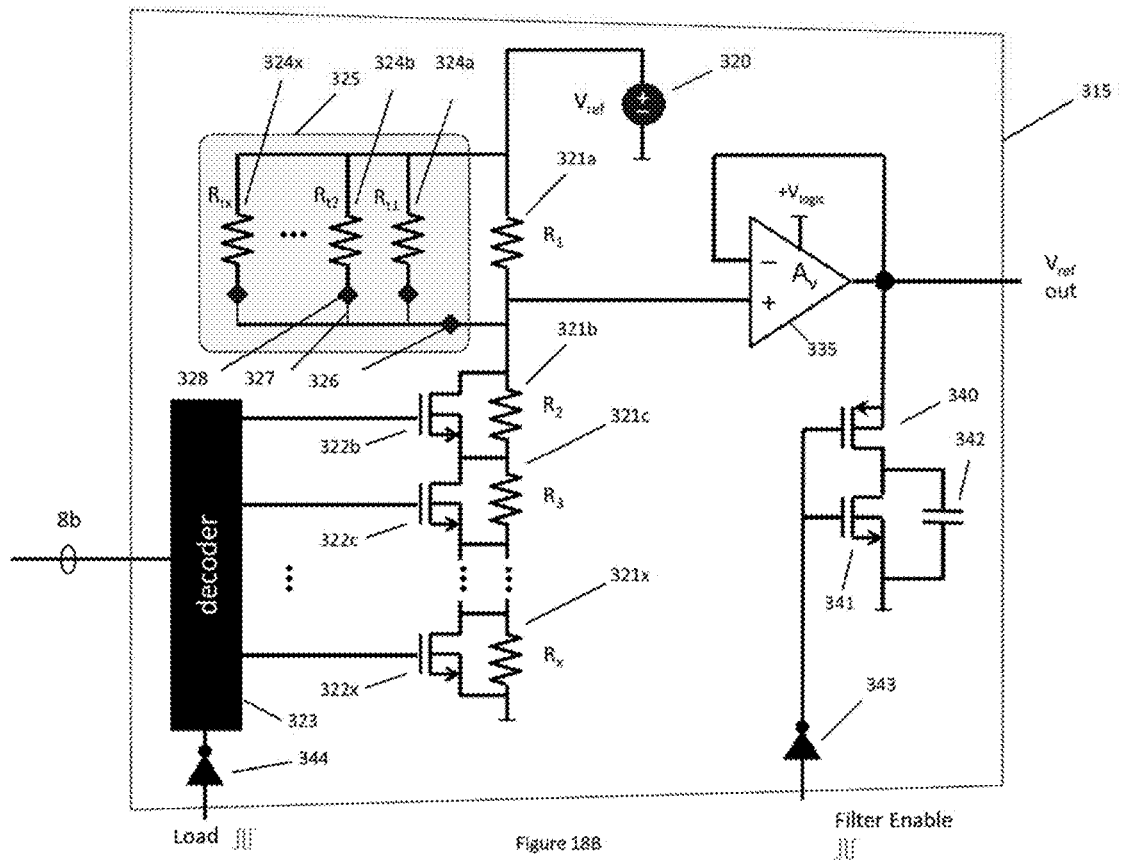
FIG. 18B schematically represents an implementation of a D/A converter using a resistor ladder.

- by a hexadecimal digital code, the input to decoder 323 in FIG. 18B, as illustrated by the hex code in the third column of the above table
- by a binary digital code shown in the second column of the above table representing the various combinations of turning on and off the MOSFETSs 322b through 322x in FIG. 18B to dynamically change the resistor divider network ratio
- by the analog output voltage output from DAC 315 and buffer 335 shown by the rightmost column in the above table, or alternatively by a current in case that voltage is divided by a resistor to make a DAC controlled current.

In operation, a sequence of increasing digital codes is fed into to the DAC at a regular time intervals to produce a rising output voltage. Conversely a sequence of declining digital codes may be used to lower the output voltage of the DAC. If this increasing and decreasing code sequence is performed repeatedly and consistently a any periodic function can be synthesized as an output of DAC 315. If codes are input into the DAC at regular time intervals according to evaluation of a sine function for fixed steps of angles, e.g. 15°, then the sequence will result in a sinusoidal output from DAC 315.

Figure 19A:
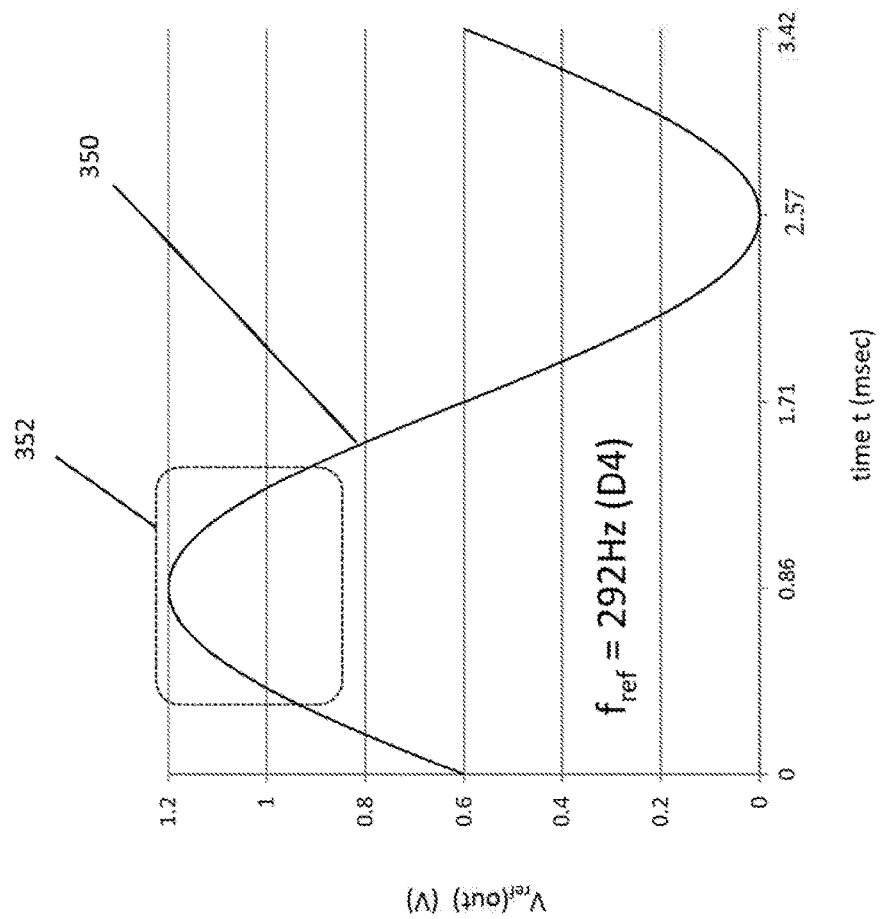
Figure 19B:
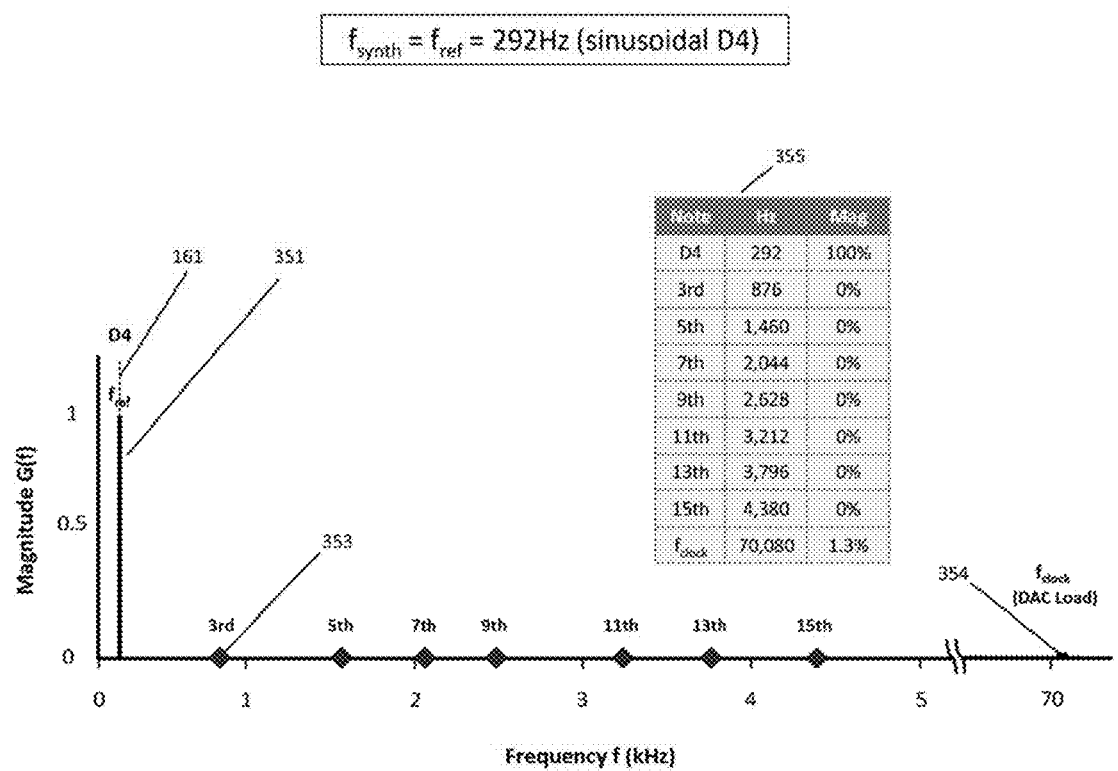
FIG. 19B illustrates the harmonic spectra of 292 Hz sine wave synthesized using a D/A converter generated reference current.

To synthesize a 292 Hz sine wave having a period of approximately T=3.42 msec, each of the 240 steps comprises 0.0142694 msec. The minimum corresponding signal used to load DAC's decoder 323 must therefore be 292 Hz·240 states/Hz or 70,080 Hz. The resulting spectra of the oscillating reference voltage is illustrated in FIG. 19B using a D/A converter to synthesize a sinusoidally oscillating reference voltage 351 having a frequency $f_{synth}=f_{ref}=292$ Hz corresponding to a pure sinusoidal D4 frequency 350. At over 70 kHz, the clock frequency 354 is well into the ultrasonic range and is therefore not a source of unwanted spectral contamination. Compared the prior art spectrum of square wave generated 292 Hz, i.e. a pulsed D4, shown in FIGS. 12A and 12B, the harmonic spectra 353 of the $3^{rd}$, $5^{th}$, $7^{th}$ through $13^{th}$ multiples of a 292 Hz sinusoid all have zero energy—meaning all spectral contamination in the audio band has been completely eliminated (see Table 355).

Figure 19C:
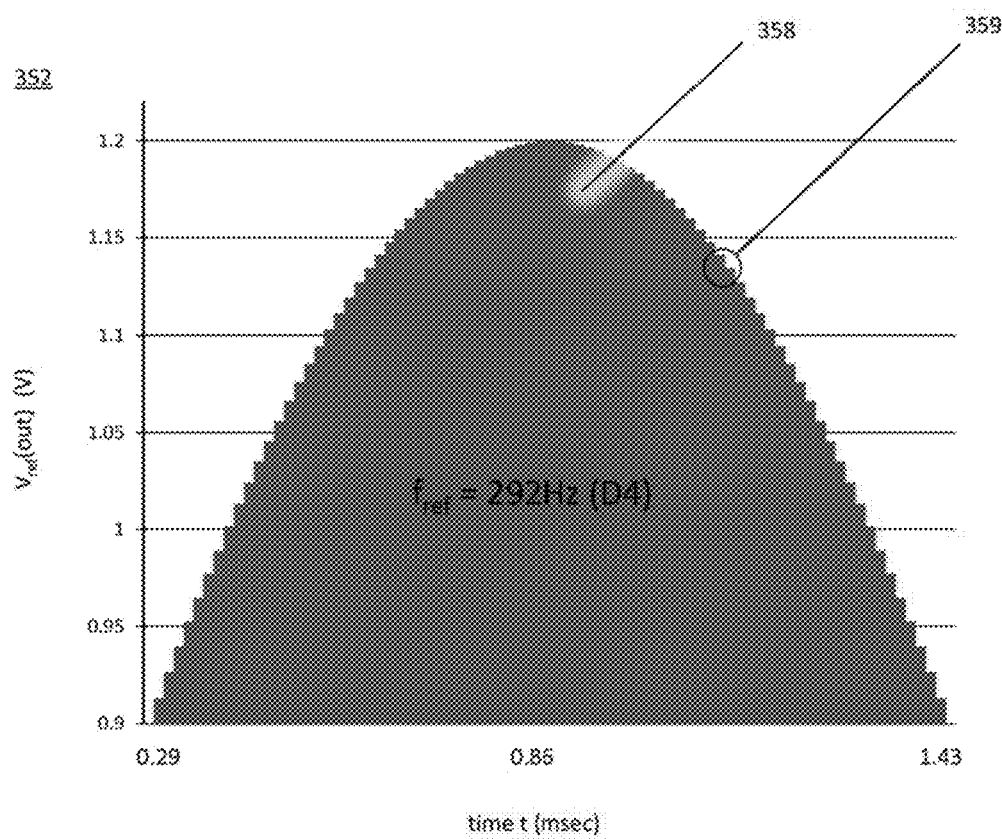
FIG. 19C illustrates an expanded view of digital steps present in a 292 Hz sine wave synthesized from a D/A converter generated reference current.
Figure 13O:
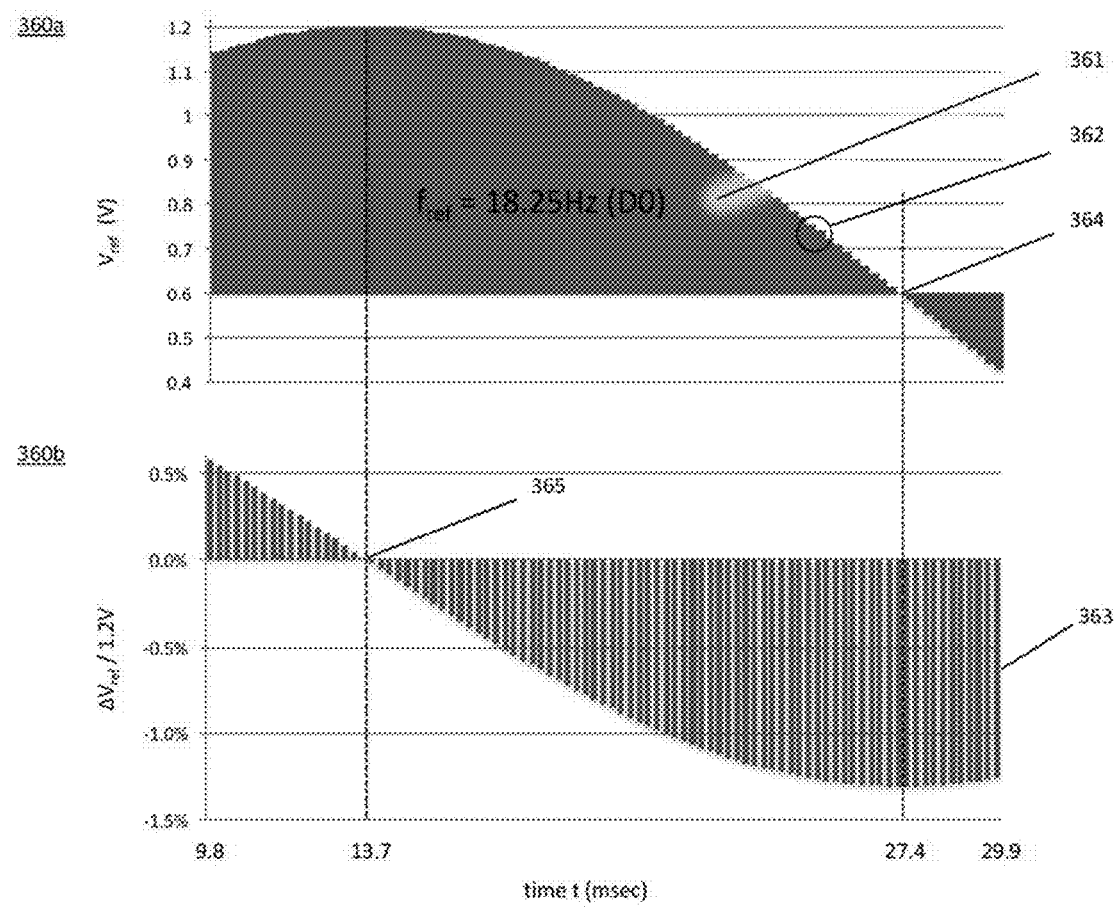

Aside from being outside the audio range, the magnitude of the noise generated by clock frequency 354 is small. A close-up view 352 of sinusoid 350 shown in FIG. 19C reveals the origin of the noise, incremental steps in voltage 359 present in the generated waveform 358 occurring each time the output of the D/A converter changes voltage. As shown, these transitions occur at the oscillating frequency of the clock used to load the decoder of the DAC. This frequency occurs at a frequency $f_{clock}=f_{ref}\cdot$(# of DAC steps) where the "# of DAC steps" corresponds to the bit resolution of the D/A converter (rounded to any convenient number of steps), although it is also possible to employ clock frequencies higher than this clock frequency.

Unless higher clock frequencies are intentionally utilized, the frequency of the clock and hence the frequency of the noise generated by the clock will scale with frequency of the sine wave being generated. As such, if the sine wave being generated is at a lower frequency, the noise spectrum of the clock will correspondingly occur at lower frequencies, possibly overlapping the audio spectrum. For example, graph 360a shown in FIG. 19D illustrates a portion of a 18.25 Hz sine wave 361 comprising a sequence of small voltage changes 362 occurring at the clock frequency of the D/A converter, specifically 4,380 Hz.

On the same time scale, graph 360b of FIG. 19D illustrates in histogram 363 the $\Delta V_{ref}$ change in voltage at each of these steps as a percentage of the oscillation's 1.2V peak-to-peak magnitude. Prior to 13.7 msec when the output voltage $V_{ref}$ is still increasing, the value of $\Delta V_{ref}$ is positive. At 13.7 msec the change diminishes to near zero and thereafter the change become negative in polarity. At approximately 27.4 msec when the sine wave passes through its average voltage of 0.6V, i.e. a point 364, the magnitude of $\Delta V_{ref}$ reaches its largest negative value and thereafter begins to diminish in magnitude. This peak magnitude represents less than 1.3% of the amplitude of the sine wave itself.

Figure 19E:
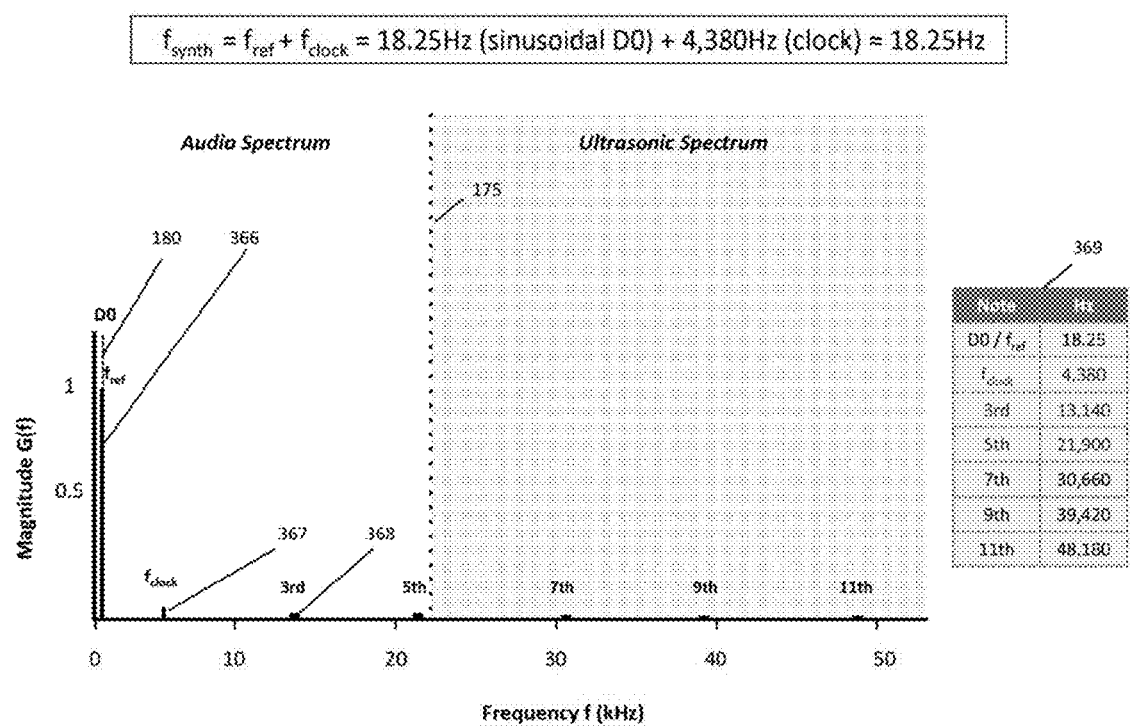
FIG. 19E illustrates the harmonic spectra of a 18.25 Hz sine wave synthesized using a D/A converter generated reference current.

The resulting spectra are shown in FIG. 19E, which indicates that the magnitude of the voltage transitions occurring at the clock frequency 4,380 Hz, represented by column 367, are small compared to the magnitude of the oscillating reference voltage at 18.25 Hz, represented by column 366. Similarly, the harmonics of these digital transitions are also negligibly small in relative magnitude. For example, the magnitude of the $3^{rd}$ harmonic of the clock frequency is represented by the column 368. Even though the clock and its $3^{rd}$ and $5^{th}$ harmonics are in the audio spectra, i.e. lower in frequency than 22,000 Hz shown by line 175, their small magnitude makes the spectral contamination of the synthesized oscillating reference insignificant, even at low frequencies. If necessary, moreover, the remaining ripple, however small, can be filtered out by the Filter Enable function biased to connect capacitor 342 to the $V_{ref}$ output by turning on MOSFET 340.

By employing analog synthesis as disclosed herein, a wide range of sine wave excitation patterns in the audio spectrum can be generated to drive LED arrays for phototherapy applications, free from harmonic contamination. Using the disclosed methods and apparatus in analog sinusoidal synthesis, dynamic control of waveforms in both frequency and in amplitude may be realized including independent control in peak and average current control.

Figure 20:
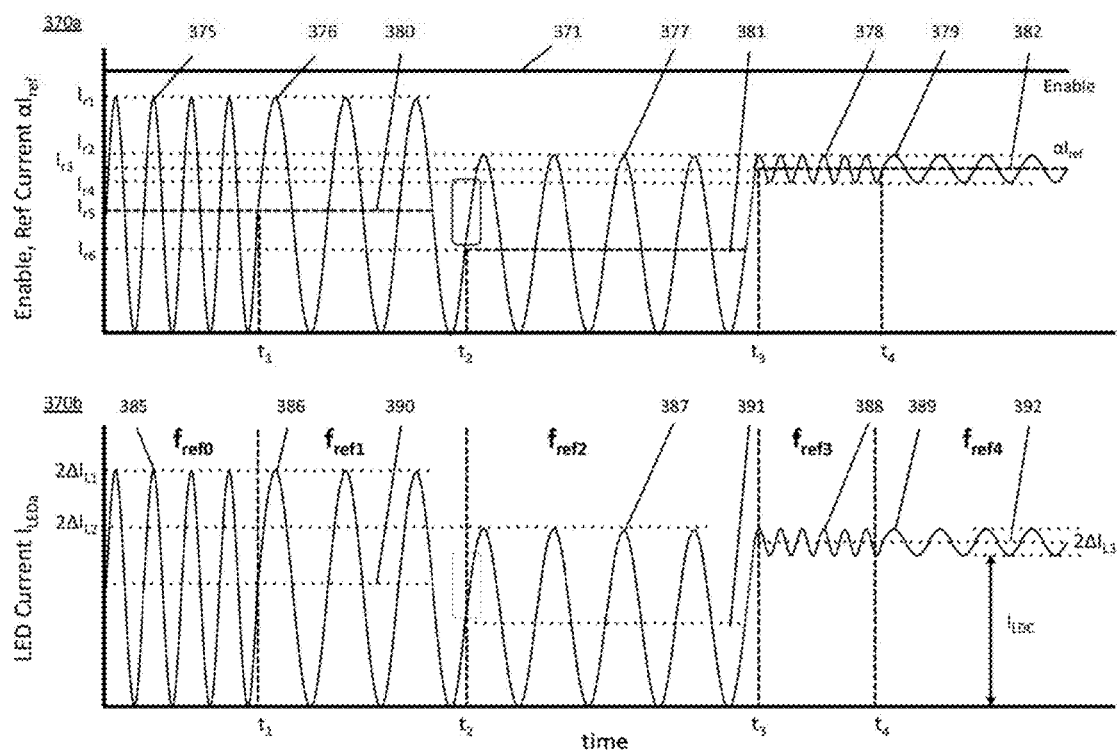
FIG. 20 illustrates various combinations of sinusoidal reference currents and resulting LED current waveforms.

As illustrated in FIG. 20, these various combinations are exemplified in graph 370a, which shows an Enable signal 371 and reference current waveforms 375-379, and graph 370b, which shows the resulting LED current waveforms 385-389. These sinusoidal waveforms, summarized in the following table, are not shown to imply a specific therapy or protocol but simply to illustrate the various current waveform combinations possible using analog synthesis.

| Time, Waveform Description | En | Peak $\alpha I_{ref}$ | Min $\alpha I_{ref}$ | Ave $\alpha I_{ref}$ | Freq | $I_{LED}$ |
|---|---|---|---|---|---|---|
| <$t_1$ Large-signal high-frequency sinusoid 375, 385 with no DC offset | on | $I_{r1}$ | 0 | $I_{r1}/2$ | $f_{ref0}$ | $\Delta I_{L1} \pm \Delta I_{L1}$ |
| $t_2$-$t_1$ Large-signal low-frequency sinusoid 376, 386 with no DC offset | on | $I_{r1}$ | 0 | $I_{r1}/2$ | $f_{ref1}$ | $\Delta I_{L1} \pm \Delta I_{L1}$ |
| $t_3$-$t_2$ Reduced-signal low-frequency sinusoid 377, 387 with no DC offset | on | $I_{r2}$ | 0 | $I_{r2}/2$ | $f_{ref2}$ | $\Delta I_{L2} \pm \Delta I_{L2}$ |

-continued

| Time, Waveform Description | En | Peak $\alpha I_{ref}$ | Min $\alpha I_{ref}$ | Ave $\alpha I_{ref}$ | Freq | $I_{LED}$ |
|---|---|---|---|---|---|---|
| $t_4$-$t_3$ Small-signal high-frequency sinusoid 378, 388 with DC offset | on | $I_{r2}$ | $I_{r4}$ | $(I_{r2} - I_{r4})/2$ | $f_{ref3}$ | $I_{LDC} + \Delta I_{L3} \pm \Delta I_{L3}$ |
| >$t_4$ Small-signal low-frequency sinusoid 379, 389 with DC offset | on | $I_{r2}$ | $I_{r4}$ | $(I_{r2} - I_{r4})/2$ | $f_{ref4}$ | $I_{LDC} + \Delta I_{L3} \pm \Delta I_{L3}$ |

Graphs 370a and 370b are broken into 5 time intervals, with a different waveform example in each interval, the intervals before time $t_3$ representing large signal behavior, where the LED current oscillates with a peak-to-peak variation that represents a significant fraction of the peak available supply current, and the intervals after $t_3$ representing a small variation in current relative to the peak available supply current and relative to the average DC current $I_{LDC}+\Delta I_{L3}$. Furthermore, the frequencies $f_{ref0}$ and $f_{ref3}$ in the intervals before $t_1$ and between $t_3$ and $t_4$ are shown to be high compared to the frequencies of the waveforms in the other intervals.

Specifically, in time intervals 0 to $t_1$ and $t_1$ to $t_2$, the magnitude of reference current waveforms 375 and 376 oscillate between zero and a peak current value of $I_{r1}$ with an average current of $I_{r5}=I_{r1}/2$ shown by dashed line 380 and with respective frequencies $f_{ref0}>f_{ref1}$. This reference current results in an LED current $\Delta I_{L1} \pm \Delta I_{L1}$ having an average LED current $\Delta I_{L1}$ illustrated by dashed line 390, a peak current $2\Delta I_{L1}$, and a minimum current of zero. In the subsequent interval from $t_2$ to $t_3$, the large signal reference current waveform 377 decreases in peak magnitude compared to the previous intervals but still remains large signal, with a reference current ranging from zero to $I_{r2}$ with an average value $I_{r6}=I_{r2}/2$ illustrated by dashed line 381. Consequentially, LED current 387 oscillates sinusoidally from zero to a peak current $2\Delta I_{L2}$ around an average current of magnitude $\Delta I_{L2}$ represented by dashed line 391. While the frequency $f_{ref2}$ of waveforms 377 and 387 can be chosen to any value, as shown it remains the same as the prior interval $t_1$ to $t_2$, namely $f_{ref2}=f_{ref1}$.

At time $t_3$ and thereafter the amplitude of the reference current waveforms 378 and 379 is reduced dramatically, waveforms 378 and 379 ranging between currents $I_{r2}$ and $I_{r4}$ symmetrically around an average current of magnitude $I_{r3}$ represented by the dashed line 392 and oscillating at frequencies $f_{ref3}>f_{ref4}$ combined with a constant DC offset $I_{r4}$. The resulting LED currents 388 and 389 oscillate sinusoidally at frequencies $f_{ref3}$ and $f_{ref4}$ respectively, and both have an peak-to-trough range of $2\Delta I_{L3}$ and an average current represented by dashed line 392, which is equal to a DC offset $I_{LDC}$ plus one-half the peak-to-trough range $2\Delta I_{L3}$ of the waveforms 388 and 389, i.e. $I_{LDC}+\Delta I_{L3}$. The resulting small signal waveform therefore is a current oscillating sinusoidally between maximum and minimum values of $I_{LDC}+\Delta I_{L3} \pm \Delta I_{L3}$, meaning that the LEDs are continuously illuminated but with sinusoidal variation in their brightness.

In conclusion, to create time varying currents of regular periodicity for phototherapy it is preferable to vary the LED current using a controlled current source or controlled current sink instead of driving the LED string with a controlled voltage source, because LED brightness varies in proportion to current in a consistent manner. In contrast, LED voltage varies in a manner independent of brightness and primarily as a consequence of variations in LED die fabrication and manufacturing. Maintaining consistency and uniformity of LED brightness using voltage drive therefore remains problematic, requiring precision trimming of each channel of LED drive.

As shown previously, to implement a controlled current sink, a programmable voltage is fed into a network of resistors and transistors to establish a reference current and to mirror this current to one or multiple channels driving separate LED strings. The value of the reference current may be actively trimmed during manufacture to set the precise value of current for a given voltage input by trimming a network of resistors as shown previously in FIG. 16C or by trimming a network of transistors as shown in FIG. 16D. The transistors may comprise either bipolar or MOSFET type.

By varying the voltage used to drive the current mirror or transconductance amplifier over time in a regular periodic manner, a time dependent or oscillatory LED current may be created. The voltage may be varied sinusoidally or by any other regular periodic function by operating the voltage reference in an oscillatory circuit. Alternatively the voltage can be constantly changed using digital control of a voltage-output type DAC to "synthesize" the desired waveforms.

An alternative means by which to produce a controlled voltage is to feed a time varying programmable voltage into a transconductance amplifier, an amplifier which naturally converts a voltage into a corresponding current, but transconductance amplifiers are larger and more expensive to implement than using current mirrors.

Still another alternative, at least theoretically, could be to bias each current sink MOSFET to operate in the constant current regime of operation, precisely driving it with the proper gate voltage for each desired drain current. To accomplish this goal, the gate drive circuitry would require calibration at the time of manufacturing. Once calibrated, driving the MOSFET gate with time-varying sequence of voltages will result in a desired periodic current waveform. Because, however, threshold voltage varies not only with manufacturing but with temperature, the calibration method to produce controlled and well matched currents across multiple channels of LED drive remains problematic. As such a current mirror is still vastly superior because the two or more mirror transistors vary with manufacturing and over temperature in the same way so that the current ratio of the transistors and the resulting LED current remains constant.

Finally, a programmable current-mode DAC can be employed to synthesize a periodic time varying current, but to drive multiple LED strings, it still is beneficial to feed the DAC output current into a transistor current mirror not only to buffer the current to a higher value but to conveniently produce multiple channels of well matched LED drive.

Analog Sinusoidal Synthesis of Chords

Referring again to the resonant graph of FIG. 10, it is well documented that many if not most physical systems exhibit more than one resonant frequency. Given the plethora of time constants present in the anatomy and cytological processes of living creatures, it is clear that multiple bioresonant frequencies exist in nature as well. While it is unproven whether the simultaneous excitation of multiple bioresonant frequencies has a beneficial impact on treatment efficacy, prior art systems utilize digital pulse excitation of the LEDs. As shown in FIG. 11 and FIG. 12, such purely-digital square-wave LED drive methods are incapable of simultaneously producing multiple frequencies, except for unwanted harmonics.

Figure 21:
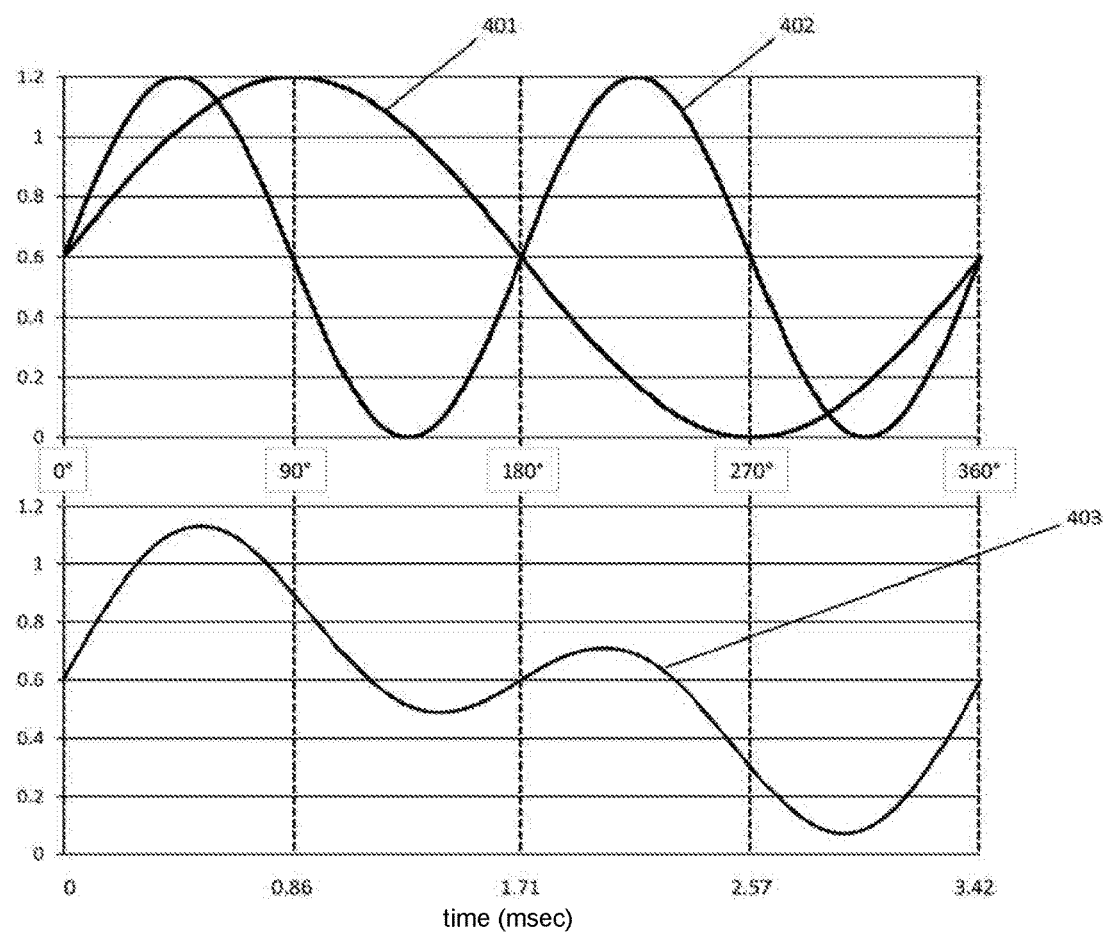
FIG. 21 illustrates the sum of two sinusoidal waveforms and the resulting waveform.

In dramatic contrast, it is well known that sine wave frequencies add algebraically without limitation, as evidenced by the existence of multiple note "polyphonic chords" in an acoustic piano. Mathematically, the sum of sine waves can be expressed by the series sum of multiple sine waves of varying magnitude $A_x$, frequency $\omega_x$ and duration (or decay rate), namely $$G(t)=A_1(t)\cdot\sin(\omega_1)+A_2(t)\cdot\sin(\omega_2)+\ldots+A_x(t)\cdot\sin(\omega_x)$$

as represented graphically in FIG. 21 where a 292 Hz sine wave 401 and a 584 Hz sine wave 402 are combined to produce a two-note chord shown by waveform 403. LEDs driven by polyphonic excitation will simultaneously and concurrently exhibit multiple frequencies, with the ability to effectively couple energy into comparable bioresonant frequencies.

Figure 22A:
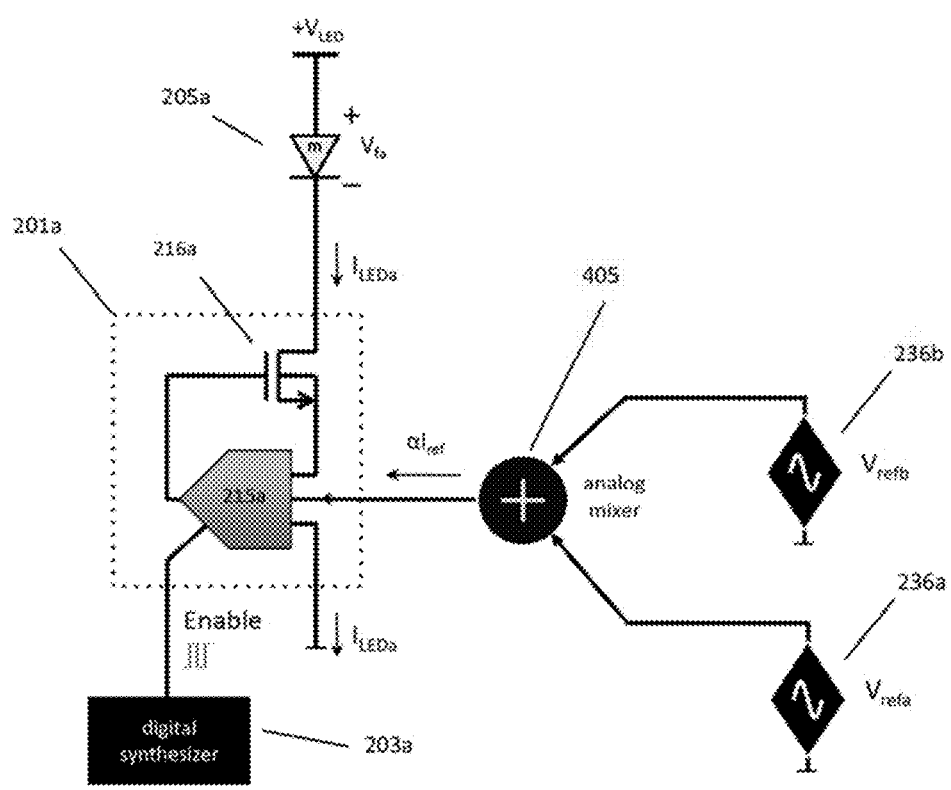
FIG. 22A schematically illustrates the use of an analog mixer to generate a polyphonic oscillatory reference current for phototherapy LED drive.

One means by which to synthesize polyphonic chords in shown in FIG. 22A comprising an analog mixer circuit 405 summing oscillating reference voltages $V_{refa}$ and $V_{refb}$ produced by oscillators 236a and 236b, respectively, to produce a time-varying voltage resulting in oscillating reference current $\alpha I_{ref}$ as an input to MOSFET driver 215a. A large variety of analog mixer circuits exist including multiple input amplifiers using adjustable resistor dividers to vary the gain of individual inputs. Oscillators 236a and 236b, having different frequencies of oscillation, may be synchronized to prevent unwanted frequency drift and aliasing.

Figure 22B:
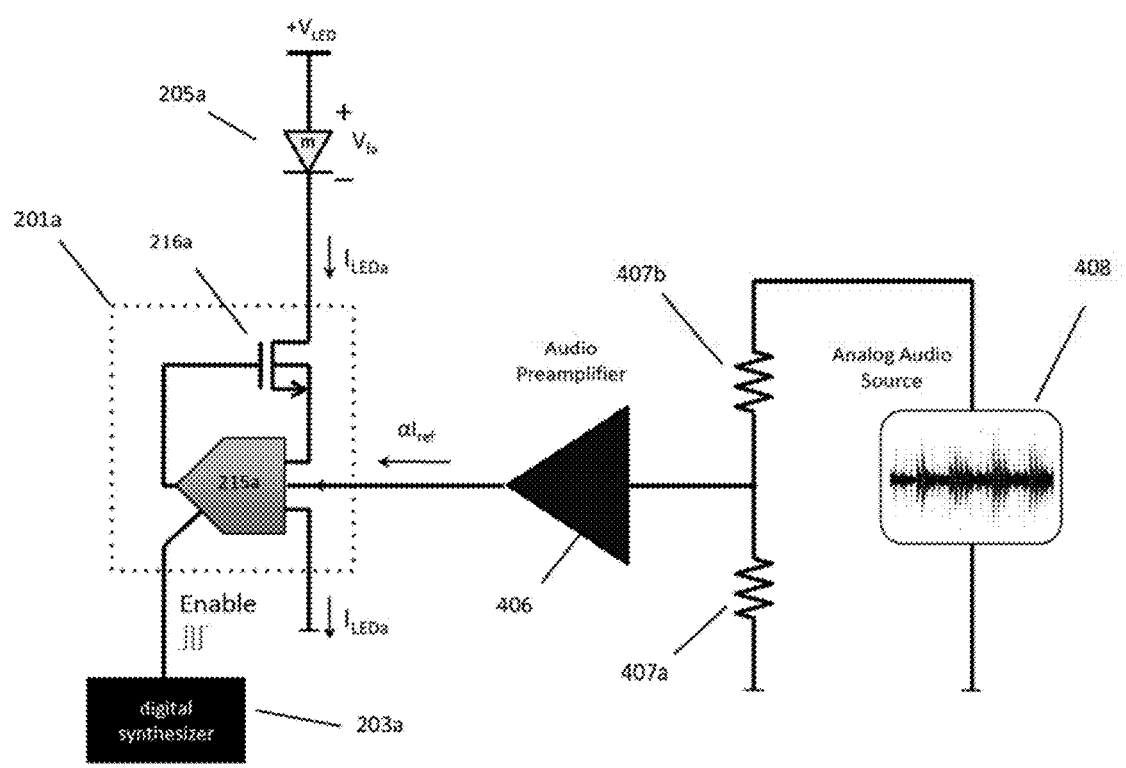
FIG. 22B schematically represents the use of an analog audio source to generate a polyphonic reference current for a phototherapy LED drive.

Other analog sources may be used to generate a polyphonic reference current comprising one or more chords or even music. For example, in FIG. 22B the analog output of any polyphonic audio source 408 including a music synthesizer, radio decoder, or audio recording player may be used to generate the reference current $\alpha I_{ref}$, provided that the analog voltage output of the audio source 408 and series resistance of the circuit are adjusted to limit the peak value of $\alpha I_{ref}$ to the input range acceptable for MOSFET driver 215a to prevent signal distortion. Conceptually, the analog voltage output of audio source 408 may be scaled in voltage by a voltage divider including resistors 407a and 407b followed by audio preamplifier 406 to produce the time varying current $\alpha I_{ref}$. One way to implement such a circuit is to employ a fixed reference current of value $I_{ref}$ and to scale this current to a higher or lower current with a current amplifier having current gain $\alpha$, where the gain $\alpha$ is modulated in response to the analog output of analog audio source 408. The analog audio source 408 may comprise a tape player, a digital audio player, a CD player, or digitally streamed music.

Figure 22C:
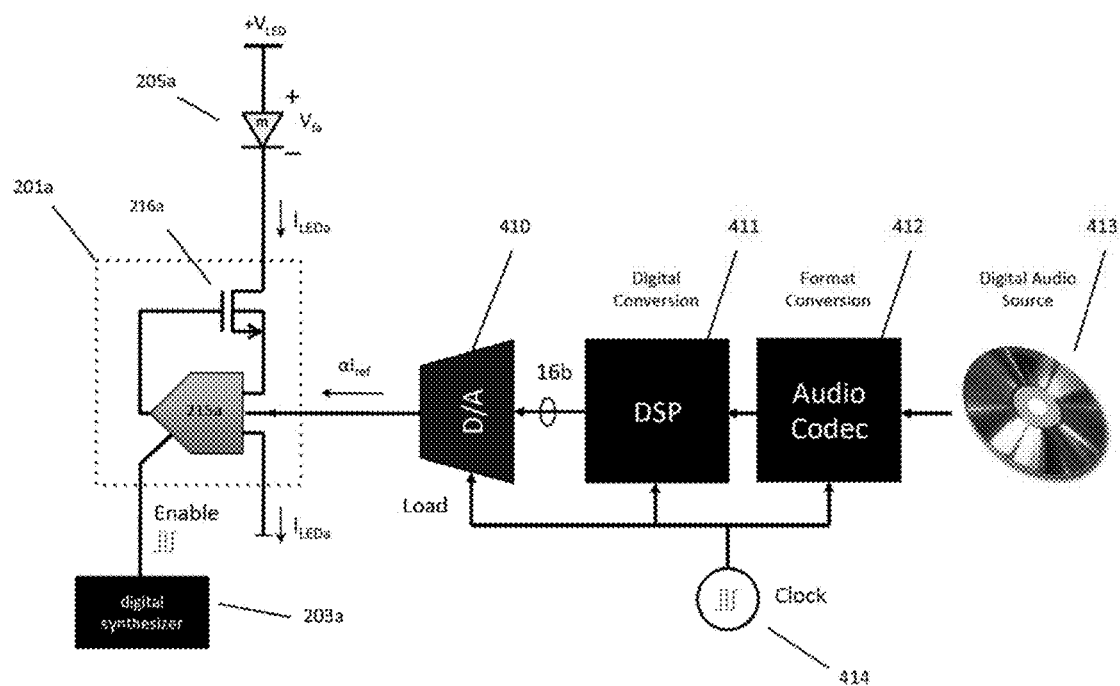
FIG. 22C schematically represents the use of a digital audio source to generate a polyphonic reference current for a phototherapy LED drive.

Another method, shown in FIG. 22C, to derive an analog audio source is to directly translate a digital source 413 such as digital streamed audio, digitally encoded data, or a CD audio and to convert the specific data encoding format into a parallel or serial digital data using format conversion in an audio codec 412. This stream of 1-bit data or sequence of 16-bit parallel words is then processed using custom algorithms in a digital signal processor (DSP) 411 and loaded at regular intervals into a D/A converter 410 to create the desired time varying reference current $\alpha I_{ref}$. To avoid audio distortion, digital words should be loaded into D/A converter 410 at a minimum frequency of 44 kHz if the entire audio spectrum is to be preserved.

One common point of confusion is that digital audio sources such as CD players or Internet streamed digital audio are often considered digital because the audio information is stored as "bits", specifically digital words describing a sequence of audio volumes commonly referred to as PCM or pulse coded modulation. During reconstruction of the analog audio signal, however, the digital PCM source is used to drive a D/A converter to produce a time-varying analog signal and as such, signal reconstruction comprises "analog" synthesis in a manner similar to the method shown in FIG. 22C.

Aside from those similarities, the function of digital audio players is to reproduce an audio signal driving a magnetic coil or piezoelectric crystal to move air and produce sound, not to produce light. The mass of a speaker or transducer acts as a natural filter, its inertia responsible for removing many unwanted frequencies and spikes. For example, combined with a filter capacitor, the inductance of a speaker coil naturally forms a simple low-pass filter. In short, audio reproduction favors low frequencies and has to be driven with high currents produced by means of power amplification, in order to faithfully reproduce high frequency tones. In many cases, such as guitar amplifiers, the amplifier is intentionally driven into distortion as long as the harmonics sound "good".

In contrast, photons are massless and not subject to inertial damping or filtering. The response time of an LED occurs with nanosecond precision and faithfully reproduces all the harmonics of the driving waveform, even when those harmonics are unwanted or detrimental to the purpose of phototherapy. As a consequence of these differences, the harmonic spectral content used for driving LEDs in phototherapy is key to achieving bioresonance with specific biophysical process such as electron conduction, ionic transport, molecular bonding, transient thermal conduction, and steady-state heating of cells, tissue and organs, regardless of whether analog or digital synthesis is used is generating the waveforms for the phototherapy.

For example, when adapting an audio source or music for LED drive, DSP 411 may be used to selectively filter certain frequencies and notes from an audio stream while suppressing other tones that may be adverse to phototherapeutic treatment, for example odd harmonics created by cymbal crashes. Therefore, the data rate at which D/A converter 410 is loaded with new data should be equal to no less than twice the highest frequency being reproduced as LED current modulation by MOSFET driver 215a. As a matter of convenience D/A converter 410, DSP converter 411, and audio codec 412 may be synchronized by a common digital clock signal 414, often generated by dividing down the oscillations of a crystal (xtal) oscillator. While digital filtering may make music and tones reproduced on a speaker or headphone sound unlistenable to the human ear, removing unwanted harmonics and spectral content from LED drive waveforms in phototherapy is important in achieving tissue specificity and high treatment efficacy during phototherapy treatments.

Another inventive method disclosed herein to avoid the complexity and added costs of analog signal processing, digital filtering, or audio mixing to produce chords of tones, is to combine an analog synthesized waveform with a second digital pulse frequency achieved by digitally "strobing" an analog oscillating waveform. Returning to the circuit of FIG. 17B, such a method employs the single frequency oscillator 236 to feed the reference current input of MOS- FET driver 215 while strobing the MOSFET driver on and off using digital synthesizer 203*a*. Two possible methods exist, namely setting the digital strobing frequency $f_{clock}$ to be higher than the frequency of the oscillating reference current $f_{ref}$, i.e. $f_{clock} > f_{ref}$ setting the frequency of the oscillating reference current $f_{ref}$ to be higher than digital strobing frequency $f_{clock}$, i.e. $f_{ref} > f_{clock}$ The waveforms produced using these two methods have differing spectral characteristics, and therefore the methods cannot be used interchangeably to perform dual-frequency LED drive.

Figure 23A:
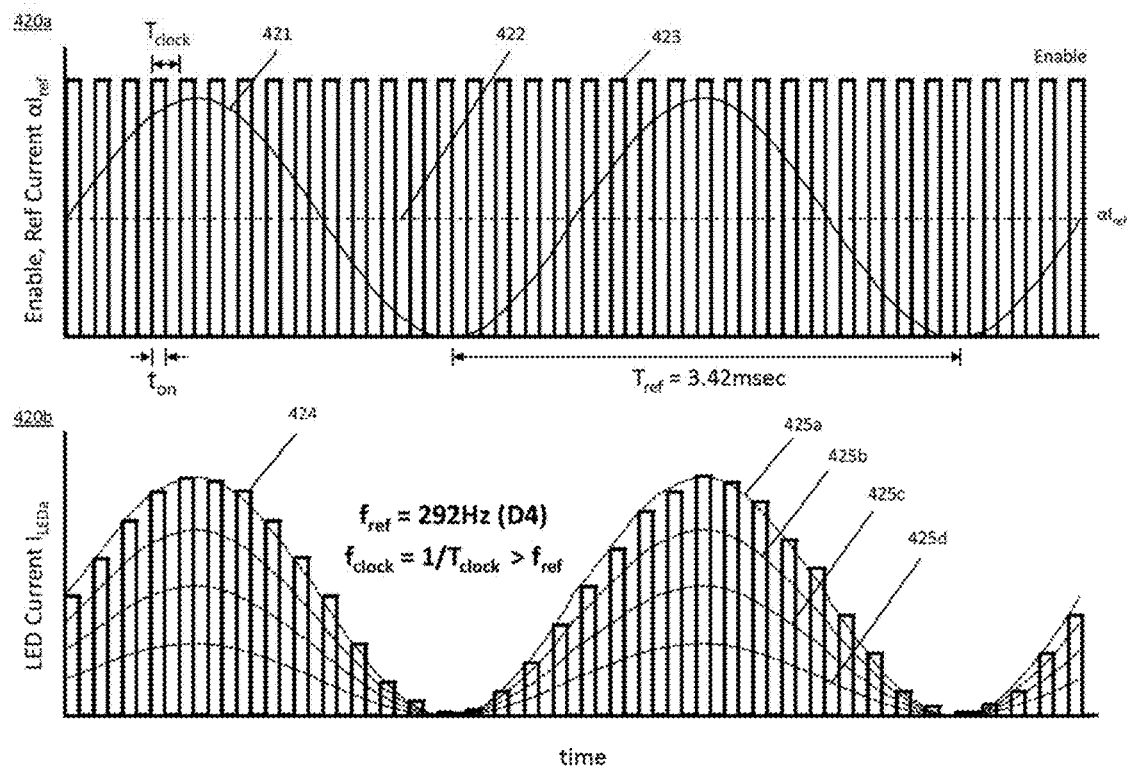
FIG. 23A illustrates the synthesized polyphonic waveform generated from a sinusoidal reference current and a higher frequency digital pulse.

FIG. 23A illustrates the case wherein the frequency $f_{clock}$ of the clock signal is higher than the frequency $f_{ref}$ of the sinusoidally oscillating reference current, i.e. the first of the methods described above. As shown in graph 420*a*, a 292 Hz oscillating sinusoidal reference current 421 (D4) with a period $T_{ref}$=3.42 msec and an average value 422, clearly has a longer period and lower frequency than the digital pulses of an Enable signal 423 having a clock period $T_{clock}$. For the purposes of this illustration, the specific frequency $f_{clock}$ of the digital pulses of Enable signal 423 may be any value provided that $f_{clock}$ is at least double the sine wave frequency $f_{ref}$. During operation, MOSFET driver 215 outputs zero volts, i.e. ground, whenever Enable 423 is at a logic zero and the analog value of oscillating reference current 421 whenever Enable signal 423 is a logic one or "high" state. The resulting waveform is equivalent to multiplying the analog sine wave by the digital multiplier of "1" or "0" for each moment of time, essentially "chopping" a sine wave into pieces.

The LED current waveform shown in graph 420*b* comprises small pulses of current of varying height, where the collection of pulses forms an envelope 425*a*, 425*b*, 425*c*, or 425*d* (individually and collectively as 425) having the same frequency and phase as oscillating reference current 421. The difference of these envelopes is a variation only in amplitude depending on the ratio of $t_{on}$ to $T_{clock}$ of Enable signal 423. The duty factor of the Enable signal 423, i.e., $t_{on}/T_{clock}$, acts as PWM brightness control, controlling the average current of the sinusoidal envelope 425 and hence LED brightness by pulse width modulation, without changing the frequency or phase of the sinusoidal reference current 421.

Figure 23B:
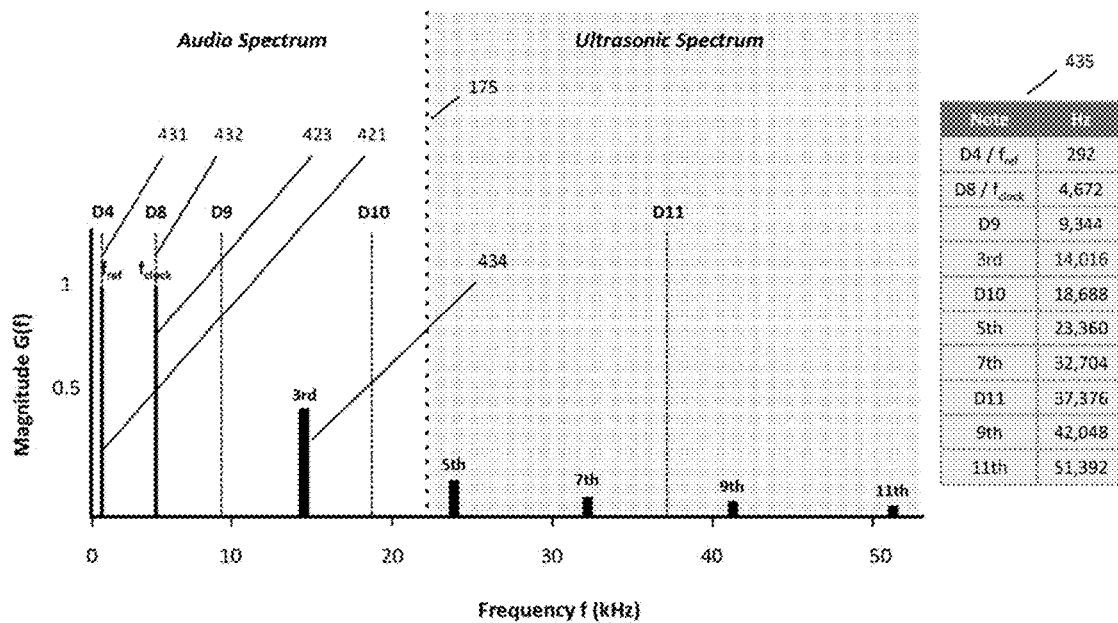
FIG. 23B illustrates the polyphonic harmonic spectra generated from a 292 Hz sinusoidal reference current and a 4,672 Hz digital pulse.

Because the higher of the two frequencies in the polyphonic chord is created "digitally", this frequency component will exhibit the previously described harmonics of a square wave, contributing to unwanted spectral contamination. This point is illustrated in FIG. 23B, where the 292 Hz reference current 421 occurs at a frequency $f_{ref}$ shown by line 431, and combines with the 4,672 Hz digitally pulsed Enable signal 423 that occurs at a frequency $f_{clock}$ shown by line 432. Because the Enable signal 423 is a square wave, it produces harmonics 434 including a $3^{rd}$ harmonic at 14,016 Hz in the audio spectrum and the remainder of its harmonics in the ultrasonic spectrum, i.e. beyond the frequency illustrated by line 175. So using this method, a chord of 292 Hz (D4) and 4,672 Hz (D8) can be generated without the need for a mixer or two analog oscillators, with the only disadvantage that an unwanted $3^{rd}$ harmonic is still present in the audio range. The resulting spectra are summarized in table 435 including other octaves of D for reference.

Figure 23C:
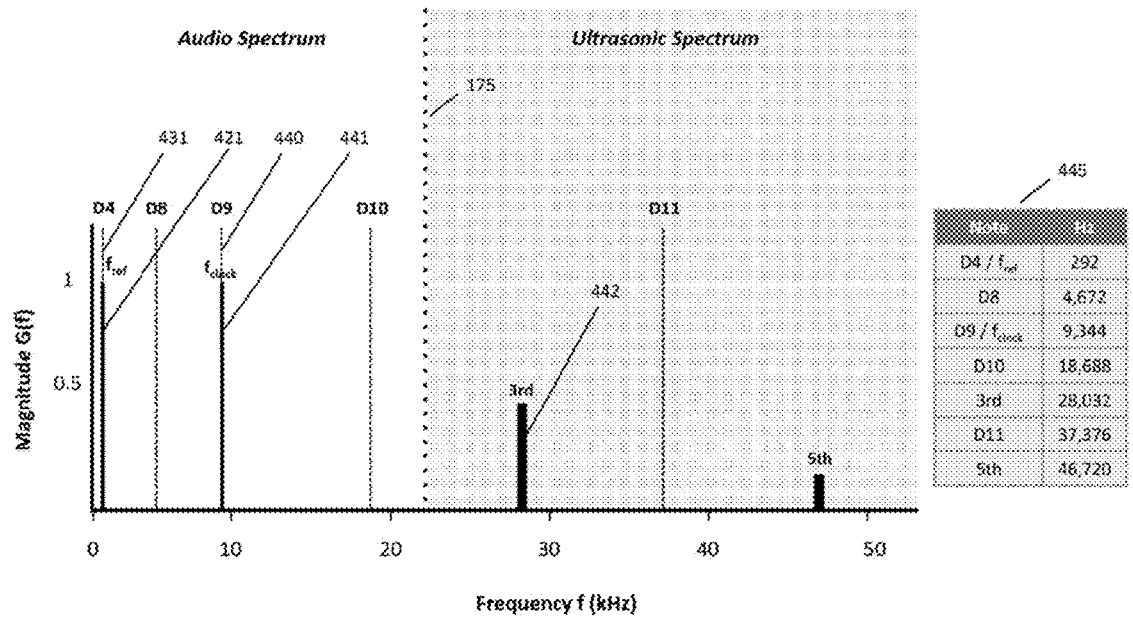
FIG. 23C illustrates the polyphonic harmonic spectra generated from a 292 Hz sinusoidal reference current and a 9,344 Hz digital pulse.

If the digital pulse rate is increased to D9 or any other note higher than approximately 7 kHz, no harmonic will be manifest in the audio spectrum. This example is shown in FIG. 23C, where the 292 Hz reference current shown by line 431 is combined with a 9,344 Hz digitally pulsed Enable signal 441 at a frequency $f_{clock}$ (D9) shown by line 440. The resulting spectra are summarized in table 445 including other octaves of D for reference.

Figure 23D:
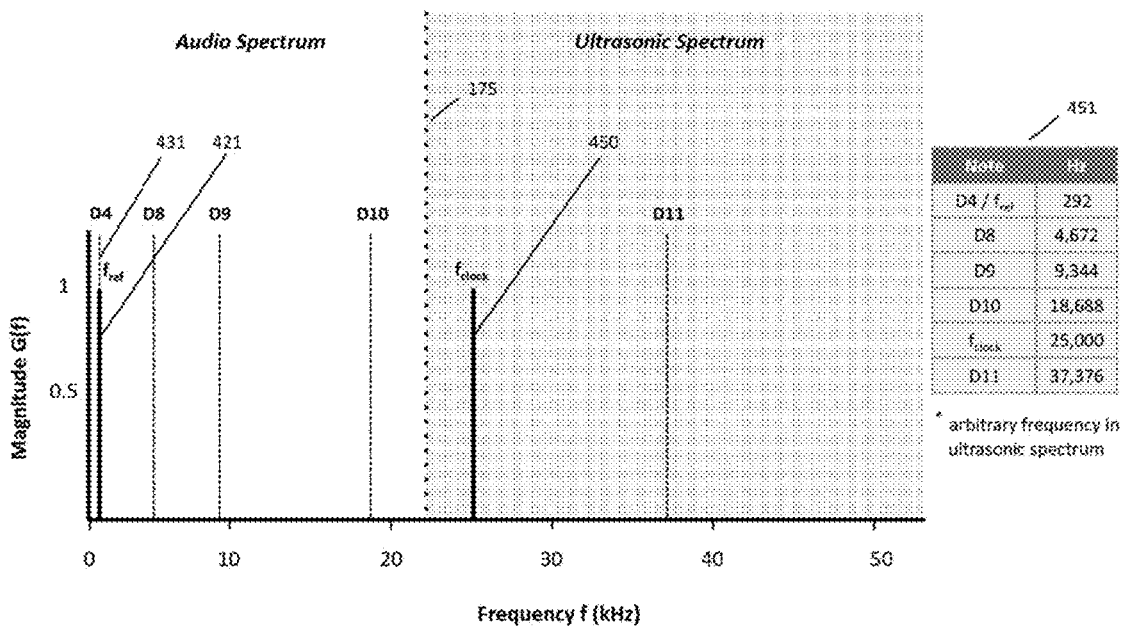
FIG. 23D illustrates the polyphonic harmonic spectra generated from a 292 Hz sinusoidal reference current and an ultrasonic digital pulse.
Figure 23E:
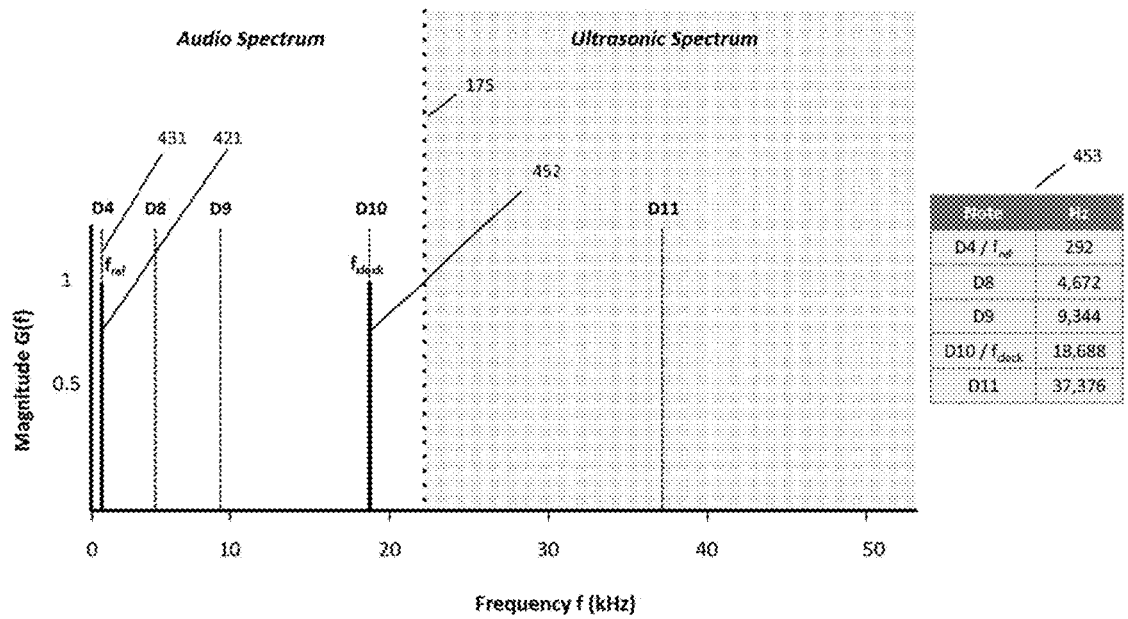
FIG. 23E illustrates the polyphonic harmonic spectra generated from a 292 Hz sinusoidal reference current and a 18,688 Hz digital pulse.

Note that, as shown in FIG. 23D, if the clock frequency $f_{clock}$ shown by line 450 can be pushed into the ultrasonic spectrum, then as shown in table 451 no harmonics of concern exist. Because this method eliminates the second note of the chord it is therefore not a method for polyphonic synthesis and confers no advantage over leaving the Enable signal on continuously. As an alternative, running the clock at 18,688 Hz, i.e. at D10, as shown by solid line 452 in FIG. 23E, eliminates all audio harmonics but still offers a second frequency as an octave of $f_{ref}$.

In summary, for polyphonic synthesis of two tones where $f_{clock} > f_{ref}$, there is no restriction of the value of $f_{ref}$ but the digital pulse generated frequency $f_{clock}$ must be chosen to avoid significant spectral contamination in the audio range.

Figure 24:
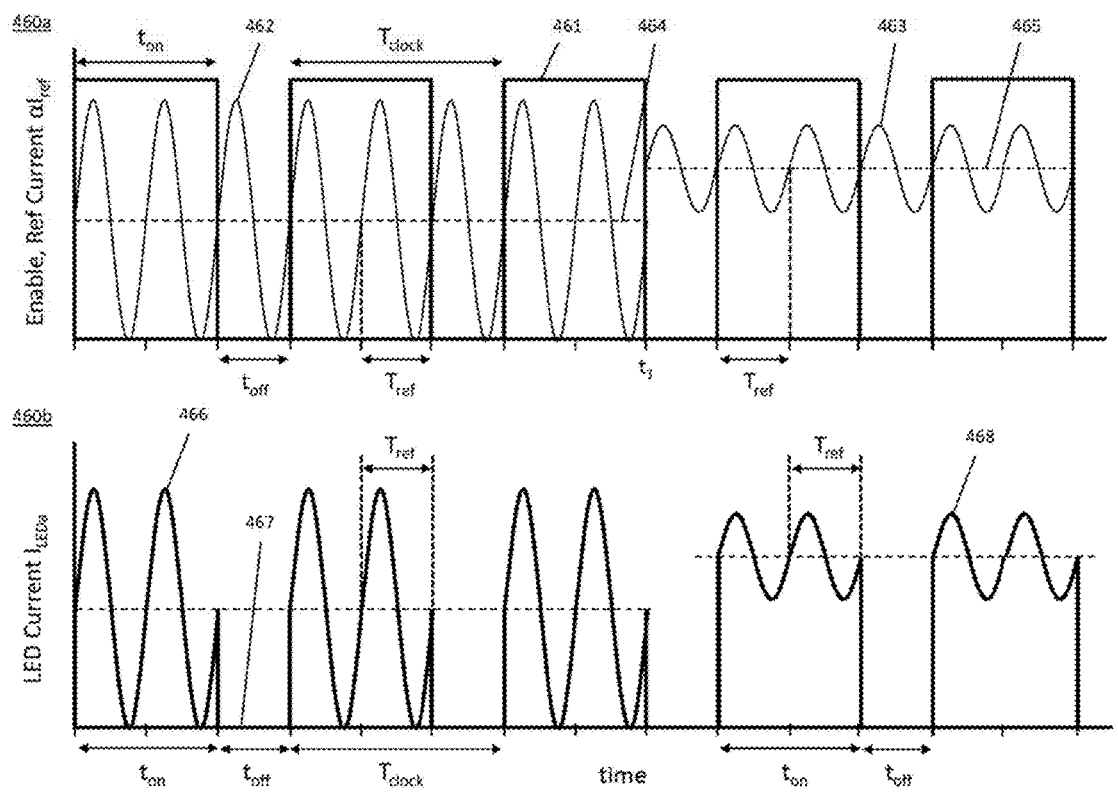
FIG. 24 illustrates the synthesized polyphonic waveform generated from a sinusoidal reference current and a lower frequency digital pulse.

FIG. 24 illustrates the case where the Enable signal is digitally strobed at a frequency $f_{clock}$ that is lower than the frequency $f_{ref}$ of the sinusoidally oscillating reference current, i.e. where $f_{clock} < f_{ref}$.

As shown in graph 460*a*, a fixed-frequency constantly oscillating reference current 462 with period $T_{ref}$ and average value 464 oscillates with longer period and lower frequency than digital pulses of Enable 461 having a clock period $T_{clock}$. Each clock period Tclock is subdivided into two intervals—$t_{off}$ when Enable 461 is at a logic zero or biased in an "off" condition, and $t_{on}$ when Enable 461 is biased at a logic one or "high" state. During operation, MOSFET driver 215 outputs zero volts, i.e. ground, whenever Enable 461 is at a logic zero. Conversely, whenever Enable 461 is a logic one or "high" state, MOSFET driver 215 outputs the time varying analog values of oscillating reference current 462.

During this $t_{on}$ interval, the output of the MOSFET driver 215*a* does not result in a single, constant LED current but whatever portion of the sinusoidal oscillation in voltage and current is occurring at that time. The resulting waveform is equivalent to multiplying the analog sine wave by the digital multiplier of "1" or "0" for each moment of time, essentially "chopping" the sine wave into short intervals or "snippets" of oscillation. The LED current waveform shown in graph 460*b* comprises the same intervals of duration $t_{on}$, where the LED current 466 completes one or several oscillating cycles before it is is shut off, as shown by line 467, for a duration $t_{off}$ and thereafter repeating the entire cycle.

In the event that reference current waveform 463 includes a DC offset with an average value 465, as shown in graph 460*a*, then the resulting LED current waveforms 468, shown in graph 460*b*, exhibit identical AC oscillatory behavior, except that the magnitude of the oscillation is reduced, resulting in oscillatory perturbations in brightness of an LED string that repeatedly conducts for a duration $t_{on}$ and then temporarily is interrupted for a duration $t_{off}$ before resuming its conduction and small signal oscillations. Note that the absence or presence of a DC offset in the oscillatory reference current has no impact on the harmonic spectra of the two-note chord.

Figure 25A:
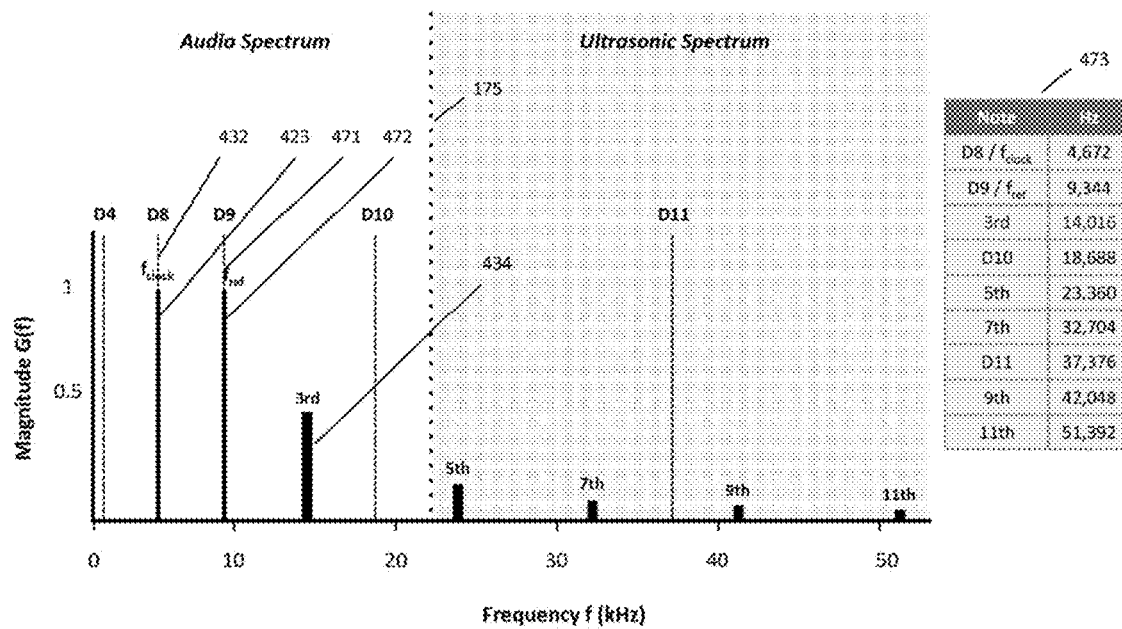
FIG. 25A illustrates the polyphonic harmonic spectra generated from a 9,344 Hz sinusoidal reference current and a 4,672 Hz digital pulse.

The resulting spectra for a chord of D8 and D9 using this disclosed method is shown in FIG. 25A, where a sinusoidal reference current at a frequency $f_{ref}$ of 9,344 Hz (D9), shown by solid line 472, combines with an Enable signal digitally pulsed at a frequency $f_{clock}$ of 4,672 Hz (D8), shown by solid line 423. Because the Enable signal is digitally pulsed, it produces harmonics 434, including a $3^{rd}$ harmonic at 14,016 Hz in the audio spectrum and higher-frequency harmonics in the ultrasonic spectrum, i.e. beyond the frequency illustrated by line 175. So, using this method, a chord of D8 and D9 can be generated without the need for a mixer or two analog oscillators, with the only disadvantage that an unwanted $3^{rd}$ harmonic is still present in the audio range. The resulting spectra are summarized in table 473, including other octaves of D for reference.

Figure 25B:
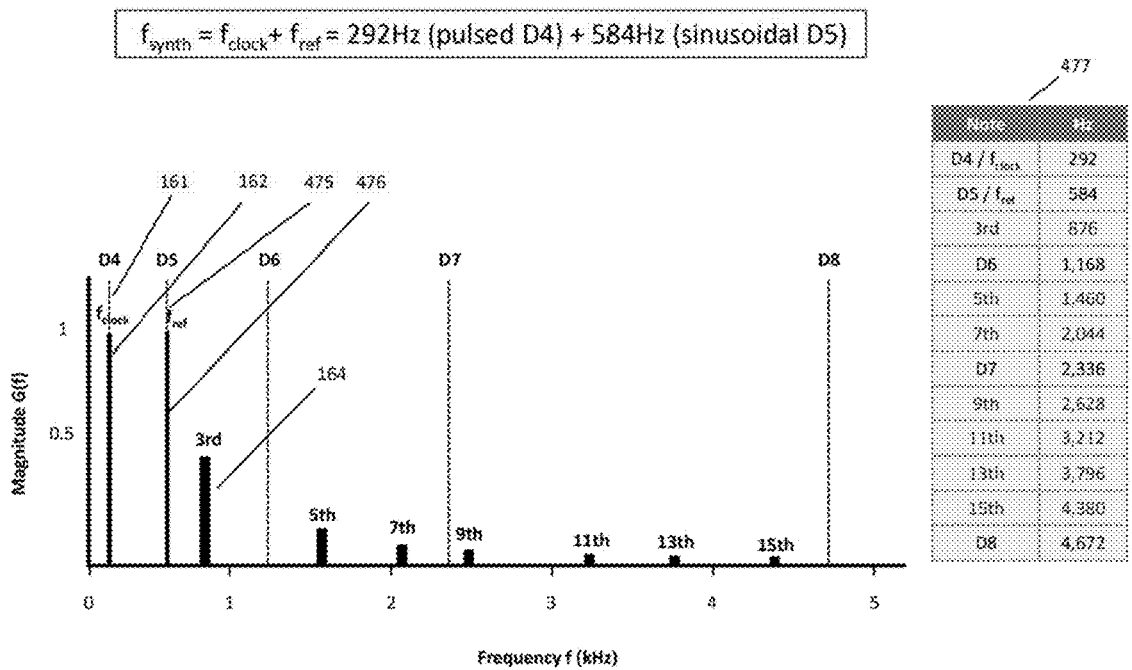
FIG. 25B illustrates the polyphonic harmonic spectra generated from a 584 Hz sinusoidal reference current and a 292 Hz digital pulse.

While this method works fine for high frequency chords, its operation is problematic when generating low frequencies because the digital clock, the origin of harmonic noise and spectral contamination, occurs at the lower frequency of the two-note polyphonic chord. This problem is illustrated in FIG. 25B, which shows the result of mixing a 584 Hz (D5) reference current (line 476) with a 292 Hz (D4) digitally pulsed Enable signal (line 161). Because of the 292 Hz square wave Enable signal, spectral contamination of harmonics 164 occur throughout the audio spectrum, as described in Table 477, identical to those shown in FIG. 12. Such a method is therefore not useful for generating low frequency polyphonic chords for LED drive in phototherapy applications.

Figure 26:
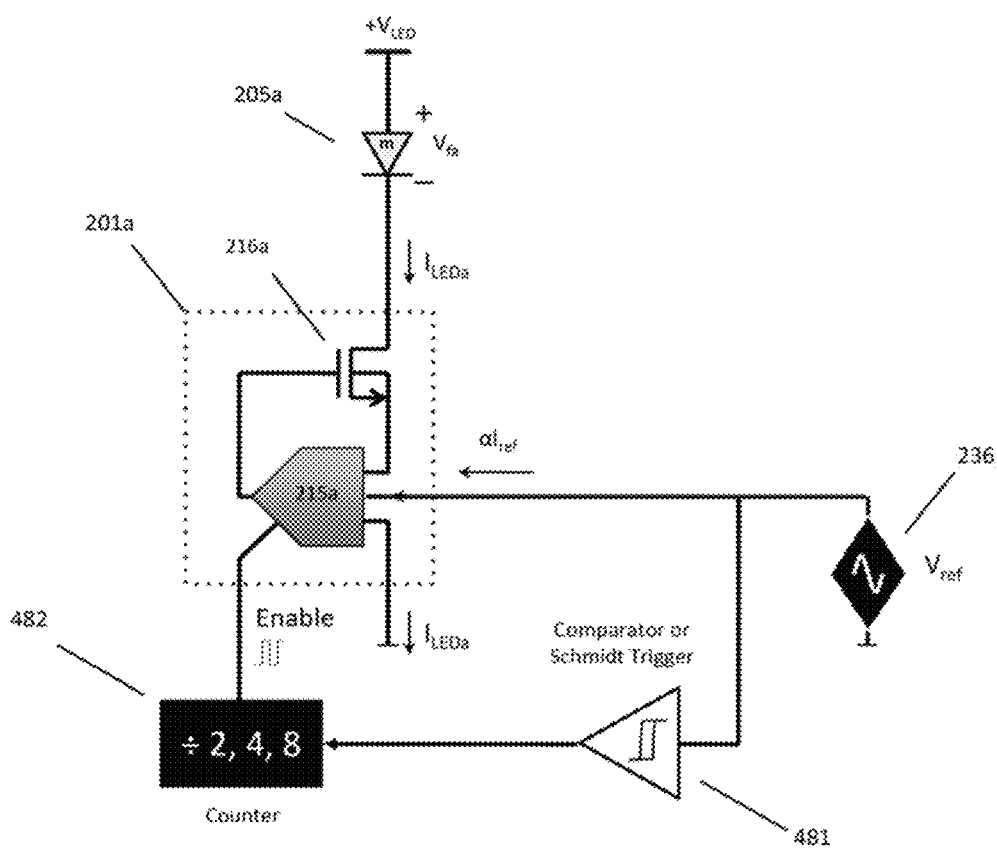
FIG. 26 schematically illustrates implementation of a polyphonic LED current drive for phototherapy from a single oscillator.

For generating high frequency polyphonic chords, the method can be implemented at low cost as shown in FIG. 26 because the oscillator 236 used to create the sine wave can also be used to drive a simple divide by 2, 4 or 8 counter 482 to simply generate the digital clock pulses needed as the Enable signal input to MOSFET driver 215a. Because the oscillating reference 236 exhibits sinusoidal transitions too slow for clearing triggering counter 482, an intervening Schmidt trigger or comparator 481 with hysteresis and high input impedance is inserted between the oscillator 236 and the counter 482. Each factor of 2 in frequency division implemented by counter 482 represents an octave in musical notes, e.g. D8 divided by 2 is D7, D8 divided by 4 is D6 and so on.

Pulse Width Modulated Digital LED Control

In addition to analog sinusoidal synthesis described above, another inventive means disclosed herein to synthesize sinusoidal waveforms with controlled harmonic content for driving LEDs in a phototherapy system is through the use of digital synthesis. While analog synthesis involves sinusoidally varying the reference or bias current to the LED current control circuit, digital synthesis involves pulsing the LED current on-and-off in constantly varying durations to synthesize a sine wave (or chords of multiple frequencies of sine waves). Pulse modulation techniques include both fixed-frequency "pulse width modulation", commonly referred to by the acronym PWM, and variable-frequency "pulse frequency modulation", referred to by the acronym PFM. While both PWM and PFM modulation techniques may be employed to control average current or voltage in electronics circuits, such as voltage regulators, the variable clock rate of PFM complicates waveform synthesis. Moreover, PFM can give rise to unwanted radio frequency noise and electromagnetic interference (EMI) which varies in frequency and is therefore difficult to filter or shield. EMI is especially problematic in medical devices because government agencies such as the FDA and the FCC strictly prohibit EMI that could dangerously interfere with other life-critical medical devices in a hospital or clinic. As a consequence, the digital synthesis section of this application mainly focuses on PWM control techniques with the understanding that, alternatively, a sequence of PFM controlled pulses may be used in waveform synthesis if so desired.

Returning to the waveform examples shown in FIG. 15, while the pulsed digital waveforms 243 through 258 do not specifically illustrate digital sinusoidal synthesis, the ability to change the average LED current from a level shown by dashed line 272 to a higher level 273 simply by increasing the LED current pulse width 267 to a longer pulse width 268. Since the frequency of both of pulses 267 and 268 is equal to $1/T_1$, this represents the principle of "pulse width modulation", also known as fixed-frequency PWM, one means by which to perform sinusoidal synthesis digitally. The alternative method of digital synthesis, "pulsed frequency modulation" or also a "PFM", is exemplified by comparing pulses 268 and 269 at times $t_8$ and $t_9$ used to increase the average LED current from a level shown by dashed line 273 to 274 by varying the LED on-time and frequency, i. e., since $T_2$ is greater than $T_1$, the frequency of pulse 268 ($1/T_1$) is greater than the frequency of pulse 269 ($1/T_2$). Variable frequency PFM methods may comprise fixed-on time or fixed-off time modulation schemes. Variable frequency PFM methods are often avoided because of concerns of time-varying signals contributing to dynamically changing electromagnetic interference resulting in noise that is difficult to filter.

Unlike analog circuits whose performance and circuit stability are sensitive to electrical loading of their outputs, in digital synthesis, the enable signal produced by the digital synthesizer circuitry has a large digital "fan-out," meaning that one digital synthesizer can be used to control many channels and MOSFET drivers. An example of a large fan-out is illustrated in FIG. 27C where digital synthesizer 203 has a single output and is used to drive the Enable input of numerous MOSFET drivers from 215a through 215n, where n is a variable representing the number of MOSFET drivers. In this example, where digital synthesizer 203 has a single output, all the channels of LED drivers will exhibit the same digital waveform and synthesize the same sinusoids synchronously. This centralized approach allows one digital synthesizer to connect to all the MOSFET drivers using a shared conductive signal path, whether a wire, conductive printed circuit board (PCB) trace, or a data bus.

Figure 27A:
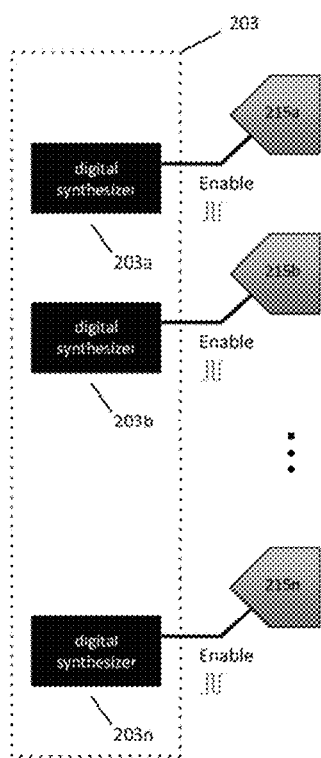
FIG. 27A schematically illustrates multiple digital synthesizers controlling multiple corresponding LED drivers.
Figure 27B:
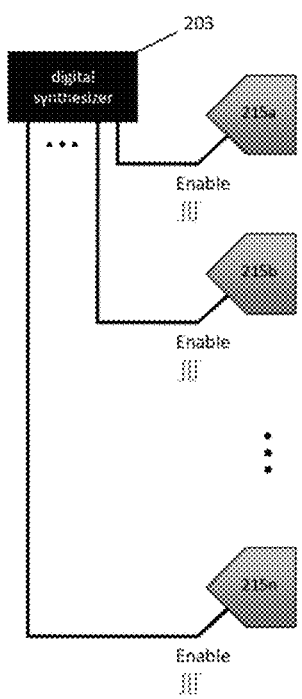
FIG. 27B schematically illustrates a centralized digital synthesizer separately controlling multiple LED drivers.
Figure 27C:
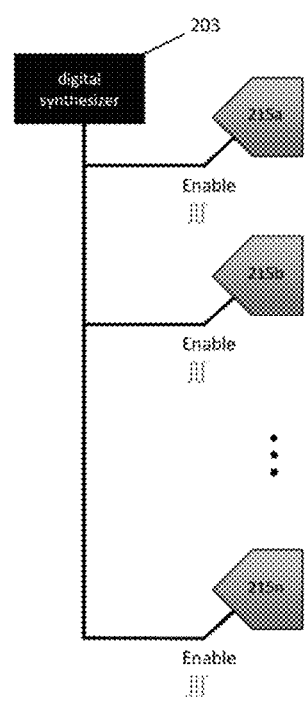
FIG. 27C schematically illustrates a single digital synthesizer controlling multiple LED drivers with a common signal.

FIGS. 27A, 27B, and 27C illustrate and contrast various combinations of digital synthesizers and independent channels of LED drive. In FIG. 27A, each MOSFET driver 215a through 215n is controlled by its own corresponding digital synthesizer 203a through 203n (collectively as digital synthesizer 203), where the subscript "n" is a mathematical variable representing the number of MOSFET drivers and digital synthesizers. These various digital synthesizers shown may occupy one, several, or completely independent integrated circuits representing either a centralized, clustered, or fully distributed system. Because each LED channel and associated MOSFET driver are controlled by their own dedicated digital synthesizer, this implementation offers complete flexibility in synthesizing sinusoids of channel-unique frequency, magnitude, and duration should it be desired. As such, it is important that the channels be synchronized to a common clock reference, or noise may result from channel-to-channel interactions and aliasing. In this independent and autonomous approach, each of digital synthesizers 203a-203n must connect to its corresponding one of MOSFET drivers 215a-215n with a dedicated wire or conductive PCB trace.

Another method which minimizes duplication of circuitry and minimizes IC real estate without sacrificing flexibility is a centralized method of control shown in FIG. 27B comprising a single digital synthesizer 203 having multiple independently controlled outputs. In this approach, the centralized digital synthesizer 203 must uniquely address every MOSFET driver with a separate and distinct wire or conductor. If discrete wires or conductive PCB traces are employed, the digital synthesizer must be located near, i.e.

in the physical vicinity of, the MOSFET drivers or otherwise a large number of conductors of extended length will be required. Alternatively a data bus may be employed to distribute the data for all channels, but then each channel requires a decoder circuit to uniquely identify its particular control signal from the others.

Figure 28A:
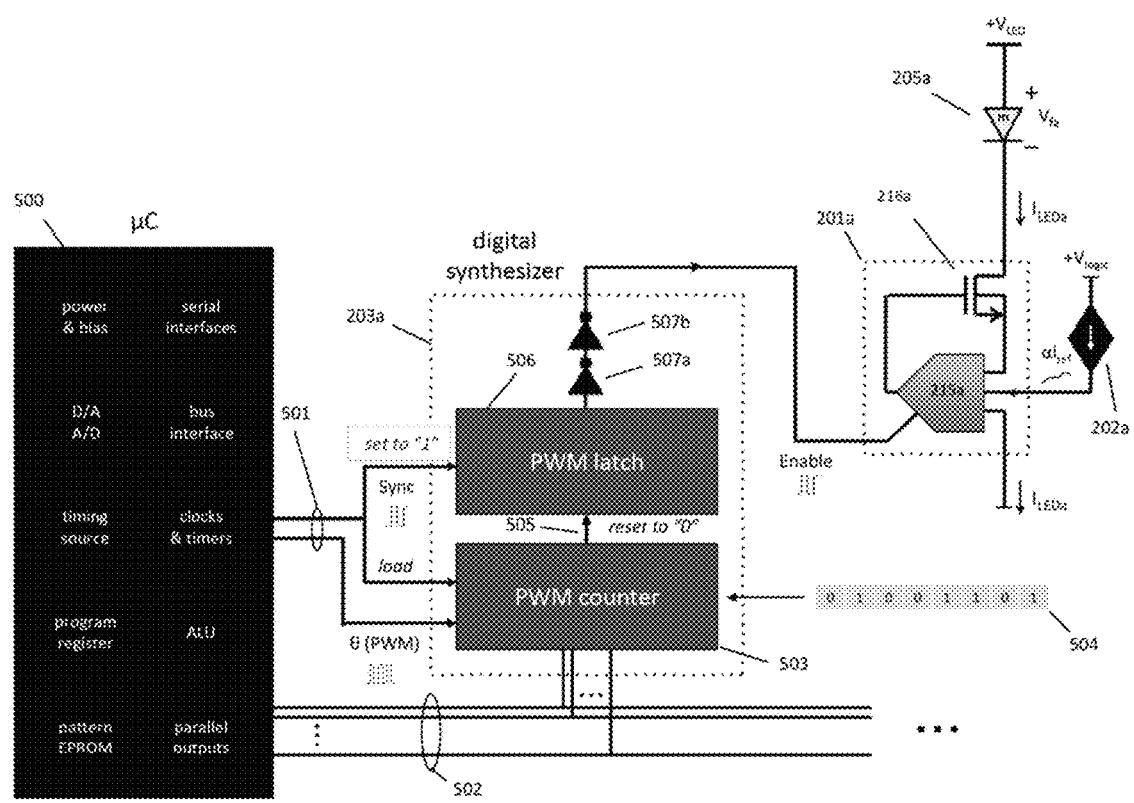
FIG. 28A illustrates a circuit diagram of a digital synthesizer.

One implementation of the digital synthesizer 203a of FIG. 27A is schematically represented in FIG. 28A, comprising a digital counter 503, a latch 506, and a digital buffer string comprising inverters 507a and 507b, with the output of digital synthesizer 203a controlled by clock signals 501 and parallel data bus 502 generated by microcontroller µC 500. Inverters 507a and 507b are shown to illustrate that the output of latch 506 comprising minimum size logic transistors must be buffered to drive the input capacitance of one or more MOSFET drivers 215a, as well as to compensate for any parasitic resistance and capacitance present in the conductive interconnect between digital synthesizer 203a and an electrical load, represented by current sink circuit 201a. As such, the current drive capability and the corresponding gate width of the MOSFETs used in inverter 507b should be sized accordingly to drive the Enable line at the requisite speed.

While the illustration shows a single inverter 507a electrically inserted between the un-buffered output of latch 506 and the input to high current inverter 507b, in practice many intermediate inverters of sequentially increasing gate widths (not shown) may be used to scale each inverter's output current with the capacitive loading of the next inverter. So long as the total number of inverters in the series of inverters (including the first inverter 507a and the last inverter 507b) is an even number, e.g. 2, 4, 6, . . . then the output of digital counter 503 and latch 506 should remain in digital phase with the output of digital synthesizer 203a. The result of employing the described sequential buffer string is a significantly larger fan out and ability to consistently drive a wide range of data lines while contributing a negligible change in signal propagation delay. Throughout this disclosure, this same technique may be used anytime a high-speed gate needs to drive a long line, high capacitance, or heavy load at a high speed, and therefore it will not be described again.

In operation, µC 500 writes data from its pattern EPROM onto parallel output lines 502. µC 500 also generates clock signals on lines 501, comprising a Sync pulse and clock signal θ. In operation, a Sync pulse sets the output of latch 506 to logic "1" which, buffered by inverters 507a and 507b enables MOSFET driver 215a into an on state, driving the gate of MOSFET 216a to produce a programmed current $I_{LED}$ and illuminating LED string 205a to a fixed brightness. Concurrently, the Sync pulse causes digital counter 503 to load the data present on parallel data bus 502 into the counter's register 504, shown by example as an 8-bit word. Pulses of clock signal θ cause digital counter 503 to count down linearly, decrementing the remaining count by one with each pulse. When the count reaches zero, digital counter 503 generates a pulse on output line 505, resetting the output of latch 506 to "0" and disabling MOSFET driver 215a.

Figure 28B:
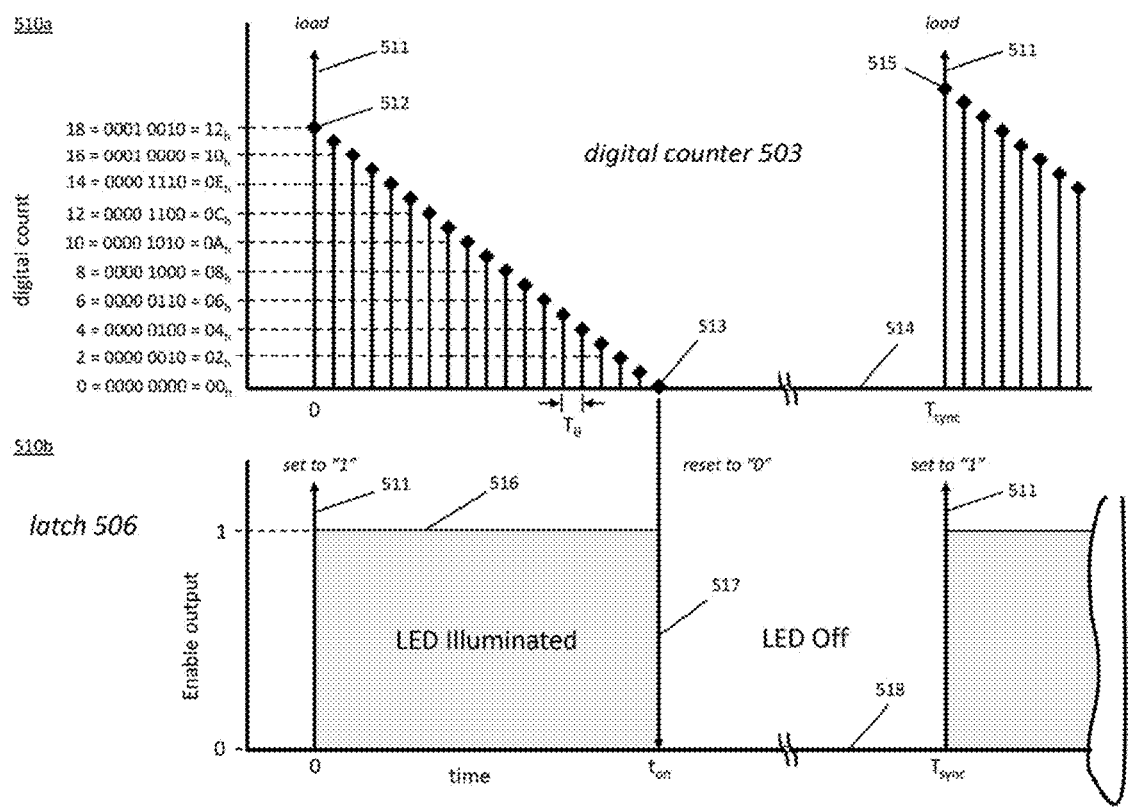
FIG. 28B is a timing diagram of digital synthesizer operation.

The timing diagram of FIG. 28B illustrates digital synthesizer operation of digital counter 503 in graph 510a and operation of latch 506 in graph 510b. As shown, digital counter 503 loads data 512 upon load instruction 511 triggered by the Sync pulse on one of clock signal lines 501. Repeated pulses of the clock signal θ subsequently decrement the counter register 504 once for each interval $T_\theta$, eventually counting down to zero count at time 513. During this time, the output of the digital synthesizer 203a outputs a logic "1" state as shown by waveform 516. When the value of the count in digital resister 503 reaches zero, the output is reset (line 517) and the LED string switches off at time 513. Until the next load pulse (line 511), the count in digital counter 503 remains at zero (line 514) or alternatively is ignored even if it continues to count.

As illustrated, digital counter 503 is binary and may comprise a ripple counter or a synchronous counter. Alternatively the counter 503 may be realized by software within µC 500, eliminating the need for hardware counters and latches, but still performing similar functions. In conclusion, the PWM counter function within digital synthesizer 203a may be implemented discretely, or using a dedicated timer function within µC 500, or implemented in software within µC 500. When software timers are employed, however, care must be maintained to insure that interrupts do not suspend or delay regular counter operation, or an incorrect frequency may be synthesized.

Figure 8A:
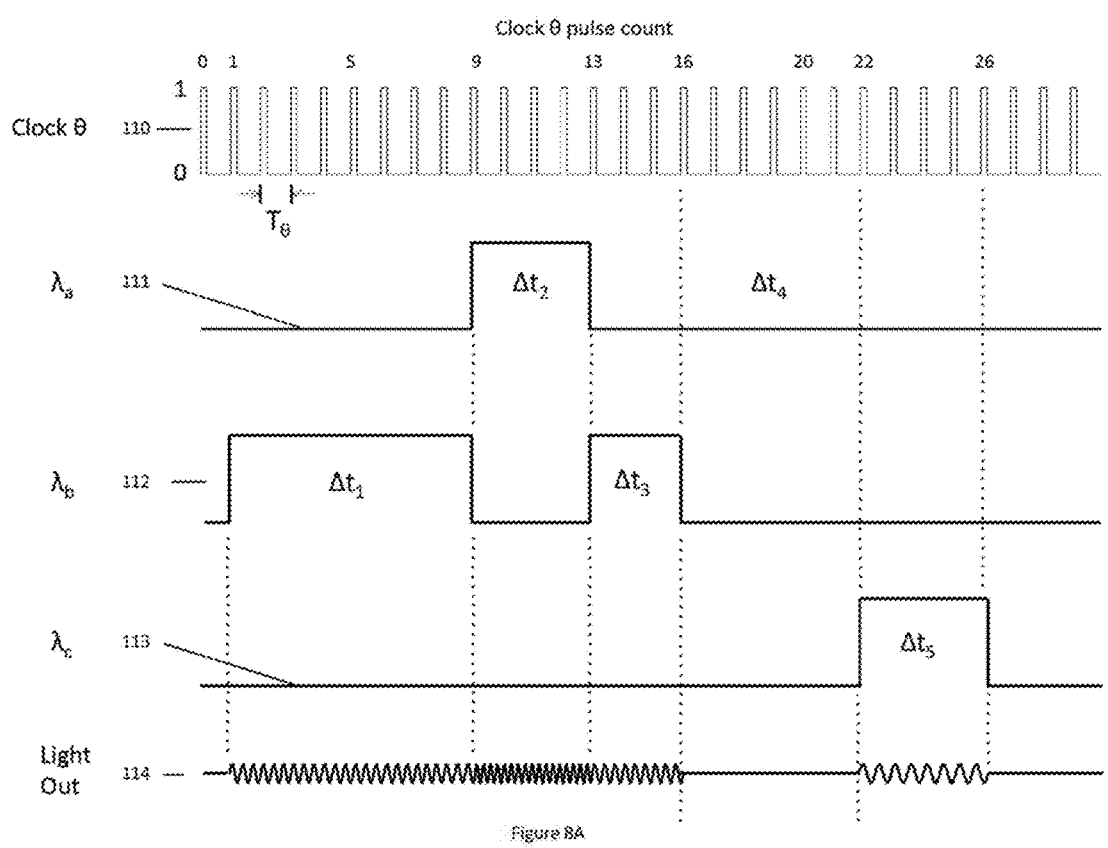
FIG. 8A is an exemplary timing diagram, showing the sequential pulsed excitation of multiple wavelength LEDs with varying durations.
Figure 8B:
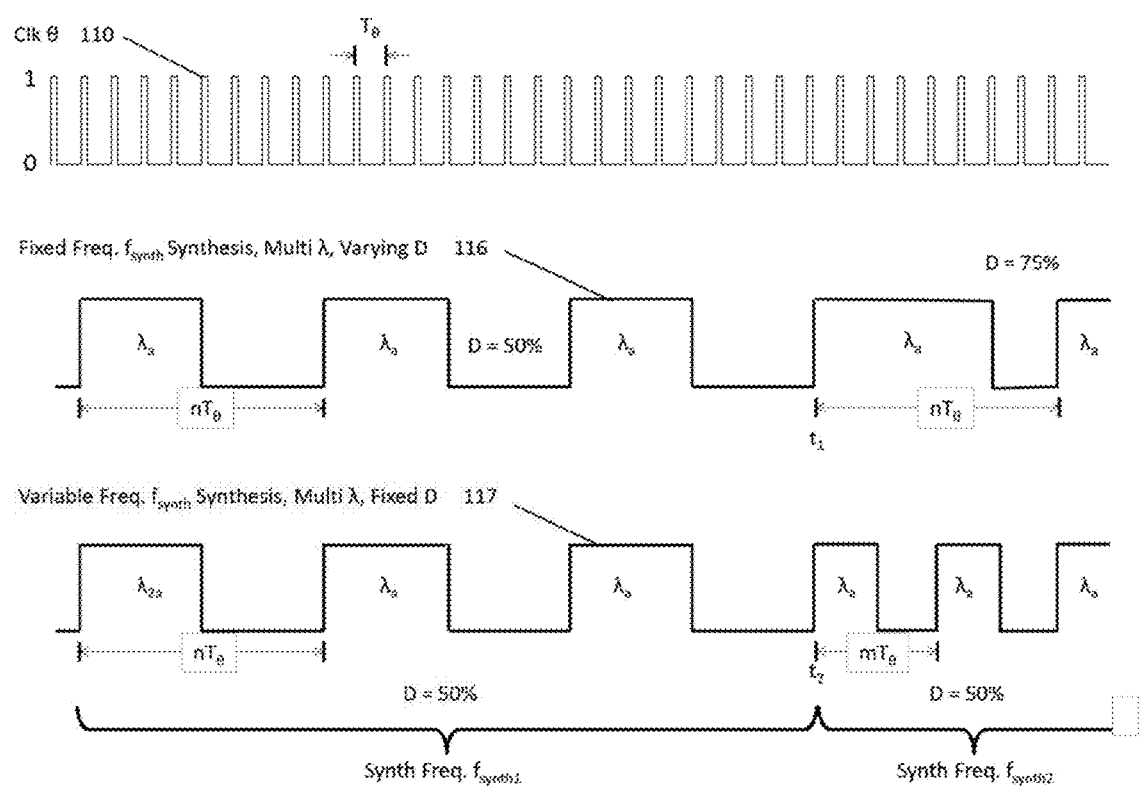
FIG. 8B is an exemplary timing diagram, showing the sequential pulsed excitation of multiple wavelength LEDs with various combinations of duty factor and frequency.
Figure 28C:
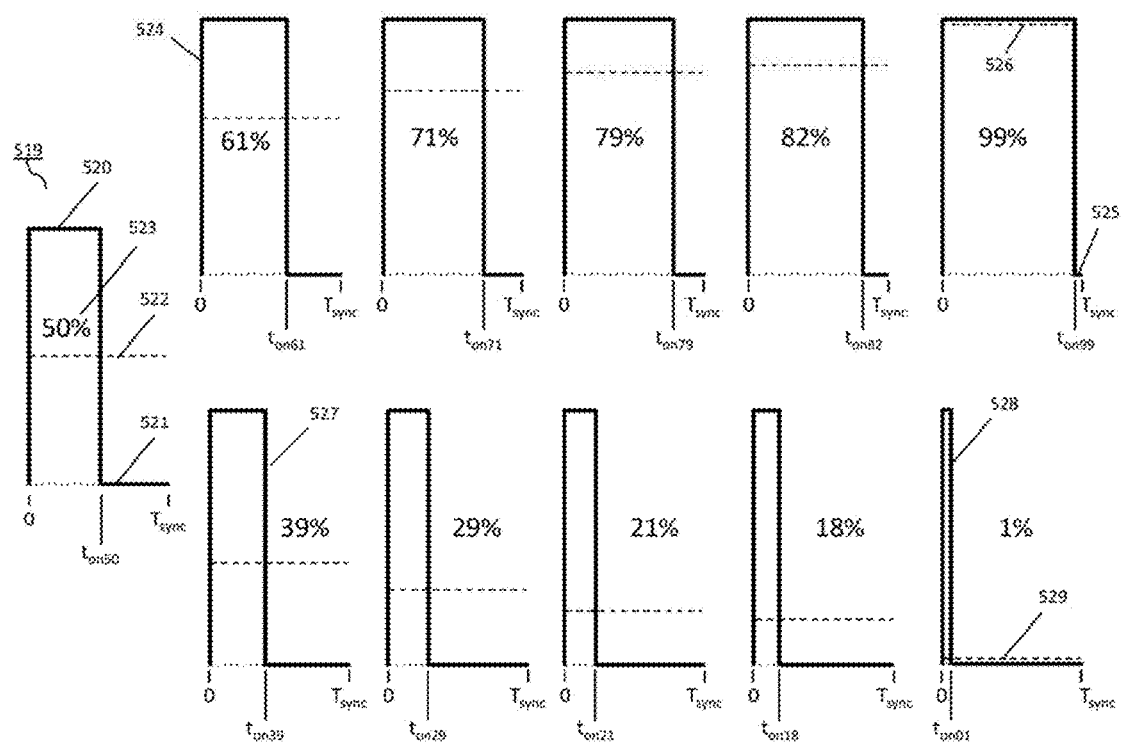
FIG. 28C illustrates synthesized pulses of a fixed frequency and varying duty factor.

The resulting LED current waveforms of the disclosed LED drive system comprise pulses of controlled widths and varying duration repeated at a fixed clock rate. By varying the on time $t_{on}$ while maintaining a fixed clock period $T_{sync}$, the average current in an LED string can be controlled digitally. Such a method can be referred to a fixed-frequency pulse width modulation or PWM control. Examples of fixed-frequency PWM generation of pulses of varying on-time are illustrated in FIG. 28C. In phototherapy applications, PWM average current control can be used for dynamic brightness adjustment of digitally pulsed LED currents as shown in FIG. 8B and described in previously cited U.S. Pat. No. 9,877,361. Alternatively, such PWM methods disclosed herein can be used for digital synthesis of sinusoidal waveforms, driving LED strings in an inventive manner free from spectral contamination in the audio spectrum.

Unlike in analog synthesis described in the previous section, where the average LED current is changed by altering the conducted LED current using a sinusoidal reference voltage, in digital sinusoidal synthesis a sequence of pulse widths varying in a prescribed manner are employed to recreate the sinusoidal waveform at a frequency far below the clock rate used to generate the pulses themselves. As shown in FIG. 28C, pulse 520 comprises an on-time $t_{on50}$ which is half that of the clock period $T_{sync}$, specifically with a digital value of "1" for the portion 520 of the waveform and with a digital value of "0" for the remaining portion 521 of the $T_{sync}$ period. As such the on-time $t_{on}=50\% \cdot T_{sync}$, the off-time $t_{off}=1-t_{on}=50\% \cdot T_{sync}$, and in this particular case $t_{on}=t_{off}$.

The average current during any PWM pulse is determined by its duty factor, defined as $D \equiv t_{on}/T_{sync}$. Accordingly, in this example the duty factor is given by $D=t_{on50}/T_{sync}=50\%$, where dashed line 522 graphically illustrates the duty factor, visually representing the average value of the waveform. Starting with waveform 523, the top row of waveforms shown in FIG. 28C illustrates pulses 524 with duty factors greater than 50%, specifically duty factors of 61%, 71%, 79%, 82% and 99%. In the 99% waveform, the dashed line 526 representing the average value and the off-time shown by line segment 525 are not drawn to scale in order to better illustrate the variables. Similarly, starting with waveform 527, the bottom row of waveforms shown FIG. 28C illustrate pulses with duty factor less than 50%, specifically duty factors of 39%, 29%, 21%, 18% and 1%. In the 1% waveform, the dashed line 529 representing the average value and the on-time shown by pulse 528 are not drawn to scale in order to better illustrate the variables. Each example in the top row is located above its complementary waveform in the bottom row, i.e. the mirror image condition around the 50% condition. For example, waveform 524 with an on-time $t_{ton61}$ and a 61% duty factor has a duty factor 11% above the 50% center value, while waveform 527 with an on-time $t_{ton39}$ and a 39% duty factor has a duty factor 11% below the 50% center value.

Figure 29A:
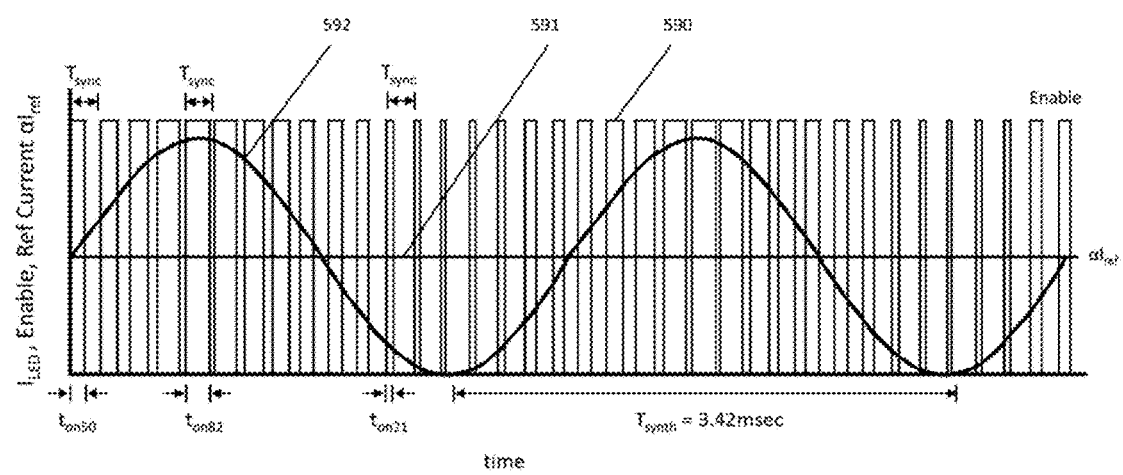
FIG. 29A illustrates an LED drive waveform comprising a fixed frequency PWM synthesized sinusoid.

By stringing together, i.e. sequencing, a series of pulses of varying duty factors and fixed period in a specific manner, any mathematical function, including sinusoidal waveforms, can be generated from PWM modulated digital pulses. For example, in FIG. 29A, a series of digital pulses 590 of varying width, e.g. $t_{on50}$, $t_{on82}$, $t_{on21}$, etc. occurring at a fixed period $T_{sync}$ results in a time-varying average value synthesizing a pure sine wave 592. During this digital synthesis, the value of analog reference current 591 remains constant and does not contribute to generation of the sine wave. In this method, sine wave 592 can be synthesized to have any frequency and period independent of the clock frequency $1/T_{sync}$, provided that the clock frequency $1/T_{sync}$ is higher than the highest frequency $1/T_{synth}$ being synthesized.

Figure 29B:
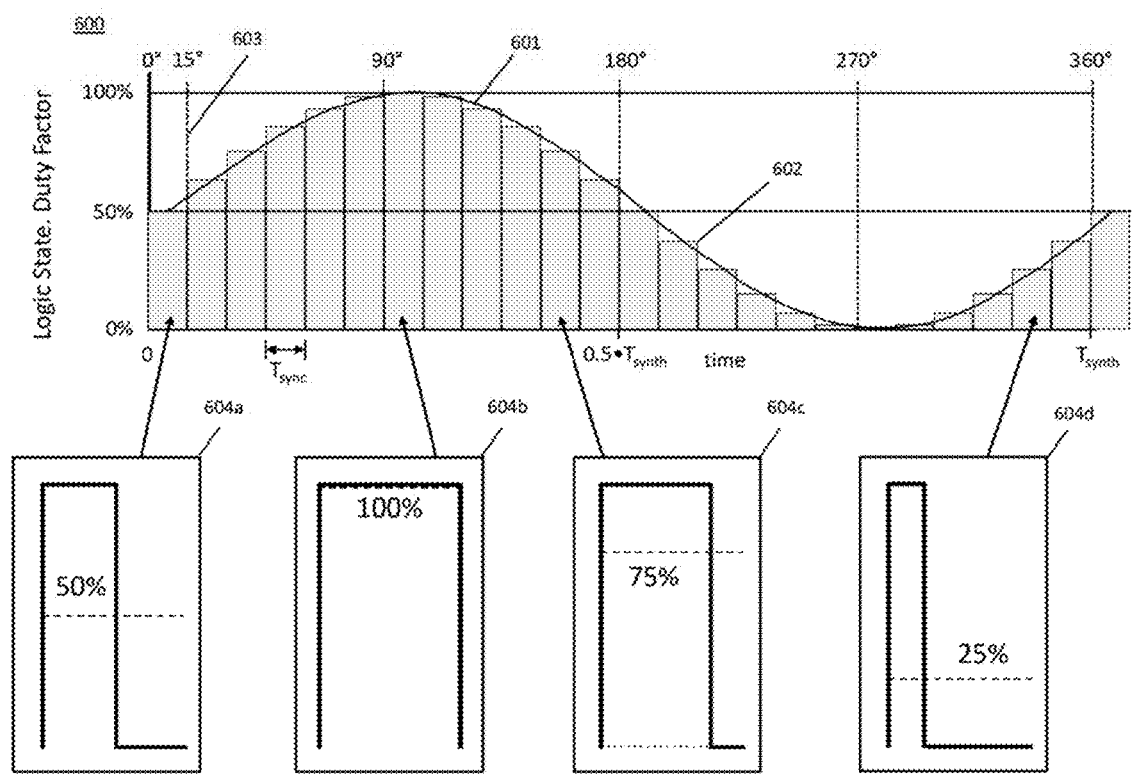
FIG. 29B illustrates examples of digitally synthesized sinusoids.

Provided that the clock frequency $f_{sync}=1/T_{sync}$ is chosen to be near or greater 22 kHz, neither the digital clock frequency nor its harmonics are present in the audio spectrum, and the resulting digital synthesis produces no spectral contamination that could adversely impact phototherapy efficacy. For example, a 28,032 Hz clock can be employed to synthesize a 1,168 Hz (D6) sine wave with 24 independent $T_{sync}$ time intervals. Such an approach is equivalent to breaking a 360° sine wave into 24 pieces of 15° and 35.7 μsec each as illustrated in graph 600 of the digital synthesizer's normalized magnitude versus time shown in FIG. 29B. Plotting the average value of sine wave 601 against elapsed time expressed in fixed 15° angle increments 602 results in a spectrum comprising the frequency $f_{synth}=1/T_{synth}$ of the generated sinusoid 602 along with the clock frequency $f_{sync}=1/T_{sync}$ used to generate it. In pulse width modulation, the magnitude of each pulse determined by the PWM duty factor has the same average amplitude as that of a D/A converter with the same resolution.

Unlike a D/A converter, however, in PWM control the actual analog value is not present in the amplitude of a waveform but in its duration determined by the time average value of the current or voltage. This duration is illustrated by waveforms 604a through 604d having PWM duty factors of 50%, 100%, 75% and 25% corresponding to arc angles of 0°, 90°, 150° and 330° respectively. The average value 602 of any 15° time increment comprises a portion of time when the output is at the full scale of 100% and a the remainder of the period where the output is at 0%. The average value shown as sinusoid 600 is in between, varying in proportion to the duty factor of each time slice.

As a practical matter, in sinusoidal synthesis using digital circuitry, negative voltages are problematic because they require dual power supply voltages, e.g. ±0.6V, where the signal must range from voltages above-ground to those "below-ground". Negative or below ground voltages are uncommon in integrated circuits, difficult to integrate because they require special electrical isolation techniques, and almost unheard of in digital circuitry. To realize a sinusoid using only positive supply voltages, the average value of the sine wave must occur above ground. For example, if sine wave 601 is realized using 1.2V logic, then for a sinusoid having a peak-to-peak voltage range of 1.2V, i.e. ±0.6V, the average voltage of the sine wave occurs at 0.6V. In digital synthesis this center voltage occurs at D=50%, equivalent to the zero state of a sine wave occurring at 0°, 180°, and at 360°.

Figure 29C:
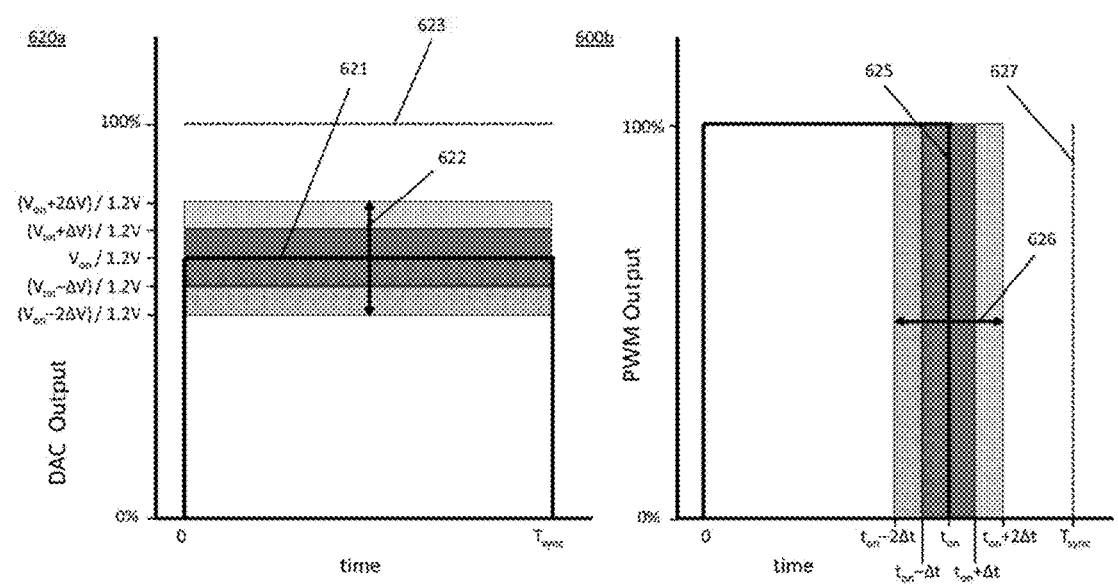
FIG. 29C illustrates a comparison of the output waveforms of a D/A converter versus PWM control over a single time interval.

A direct comparison between analog synthesis and fixed-frequency PWM digital synthesis of a sinusoid is shown in FIG. 29C, where the vertical axis represents the amplitude of the synthesized sine wave in a given interval while the horizontal axis represents time within the interval. In analog synthesis using a D/A converter (DAC), the amplitude of the signal shown in graph 620a controlled by the DAC output remains at a constant voltage for the entire period $T_{sync}$. In any given interval, the normalized DAC output has a value $V_{on}/1.2V$ ranging from 0% to 100% and may vary in the next time increment by a change in magnitude 622. These magnitude changes generally comprise linear steps of ±ΔV, ±2ΔV, etc. according to any desired resolution comprising 256 levels for an 8-bit DAC, 4096 levels for a 12-bit DAC and 65,536 steps for a 16-bit DAC. Since the instantaneous voltage of the waveform is set by the DAC and not by a PWM counter, then the highest required clock frequency to implement analog synthesis is $1/T_{sync}$ with the period $T_{sync}$ adjusted in accordance with the highest frequency to be reproduced with fidelity.

In contrast, using PWM digital synthesis, in a plot of voltage versus time shown in graph 600b, at the beginning of each time interval the voltage jumps from 0% up to 100% with no intermediate values except for transitions, and remains at this voltage for some fractional $t_{on}$ time 625 of the $T_{sync}$ period 627. The on-time $t_{on}$ is dynamically adjusted in linear increments of time±Δt, ±2Δt, etc. set by a 8-bit, 12-bit, or 16-bit counter having a resolution of 256, 4096 or 65,536 steps respectively according to the desired resolution unless otherwise limited by available clock frequencies. Because the average value of the sinusoid is set by a clock counting time and further subdividing the pulse shown in graph 600b, then a higher clock rate is needed to synthesize a sine wave than is required using a D/A converter. So, while analog synthesis achieves its resolution with steps in voltage, PWM digital synthesis achieves its resolution by steps of time. As such, the maximum frequency of the clock required for PWM digital synthesis is $1/T_\theta$ where this frequency is the sync clock frequency $1/T_{sync}$ times the desired resolution desired. In PWM synthesis, each time interval, e.g. 604a, includes a portion of the time current is flowing in the LED and a portion of time where the drive current is zero. Provided the clock frequency $f_{sync}$ is sufficiently high to be beyond the audio spectrum, then the cells in living tissue cannot respond to the presence of this high frequency, especially since it represents a small signal change in the average current from one interval to the next. In essence the cells provide natural filtering. Another filtering effect occurs because of capacitance in the LEDs and the MOSFET drive circuit which unavoidably softens the driving current waveform edges and filters high frequency noise, particularly harmonics beyond the audio spectrum, Lastly additional capacitance can be added to the LED drive channels if required.

Sinusoidal reconstruction with good fidelity, i.e. sinusoidal synthesis with minimal harmonics from distortion of the waveform from its mathematically ideal shape, requires a sufficient number of intervals of the highest sinusoidal frequency being reproduced $f_{synth}(max)$. For analog synthesis this clock frequency $f_{sync}$ is given by the relation $$f_{sync}=1/T_{sync}=(\#intervals) \cdot f_{synth}(max)$$

where the variable "#intervals" is the number of time intervals per 360° for the highest frequency waveform being synthesized and $f_{synth}$(max) is the highest frequency waveform being synthesized. One means by which the #intervals can be chosen is by the desired width of each time interval in degrees using the following relation: #intervals=360°/(arc angle of each time interval). For example if each arc angle is 36° then #intervals=10, if each arc angle is 20° then #intervals=18, if each arc angle is 15° then #intervals=24, if each arc angle is 6° then #intervals=60, and so on. This hyperbolic relationship, that smaller angles require more time intervals to describe one full 360° cycle of a sine wave, means in PWM synthesis higher resolution, requires a faster clock.

To summarize the comparison, digital PWM synthesis requires a higher frequency clock $f_\theta$ than analog synthesis because each time interval $T_{sync}$ must be further subdivided into smaller snippets of time of duration $T_\theta$, meaning for digital PWM synthesis the same bit resolution requires a higher clock frequency than analog synthesis. The required frequency $f_\theta$ of this faster clock, the one used for counting the increments of the on-time and setting the duty factor, is given by the relation $$f_\theta = 1/T_\theta$$
$$= (\text{bit resolution}) \cdot f_{sync}$$
$$= (\text{bit resolution})/T_{sync}$$
$$= (\text{bit resolution}) \cdot (\text{\#intervals}) \cdot f_{sync}(\text{max})$$

essentially describing how many thin rectangles of fixed time intervals are used to reconstruct one cycle of the highest frequency to be synthesized. This faster PWM clock signal $f_\theta$ may be generated from an even higher fixed frequency oscillator $f_{osc}$, preferably temperature compensated to minimize drift, using either a constant or dynamically adjustable frequency ratio. The process of dividing the synthesized sinusoidal waveform into small rectangles of fixed duration and of height equal to the magnitude of the function is analogous to the mathematical procedure called "integration" in calculus. In integral calculus, as the time increments "dt" become infinitely thin, the synthesized waveform is reproduced precisely and the area under the curve, the energy and harmonic content of the phototherapy excitation, is precisely controlled. Also it should be noted that the value of $T_{sync}$ is identical for both analog and digital synthesis. For example, using 18 intervals of 20° each to synthesize a 1,168 Hz (D6) sinusoid, the Sync clock used to load D/A converters in analog synthesis or to load the digital counter in digital PWM synthesis has a frequency $f_{sync}$ of 21,024 Hz, a frequency sufficiently high that it and all its harmonics occur at the extreme upper range of the audio frequency range and beyond.

Figure 29D:
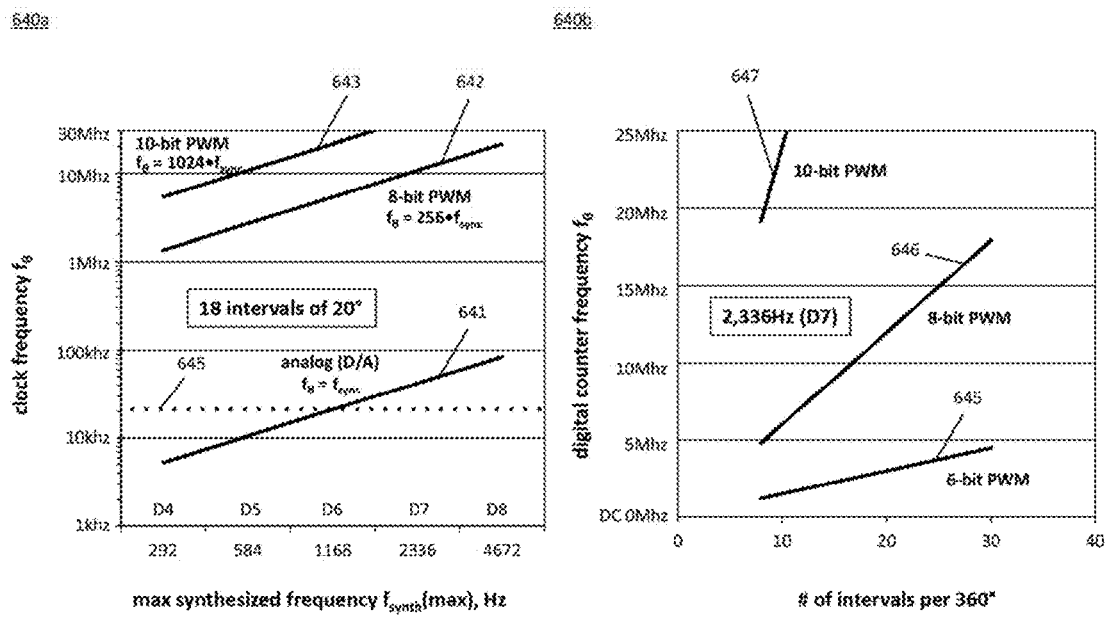
FIG. 29D graphically illustrates interrelationship between PWM bit resolution, the number of time intervals, and the maximum frequency being synthesized to the required counter clock frequency.

Graph 640a in FIG. 29D illustrates a plot of the clock frequency required in the system as a function of the maximum frequency sine wave to be synthesized, shown ranging from D4 to D8. The y-axis represents the highest frequency clock which in the case of analog synthesis represented by line 641 is the sync pulse used to load the D/A converter at a frequency of $f_{sync}$ and in the case of digital PWM synthesis is the digital counter clock having a frequency $f_\theta$. Using digital synthesis of the same 1,168 Hz waveform, the digital clock rate of the PWM digital counter for 8-bit, and 10-bit resolution shown by lines 642 and 643 respectively requires corresponding clock frequencies $f_\theta$ of approximately 5.38 MHz and 21,529 MHz. For 12-bit resolution, the digital counter clock is 4,096 times that of $f_{sync}$ or over 86 MHz, too high to be shown on the graph.

Graph 640b also shown in FIG. 29D illustrates the linear impact of increasing the number of time intervals used to synthesize 360° of the highest frequency sine wave being generated, where the number of intervals varies from 8 to 30. As shown by line 645 the clock rate required to synthesize a 2,336 Hz (D7) sine wave remains below 5 MHz for employing a 6-bit counter offering 64 magnitudes for a 1.2V sine wave, i.e. where each step represents 18.8 mV or 1.6% increments of the signal. Line 646 illustrates an 8-bit counter offering 256 steps and a precision of 4.69 mV or 0.4% step increments can be achieved over the full range without exceeding 20 MHz.

Considering that practical commercial microcontrollers typically operate at clock frequencies between 10 and 25 MHz, line 647 illustrates that a 10-bit PWM counter can only be used with a small number of intervals, 8 or less, while remaining below 25 MHz. Using fewer than 12 intervals per 360° results in distortion in the synthesized sinusoid not compensated for by higher bit precision, meaning the benefit of more precisely setting the average voltage in a given time interval by using 12-bit PWM counters or larger, is not worth sacrificing the number of time intervals used to construct the sinusoid. For high fidelity synthesis of a sinusoid free from unwanted audio spectrum harmonics, the number of time intervals for practical considerations ranges from 12 time-intervals each 30° wide, to 24 intervals of 15°. The following tables details the clock frequency required to synthesize a 4,672 Hz (D8) sinusoid using a various sized PWM counters.

| bit accuracy | 8 × 45° | 12 × 30° | 15 × 24° | 18 × 20° | 24 × 15° |
|---|---|---|---|---|---|
| 6-bits | 2.4 MHz | 3.6 MHz | 4.5 MHz | 5.4 MHz | 7.2 MHz |
| 8-bits | 9.6 MHz | 14.4 MHz | 19.9 MHz | 21.5 MHz | 28.7 MHz |
| 10-bits | 38.3 MHz | 57.4 MHz | 71.8 MHz | 86.1 MHz | 115 MHz |

Of the above conditions, the shaded boxes are not viable either because the clock frequency exceeds 25 MHz or because the number of time intervals are too few. This analysis suggests that the optimum condition is a 21.5 MHz PWM clock driving a 8-bit PWM counter to synthesize a 4,672 Hz (D8) sinusoid from 18 time intervals, each 20° in width. The corresponding PWM clock has a period $T_\theta=1/f_\theta=1/(21.529 \text{ MHz})=46.5$ nsec and sync period of $T_{sync}=256/f_\theta=11.9$ µsec with a corresponding frequency $f_{sync}=83.9$ kHz.

Figure 30:
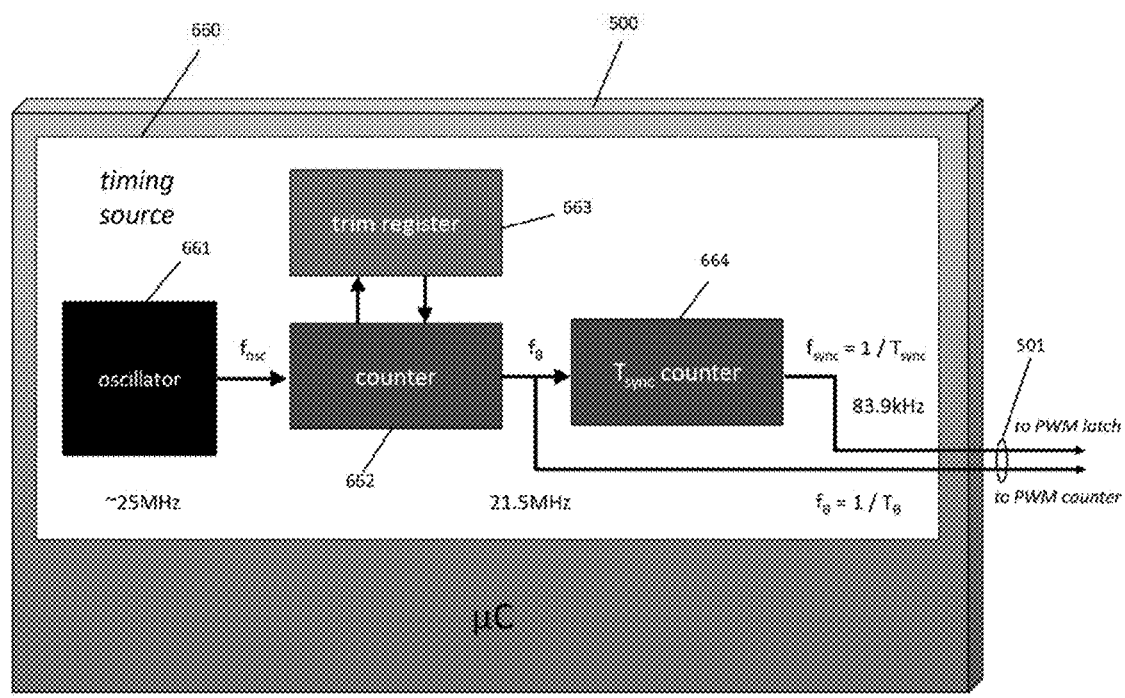
FIG. 30 schematically illustrates a clock generator circuit.

While discrete oscillator solutions can be utilized, in many cases the accuracy and cost is unwarranted, especially considering that many such solutions were developed for radio communications. On the other hand, 25 MHz oscillators are relatively easy to manufacture discretely or in conjunction with common microcontrollers because this oscillating frequency is commonly used in Ethernet communications. One timing source and clock generator circuit 660 made in accordance with this invention is illustrated in FIG. 30, comprising oscillator 661, digital counters 662 and 664 and trim register 693 to create clock signals 501 used to drive the digital synthesizer 203a shown in FIG. 28A.

Oscillator 661 may be realized using a crystal oscillator, an R-C relaxation oscillator, a ring oscillator, or a silicon MEMs oscillator. A crystal oscillator, comprising a crystal shard of quartz mechanically tuned to resonate a specific frequency is advantageous for its temperature independence, but it is unfortunately relatively fragile compared to semiconductors. An R-C relaxation oscillator employs a resistor-capacitor network to charge the capacitor at a set rate, discharging the capacitor rapidly after reaching a comparator or Schmidt trigger threshold, and repeating the process interminably. In many cases, the circuit elements to implement timing source 660 are fully integrated into μC 500 (shown in FIG. 28A) and are entirely user-programmable in firmware or software.

the clock frequency is increased in proportion to $f_{synth}$(max), using PWM methods to synthesize sinusoids above this frequency means the aggregate resolution must be reduced hyperbolically, i.e. where $f_{osc}/f_{synth}$(max) sacrificing fidelity either by lowering the bit-resolution or the number of time intervals. This tradeoff between the maximum frequency synthesized and its aggregate resolution is illustrated in the following table:

| description | D8 | bandwidth | D9 | D10 | ultrasonic |
|---|---|---|---|---|---|
| waveform $f_{synth}$(max) | 4,672 Hz | 5,425 Hz | 9,344 Hz | 18,688 Hz | 22,000 Hz |
| oscillator $f_{osc}$ | 25 MHz | 25 MHz | 25 MHz | 25 MHz | 25 MHz |
| $f_{osc}/f_{synth}$(max) ratio | 5,351 | 4,608 | 2,676 | 1,338 | 1136 |
| waveform resolution | 4,608 | 4,608 | 2,676 | 1,338 | 1136 |
| equivalent resolution | 12-bit | 12-bit | 11-bit | 10-bit | 10-bit |

Clock precision is achieved by trimming the resistor in an R-C oscillator and/or using materials that are relatively temperature independent. Another alternative is the to create a time source using a large number of inverters connected head-to-tail, i.e. output to input, to form a loop or ring. When powered, the signal propagates around the inverter ring at a frequency in accordance to the inverters' propagation delays. An odd number of inverters are required to insure the oscillations continue. The newest solution available today is the use of silicon micromachine devices or MEMs, used to create a small vibrating spring or diving board (cantilever) monitored electrically by capacitive coupling or peizo-resistive variation and tuned to resonate according to its specific mass.

Regardless of the technique employed, the oscillator 661 produces a 25 MHz oscillating signal which is then adjusted to any lower desired frequency, e.g. 21.5 MHz, by digital counter 662. If oscillator 661 is trimmed during manufacturing then counter 662 can be preset to a fixed value by software. If however, the frequency of oscillator 661 varies with manufacturing, functional trimming using trim register 663 is normally performed during manufacturing. In functional trimming, measurement of frequency $f_\theta$ is made repeatedly while the count being loaded into counter 662 by the digital value stored in trim register 663 is adjusted until the desired frequency is achieved and the frequency source calibrated.

This PWM clock frequency is supplied to the digital synthesizer and also to the input of programmable counter 664, converting the PWM clock frequency $f_\theta$ into the Sync pulse having a frequency $f_{sync}$ that is, as shown, 256 times lower than $f_\theta$. The divide by factor for counter 664 should match the desired resolution of the PWM output, e.g. 8-bits, 10-bits etc. In this manner the PWM digital counter 664 will count pulses corresponding to the frequency $f_\theta$ and the Sync pulse occurring 256 pulses later will reset the LED driver and restart the count.

As applied to LED drive in phototherapy, the effective resolution of sinusoidal generation using the disclosed invention can be estimated by multiplying the number of time intervals used in constructing the sinusoid times the number of PWM duty factors possible, i.e. the bit resolution of the PWM counter. Multiplying 18 time increments, approximately equivalent to 4-bit precision, times 256 possible values of D generated from an 8-bit counter means for sinusoids up to 5,425 Hz, the total resolution is approximately equivalent to 12-bits or 4096 combinations. Unless The table illustrates that for synthesizing sinusoids up to approximately 5.4 kHz, the overall resolution of the digital synthesizer is 4608 combinations, greater than 12-bit resolution. Above this frequency, referred herein as the synthesizer's "bandwidth", the digital synthesizer's resolution declines in proportion to the sinusoid's frequency, declining to 11-bit precision at 9,344 Hz (D9) and maintains at least 10-bit resolution all the way to the upper edge of the audio spectrum. The bandwidth limitation and its impact is illustrated graphically in FIG. 31 wherein curve 671 shows the aggregate synthesizer resolution versus the maximum synthesized frequency $f_{synth}$ (max) in both the number of possible combinations and in their bit equivalence. As shown, the accuracy of digital synthesizer 203a remains constant at a value exceeding 12-bits until the frequency of 5.425 kHz, the digital synthesizer's bandwidth, is reached (line 673), above which the resolution declines proportionately with $f_{synth}$(max). At the edge of the ultrasonic spectrum (line 175), the digital synthesizer 203a still maintains an overall resolution of 10-bits. If the number of time intervals used to synthesize the highest frequency sine wave is maintained at #intervals=18, then the drop in aggregate resolution 671 must be accompanied by a decrease in PWM counter resolution as shown by line 672. Even operating above synthesizer 203a's bandwidth, up to the edge of the ultrasonic spectrum 175, the PWM counter resolution still exceeds 6-bits.

Clearly, above synthesizer 203a's bandwidth, as the resolution declines the fidelity of the synthesized sine wave suffers. While for audiophiles listening to music, subtle distortion and phase artifacts of the digital audio reproduction process may be noticeable to the trained ear, in an LED drive for phototherapy the resulting distortion is essentially insignificant, carrying little energy and occurring at harmonic frequencies outside the audio spectrum. No adverse impact is expected in this frequency range.

Figure 31:
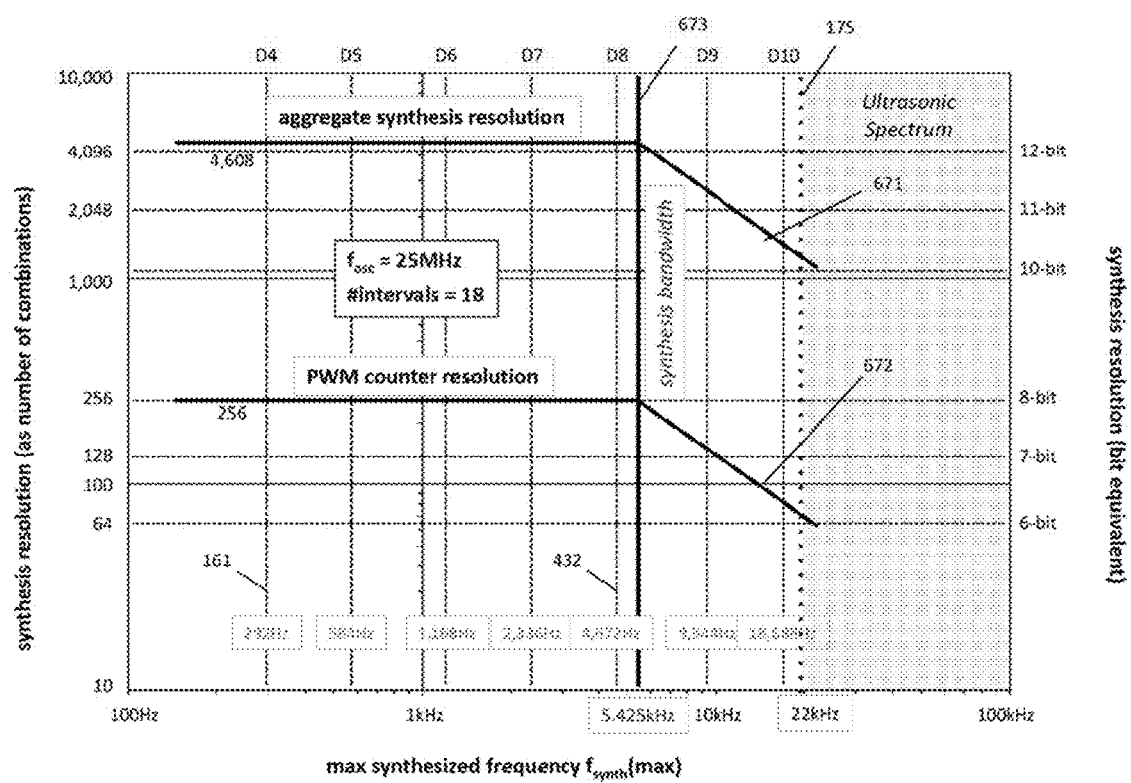
FIG. 31 graphically illustrates the dependence of overall digital synthesis resolution and PWM bit resolution on the maximum frequency being synthesized.
Figure 32A:
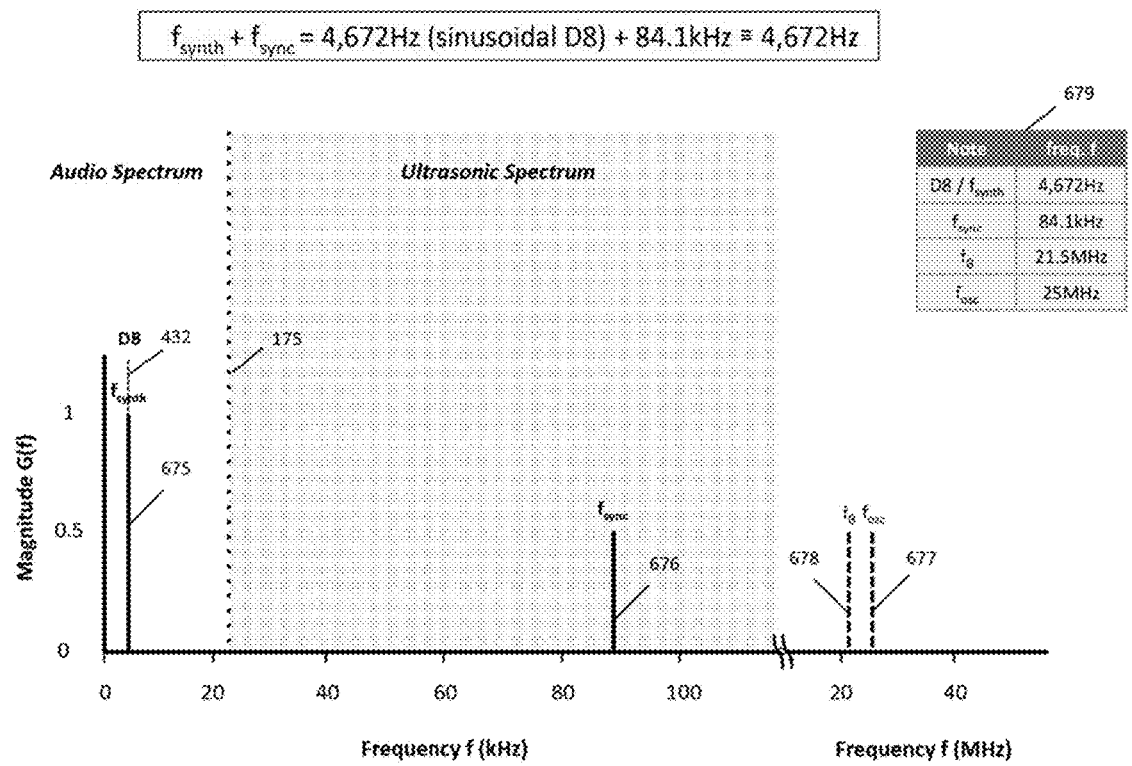
FIG. 32A illustrates the frequency spectrum of a digitally synthesized 4,672 Hz sinusoid.

As described previously, at a frequency slightly above 7 kHz, even the lowest harmonics of a square wave are outside the audio spectrum and not expected to affect photobiomodulation and phototherapy efficacy. So at frequencies above the threshold frequency shown by line 673 in FIG. 31 the disclosed invention may continue PWM synthesis with reduced fidelity, switch to pulsed digital operation, or switch to analog synthesis described previously. The resulting harmonic spectra, shown in FIG. 32A, illustrate that using PWM digital synthesis of a sinusoid results in only the synthesized frequency represented by line 675 in the audio range. The sync frequency $f_{sync}$ used to load the data stream into the PWM digital counter, represented by line 676, occurs at a frequency far into the ultrasonic spectrum beyond the upper limit of the audio spectrum (line 175). The clock pulses used to control the PWM on-time (line 678) and the clock pulses used to generate it (line 677) occur in the MHz range and are not present in the LED drive excitation waveforms whatsoever.

Figure 32B:
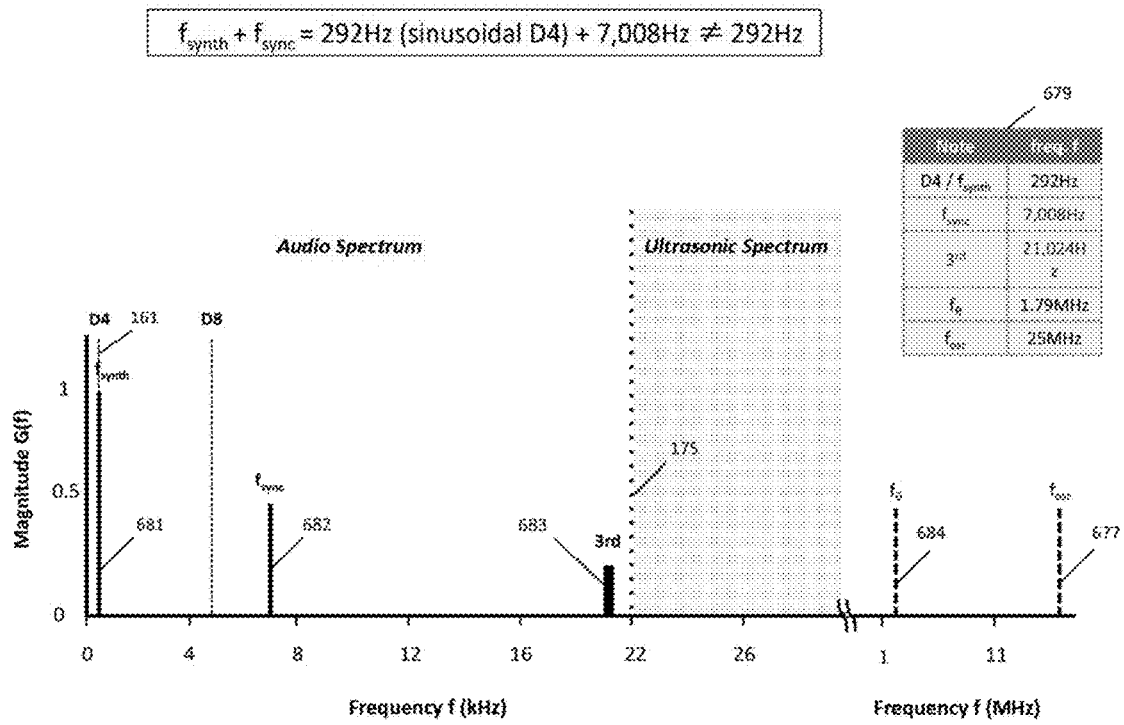
FIG. 32B illustrates the frequency spectrum of a digitally synthesized 292 Hz sinusoid.

When the same approach is employed to synthesize a lower frequency sine wave, e.g. $f_{synth}$=292 Hz (D4) shown by line 681 in FIG. 32B, a potentially serious noise problem results. If the synthesized frequency of 292 Hz is generated using the minimum required Sync clock frequency (line 682), the resulting clock frequency $f_{sync}$ occurs at 7,078 Hz in the middle of the audio spectrum and with relatively high energy content. Moreover as described by table 679 in FIG. 32B, the third harmonic of the Sync clock (line 683) also falls at a frequency below the lower limit of the ultrasonic spectrum (line 175), in the upper part of the audio spectrum. So while using the minimum possible clock frequency is beneficial in synthesizing high frequency waveforms, it is not advantageous in generating lower frequency sinusoids.

Figure 32C:
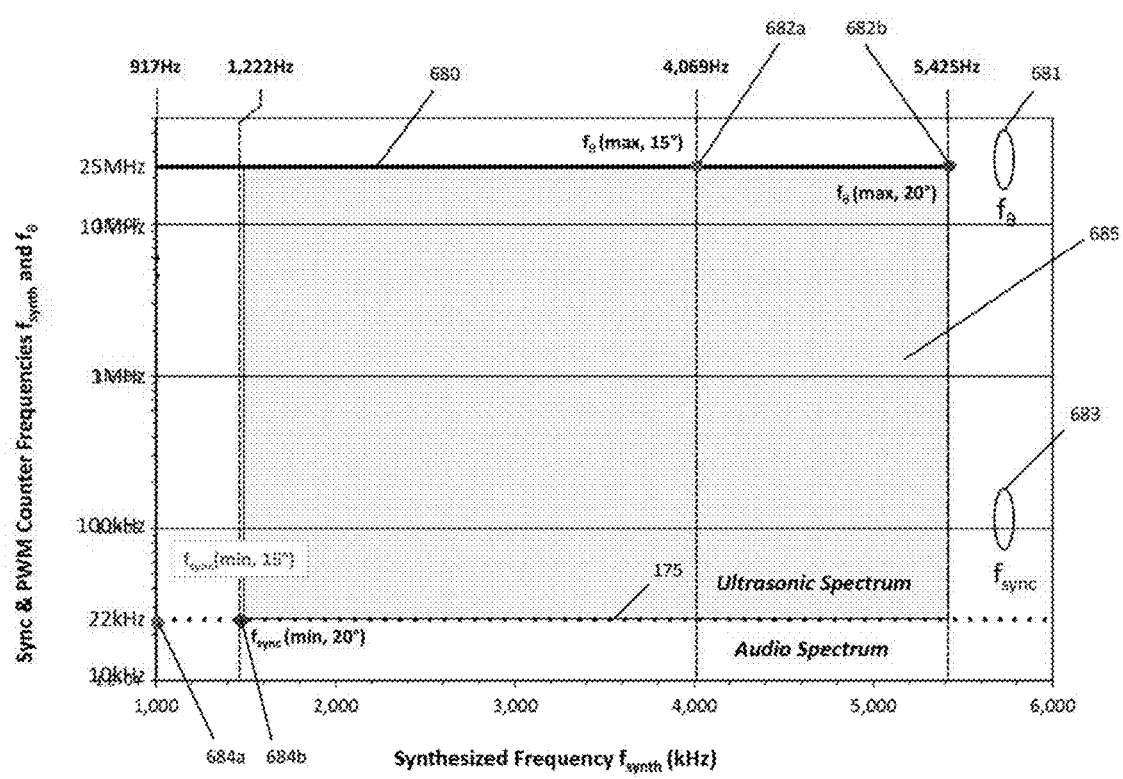
FIG. 32C graphically illustrates the dependence of the Sync and PWM counter frequencies on the synthesized frequency.

As illustrated in FIG. 32C, requiring the upper limitation in PWM clock frequency $f_\theta$ not to exceed the preferred oscillator frequency 25 MHz, and the lower limitation in the Sync pulse frequency $f_{sync}$ not to fall within the audio spectrum puts practical constraints on the range of frequencies $f_{synth}$ that can be synthesized using the fixed clock ratio described previously, namely $$f_\theta = (\text{bit resolution}) \cdot f_{sync} = (\text{bit resolution}) \cdot (\#\text{intervals}) \cdot f_{synth}(\text{max})$$

For the PWM clock frequency for synthesized sine waves formed of twenty-four 15° time intervals or eighteen 20° time intervals to remain at or below 25 MHz, shown by horizontal line 680, the maximum frequency sinusoid $f_{synth}$ (max) is limited to 4,069 Hz and 5,425 Hz respectively, as shown by points 682a and 682b and consistent with FIG. 31. According to the above relation at the other extreme, synthesizing any sine wave having a frequency $f_{synth}$ below 917 Hz with 15° time intervals or below 1,222 Hz with 20° time intervals means that the Sync clock pulse frequency $f_{sync}$ will be sufficiently low that it falls below the frequency represented by line 175 and into the audio band, specifically shown as points 684a and 684b, creating the potential for unwanted spectral contamination affecting phototherapy efficacy. The resulting range bounded by the audio spectrum's limitation of the Sync clock $f_{sync}$ on the low-end and the practical limit of the oscillator's 25 MHz frequency on the PWM clock frequency $f_\theta$ on the upper end (shown by shaded region 685 for the 20° synthesis example). Assuming the oscillator frequency and audio boundaries are fixed, operating outside of the allowed range means resolution must be sacrificed for synthesizing high sinusoidal frequencies and at the other extreme, a higher than minimum, i.e. an "over-sampled" Sync clock frequency must be maintained when synthesizing low frequency sinusoids.

In conclusion, when the required clock frequency for PWM digital synthesis is impractically high, the options available using the disclosed invention include
- limit the maximum frequency of the synthesized sine wave
- compromise the harmonic fidelity of the synthesized waveform by limiting PWM bit resolution, i.e. reducing the resolution of the duty factor
- compromise the harmonic fidelity of the synthesized waveform by employing larger time intervals, thereby reducing the number of time intervals per $T_{synth}$
- switch from digital synthesis to analog synthesis above a certain clock frequency, using a D/A converter as described previously including to vary the magnitude of the LED current in accordance with analog, digital and PCM sources
- Combinations of the above methods Conversely, when the frequency of the sine wave being synthesized is too low, the minimum Sync clock frequency must be maintained above a set frequency limit and cannot scale in proportion to the synthesized frequency. Using the inventive methods disclosed herein a sinusoid of controlled and dynamically adjustable frequencies for LED phototherapy can therefore be generated using digital synthesis free from spectral contamination of unwanted harmonics in the audio spectrum.

Digital Sinusoidal Synthesis

Given the aforementioned description of the apparatus and methods of pulsed width modulation control of LED current, frequency, and brightness, any sinusoid, series of sinusoids, or chords of multiple sinusoids may be dynamically synthesized.

Referring again to the apparatus of FIG. 28A, in sinusoidal synthesis, a particular control sequence, i.e. a specific series of PWM counts, is sequentially loaded from any digital controller such as μC 500 into register 504 of digital synthesizer 203a. The digital synthesis of sinusoids in accordance with the methods described herein controls the harmonic content and brightness of one or more LED strings used in phototherapy. While microcontroller μC 500 is shown as the source of these instructions, any programmable logic or logic array, custom digital circuitry or custom integrated circuit may also be used to generate the control sequence.

Figure 33:
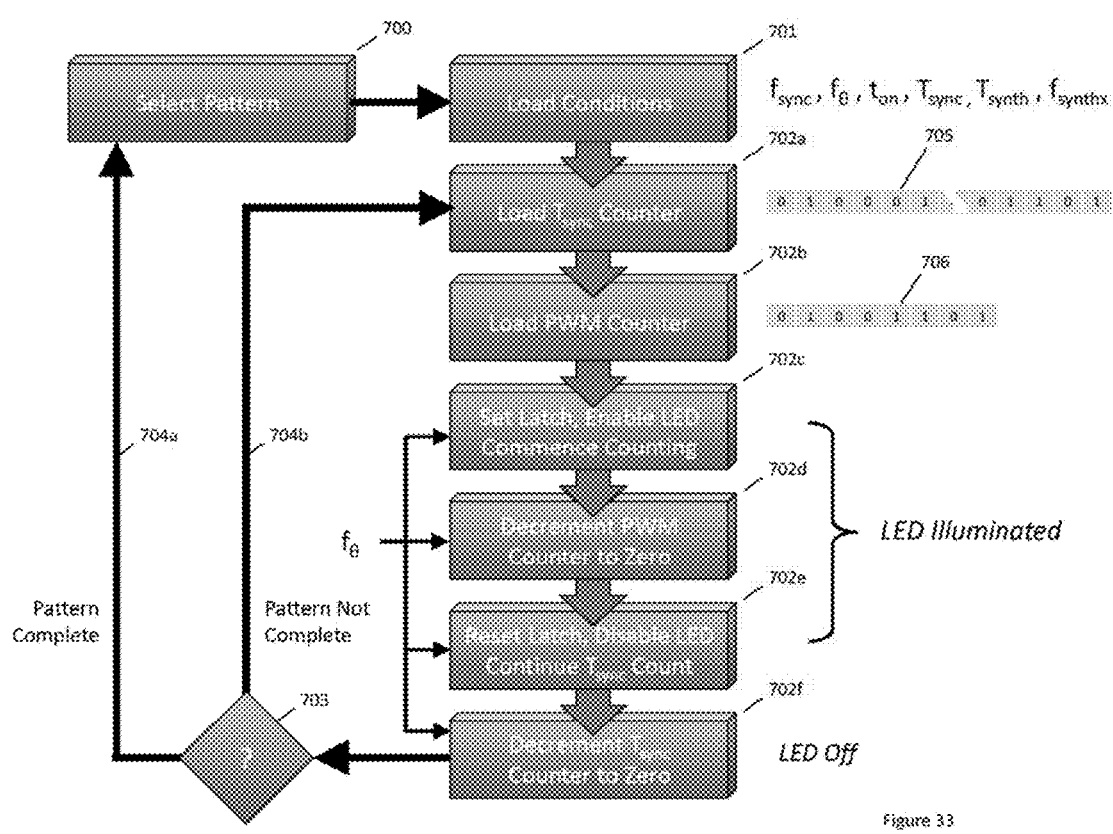
FIG. 33 illustrates a flow chart of sinusoidal waveform generation using the disclosed digital synthesis methods.

Whether by hardware, software or some combination thereof, execution of the digital synthesis involves a sequence of steps such as those shown in FIG. 33. Starting with the step "Select Pattern" (step 700), the LED wavelengths, channels, and driving algorithms are chosen. In "Load Conditions" (step 701), these settings including $f_{sync}$, $f_\theta$, $t_{on}$, $T_{sync}$, $T_{synth}$, and the various synthesis patterns are loaded into the appropriate registers within μC 500 and in associated hardware, counters, buffers, etc. If a single-frequency sinusoid $f_{synth1}$ is to be synthesized, the sequence of digital codes required is recalled from non-volatile memory files and then saved in a data register or stack. These codes represent the counts loaded sequentially into the PWM counter each time a $T_{sync}$ pulse occurs. If a chord of multiple sinusoids $f_{synth1} + f_{synth1} + \ldots + f_{synthx}$ is to be synthesized, a different sequence of digital codes is recalled from nonvolatile memory file comprising and loaded into a data register or stack. Data registers may comprise static or dynamic memory, i.e. SRAM or DRAM, but since they are modified, i.e. "written" frequently and rapidly during synthesis, the data registers operate at a frequency too high for non-volatile memory such as EPROM, $E^2$PROM or flash, used to store the phototherapy patterns and algorithms.

After the conditions are loaded into registers or stacks for quick access, in "Load Tsync Counter" (step 702a) the register 705 containing data that represents the first time interval $T_{sync}$ is loaded into the $T_{sync}$ counter 664, shown in FIG. 30. In tandem, in "Load PWM Counter" (step 702b), the data in register 706, representing the on-time of the pulse within the time interval $T_{sync}$, is loaded into PWM counter 503 shown in FIG. 28A. In the step entitled "Set Latch, Enable LED, Commence Counting" (step 702c) the output of PWM latch 506 is set "high" enabling MOSFET driver 215a and illuminating LED string 205a. Concurrently, $T_{sync}$ counter 664 and PWM counter 503 commence counting pulses from the $f_\theta$ clock. In the step entitled "Decrement PWM Counter to Zero" (step 702d), PWM counter 503 counts down to zero while the $T_{sync}$ counter continues unabated. When the PWM counter 503 reaches zero, the output of PWM latch 506 is reset "low" disabling MOSFET driver 215a and turning off LED string 205a as described by the step entitled "Reset Latch, Disable LED, Continue $T_{sync}$ Count" (step 702c). As the name describes, the $T_{sync}$ counter continues to count through the step entitled "Decrement $T_{sync}$ Counter to Zero" until the Tsync count reaches zero.

Once $T_{sync}$ counter 664 reaches zero, a program decision (step 703) is made in accordance with the algorithm prescribed by files originally loaded during the "Select Pattern" step 700. If the pattern has been completed in the "Pattern Complete" case (arrow 704a), the sequence is finished and a new pattern must be selected to continue. Otherwise, in the case "Pattern Not Complete" (arrow 704b) a new set of counts comprising the data in register 705, representing the new time interval $T_{sync}$ 705, and the data in register 706, representing the on-time of the pulse within the time interval $T_{sync}$, are respectively loaded into $T_{sync}$ counter 664 and PWM counter 503, and steps 702a through 702f are repeated. The process continues until decision 703 determines the pattern is complete, whereby program execution terminates and digital synthesis of a sequence of sinusoids or sinusoidal chords is complete.

In software implementations, the size of counters 702a and 702b are adjustable, able to synthesize a single cycle of a sinusoid or multiple cycles. The duty factor of a given pulse may be calculated as the ratio of the on-time determined by the count stored in register 706 and the $T_{sync}$ time interval stored in register 705. While in fixed frequency PWM synthesis, the $T_{sync}$ time interval in register 705 remains constant and the on-time in register 706 is adjusted to control the duty factor, the $T_{sync}$ period can be adjusted to synthesize any given sinusoid of an arbitrary frequency $f_{synth}$. The algorithm shown in FIG. 33 accommodates changing the value of $T_{sync}$ in accordance with the frequency of the sinusoid being synthesized and to maintain a desired resolution. For example, $f_{sync}$ can be decreased in proportion to the maximum frequency $f_{synth}$(max) of the sinusoid being synthesized. Alternatively, a higher value of $f_{sync}$ than required may be employed.

Figure 34A:
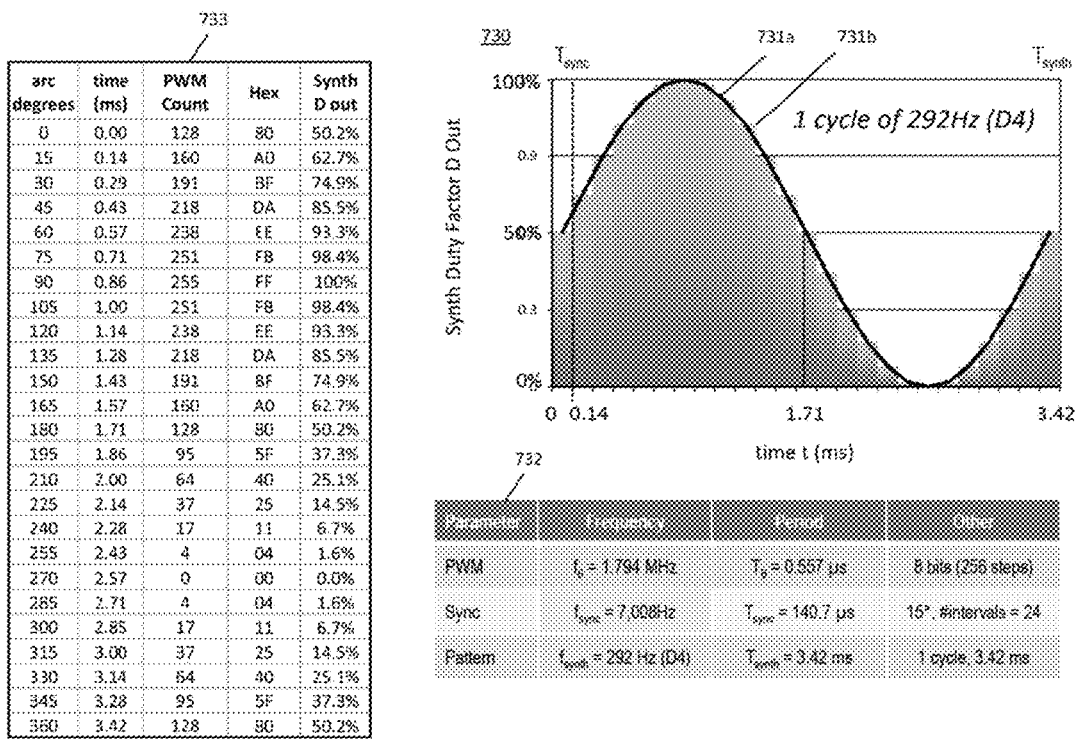
FIG. 34A graphically illustrates digital synthesis of a 292 Hz (D4) sine wave using 15° intervals.
Figure 348:
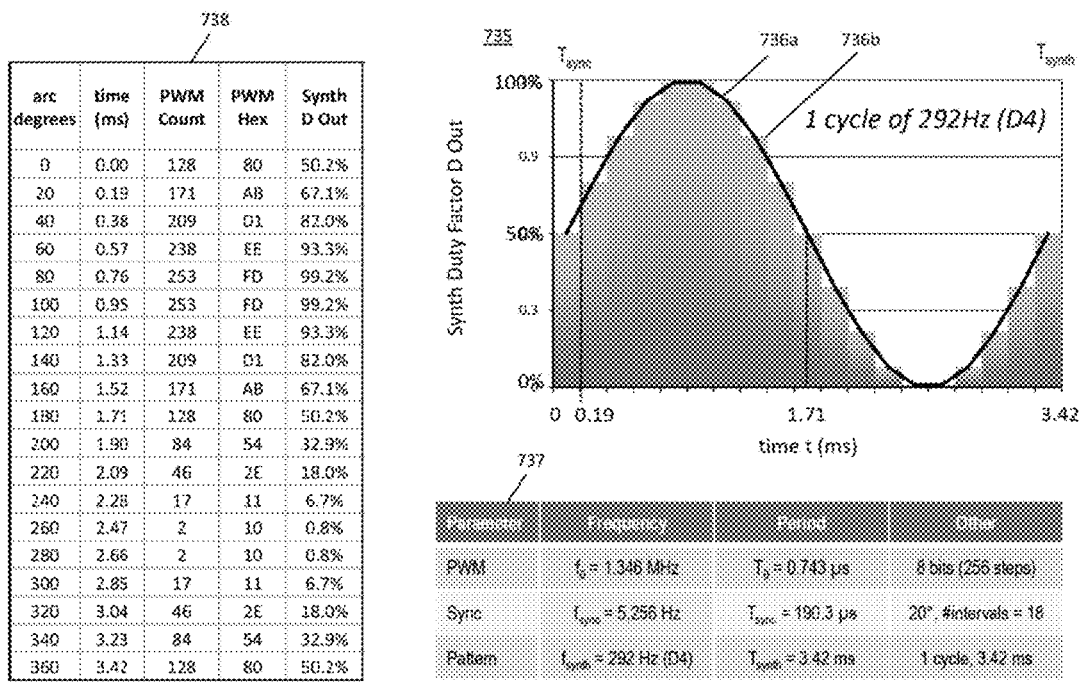

For example, except for the aforementioned of audio frequency noise issue, a 292 Hz (D4) sinusoid may be synthesized using an 8-bit PWM counter and either 24 or 18 time intervals. In graph 730 of FIG. 34A, sinusoid 731a is synthesized using 24 evenly-spaced intervals each corresponding to 15° of arc and having a duration of 140.7 µsec. Each interval has an average value shown by steps 731b determined by an 8-bit PWM counter having 256 durations summarized in table 732. By successively loading the PWM counter with the binary equivalent of the decimal number in the "PWM count" column or the hexadecimal number in the "hex" column of table 733, the sinusoidal waveform 731a will result. In operation, at the first time point representing 0°, the PWM counter is loaded with hex number 80 for 50%, the sin of 50°. Because of a quantization error in the counter, i.e. 128/255, the nearest duty factor is 50.2%, the synthesizer exhibiting a slight discrepancy from its ideal average output. After 140 µsec, one $T_{sync}$ time interval, the PWM counter is loaded with a new value A0 hex (160 decimal) changing the duty factor to 62.7%.

The process continues sequentially driving the average magnitude higher till at 0.86 ms the PWM counter is loaded with FF hex reaching a duty factor of 100%. Thereafter the PWM duty factor declines reaching a minimum value at 2.57 ms of 0 corresponding to the sine of 270°. The process then repeats to synthesize additional cycles of sinusoids. The major negative aspect of this sinusoidal synthesis is the noise generated by $f_{sync}$=7,008 Hz shown in table 732. While it does not comprise an entire spectrum of audio frequency harmonics present in present day digital pulsed systems intentionally operating in the audio band, it still represents audio spectral contamination.

In graph 730 of FIG. 34B, sinusoid 736a is synthesized using 18 evenly-spaced intervals each corresponding to 20° of arc and having a duration of 190.3 µsec. Each interval has an average value shown by steps 736b determined by an 8-bit PWM counter having 256 durations summarized in table 737. By successively loading the PWM counter with the binary equivalent of the decimal number in the "PWM count" column or the hexadecimal number in the "hex" column of table 738, the sinusoidal waveform 736a will result. The advantage of dividing a sine wave into 20° intervals of time over that of 15° intervals is the lower resolution allows a higher frequency sinusoid to be synthesized with a clock frequency $f_\theta$. The disadvantage of employing 20° intervals is that the nearest points to the maximum and minimum values on the sinusoid at 90° and 270° occur at 80°, 100°, 260° and 280° causing some flattening of the synthesized sine wave, slight distortion appearing as if the waveform was "clipped". Another negative aspect of this sinusoidal synthesis is the noise generated by $f_{sync}$=5,256 Hz shown in table 737. While it does not comprise an entire spectrum of audio frequency harmonics present in present day digital pulsed systems intentionally operating in the audio band, it still represents audio spectral contamination.

Figure 34C:
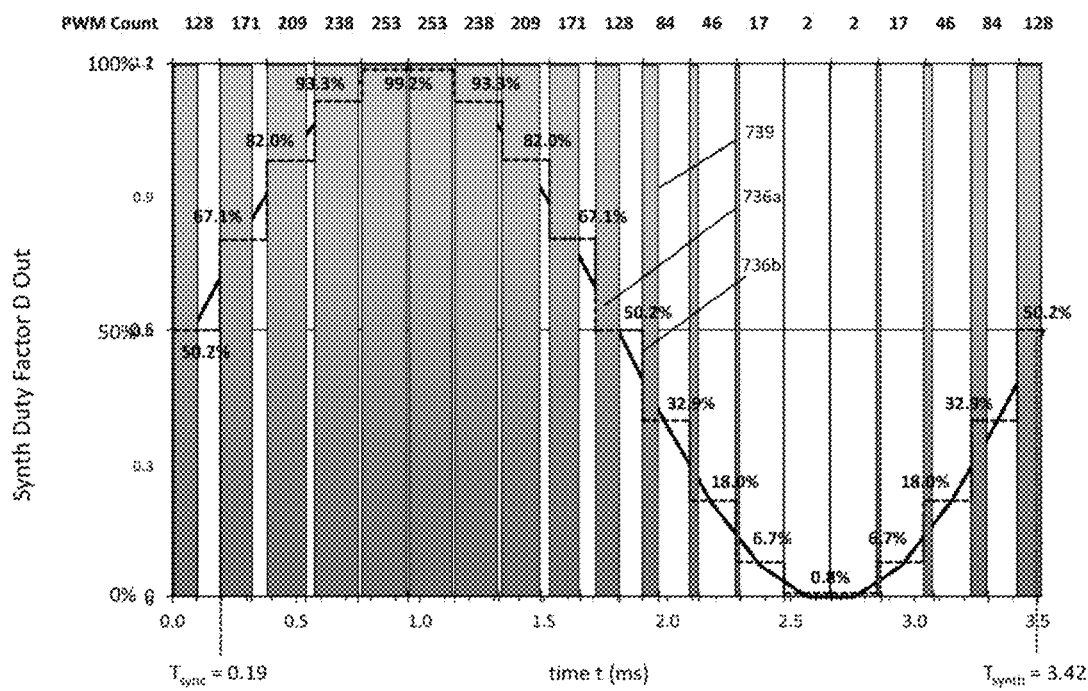
FIG. 34C graphically illustrates the PWM intervals used in the digital synthesis of a 292 Hz (D4) sine wave using 20° intervals.

A time graph of PWM pulses 739 used to synthesize sinusoid 736a and its sequence of average value steps 736b is shown in greater detail in FIG. 34C. For clarity the average value of each step 736b is listed as a percentage for each interval along with the corresponding decimal equivalent of the binary count loaded into the 8-bit PWM counter.

Figure 34D:
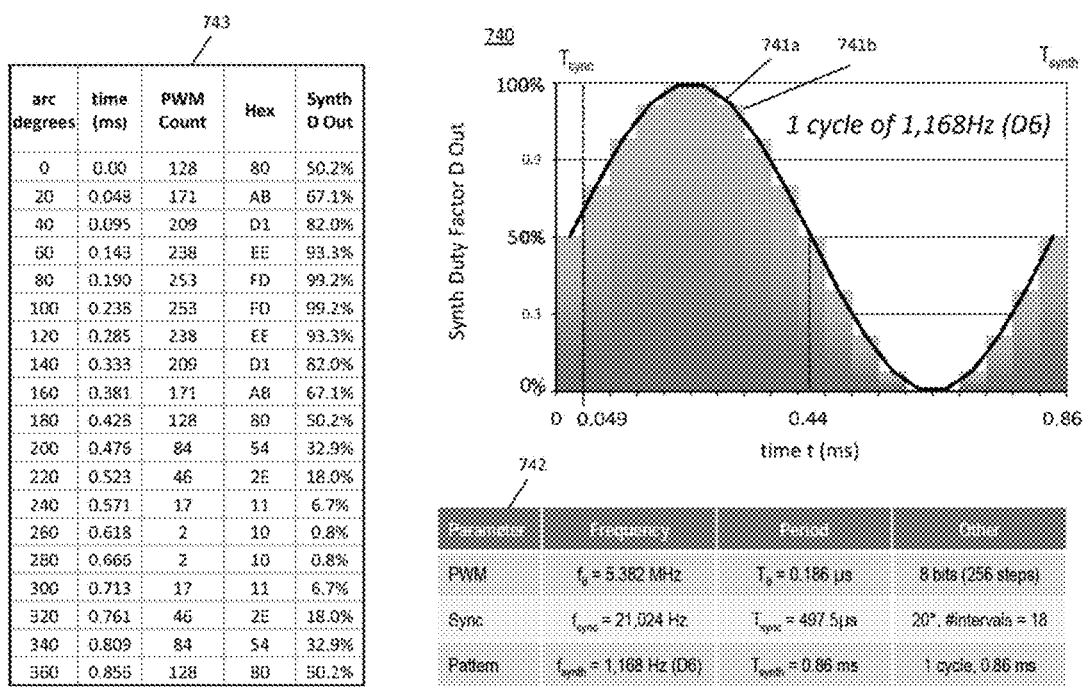
FIG. 34D graphically illustrates the digital synthesis of a 1,168 Hz (D6) sine wave using 20° intervals.

FIG. 34D illustrates synthesis of a single cycle of 1,168 Hz (D6) sinusoid 741a with PWM average value shown by steps 741b comprising 18 time intervals of 20°. In this case, the PWM clock frequency $f_\theta$ and the sync interval $T_{sync}$ are adjusted from $f_\theta$=1.346 Mhz to 5.198 MHz and from $T_{sync}$=190.3 µs to 49.3 µs, commensurate with the decrease in the period of the synthesized sinusoid from 3.42 ms to 0.86 ms as summarized in table 742. The PWM counter sequence used to synthesize sinusoid 741a is described in table 743 both in hexadecimal form and its decimal equivalent. Since the Sync frequency is $f_{sync}$=20,304 Hz, no audio spectrum noise is generated.

Figure 34E:
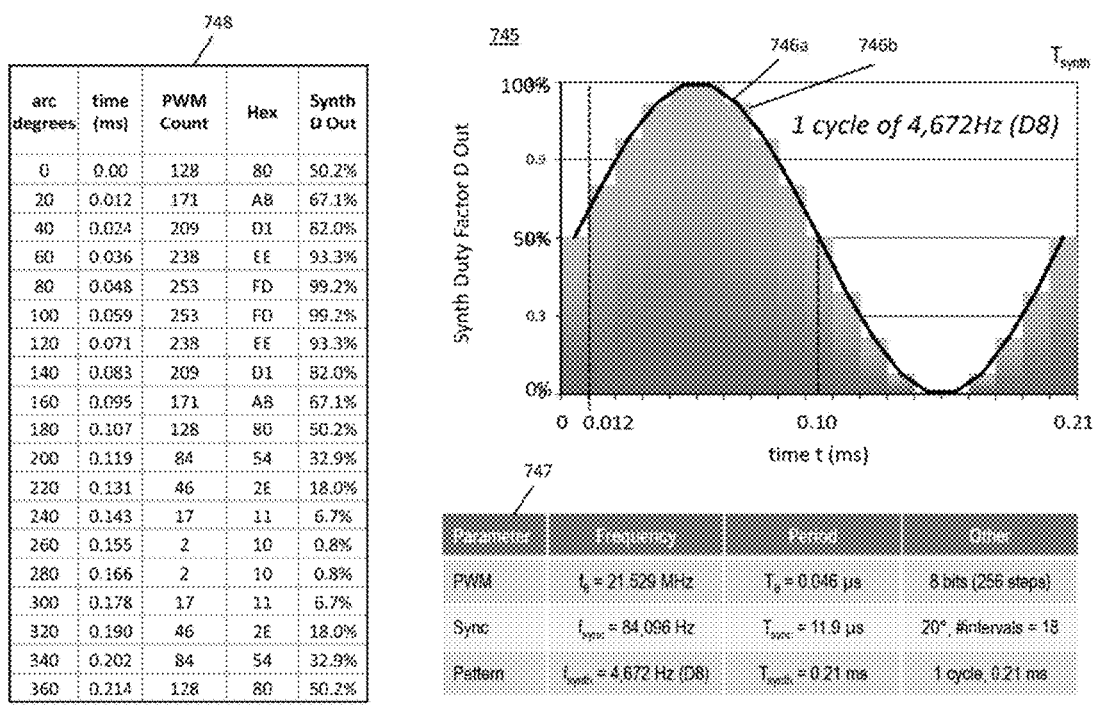
FIG. 34E graphically illustrates the digital synthesis of a 4,672 Hz (D6) sine wave using 20° intervals.

FIG. 34E illustrates the same data for synthesizing a 4,672 Hz (D8) sinusoid 746a shown in graph comprising steps 746b formed in accordance with PWM count sequence shown in table 748 and clock periods shown in table 747. Comparing these conditions with the synthesis of lower frequency sinusoids illustrates that the minimum frequency clock rate requirements for the PWM clock $f_\theta$ change with synthesis accuracy, i.e. the number of time intervals used to synthesize the sinusoid (#intervals), and with the frequency of the sinusoid being synthesized $f_{synth}$.

| | Frequency $f_{synth}$ (Note) | | | | | |
|---|---|---|---|---|---|---|
| | 292 Hz (D4) | | 1,168 Hz (D6) | | 4,672 Hz (D8) | |
| Period $T_{synth}$ | 3.42 ms | | 0.86 ms | | 0.21 ms | |
| #intervals (degrees) | 18 of 20° | 24 of 15° | 18 of 20° | 24 of 15° | 18 of 20° | 24 of 15° |
| Sync clock period $T_{sync}$ | 190.3 μs | 140.7 μs | 47.6 μs | 35.7 μs | 11.9 μs | 8.9 μs |
| Sync clock freq. $f_{sync}$ | 5,256 Hz | 7,008 Hz | 21,024 Hz | 28,032 Hz | 84,096 Hz | 112,128 Hz |
| PWM clock freq. fe | 1.35 MHz | 1.79 MHz | 5.38 MHz | 7.18 MHz | 21.53 Mz | 28.70 MHz |

As the above table reveals, the PWM clock frequency $f_\theta$ increases in proportional to the frequency being synthesized with synthesis at 15° increments carrying a 33% overhead in added clock rate compared to 20° resolution. This added accuracy only becomes limiting when synthesizing the 4,672 Hz (D8) frequency or higher, because 28.7 MHz exceeds the common clock frequency 25 MHz used in microcontrollers and for Ethernet. The table also clarifies that synthesis of a 292 Hz sine wave using the minimum frequency $f_{sync}$ results in noise in the audio spectrum, at approximately 5 kHz and 7 kHz. This problem can be avoided using oversampling, discussed below.

Figure 35A:
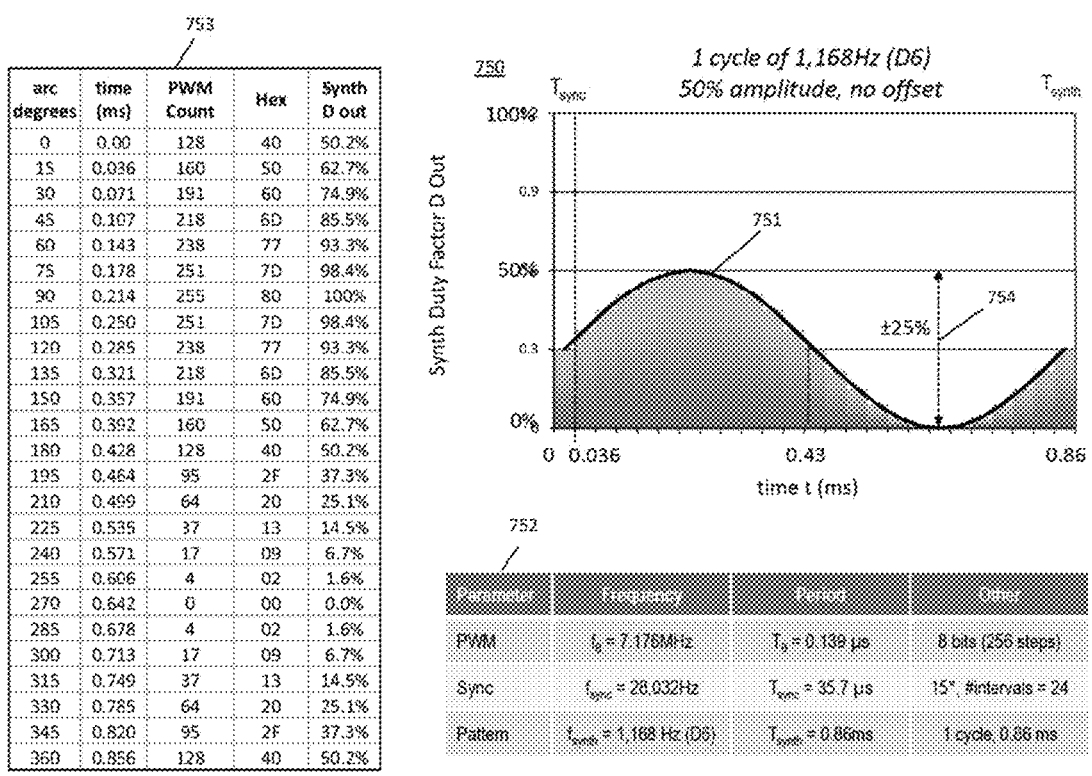
FIG. 35A graphically illustrates the digital synthesis of a 1,168 Hz (D6) sine wave with a 50% amplitude.

While the aforementioned waveforms comprised sinusoids with peak-to-peak amplitudes representing 100% of the digital scale, the magnitude of the synthesized sine wave can be reduced simply by changing the sequential PWM code, as shown in table 753 in FIG. 35A. In the digital synthesized waveform 751 shown in graph 750, the average value of the function is +25% and varies with an amplitude 754 of ±25%, ranging in total from 0% to 50%, i.e. with a sinusoidal output of 25%±25%. Without changing the operating conditions in table 752 from that of a full-scale sinusoid specified previously in table 732, the magnitude and the mean value of the digitally synthesized sinusoid can be controlled simply by adjusting the PWM code sequence labeled "Hex" in table 753 to lower magnitude numbers.

Figure 35B:
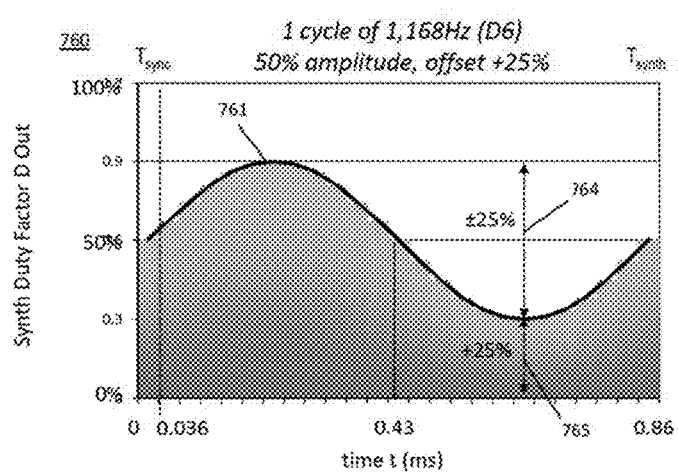
FIG. 35B graphically illustrates the digital synthesis of 1,168 Hz (D6) sine wave with a 50% amplitude offset by +25%.

Although this reduced magnitude sine wave shown in FIG. 35A extended down to 0% at its minimum, as shown in FIG. 35B, even with a reduced magnitude sinusoid of ±25% shown by line 764, the entire curve can be shifted up by a DC offset 765, in this example by +25%, to produce resulting offset sinusoid 761 with a DC bias offset. In phototherapy this waveform modulates the LED brightness while maintaining some illumination at all time. The shift is the average value and the smaller magnitude of the oscillation is accomplished entirely by minimizing the variation in the sequential PWM code described in table 763.

Figure 35C:
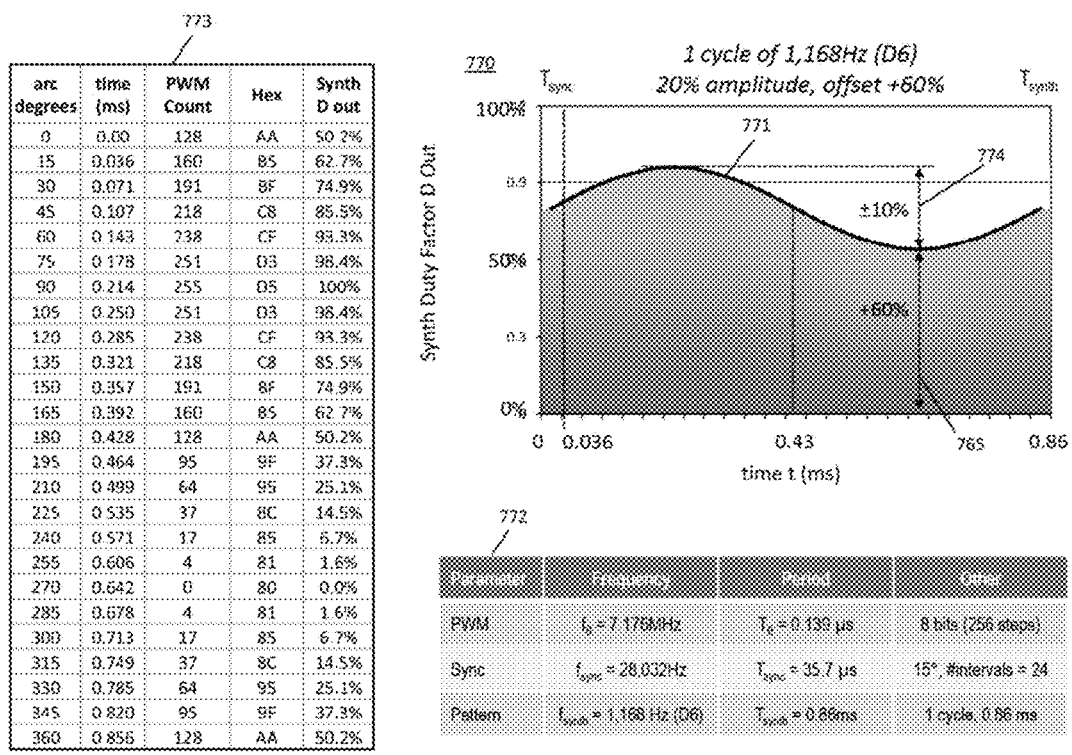
FIG. 35C graphically illustrates the digital synthesis of a 1,168 Hz (D6) sine wave with a 20% amplitude offset by +60%.
Figure 350:
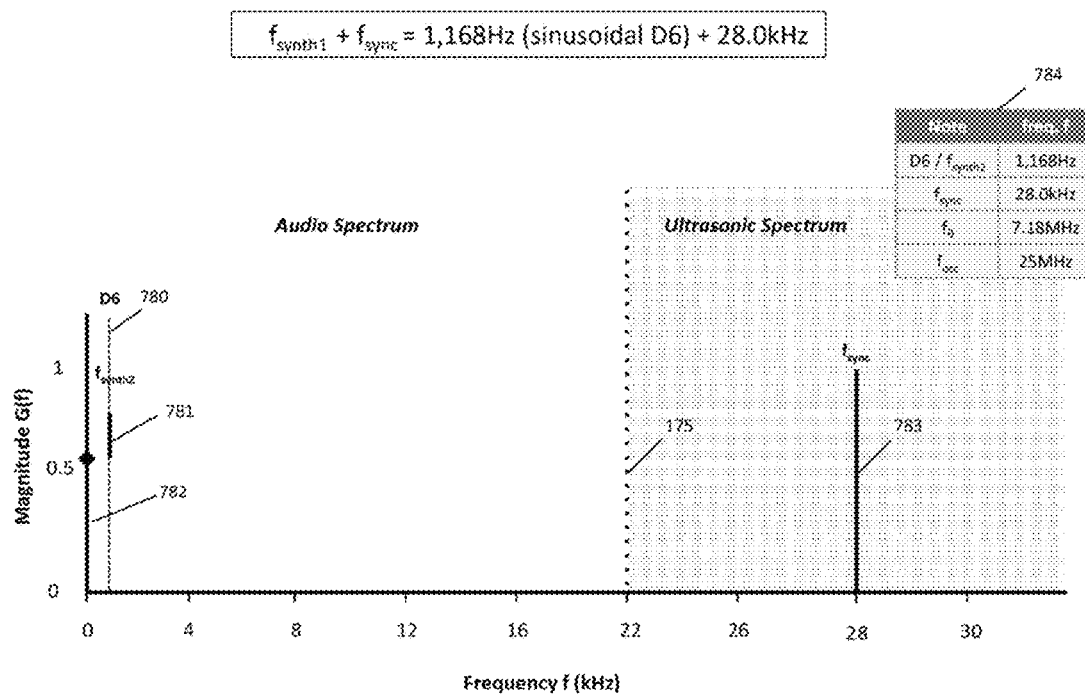

As FIG. 35C reveals, modification of the PWM code as shown in table 773 can be used to further limit the AC swing to a small signal level, e.g. ±10% variation. This AC component 774 can be considered small signal when compared to the DC component 765 of the waveform 771, comprising a +60% offset 765 in the entire sinusoid. The resulting spectrum is shown in FIG. 35D illustrating a sinusoid of limited amplitude (line 781) at frequency of 1,168 Hz (D6) (line 780). As graphically represented, the sinusoid of limited amplitude (line 781) sits atop a DC offset (line 782). By definition, direct current or DC has a frequency of zero Hertz. The Sync clock has a frequency (line 783) of 28 kHz, well outside the audio spectrum.

Digital Sinusoidal Synthesis of Chords

An LED phototherapy drive system made in accordance with this invention is also capable of digitally synthesizing chords of multiple frequencies for driving LED strings. When more than one frequency pattern is present, e.g. a higher-frequency sine wave of period $T_{synth1}$ and a lower-frequency sine wave of period $T_{synth2}$, the duration of the pattern is chosen to synthesize at least one cycle of the lower frequency. This means the overall time of the pattern has a duration of at least $T_{synth2}$ and over the same interval more than one 360° cycle of the higher frequency sinusoid will necessarily occur. Assuming for simplicity's sake that the ratio of the sinusoids is an integer, i.e. where $T_{synth2}=\beta T_{synth1}$, then more than β cycles of the higher frequency sinusoid will occur is the same time that only one cycle of the lower frequency sinusoid occurs. For example, a single cycle of a 1,168 Hz (D6) sine wave requires 0.856 ms to complete 360° while a 4,672 Hz (D8) sine waves requires only 0.214 ms. The ratio of their sinusoidal periods is therefore β=4, meaning four complete cycles of the 4,672 Hz (D8) sine wave is completed in the same time interval that only one cycle of the 1,168 Hz sinusoid is completed.

Figure 36:
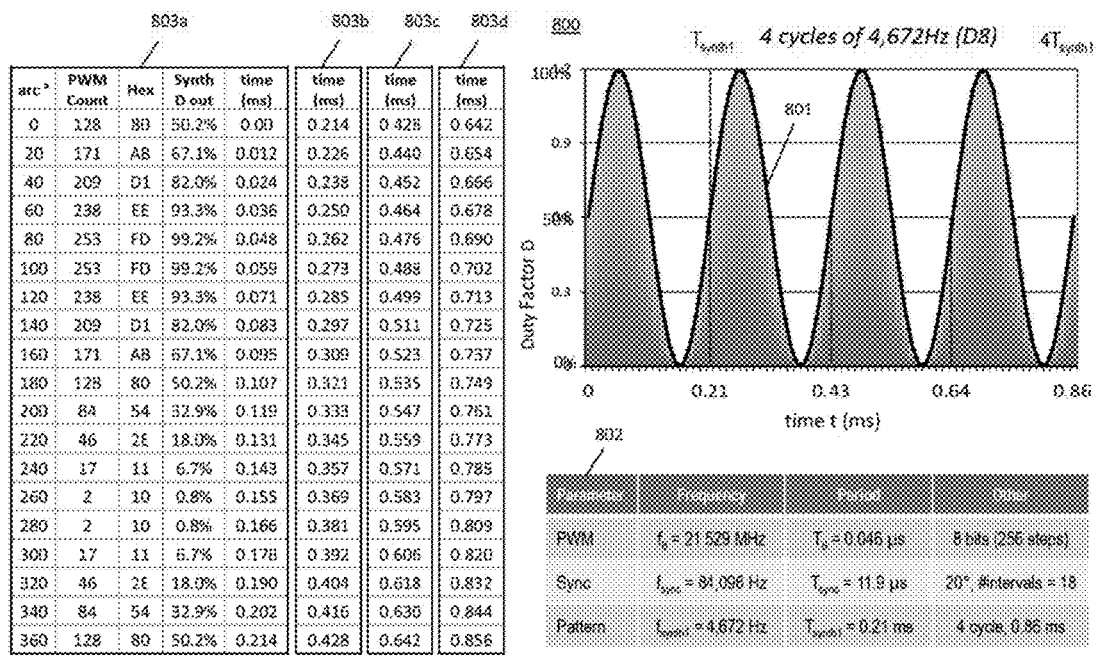
FIG. 36 graphically illustrates the digital synthesis of 4-cycles of a 4,472 Hz (D8) sine wave using 20° intervals.

An example of this higher frequency component is shown in FIG. 36 where an individual cycle of a 4,572 Hz sinusoid having a period $T_{synth1}$=0.214 ms is repeated four cycles having a total period for the pattern synthesized of $\beta T_{synth1}=4T_{synth}=4\cdot0.214$ ms=0.856 ms. The resulting curve 801 shown in graph 800 comprises the same pattern of synthesized duty factor and digital PWM codes described in table 803a for the duration from 0 to 0.214 ms and then repeats in columns 803b, 803c, and 803d for the corresponding time intervals from 0.214 ms to 0.428 ms, from 0.428 ms to 0.642 ms, and from 0.642 ms to 0.856 ms. All told, synthesis of four cycles of a 4,672 Hz sinusoid requires 4·0.214=0.856 ms to complete, comprising 4·18=72 time intervals.

In order to accurately add two or more waveforms together to form a chord in digital synthesis disclosed herein, each function must have a defined value at the same time points, even if the value must be interpolated from other time points. For example to add the values of a 1,168 Hz sine wave together with that of four cycles of a 4,672 Hz sine wave 801, both sine waves must have a corresponding value at each time increment of 0.214 ms. So while synthesis of one 360° cycle of higher-frequency sine wave 801 will comprise only 18 time intervals, the lower frequency sine wave will comprise 72 time intervals, many more than required for its high-fidelity synthesis. Synthesis of a waveform with more time intervals than is practically needed for high fidelity reproduction is herein referred to as "oversampling".

Figure 37A:
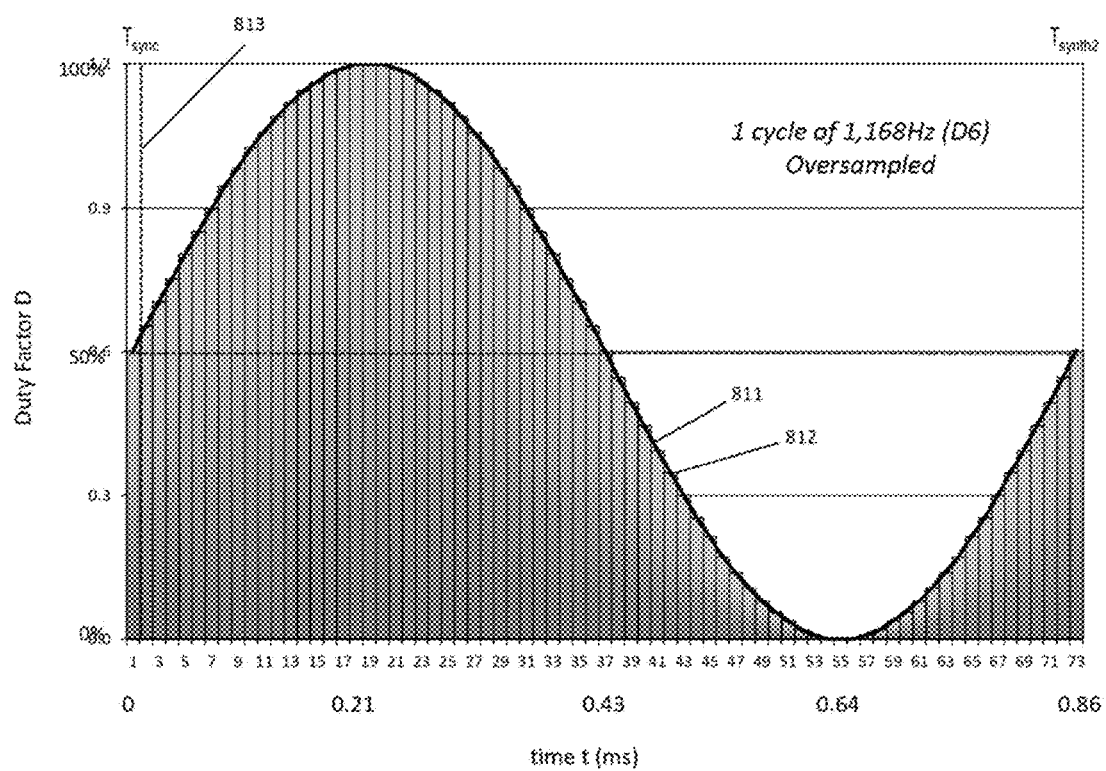
FIG. 37A graphically illustrates the digital synthesis of a 1,168 Hz (D6) sine wave using 4× oversampling.

An example of an oversampled sinusoid is illustrated in FIG. 37A comprising a 1,168 Hz sinusoid 811 generated from the PWM average value 812 of 72 distinct time intervals, 4× the number needed to faithfully synthesize sinusoid 811 with high fidelity. The benefit of oversampling includes reducing output ripple
  simplifying filtering of high frequency clock signals preventing the Sync clock frequency from falling into the audio spectrum when synthesizing low frequency sinusoids increasing the resolution to include common time points where the amplitude of two or more sinusoids of differing frequencies may be added to digitally synthesize a chord of frequencies.

For example, in pattern tables 815a, 815b, and 815c shown in FIG. 37B defining the PWM counts used to synthesize sinusoid 811, only the shaded rows are needed to synthesize the waveform with fidelity. The rest of the PWM counts represent oversampled data. Since only one-in-four PWM counts are needed to accurately produce the desired sine wave, the drive data is 4×, i.e. four-times, oversampled.

In this case, such a waveform can be directly added together with sinusoid 801 of FIG. 36 to produce a new waveform comprising a chord of two sine waves. The process of adding waveforms to produce a new waveform comprising a chord of the two component frequencies is shown graphically in FIG. 38 where graph 820a illustrates the two component frequencies of the chord, namely one cycle of 1,168 Hz (D6) sinusoid 811 and four-cycles of 4,672 Hz (D8) sinusoid 801, each equal in amplitude having a peak-to-peak amplitude of 100% and an average duty factor of 50%. While 4-cycle sinusoid 801 has a period $T_{synth1}$=0.21 ms shown by line 821, lower frequency sinusoid 811 has a period $T_{synth2}$=0.86 shown by line 822, four times longer than $T_{synth1}$. Because the two curves are integral multiples of one another, oversampling facilitates easy addition of the PWM counts at each time interval in order to synthesize the chord of the two notes.

Figure 38:
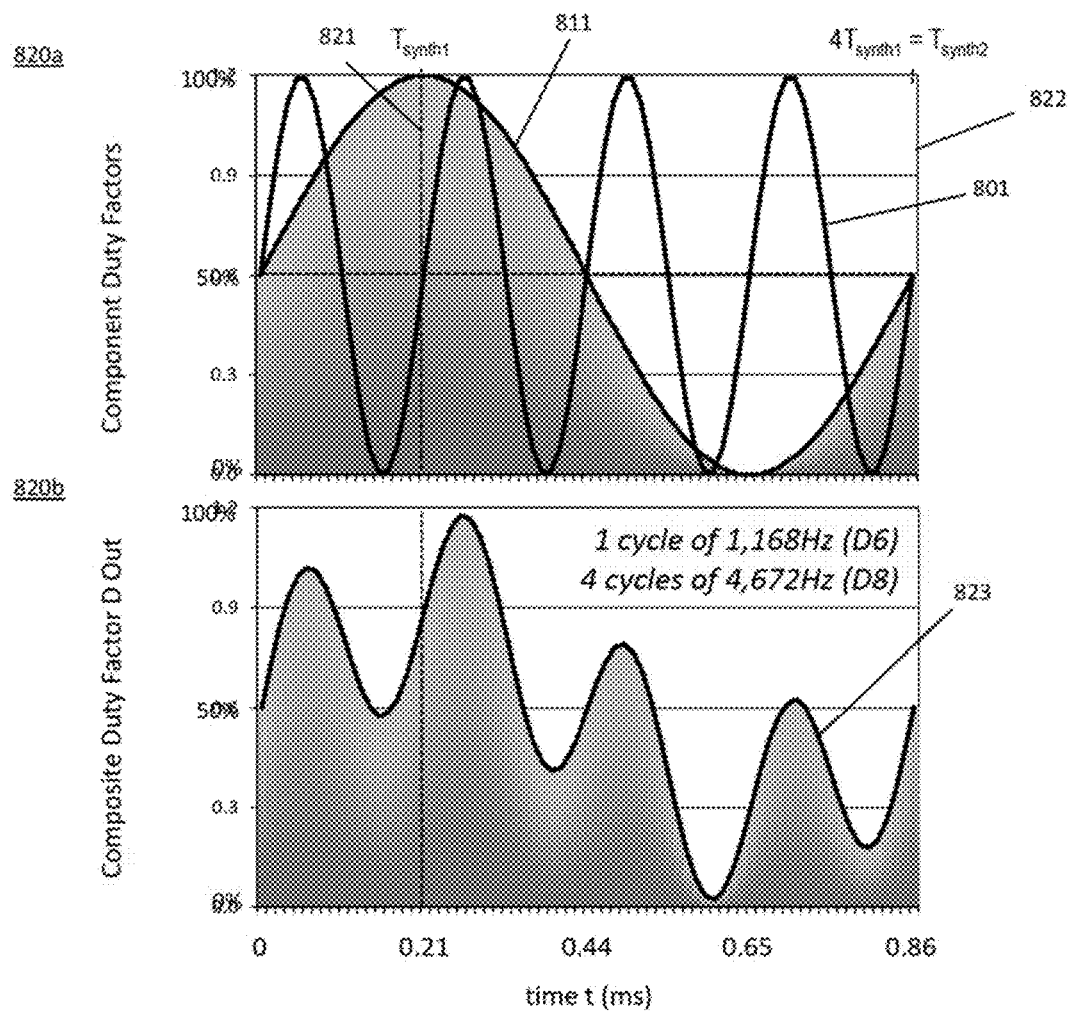
FIG. 38 graphically illustrates the digital synthesis of a chord of 4,472 Hz (D8) and 1,1672 Hz (D6) sinusoids of equal amplitude.
Figure 39:
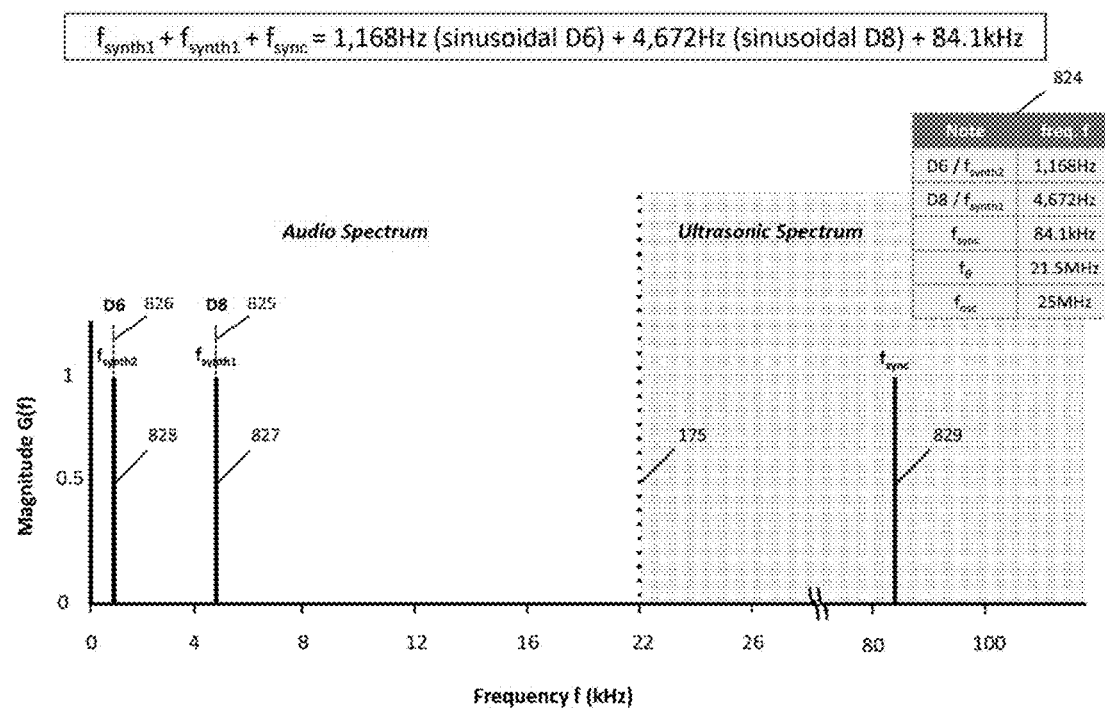
FIG. 39 illustrates the frequency spectrum of digitally synthesized chord of 4,472 Hz (D8) and 1,1672 Hz (D6) sinusoids of equal amplitude.

The resulting composite frequency representing a chord of the component frequencies is shown by waveform 823 in graph 820b in FIG. 38. The sinusoidal nature of the waveform and its constituent frequencies are not easily identified from the time waveform shown in graph 820b. In the frequency spectrum shown in FIG. 39, however, it can readily be seen that the synthesized frequencies represented by lines 828 and 827 equal to the $6^{th}$ and $8^{th}$ octaves of D are of equal amplitude and the only synthesized frequency below the upper limit of the audio spectrum (line 175). The sync clock occurs at a frequency 18 times that of the highest frequency, i.e. 18·4,672 Hz=84,096 Hz (line 829) well into the ultrasonic spectrum.

Figure 40:
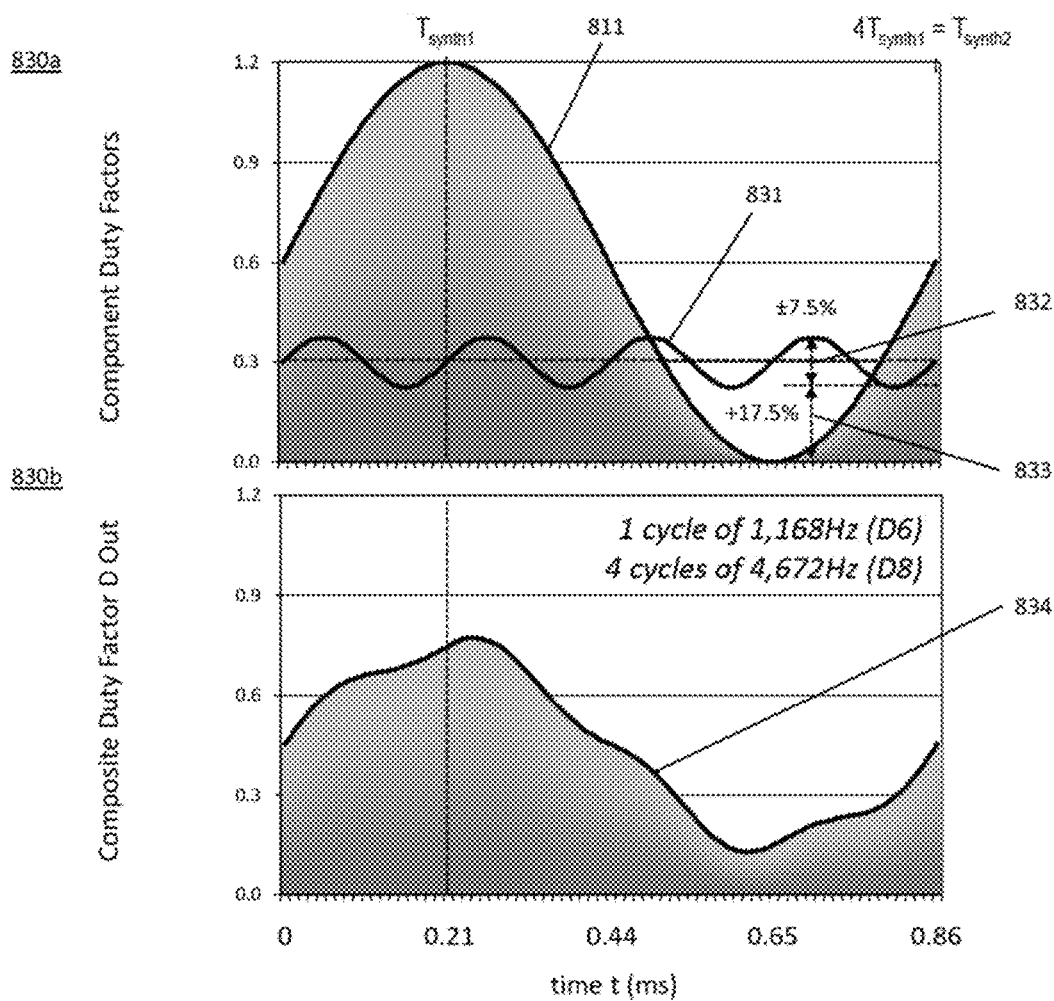
FIG. 40 graphically illustrates the digital synthesis of a chord of 4,472 Hz (D8) and 1,1672 Hz (D6) sinusoids of differing amplitudes.

As more notes are added to the chord or if the constituent frequencies have different amplitudes, the waveform becomes even more complex visually. An example of mixing sinusoids of differing frequency and amplitude is illustrated in graph 830a of FIG. 40 where a 1,168 Hz (D6) sinusoid 811 having a peak-to-peak amplitude of ±50% around a 50% average value is mixed, i.e. algebraically added, to 4 cycles of a 4,672 Hz sinusoid 831 having an attenuated AC magnitude 852 of ±7.5%, with sinusoid 831 sitting atop a DC offset 833 of +17.5%, meaning sinusoid 831 ranges from a low value of 17.5% to an upper value of 32.5%. In phototherapy, a DC offset can be interpreted as a minimum current and corresponding brightness which an LED will never drop below. The resulting waveform 834 from the summation of the two sinusoids into a chord is shown in graph 830b of FIG. 40. Despite the fact that waveform 834 and waveform 823 of FIG. 38 both comprise identical frequency components and harmonic spectra, specifically the notes of D6 and D8, the time waveforms appear entirely different.

Figure 41:
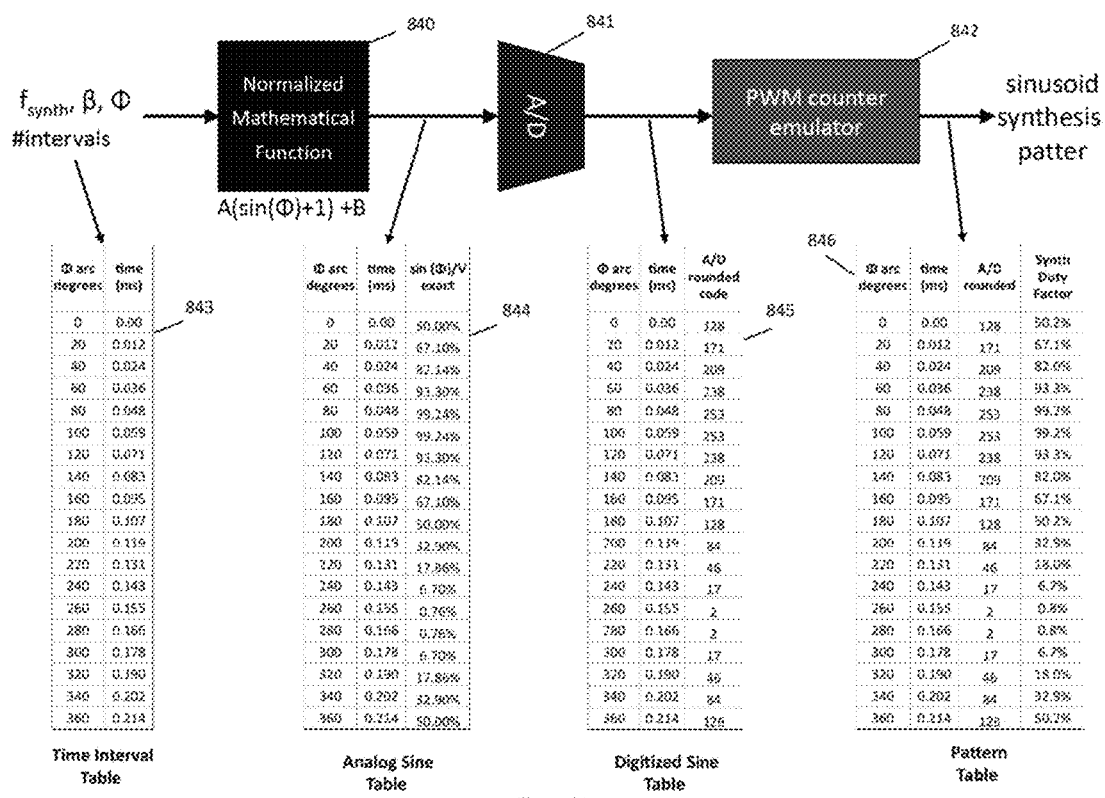
FIG. 41 illustrates an algorithm for generating a synthesis pattern file.

A process by which the pattern tables used for sinusoidal synthesis, e.g. tables 815a through 815c, are created involves an algorithm shown in FIG. 41 or some modification thereof. In this method, starting with the number of time intervals, e.g. #intervals=18, then the arc degree column of data is calculated using a fixed angle namely Φ=360/18=20°. The column arc degrees Φ, combined with the frequency of the synthesized waveform $f_{synth}$, e.g. $f_{synth}$=4,672 Hz, results in a calculated time interval $T_{sync}$=1/$T_{synth}$= (20°/360°)/4,672 Hz=0.012 ms. Given the foregoing, if the number of cycles β=1, the total period β$T_{synth}$ is then β$T_{synth}$ 1·(18·0.012 ms)=0.214 ms. The result is time interval table 843 comprising a column of angles versus corresponding time points. If two cycles are desired, i.e. number of cycles β=2, then the height of time interval table 843 is doubled where the time column extends from 0 ms to 0.428 ms in increments of 0.012 ms and the corresponding arc angle ranges from 0° to 720° in increments of 20°.

The time interval table 843 of time versus arc angle Φ is next processed line-by-line by normalized mathematical function 840, in the example by sinusoid function [A·(sin (Φ)+1)+B]≤100%. As indicated, the function is normalized, i.e., represented as a percentage from 0% to 100%. A represents the amplitude and B the offset of the sine wave. The amplitude A is calculated from the vertical midpoint between the peak-to-peak amplitude of the sine wave; the offset B is calculated from the minima of the sine wave. Thus, 0>A≤0.5 and 0≤B<1, and when A=0.5, B=0. The result is analog sine table 844 comprising columns of time with corresponding arc angle Φ and the output of normalized mathematical function 840, the exact normalized value of the sine function at each arc angle, provided the function does not exceed 100%.

For example, in the un-scaled sine wave with no DC offset shown in FIG. 34D, the multipliers A=0.5 and B=0 so that the output of normalized mathematical function 840 is [0.5·(sin(Φ)+1)+0] having values ranging from 0% to 100% with an average value of 50%. In the case of an attenuated sine wave with a scaled amplitude A=0.25 and no DC offset B=0 as shown in graph 750 of FIG. 35A, the output of normalized mathematical function 840 is [0.25·sin(Φ)+1)+ 0] and ranges from 0% to 50% with an average value of 25%. In the case of an attenuated sine wave with a DC offset as shown in graph 750 of FIG. 35B, A=0.25 and B=0.25, the output of normalized mathematical function 840 is [0.25· (sin(Φ)+1)+0.25] having values ranging from 25% to 75% with an average value of 50%. In the example shown in graph 770 of FIG. 35C illustrating a highly attenuated sine wave with a large DC offset, A=0.10 and B=0.60, whereby the output of normalized mathematical function 840 is given by [0.10·(sin(Φ)+1)+0.60] with values ranging from 60% to 80% and an average value of 70%.

In the event that the calculated value of normalized mathematical function 840 exceeds 100%, e.g. [(A·sin(Φ)+ 1)+B]>100%, then the output of mathematical function 840 is pinned at a 100%, the maximum value of the function. In such cases the top portion of the waveform will "clipped" at a maximum value of 100%, and the resulting waveform distortion will likely produce unwarranted harmonics and spectral contamination. For stimulating healing in phototherapy where spectral control and the prevention of unwanted harmonics is important, the preferred LED excitation pattern is a distortion free sinusoidal waveform with even harmonics. In other cases such as photodynamic therapy, i.e. using photons to excite or chemically activate a chemical compound or pharmaceutical, or in efforts to target cellular destruction of bacteria or viruses, other waveforms may also be beneficial. The mathematical operation performed by normalized mathematical function 840 may therefore represent any time varying and preferably cyclical, function and is not limited to sinusoids. Regardless of the function, it is convenient to scale the analog output of this operation to "exact values" ranging between 0% to 100%, i.e. normalized data. While normalization is not actually required, limiting the data range by scaling and normalization to a range of 0% to 100% makes subsequent data processing of the analog table 844 more convenient in avoiding signals greater than the input range of any subsequent mathematical operations.

The term "exact values" for the purposes of this disclosure means greater accuracy than the LSB, i.e. the least significant bit of the digitization process in subsequent steps of the pattern generating process. The resulting output includes an analog duty factor ranging from 0% to 100%. In the event that the sinusoid has an attenuated amplitude A<50%, e.g. A=25%, results in an output that is limited to a range of duty factors less than full scale.

Referring again to FIG. 41, analog sine table 844 is then inputted into an analog-to-digital converter 841, wherein each percentage value of the function $(A\cdot\sin(\Phi)+1)+B$ is converted into an equivalent digital duty factor to later be used in a PWM counter to generate sinusoids. The conversion process is chosen to match the bit resolution of the intended PWM counter. For example, in digitizing the analog output of normalized mathematical function 840 using 8-bit conversion for use in an 8-bit counter, the duty factor is a digitized value or count ranging from 0 to 255 in decimal format shown in digitized sine table 845. The data may also be represented by a hexadecimal equivalent of this count ranging from 00 to FF, but in actual use, the PWM counter operates digitally using base-2 Boolean logic. The process of digitization naturally rounds the exact analog value to its nearest digital equivalent value, the PWM count with an analog value closest to the original analog value input to analog-to-digital converter 841.

The decimal equivalent of the analog value stored in analog sine table 844 is then loaded into PWM counter emulator 842 to generate the quantized output "synthesized duty factor" a key component of pattern table 846 used to synthesize sinusoids in real time. The synth duty factor column in pattern table 846 represents the analog synthesized value closest to the original exact value in analog sine table 844, the small difference being the digitization error resulting by the conversion process of analog-to-digital converter 841. This error can be reviewed when creating pattern table 846 to determine if the agreement with the original is acceptable. If not, a higher bit resolution may be used with the caveat that the maximum frequency of the synthesized sinusoid may be reduced by employing higher resolution data conversion. While the decimal equivalent of the duty factor is used to drive the PWM counter controlling LED drive, the analog value in pattern table 846 is useful to drive display graphics.

While the algorithmic process to generate a pattern file shown in FIG. 41 can be performed in real time "on the fly" or in advance, it is beneficial to perform the process in advance for commonly used frequencies and to store the collection of pattern files in a "pattern library" for convenient access during normal machine operation in phototherapy treatments.

Figure 42A:
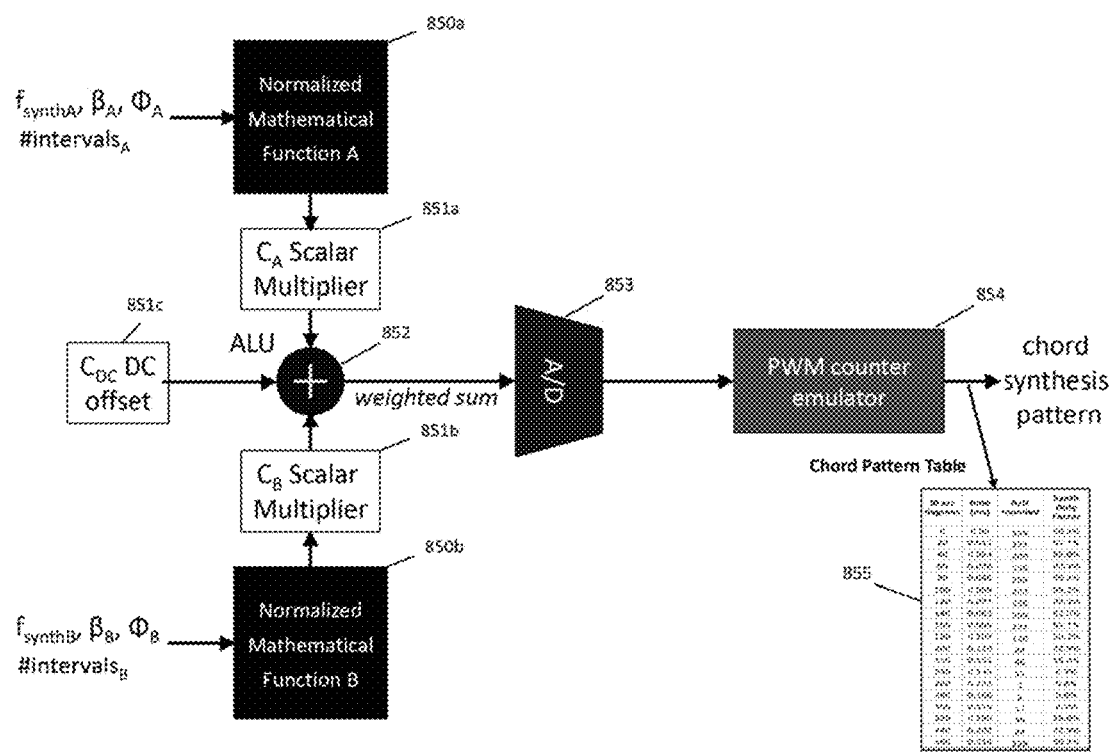
FIG. 42A illustrates an algorithm for generating chords of two or more sinusoids in real time or in advance for storage in a pattern library.
Figure 428:
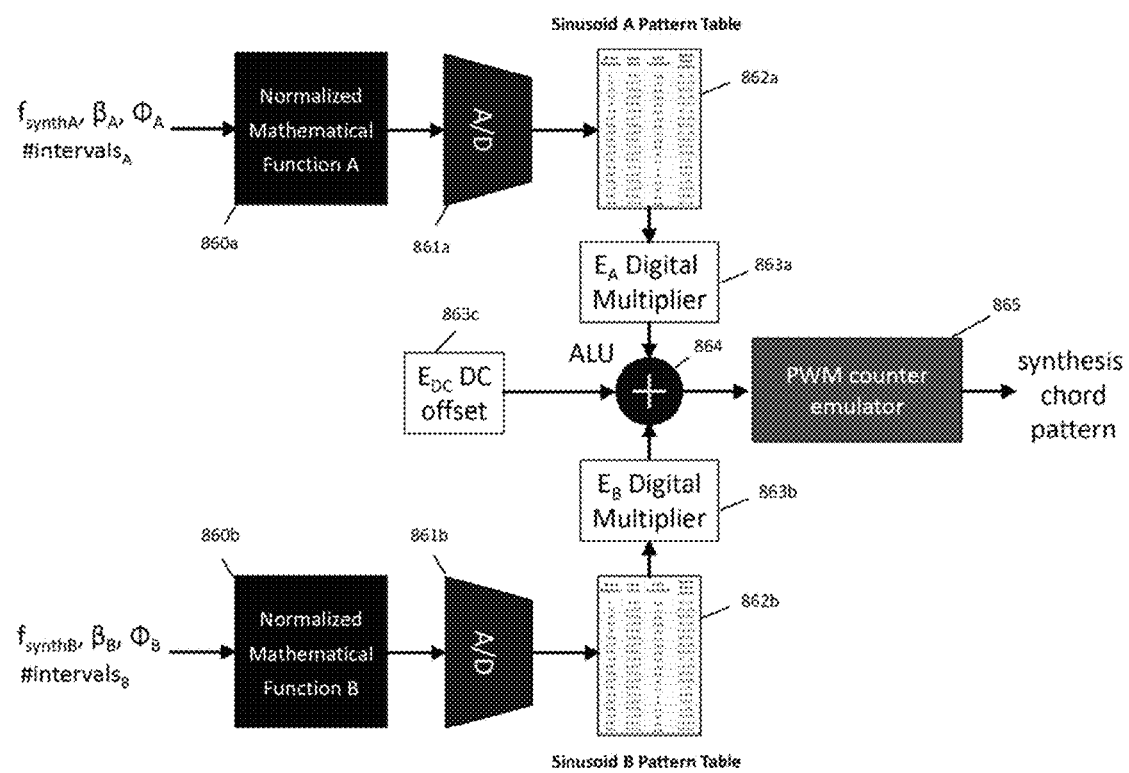

In the same manner, chords of two or more sinusoids can be generated in real time or made in advance and stored in the pattern library as shown in the algorithm of FIG. 42A. In this process the time interval table is generated from the input conditions for both sinusoid A having frequency $f_{synthA}$ and sinusoid B having frequency $f_{synthB}$. The number of time intervals and hence the gradation of arc angle $\Phi$ must be chosen to meet the minimum acceptable number of intervals on the higher frequency sinusoid. To add the amplitudes of different frequency sinusoids the two sine waves should have the same time scale. As a consequence, the lower frequency sine wave will be oversampled such as the one shown in FIG. 37A, having a greater number of time intervals and a finer gradation of arc angles $\Phi$ than is required for synthesis with high fidelity. Each time-interval table is then converted into exact values of magnitude $G(\Phi)$ using normalized mathematical functions 850a and 850b and output in their corresponding analog sine tables (not shown) whereby $$G_A(\Phi)=[A\cdot(\sin(\Phi)+1)+B]_A$$

$$G_B(\Phi)=[A\cdot(\sin(\Phi)+1)+B]_B$$

corresponding to two sine waves of differing frequencies.

These amplitude values are then scaled by scalar multipliers 851a and 851b $C_A$ and $C_B$. After scaling, the magnitudes are added arithmetically together with any DC offset $C_{DC}$ using arithmetic logic unit (ALU) 851 or equivalent programs to facilitate a weighted-sum addition of the component analog waveform data outputted from the normalized mathematical function generators 850a and 850b. The weighted average of these waveforms in ALU 852 is given by $$\text{Weighted Average}=\{C_A\cdot G_A(\Phi)+C_B\cdot G_B(\Phi)+C_{DC}\}/(C_A+C_B+C_{DC})$$

In the event that $C_A=C_B=1$ and $C_{DC}=0$, then the Weighted Average=$\{G_A(\Phi)+G_B(\Phi)\}/2$ and the output is the average of the two values. In the case of a weighted average, e.g. where $C_A=2$ and $C_B=1$, sinusoid A contributes twice as much to the chord as sinusoid B does, in which case $$\text{Weighted Average}=\{2G_A(\Phi)+G_B(\Phi)\}/3$$

If a DC offset comprising a quarter of the maximum amplitude is added the signal, the above equation becomes $$\text{Weighted Average}=\{2G_A(\Phi)+G_B(\Phi)+1\}/4$$

After mixing, the output of ALU 852 is then digitized using analog-to-digital converter 853, resulting in the signal magnitude represented by a digital code used to control the on-time of a PWM counter. To complete the chord pattern table 855, the digital code is converted by PWM counter emulator 854 back into an analog value representing the duty factor. The only error introduced by this process is the single digitization error that occurs from rounding the weighted average output of ALU 852.

Because numerical errors are introduced only once, i.e. when generating the chord pattern file, the algorithm of FIG. 42A offers superior accuracy. This accuracy is especially beneficial when synthesizing complex pattern files for inclusion in a pattern library and used later for subsequent playback. One disadvantage of the algorithm is complexity introduced by numerical weighted averaging of multiple analog values and requiring subsequent digitization, making it less amenable to real time synthesis of chords than purely digital signal reconstruction methods.

An alternative approach using purely digital reconstruction to create chords, shown in FIG. 42B, utilizes the algorithm described in FIG. 41 to generate individual sinusoidal pattern files using normalized mathematical function A 860a and analog-to-digital conversion 861a to create sinusoid A pattern table 862a and similarly using normalized mathematical function B 860b and analog-to-digital conversion 861b to create sinusoid B pattern file 862b. These individual pattern tables can be saved in digital form in the pattern library and used later for generating chords.

As shown in FIG. 42B, to generate a chord, the individual sinusoid pattern tables 862a and 862b are scaled, i.e. multiplied digitally by $E_A$ digital multiplier 860a and $E_B$ digital multiplier 860b respectively. These scaled files are then added digitally to the digital $E_{DC}$ DC offset 863c and added using Boolean algebra in ALU 864, whose output is converted into a synthesis chord pattern by PWM counter emulator 854. Alternatively, the data can be fed directly into a PWM counter to provide real time control of LEDs.

Figure 43:
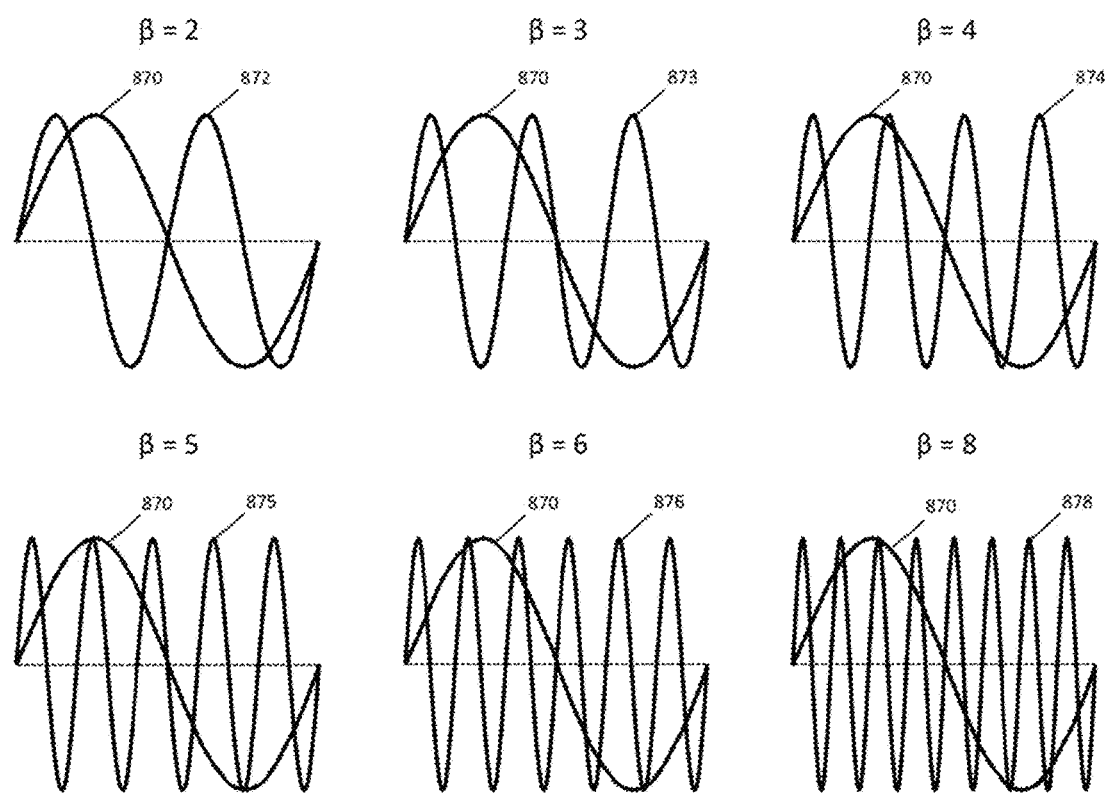
FIG. 43 illustrates sinusoids of frequencies that are integral multiples of one another.

One complexity of digital chord synthesis is creating files wherein the mathematical function of the composite waveform is continuous in amplitude and in slope, i.e. in its $1^{st}$ derivative, from the end of one pattern and the beginning of the next pattern. This goal is most easily addressed by sinusoids having composite frequencies that are integral multiples of one another, i.e. where β is an integer, as illustrated in the examples of FIG. 43. In all the examples, the lower frequency sinusoid 870 is combined with higher frequency sinusoids 872, 873, 874, 875, 876 and 878 representing higher frequencies that are integral β multiples of the frequency of sinusoid 870, specifically where β equals 2, 3, 4, 5, 6, and 8, respectively.

Because the frequencies of the sinusoids 872, 873, 874, 875, 876 and 878 are integral multiples of the frequency of the sinusoid 870, each of the sinusoids begins and ends at the same value, namely D=50.2%. The reason the duty factor is 50.2% rather than 50% is an artifact of the digitization process. Even through the PWM counter has 256 levels including 0 volts for a zero code, the number of maximum intervals is 255 steps, i.e. that 255 represents 100%. So code 128 is not exactly half of 255 steps, but instead is 128/255=50.2%

As such, a chord comprising any mix of these two component frequencies will have the same amplitude at the beginning and end of the synthesized pattern and when repeated sequentially will form a piecewise continuous waveform in amplitude and in its $1^{st}$ derivative function. In accordance with the prior discussions of even harmonics and their importance in phototherapy efficacy, even multiple sinusoids 872, 874, 876 and 878 are preferred. The sinusoids 872, 874, and 878, specifically being multiples of two of the frequency of sinusoid 870, represent octaves of the fundamental.

In the event that component frequencies of a chord have a ratio that is non-integral, using a pattern comprising a single cycle of the lower fundamental frequency will not achieve a continuous function across repeated patterns. Any discontinuity across repeated patterns causes a sudden jump in LED current and results in unwanted harmonics, harmonics present constantly because of repeated sequencing of a single pattern for durations ranging from three to over 20 minutes.

One simple solution to overcoming discontinuities in fractional values of β>1 is to employ more than one cycle of the lower fundamental frequency $f_{synth2}=1/T_{synth2}$ to define the total period of the pattern $\beta T_{synth2}$. The minimum number of required cycles can be determined by converting the decimal ratio into a fraction with the lowest common denominator. This lowest common denominator defines the number of cycles of the lower frequency fundamental in the pattern while the numerator defines the number of the complete cycles of the higher frequency.

Figure 44:
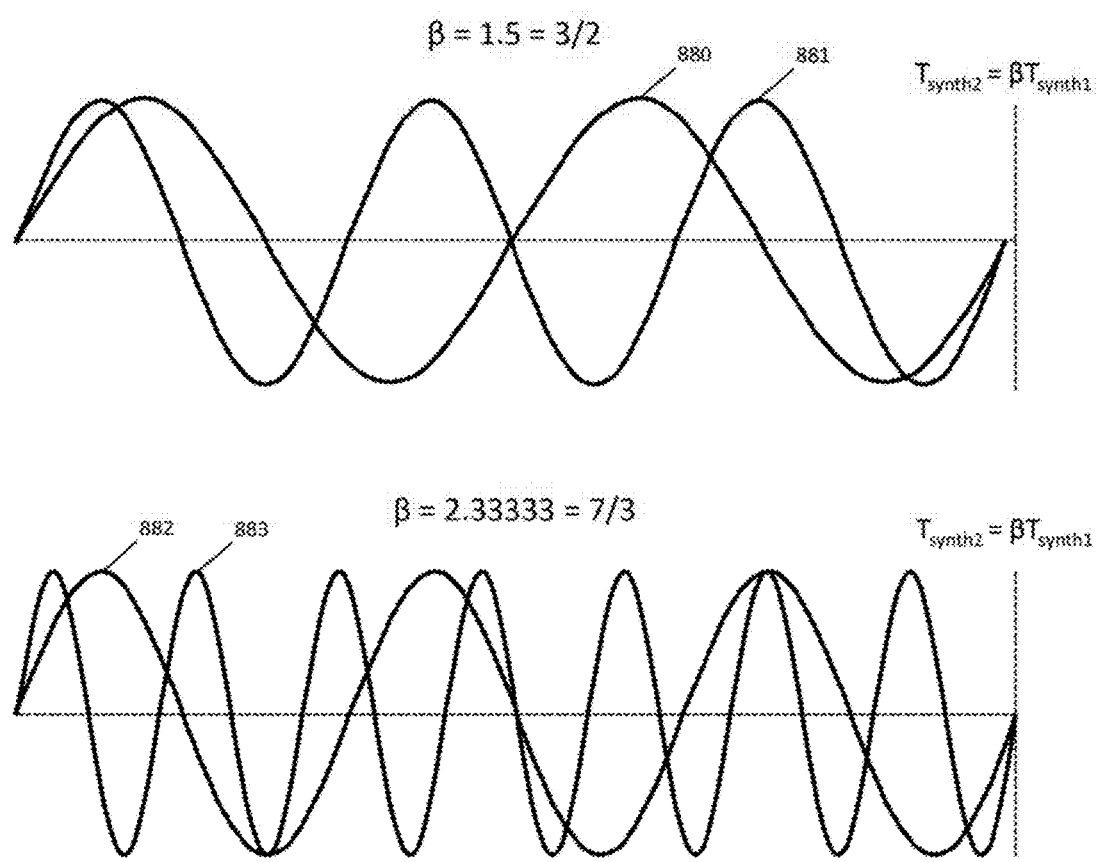
FIG. 44 illustrates sinusoids of frequencies that are fractional multiples of one another.

For example, in the topmost graphic example in FIG. 44 labeled β=1.5=3/2, two sinusoids having a frequency ratio of 1.5 or fractionally as 3/2 comprises two-cycles of lower frequency sinusoid $f_{synth2}$ shown by curve 880 and three-cycles of high frequency sinusoid $f_{synth1}$ shown by curve 881 having the same start and end values. Because the component sinusoids start and end with the same value, any chord combining the two will also be continuous in magnitude and in its slope, i.e. its $1^{st}$ derivative, across repeated patterns. While the pattern may also be stored comprising an integer multiple of this fraction, e.g. 6/4, 12/8, or 24/16, the data sets are substantially larger without adding any additional information or improving resolution. Patterns comprising scalar multiples of lowest-common-denominator based fractions are therefore only beneficial in matching other patterns in a pattern library having the same total pattern duration and not for their fidelity or harmonic content.

Fractions comprising the lowest-common-denominator are applicable for any frequency where the total pattern duration and underlying data file is manageable. For example, the bottommost graphic example in FIG. 44 labeled β=2.33333=7/3 comprises two sinusoids having a frequency ratio of 2.33333 or fractionally as 7/3. In this example, the component of the chords comprise three-cycles of lower frequency sinusoid $f_{synth2}$ shown by curve 882 and seven-cycles of high-frequency sinusoid $f_{synth1}$ shown by curve 883 having the same start and end values. Because the component sinusoids start and end with the same value, any chord combining the two will also be continuous in magnitude and in slope, i.e. in its $1^{st}$ derivative, across repeated patterns. Because more cycles are required to construct a repeating pattern maintaining continuity throughout than in the example of where β=1.5, the data file of such a pattern is naturally larger and longer. While even long duration patterns have manageable file sizes, they are less flexible in forming new combinations.

Figure 45:
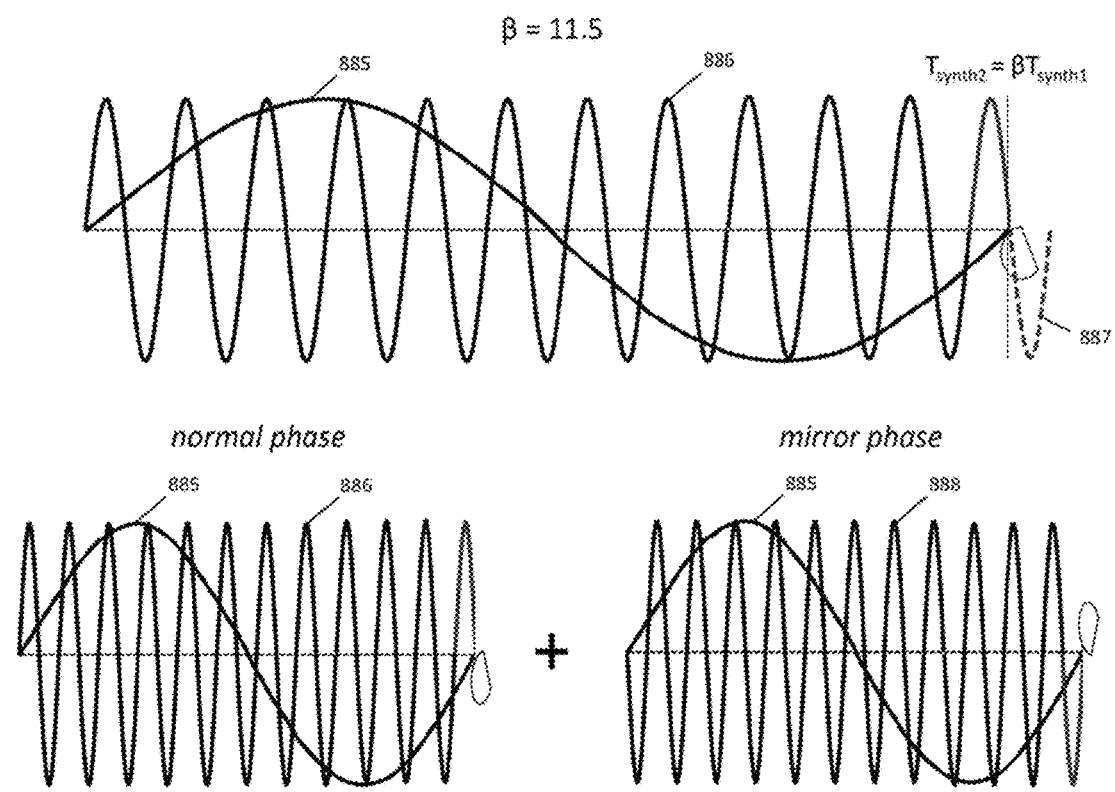
FIG. 45 illustrates the use of mirror phase symmetry to generate a chord consisting of sinusoids whose frequencies have a ratio of 11.5.

Another means to reduce file size and pattern length is to utilize the principal of mirror phase symmetry. For example, in the topmost waveform in FIG. 45 labeled β=11.5 a single-cycle of lower frequency sinusoid of period $T_{synth2}$ is combined with sinusoid 886 having a frequency 11.5 times higher. Sinusoid 886 is one-half a cycle short of being 12 full sinusoidal cycles, as shown by missing piece 887. Even though both sine waves have the same amplitude at the beginning and end of the pattern, the slope of sinusoid 886 is negative at the end of the pattern, meaning the function is positive and declining in magnitude at the end of the pattern. Repeating the pattern will result in two positive "humps" in the sine wave producing an unwanted higher harmonic spectral component.

Rather than doubling the length of the pattern to its lowest common denominator fraction β=23/2 to avoid this issue, another option is to numerically synthesize a mirror phase pattern. This inventive method as disclosed herein is shown in the bottommost graphs of FIG. 45 whereby fundamental sine wave 885 remains the same in both normal phase and mirror phase patterns, while higher frequency sinusoid 886 shown in the normal phase pattern is inverted to form sinusoid 888 in the mirror phase. The alternating combination of normal phase and mirror phase patterns results in sinusoids continuous in magnitude and in slope, i.e. in its $1^{st}$ derivative, without the need for storing long inflexible patterns in the pattern library.

Figure 46:
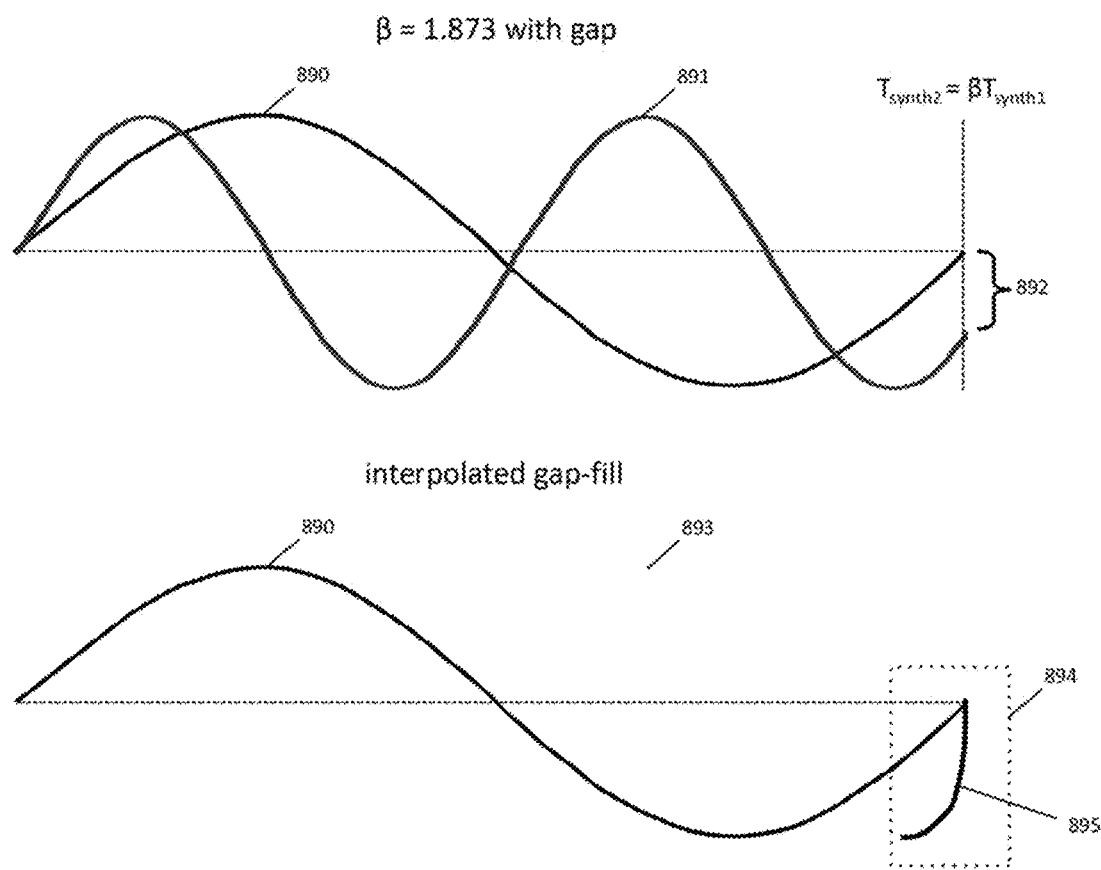
FIG. 46 illustrates the use of an interpolated gap fill to generate a chord consisting of sinusoids having frequencies that are in an irregular ratio (1.873) to one another.

In the event that frequencies of irregular fractions are combined, it can be impractical to find a convenient fraction for constructing two or more sinusoids of full cycles. For example, FIG. 46 illustrates that the frequency of sinusoid 891 is not an integral or even fractional multiple of the frequency of fundamental sine wave 890. Instead, sinusoid 891 exhibits a gap in amplitude 892 between its value at the start of the pattern and the end. Repeating this pattern will result in a severe discontinuity in amplitude and slope at the transition between the end of one pattern and the beginning of the next pattern. Moreover, because of the non-integral fractional multiple in frequency β=1.873, even a large number of cycles will not converge on a discontinuity-free transition. One brute-force solution is to employ an interpolated gap fill 894 where sinusoid 891 is modified into curve 893 with a constructed interpolated line segment 895, created manually or by some mathematical means. The shape of interpolated line segment 895 results in no discontinuity in the amplitude of the pattern and minimal discontinuity in the slope. While the edit does create some harmonics, it can be designed using Fourier analysis to minimize any adverse impact of harmonic spectra.

The disclosed apparatus and methods for synthesizing sinusoidal and chord excitation patterns for LED drive in phototherapy systems using digital synthesis were described in the context wherein the reference current used in the LED drive circuitry remained constant throughout the generation of various patterns. Changes in frequency, amplitude and DC offset can all be generated entirely in the digital domain without the use of analog synthesis. Pure digital synthesis in the context of this application means the use of PWM synthesis not including PCM audio methods. In contrast, because it employs digital-to-analog conversion outputting a time-varying analog output, pulse coded modulation is considered herein as analog synthesis. Previous sections of this disclosure also described a range of options for generating LED drive using both purely analog and such PCM and other digitized analog synthesis methods. Nothing in this application precludes the combination of using both digital and analog synthesis to generate sinusoids and chords thereof.

Figure 47:
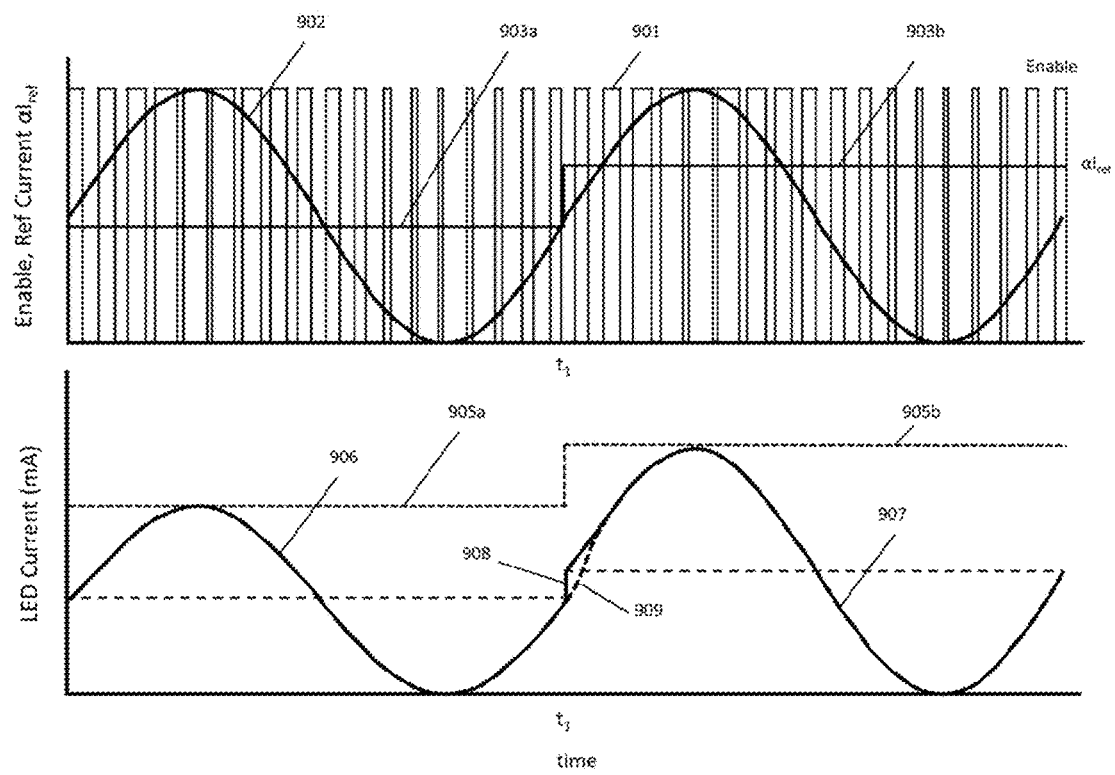
FIG. 47 illustrates generating a sinusoid using PWM while varying the reference current $\beta I_{ref}$.

The discussion of such mixed-mode synthesis is beyond the scope of this application and will not be described further except in the context of using the reference current as a means to adjust the full scale value of sinusoids generated using digital PWM synthesis. An example of this point is illustrated in FIG. 47, wherein the topmost waveform illustrates a PWM generated sine wave 902 using pulses 901 of varying pulse width in accordance with the previously disclosed methods. As shown, the reference current $αI_{ref}$ has a value 903a that at time $t_1$ increases to a higher current 903b. The result of this change in reference current is illustrated in the bottommost graph of FIG. 47 showing the LED current resulting from the described synthesis waveforms.

In the interval prior to time $t_1$ when the reference current is biased at current 903a, the full scale output current of the LED driver is shown by line 905a. After time $t_1$ when the reference current is increased to current 903b, the full scale output current of the LED driver correspondingly increases to current level 905b. Since digital synthesis only controls the LED enable signal of the driver, the actual current flowing when the LED driver is conducting is set by the reference current value. As a result, prior to time $t_1$ the peak-to-peak value of sinusoid 906 ranges from zero to current level 905a while after time $t_1$ the peak-to-peak value of sinusoid 907 ranges from zero to current level 905b, thereby increasing the magnitude of the output without changing the digital pattern code used in sinusoidal synthesis. At the transition at time $t_1$ a discontinuity 908 may occur, which with capacitance present in the LED drive circuit may appear filtered into transition 909. Since changing the reference current is an infrequent event in phototherapy, the non-repeating transition has no significant impact on the frequency spectrum of the LED drive.

Bus Architecture Based Control

Referring to FIG. 27A, a distributed LED driver system comprises separate digital synthesizers 203a through 203n independently controlling the current in multiple channels of LEDs through the enable input of MOSFET drivers 215a through 215n. Constructed using dedicated counters and latches, these digital synthesizers can operate independently but require a proper sequence of PWM codes to be repeatedly loaded into the counters to synthesize the desired sinusoid. In this regard, collectively digital synthesizers 203 therefore require some centralized control able to uniquely access each digital synthesizer 203a through 203n at high speeds. One such means to implement this kind of control and communication is through a high-speed digital bus.

Figure 48:
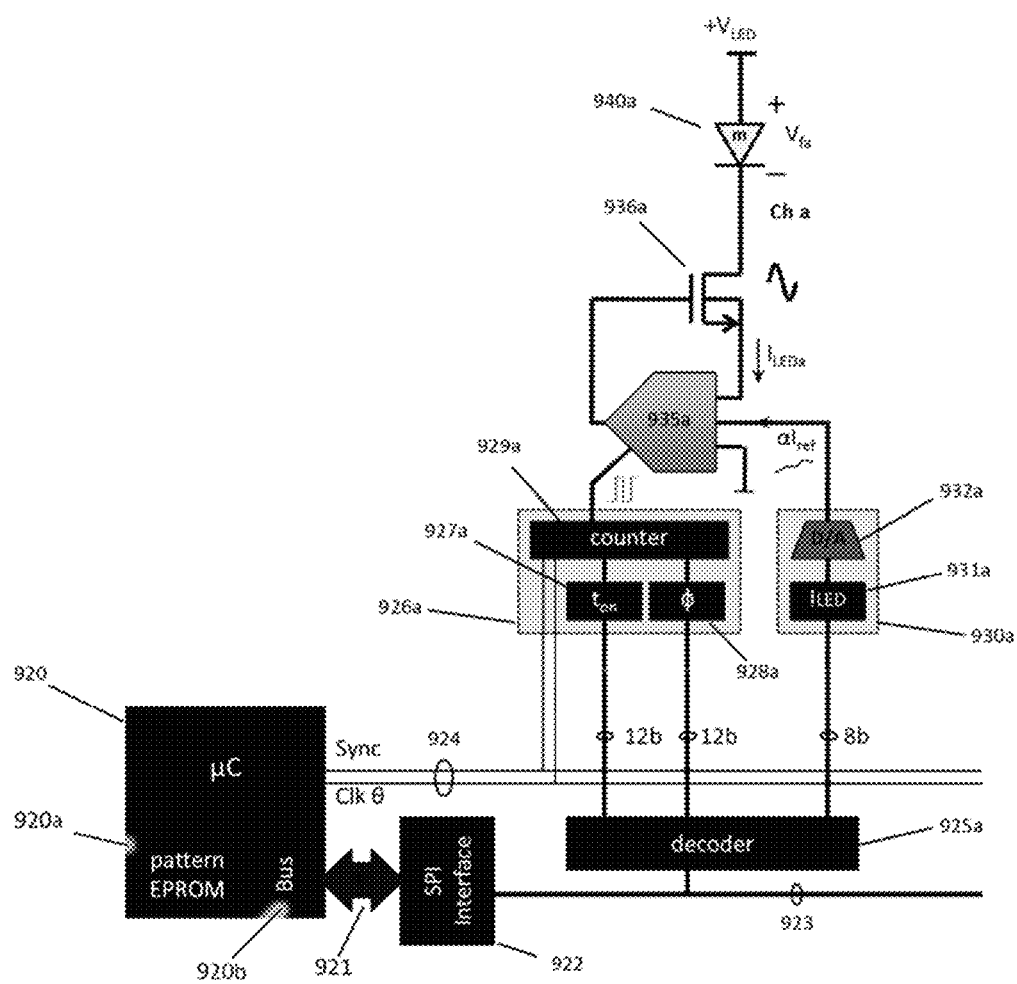
FIG. 48 illustrates how a prior art digital pulse circuit used to drive LED strings may be repurposed for the synthesis of sinusoidal waveforms.

As described in the previously-cited U.S. Pat. No. 9,877,361, a bus-controlled LED driver is used to generate programmable square wave pulses. By utilizing the methods disclosed herein, any digital pulse drive circuit used in LED drives may be repurposed for sinusoidal synthesis. For example the circuit of FIG. 48 illustrates one such implementation of an LED driver including a bus-programmable reference current source 930a comprising a D/A converter 932a, which converts an 8-bit digital word stored in I$_{LED}$ register 931a into an analog current $αI_{ref}$ quantized into 256 levels. If greater resolution is required a greater number of bits, e.g. 12 bits for 4096 quantized levels or 16 bits for 65,536 quantized levels, may be used.

As shown, the data setting the current $αI_{ref}$ may be loaded into the latch of I$_{LED}$ register 931a from a software or firmware program residing in a central controller or microprocessor 920 and passed to $I_{LED}$ register 931a through digital communication bus 923. Because more than one channel is generally controlled by the same microcontroller 920 and connected to the same common data bus 923, a decoder 925a is included to detect and store "channel-a" only analog information into digital registers 931a (along with digital synthesis data for registers 927a and 928a), thereby ignoring data for other channels.

Control of the bus is managed through bus control circuitry 920b contained within microcontroller 920. This information is communicated by a data bus 921 generally using a standardized protocol such as SPI (serial peripheral interface) or other high-speed alternatives to the various ICs connected to the bus. Each IC communicates with the bus through an SPI interface 922 and translates the serial information into serial or parallel data specifically formatted for communication inside the integrated circuit, delivering the information to decoder 925a and other channels through an internal bus 923. Internal bus data structures such as internal bus 923 generally comprise parallel data needing a large number of conductors while system bus protocols such as SPI bus 921 used to connect various ICs together generally comprise high-speed serial data in order to minimize the number of connecting wires. The information relayed from microcontroller 920 to SPI interface 922 through SPI bus 921, while it could contain algorithmic information and programs, generally only comprises the operating settings needed to instruct the LED driver IC how to drive the LEDs, e.g. the register data for data registers 927a, 928a and 930a. These settings may be stored in tabular form in pattern EPROM 920a contained within microcontroller 920.

In addition to communicating the digital data for I$_{LED}$ register 931a, the data decoded in decoder 925a loads on-time data into $t_{on}$ register 927a and phase delay data into register 928a Regardless of how programmable current control is achieved for each specific channel, the independent control of an array of multiple strings of LEDs can be achieved by combining or integrating multiple channels of the disclosed LED current driver and controlling them from a central controller or microprocessor.

For example, microcontroller 920 contains within its pattern library 920a the waveform synthesis algorithms executed by the LED driver channel as shown by precision gate bias and control circuit 935a and high-voltage MOSFET 936a. This waveform pattern information generated by microcontroller 920 is relayed from its internal bus control circuitry 920b to one or more LED driver ICs, using the high-speed SPI bus 921. While other digital interfaces may be employed, the SPI bus has become an industry standard in LCD and HDTV backlighting systems, and a common interface for LED driver ICs in large displays (but not in small displays used in handheld electronics). As such, this drive electronics can be repurposed for LED drive in phototherapy, and in accordance with the methods disclosed herein, may be adapted for sinusoidal synthesis despite the fact that such ICs were never intended for such purposes.

Using the SPI protocol, each LED driver IC has its own unique chip ID code. All data packets broadcast from microcontroller 920 on SPI bus 921 include this unique chip ID in the header of the data stream as an a type of address—an address employed to direct the data to one and only one LED driver IC, i.e. the target LED driver IC. Only data matching a particular chip ID will be processed by the corresponding target LED driver IC even though all driver ICs receive the same data broadcast. The chip ID is typically hardware-programmed for each LED driver IC with one or two pins on the IC. Using a four-state input where each pin can be either grounded, tied to $V_{logic}$, left open, or grounded through a resistor, an multistate analog comparator interprets the analog level and outputs a 2-bit digital code. Using two pins, a 4-bit binary word (i.e., a binary nibble) uniquely identifies one of $4^2$ or 16 chip IDs. Whenever a data broadcast is received on SPI bus 921 matching the chip ID of any specific LED drive, i.e. the specific IC is "selected", meaning the particular LED driver IC responds to the broadcast instructions and settings. Data broadcasts whose data header do not match a particular LED driver IC's chip ID are ignored. In summary, each LED driver channel comprising a set of "n" channel drive circuits is generally realized as a single integrated circuit with its own unique "chip ID" used to direct instructions from the microcontroller 920 directly to that specific IC and to the LED drive channels contained within. The same communication from microcontroller 920 is ignored by all other LED drivers made in integrated circuits without the matching chip ID.

Within a selected LED driver IC, SPI interface 922 receives the instructions from SPI bus 921 then interprets and distributes this information to decoder 925a and other channel decoders through internal digital bus 923, which instructs the individual LED driver channels on drive conditions (including channel by channel timing and LED biasing). For high-speed data transmission with a minimal number of interconnections, internal digital bus 923 comprises some combination of serial and parallel communication. Since bus 923 is dedicated and internal to the LED driver of an LED pad, bus 923 may conform to its own defined standards and is not subject to complying with any pre-established protocol.

The digital information from digital bus 923, once decoded by decoder 925a and other channels, is next passed to digital data registers present within each individual LED driver channel. For clarity of identification, respective elements within a given channel utilize the same letter designator as the channel, for example, counter 227 is labeled as 227a in channel-a and as 227b in channel-b (not shown). These registers may be realized with S-type or D-type flip-flops, static latch circuitry, or SRAM cells known to those skilled in the art.

In the particular driver IC shown, the decoded data for each channel includes a 12-bit word defining the channel's on-time $t_{on}$, a 12-bit word defining the phase delay $\phi$, and a 8-bit word defining the LED current, stored respectively in $t_{on}$ register 927a, $\phi$ register 928a, and LED register 931a and corresponding $t_{on}$, $\phi$ and $I_{LED}$ registers in the other channels (not shown). For example the decoded output of decoder 925a comprising the $t_{on}$, $\phi$, and $I_{LED}$ data for channel-a is loaded into registers 927a, 928a, and 931a, respectively.

As previously described, the on-time $t_{on}$ of LED string 940a, along with the signals Clk θ and Sync on clock line 924 combine to set the LEDs' brightness through the corresponding PWM duty factor D, and in waveform synthesis to set the pulsed frequency $f_{synth}$ of the synthesized pattern of photoexcitation. While in pulse synthesis the $t_{on}$, $\phi$, and $I_{LED}$ data loaded in their corresponding registers change infrequently, in sinusoidal synthesis they are updated with every Sync pulse to load a new PWM value into counter 929a.

Similarly, the decoded output of decoder 925b (not shown) comprising the $t_{on}$, $\phi$, and $I_{LED}$ data for channel-b is loaded into its corresponding registers 927b, 928b, and 931b (not shown) respectively, and the decoded output of decoder 925n comprising the $t_{on}$, $\phi$, and $I_{LED}$ data for channel-n is loaded into registers 927n, 928n, and 931n respectively (also not shown).

These data registers may operate as clocked latches loading data only at predefined times, e.g. whenever a Sync pulse occurs, or may be changed continuously in real-time. Synchronizing the data loading and execution to a clock pulse is known herein as "synchronous" or "latched" operation while operating the latches and counter where the data can be changed dynamically at any time is referred to as "asynchronous" or "non-latched" operation. Latched operation limits the maximum operating frequency but exhibits greater noise immunity than asynchronous operation. In this invention disclosure, sinusoidal waveform synthesis performed by LED drive can be realized by either method—using either latched or asynchronous methods. In display applications, however, only latched operation is employed because of an LCD image's severe sensitivity to noise.

In non-latched or asynchronous operation, the data received over SPI bus 921 for channel-a is decoded and immediately loaded into the $t_{on}$, $\phi$, and $I_{LED}$ registers 927a, 928a and 931a and the corresponding registers in the other channels b through n, up to and including registers 927n, 928n and 931n in channel-n. Depending on the LED driver IC's implementation, two possible scenarios can occur thereafter. In the first case the count being executed in counter 929a is allowed to complete its operation, before new data is loaded into counter 927a and a new count commences.

By example, in non-latched operation data freshly loaded from decoder 925a into $t_{on}$, $\phi$, and LED registers 927a, 928a, and 931a would wait until the ongoing count in counter 929a is completed. After the count is completed the updated data for $t_{on}$ and $\phi$ in registers 927a and 928a are loaded into counter 929a and simultaneously the updated LED data in register 931a is loaded into D/A converter 932a changing the bias condition on precision gate bias and control circuit 935a. After loading the data, counter 929a commences immediately counting pulses on the Clk θ line of clock line 924, first by turning off LED string 940a if it was on, then counting the number of pulses in φ register 928a before toggling precision gate bias and control circuit 935a and MOSFET 936a back on. After turning LED string 940a back on, counter 929a then counts the number of counts loaded from $t_{on}$ register 927a on Clk θ line 223b before shutting LED string 940a off again. The counter 929a then waits for another instruction.

In the second alternative for non-latched or asynchronous operation the system behaves exactly the same as the non-latched operation described previously except that whenever an instruction is received via a broadcast on SPI bus 921, the latch is immediately rewritten and simultaneously restarted. Other than cutting short the ongoing count cycle at the time the register data was rewritten, the operating sequence is identical. Regardless of which asynchronous method is used, it takes time to broadcast, decode, and commence operation for each and every channel on a one-by-one basis. In display applications, the delay in writing new data (and changing an LED string's operating conditions) between the first and last channel of an LCD panel may result in flicker and jitter. As such, asynchronous operation is not a viable option in LCD backlighting. In LED phototherapy, however, where a fixed condition may be maintained for minutes, non-latched operation is a viable option especially for generating higher frequency LED excitation patterns, i.e. for higher values of $f_{synth}$.

Unlike in asynchronous operation, where data is updated continually, in latched or synchronous operation the LED operating conditions are updated only a predetermined occasions, either synchronized to fixed times, or prescribed events. In latched operation of the circuit shown in FIG. 48, whenever the Sync pulse occurs on line 924, the data most recently loaded into $t_{on}$ register 927a and φ register 928a is loaded into counter 929a. Counter 929a then commences counting a number of pulses on the Clk θ line 924 equal to the number stored in φ register 928b before toggling precision gate bias and control circuit 935a on. After completing the count, the counter 927a toggles on precision gate bias and control circuit 935a, biasing the gate of current sink MOSFET 936a to conduct a prescribed amount of current $I_{LEDa}$ thereby illuminating LED string 940a to a desired level of brightness. Counter 929a subsequently counts the number of Clk θ pulses loaded from $t_{on}$ register 927a until the count is complete, and then toggles precision gate bias and control circuit 935a to shut off current MOSFET 936a and terminate illumination. At this point, depending on LED driver IC's design, LED string 940a may remain off for the remainder of the $T_{sync}$ period, i.e. until the next Sync pulse appears on clock line 924, or alternatively repeatedly toggle on and off at the value loaded into $t_{on}$ register 927a until the next Sync pulse occurs on line 223a.

In latched systems the Sync pulse serves several purposes. First, it is an instruction to load the data from the $t_{on}$ register 927a and the φ register 928a into the programmable digital counter 227a. Second, it is an instruction to reset the counter 929a and commence counting in counter 929a, first to pass a period of time corresponding to the phase delay φ, and then to turn on the LED string 940a for the number of clock counts loaded into the corresponding $t_{on}$ register 927a. Thirdly, it is an instruction to load the value in the $I_{LED}$ register 931a into the D/A converter 932a, precisely setting the analog value of current $\alpha L_{ref}$. Similar operations are performed in the corresponding counters, D/A converters, and $t_{on}$, φ and $I_{LED}$ registers in the other channels. Finally, it prevents noise from overwriting the data in the registers 927a, 928a and 931a midstream jumbling the count.

Phototherapeutic Strategy

Using the described inventions to facilitate sinusoidal synthesis of LED drive and illumination patterns for phototherapy applications, photobiological processes in tissue repair and immune response can be stimulated with a greater degree of precision, control and tissue specificity, free from spectral contamination present in pulsed LED drives. The generation of sinusoidal drive waveforms may be performed using analog synthesis, digitally-controlled analog synthesis (PCM), or by purely digital synthesis methods, preferably using fixed frequency PWM techniques. The LED driving waveforms may include a simultaneous mix and/or a programmed sequence of audio-frequency square wave pulses, sine waves, chords of sinusoids, and any other time-varying waveforms such as ramp and triangle waves, filtered audio sources, or combinations thereof.

The disclosed methods may be used for driving any wavelength LED or laser diode, including long infrared, near infrared, visible light including deep red, red, blue and violet, as well as driving near ultra-violet LEDs. Far UV and beyond are excluded because of the detrimental health risks of ionizing radiation.

As disclosed, the methods and apparatus facilitate control of key parameters for phototherapy, namely Magnitude of oscillating LED current drive (AC amplitude)

Frequencies of synthesized sinusoidal oscillations in LED drive

Magnitude of continuous LED current drive (DC offset)

Chords of multiple sinusoidal frequencies

The control may be performed dynamically or in prescribed patterns made in advance of their use and stored in pattern libraries. By controlling the above variables without the potential adverse impact of unwanted audio frequency harmonics, particularly of odd harmonic multiples, a strategy consistent with the principles of bioresonance and photobiological time constants can be realized.

Figure 49:
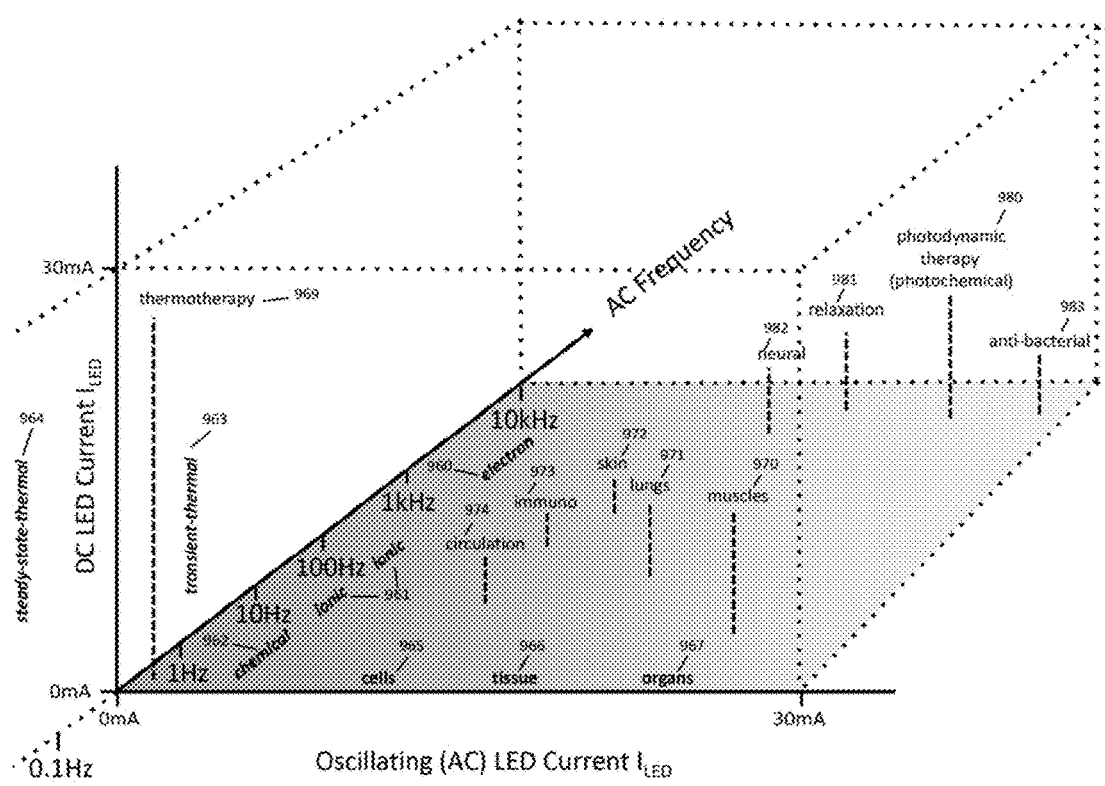
FIG. 49 illustrates various physiological structures and conditions that may be amenable to treatment with phototherapy, as a function of the amplitude, frequency and DC component of the sinusoidal current used to illuminate the LEDs.

An example of a phototherapeutic strategy is graphically illustrated in 3D in FIG. 49, where the x-axis represents the peak-to-peak amplitude of an oscillating LED current from 0 mA to 30 mA, the y-axis represents the constant DC component of the LED current ranging from 0 mA to 30 mA, and the z-axis represents the AC frequency of sinusoidal oscillations ranging from 0.1 Hz (nearly DC) to over 10 kHz. The locations of the various physiological structures and conditions, shown by the numerals 960 through 983, illustrate the areas of possible maximum beneficial effects from particular combinations of the amplitude, sinusoidal frequency and DC component of the current used to illuminate the LED string. The graph illustrates in general terms the prior observation that electron transport 960 can occur at higher frequencies, in the range of kHz and beyond, ionic transport 961 occurs in tens-to-hundreds of Hertz, and chemical transformations 962 occur in the single-digit Hertz range. Also in the single-digit range, albeit specifically at higher DC currents or higher low-frequency AC currents, transient thermal effects are manifest. Steady state thermal processes 964 occur at even higher DC currents from increased heating at frequencies from 0.1 Hz to DC, i.e. 0 Hz.

Also, as shown, higher magnitude AC is required to stimulate entire organs 967, while lesser current is need to treat patches of tissue 966, and even smaller current to affect concentrated groups of cells 965. Using too high of AC amplitude may actually reduce efficacy by introducing energy at a rate higher than a specific photobiological process can absorb or use. Among the treatments shown in an exemplary fashion in FIG. 49, muscles 970 and thermotherapy 969 benefit from greater heating and therefore require a higher continuous LED illumination, i.e. a greater DC offset.

Neurological response such as neural 982 and relaxation 981 benefits from higher frequencies and moderate AC currents with minimal DC offset. Photodynamic therapy 980, where photons are being used to stimulate or activate a photochemical process, or anti-bacterial treatments where energy is attempting to impede normal bacterial metabolism require a combination of high excitation frequencies and high AC LED current. Photodynamic therapy also benefits from high total light intensity, meaning brighter and hence higher DC currents are better.

At moderate frequencies and AC current levels with little or no DC contents a variety of remedies exist including treatment therapies for circulation and angiogenesis 974, immune system and hormonal stimulation 973 and skin 972, exhibiting treatment mechanisms at both the cellular and tissue level. Lungs 971, heart, kidney, liver, pancreas and other major bodily organs benefit from an increased AC current invoking mechanisms at both the tissue and organ levels.

Regardless of whether the specific treatments offer efficacies consistent with the 3D graph as depicted, prior pulsed light experiments with their spectral contamination still reveal a significant influence of pulse frequency and LED brightness of treatment efficacy. Using the analog and digital synthesis methods disclosed herein, the ability of the disclosed apparatus of methods to generate and control the frequency and amplitude of sinusoidal excitation of LEDs is expected to profoundly improve phototherapy control and efficacy beyond that of any prior art digitally pulsed LED or laser system.

We claim:

1. A phototherapy process comprising:
   providing a flexible LED pad, the flexible LED pad comprising a plurality of light-emitting diodes (LEDs);
   positioning the flexible LED pad adjacent the skin of a living human being or animal;
   causing the LEDs to emit light through the skin into the human being or animal so as to produce a medically therapeutic effect in an organ, tissue or physiological system of the human being or animal by means of a photobiomodulation process; and
   varying an intensity of the light emitted by the LEDs in accordance with a sinusoidal function, wherein the sinusoidal function comprises a chord comprising a plurality of sine waves, each of the sine waves in the chord having a frequency in the audio range, the frequency of each of the sine waves the chord being different from the frequency of each of the other sine waves in the chord.

2. The phototherapy process of claim 1 wherein the frequency of each of the sine waves is greater that 20 Hz and less than 20 kHz.

3. The phototherapy process of claim 1 wherein varying an intensity of light emitted by the LEDs in accordance with a sinusoidal function comprises connecting the LEDs to a controlled current element, the controlled current element comprising a current source or a current sink, the controlled current element operating through feedback to maintain a current of a prescribed magnitude in the LEDs.

4. The phototherapy process of claim 1 comprising creating the chord by delivering an electrical signal representing each of the plurality of sine waves to an analog mixer.

5. The phototherapy process of claim 1 comprising varying the frequency of at least one of the sine waves while the process is being performed on the human being or animal.

6. The phototherapy process of claim 1 comprising creating the chord by strobing an analog sine waveform ON and OFF at a strobe frequency.

7. The phototherapy process of claim 1 wherein varying an intensity of light emitted by the LEDs in accordance with a sinusoidal function comprises:
   connecting the LEDs to a controlled current element, the controlled current element comprising a current source or a current sink, the controlled current element operating through feedback to maintain a current of a prescribed magnitude in the LEDs when the controlled current element is turned on and to prevent current from flowing in the LEDs when the controlled current element is turned off; and
   controlling the controlled current element such that the LEDs emit light in accordance with the sinusoidal function.

8. The phototherapy process of claim 7 wherein controlling the controlled current element comprises:
   generating a reference current; and
   using the controlled current element to provide a current in the LEDs having a magnitude greater than a magnitude of the reference current by a predetermined ratio.

9. The phototherapy process of claim 8 wherein the controlled current element comprises a first current mirror MOSFET and a second current mirror MOSFET, the first current mirror MOSFET being threshold connected, the process comprising:
   causing the reference current to flow through the first current mirror MOSFET; and
   causing the current in the LEDs to flow through the second current mirror MOSFET.

10. The phototherapy process of claim 9 wherein the controlled current element comprises a current control MOSFET, the process comprising causing the current in the LEDs to flow through the current control MOSFET.

11. The phototherapy process of claim 10 wherein varying an intensity of light emitted by the LEDs in accordance with a sinusoidal function comprises using the current control MOSFET to switch the current in the LEDs ON and OFF so as to generate a sequence of current pulses, each pulse in the sequence having a duty factor equal to $t_{on}/T_{sync}$, wherein $T_{sync}$ represents a time between a leading edge of the pulse and a leading edge of a next pulse in the sequence and $t_{on}$ represents a duration of the pulse, the respective duty factors of the pulses representing values of the sinusoidal function at successive points in time.

12. The phototherapy process of claim 11 wherein a sync frequency is greater than 20 kHz, the sync frequency being equal to $1/T_{sync}$.

13. The phototherapy process of claim 11 wherein switching the current in the LEDs ON and OFF so as to generate a sequence of current pulses comprises applying an enable signal to the gate terminal of the current control MOSFET so as to turn the current control MOSFET ON and OFF.

14. The phototherapy process of claim 13 comprising generating the enable signal as a series of pulses, the leading edges of the pulses of the enable signal being separated by $T_{sync}$, each of the pulses of the enable signal having a duration equal to $T_{on}$.

15. The phototherapy process of claim 14 comprising varying the reference current in accordance with the sinusoidal function and generating the pulses of the enable signal from the reference current such that the frequency of the enable signal is an integral multiple of the frequency of the sinusoidal function.

16. The phototherapy process of claim 14 wherein applying an enable signal to the gate terminal of the current control MOSFET comprises:
loading data representing $T_{sync}$ into a $T_{sync}$ counter;
loading data representing $T_{on}$ into a pulse-width modulation (PWM) counter;
supplying clock pulses at a clock frequency $f_\theta$ to the $T_{sync}$ and PWM counters;
turning the current control MOSFET ON;
decrementing the $T_{sync}$ and PWM counters at the clock frequency $f_\theta$ when the current control MOSFET is turned on; and
turning the current control MOSFET OFF when the data in the PWM counter reaches a first preselected value.

17. The phototherapy process of claim 16 comprising, after turning the current control MOSFET OFF, turning the current control MOSFET ON again when the data in the $T_{sync}$ counter reaches a second preselected value.

18. The phototherapy process claim 17 wherein each of the first and second preselected values is equal zero.

19. The phototherapy process of claim 16 wherein the clock frequency $f_\theta$ is greater than 20 kHz.

20. The phototherapy process of claim 10 comprising:
detecting a voltage difference between a first voltage at a drain terminal of the first current mirror MOSFET and a second voltage at a drain terminal of the second current mirror MOSFET;
using the voltage difference to generate a gate drive voltage; and
delivering the gate drive voltage to a gate terminal of the current control MOSFET.

21. The phototherapy process of claim 20 comprising varying the reference current in accordance with the sinusoidal function.

22. The phototherapy process of claim 21 wherein varying the reference current in accordance with the sinusoidal function comprises supplying an input terminal of a digital-to-analog (D/A) converter with a series of digital values, each of the digital values representing a value of a sine wave at an instant in time.

23. The phototherapy process of claim 9 wherein the predetermined ratio is equal to a ratio of the respective gate widths of the first and second current mirror MOSFETs.

24. The phototherapy process of claim 1 comprising generating each of the sine waves using pulse width modulation with pulses at a frequency $f_{sync}$, wherein a frequency of each of the plurality of sine waves is less than 20 kHz and the frequency $f_{sync}$ is greater than 20 kHz.

25. The phototherapy process of claim 1 wherein at least one of the plurality of sine waves has an audio frequency selected from the group consisting of 292 Hz and integral multiples of 292 Hz.

26. The phototherapy process of claim 1 wherein the photobiomodulation process produces a photobiological process within a mitochondrion in a eukaryotic cell in the human being or animal.

27. The phototherapy process of claim 26 wherein the photobiomodulation process comprises a photon impinging on a cytochrome-c oxidase (CCO) molecule within a mitochondria of a cell, thereby increasing the energy content of the cell by transforming an adenosine monophosphate (AMP) molecule into an adenosine diphosphate (ADP) molecule, the ADP molecule having an energy higher than an energy of the AMP molecule, and converting the ADP molecule into an adenosine triphosphate (ATP) molecule, the ATP molecule having an energy higher than the energy of the ADP molecule.

28. The phototherapy process of claim 27 wherein the photobiomodulation process comprises the release of nitric oxide from the CCO molecule.

* * * * *